US011065311B2

(12) United States Patent
Gruber et al.

(10) Patent No.: US 11,065,311 B2
(45) Date of Patent: Jul. 20, 2021

(54) RETROVIRAL VECTOR WITH MINI-PROMOTER CASSETTE

(71) Applicant: DENOVO BIOPHARMA LLC, San Diego, CA (US)

(72) Inventors: Harry E. Gruber, Rancho Santa Fe, CA (US); Douglas J. Jolly, Encinitas, CA (US); Amy H. Lin, San Diego, CA (US); Christopher R. Logg, South Pasadena, CA (US); Noriyuki Kasahara, Los Angeles, CA (US)

(73) Assignee: DENOVO BIOPHARMA LLC, San Diego, CA (US)

( * ) Notice: Subject to any disclaimer, the term of this patent is extended or adjusted under 35 U.S.C. 154(b) by 989 days.

(21) Appl. No.: 14/438,564

(22) PCT Filed: Oct. 24, 2013

(86) PCT No.: PCT/US2013/066709

§ 371 (c)(1),
(2) Date: Apr. 24, 2015

(87) PCT Pub. No.: WO2014/066700

PCT Pub. Date: May 1, 2014

(65) Prior Publication Data

US 2015/0273029 A1 Oct. 1, 2015

Related U.S. Application Data

(60) Provisional application No. 61/718,610, filed on Oct. 25, 2012.

(51) Int. Cl.

| | |
|---|---|
| ***C12N 15/86*** | (2006.01) |
| ***A61K 48/00*** | (2006.01) |
| ***A61K 38/50*** | (2006.01) |
| ***A61K 35/768*** | (2015.01) |
| ***C12N 15/867*** | (2006.01) |
| ***A61K 31/513*** | (2006.01) |
| ***A61K 45/06*** | (2006.01) |

(52) U.S. Cl.

CPC ............ *A61K 38/50* (2013.01); *A61K 31/513* (2013.01); *A61K 35/768* (2013.01); *A61K 45/06* (2013.01); *A61K 48/00* (2013.01); *C12N 15/86* (2013.01); *C12N 15/867* (2013.01); *C12N 2740/10042* (2013.01); *C12N 2740/10045* (2013.01); *C12N 2740/13032* (2013.01); *C12N 2740/13043* (2013.01); *C12N 2830/00* (2013.01); *C12N 2830/60* (2013.01); *C12Y 305/04001* (2013.01)

(58) Field of Classification Search

CPC .... A61K 38/50; A61K 31/513; A61K 35/768; A61K 45/06; A61K 48/00; C12N 15/86; C12N 2740/10042; C12N 2740/10045; C12N 2740/13032; C12N 2740/13043; C12N 2830/00; C12N 2830/60; C12Y 305/04001

See application file for complete search history.

(56) References Cited

U.S. PATENT DOCUMENTS

| | | | |
|---|---|---|---|
| 4,937,190 | A | 6/1990 | Palmenberg et al. |
| 5,585,096 | A | 12/1996 | Martuza et al. |
| 5,674,486 | A | 10/1997 | Sobol et al. |
| 5,770,428 | A | 6/1998 | Boris-Lawrie |
| 5,830,458 | A | 11/1998 | Gruber et al. |
| 5,888,502 | A | 3/1999 | Gruber et al. |
| 5,925,345 | A | 7/1999 | Blaese et al. |
| 5,948,675 | A | 9/1999 | Klatzmann et al. |
| 5,997,859 | A | 12/1999 | Barber et al. |
| 6,025,192 | A | 2/2000 | Beach et al. |
| 6,033,902 | A | 3/2000 | Haseltine et al. |
| 6,033,905 | A | 3/2000 | Eiden et al. |
| 6,117,681 | A | 9/2000 | Salmons et al. |
| 6,207,455 | B1 | 3/2001 | Chang |
| 6,241,982 | B1 | 6/2001 | Barber et al. |
| 6,248,721 | B1 | 6/2001 | Chang |
| 6,303,380 | B1 | 10/2001 | Lin et al. |
| 6,322,696 | B1 | 11/2001 | McKee et al. |
| 6,410,313 | B1 | 6/2002 | Kasahara et al. |
| 6,410,326 | B1 | 6/2002 | Gruber et al. |
| 6,448,390 | B1 | 9/2002 | Albritton et al. |
| 6,451,304 | B1 | 9/2002 | Friedmann et al. |
| 6,485,965 | B1 | 11/2002 | Klatzmann et al. |
| 6,489,142 | B1 | 12/2002 | Torrent et al. |
| 6,576,463 | B1 | 6/2003 | Kasahara et al. |
| 6,761,884 | B1 | 7/2004 | Blaese et al. |
| 6,806,080 | B2 | 10/2004 | Kasahara et al. |
| 6,899,871 | B2 | 5/2005 | Kasahara et al. |
| 6,953,688 | B2 | 10/2005 | Ferrick et al. |

(Continued)

FOREIGN PATENT DOCUMENTS

| | | | |
|---|---|---|---|
| EP | 3361749 | A1 | 4/1990 |
| EP | 0598029 | B1 | 5/1994 |

(Continued)

OTHER PUBLICATIONS

Communication Pursuant to Rules 161(2) and 162 EPC, European Patent Application No. 13849839.9, dated Jun. 5, 2015.
Heo, Joo Hyung, International Search Report and Written Opinion, PCT/US2013/066709, Korean Intellectual Property Office, dated Jan. 28, 2014.
Bai, Lingfei, International Preliminary Report on Patentability and Written Opinion, PCT/US2013/066709, The International Bureau of WIPO, dated May 7, 2015.
Paar et al., "Influence of vector design and host cell on the mechanism of recombination and emergence of mutant subpopulations of replicating retroviral vectors," BMC Molecular Biology 10(8) (2009).

(Continued)

*Primary Examiner* — Catherine S Hibbert
(74) *Attorney, Agent, or Firm* — Rimon, P.C.

(57) ABSTRACT

This disclosure provides a retroviral replicating vector for gene delivery comprising a therapeutic cassette containing at least one mini-promoter linked to a gene to be expressed.

40 Claims, 12 Drawing Sheets

Specification includes a Sequence Listing.

(56) References Cited

U.S. PATENT DOCUMENTS

| | | | | |
|---|---|---|---|---|
| 7,056,730 | B2 | 6/2006 | Pedersen et al. | |
| 7,211,247 | B2 | 5/2007 | Borok et al. | |
| 8,722,867 | B2 | 5/2014 | Gruber et al. | |
| 8,829,173 | B2 * | 9/2014 | Gruber | A61K 38/2292 424/93.6 |
| 2002/0042137 | A1 | 4/2002 | Richards et al. | |
| 2002/0068362 | A1 | 6/2002 | Murray et al. | |
| 2002/0137889 | A1 | 9/2002 | Soong et al. | |
| 2003/0003565 | A1 | 1/2003 | Dubensky | |
| 2003/0022378 | A1 | 1/2003 | Ehrhardt et al. | |
| 2003/0121068 | A1 | 6/2003 | Orchard et al. | |
| 2003/0124136 | A1 | 7/2003 | Hadden | |
| 2003/0157070 | A1 | 8/2003 | Jolly | |
| 2003/0157718 | A1 | 8/2003 | Pedersen et al. | |
| 2003/0165466 | A1 | 9/2003 | Gromeier et al. | |
| 2003/0219410 | A1 | 11/2003 | Calatrava | |
| 2004/0068762 | A1 | 4/2004 | Attar et al. | |
| 2004/0096972 | A1 | 5/2004 | Audit et al. | |
| 2004/0142449 | A1 | 7/2004 | Tonjes et al. | |
| 2004/0146489 | A1 | 7/2004 | Yu et al. | |
| 2004/0197308 | A1 | 10/2004 | Takahashi et al. | |
| 2004/0248827 | A1 | 12/2004 | Zheng et al. | |
| 2005/0002903 | A1 * | 1/2005 | Kasahara | A01K 67/0271 424/93.2 |
| 2005/0059004 | A1 | 3/2005 | Atabekov et al. | |
| 2005/0063945 | A1 | 3/2005 | Paul | |
| 2006/0084791 | A1 | 4/2006 | Pedersen et al. | |
| 2006/0147420 | A1 | 7/2006 | Fueyo et al. | |
| 2006/0147429 | A1 | 7/2006 | Diamond | |
| 2007/0003522 | A1 | 1/2007 | Albritton | |
| 2007/0254357 | A1 | 11/2007 | Gregory et al. | |
| 2007/0281898 | A1 | 12/2007 | Slade et al. | |
| 2008/0008685 | A1 | 1/2008 | Kasahara | |
| 2008/0227736 | A1 | 9/2008 | Chen et al. | |
| 2009/0028842 | A1 | 1/2009 | Gojkovic et al. | |
| 2009/0111106 | A1 | 4/2009 | Mitrophanous et al. | |
| 2009/0169580 | A1 | 7/2009 | Whelan et al. | |
| 2009/0275508 | A1 | 11/2009 | Romani et al. | |
| 2011/0217267 | A1 | 9/2011 | Gruber et al. | |
| 2011/0287020 | A1 | 11/2011 | Gruber et al. | |
| 2012/0052554 | A1 | 3/2012 | Kasahara et al. | |
| 2012/0087894 | A1 | 4/2012 | Jolly et al. | |
| 2013/0130986 | A1 | 5/2013 | Gruber et al. | |

FOREIGN PATENT DOCUMENTS

| | | | |
|---|---|---|---|
| EP | 1059356 | B1 | 12/2000 |
| JP | 2005537021 | A | 12/2005 |
| JP | 200754069 | A | 3/2007 |
| JP | 2012503987 | A | 2/2012 |
| NO | 2006048749 | A1 | 5/2006 |
| WO | 9411524 | | 5/1994 |
| WO | 9732026 | | 9/1997 |
| WO | 1999020742 | A2 | 4/1999 |
| WO | 1999036561 | A1 | 7/1999 |
| WO | 9960008 | A1 | 11/1999 |
| WO | 0018240 | A2 | 4/2000 |
| WO | 01/04266 | A1 | 1/2001 |
| WO | 03060101 | A2 | 7/2003 |
| WO | 2005047505 | A2 | 5/2005 |
| WO | 2005086922 | A2 | 9/2005 |
| WO | 06058231 | A2 | 6/2006 |
| WO | 2006/127980 | A2 | 11/2006 |
| WO | 2007041350 | A2 | 4/2007 |
| WO | 2007065690 | A1 | 6/2007 |
| WO | 2007081740 | A2 | 7/2007 |
| WO | 2007095201 | A2 | 8/2007 |
| WO | 2007107156 | A2 | 9/2007 |
| WO | 2008011636 | A2 | 1/2008 |
| WO | 2008151633 | A2 | 12/2008 |
| WO | 2010002937 | A1 | 1/2010 |
| WO | 2010036986 | A2 | 4/2010 |
| WO | 2010045002 | A2 | 4/2010 |
| WO | 2010148203 | A2 | 12/2010 |
| WO | 2010148203 | A3 | 8/2011 |
| WO | 2011/126864 | A2 | 10/2011 |
| WO | 2012/021794 | A1 | 2/2012 |
| WO | 2011126864 | A3 | 4/2012 |

OTHER PUBLICATIONS

Pao et al., "Use of avian retroviral vectors to introduce transcriptional regulators into mammalian cells for analyses of tumor maintenance," PNAS 100(15):8764-8769.

Paola et al., "Suicide Gene Therapy With the Yeast Fusion Gene Cytosine Deaminase/Uracil Phosphoribosyltransferase is Not Enough for Pancreatic Cancer," Pancreas 35(3):224-231 (2007).

Poon et al. "Nucleocapsid and matrix protein contributions to selective human immunodeficiency virus type 1 genomic RNA packaging," J. Virol. 72:1983-1993 (1998).

Qiao et al. "VSV-G pseudotyped, MuLV-based, semi-replication-competent retrovirus for cancer treatment. Gene Ther," 13:1457-1470 (2006).

Rainov et al., "Clinical trials with retrovirus mediated gene therapy—what have we learned?," J. Neurooncol. 65:227-236 (2003).

Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).

Robson et al., "Selection of optimal polypurine tract region sequences during Moloney murine leukemia virus replication," J. Virol. 74:10293-10303 (2000).

Roscigno et al., "A mutational analysis of the polypyrimidine tract of introns. Effects of sequence differences in pyrimidine tracts on splicing," J. Biol. Chem. 268:11222-11229 (1993).

Saavedra et al., "The simian retrovirus-1 constitutive transport element, unlike the HIV-1 RRE, uses factors required for cellular mRNA export," Curr. Biol. 7:619-628 (1997).

Sanders, D. A. "No false start for novel pseudotyped vectors," Curr. Opin. Biotechnol. 13, 437-442 (2002).

Segall et al., "Characterization and Detection of Artificial Replication-Competent Lentivirus of Altered Host Range," Molecular Therapy 8:118-129 (2003).

Shikova-Lekova et al. "Replication-competent hybrids between murine leukemia virus and foamy virus," J. Virol. 77, 7677-7681 (2003).

Shin et al., "Replication of lengthened Moloney murine leukemia virus genomes is impaired at multiple stages," J. Virol. 74:2694-2702 (2000).

Short et al., "Correlation of leukemogenic potential of murine retroviruses with transcriptional tissue preference of the viral long terminal repeats," J. Virol. 61:1067-1072 (1987).

Sliva et al., "Stable integration of a functional shRNA expression cassette into the murine leukemia virus genome," Virology 351(1):218-225 (2006).

Sodroski et al., "Repetitive structure in the long-terminal-repeat element of a type II human T-cell leukemia virus," Proc. Natl. Acad. Sci. USA 81:4617-4621 (1984).

Soifer et al., "A Novel, Helper-Dependent, Adenovirus-Retrovirus Hybrid Vector: Stable Transduction by a Two-Stage Mechanism," Molecular Therapy 5(5):599-608 (2002).

Solly et al., "Replicative retroviral vectors for cancer gene therapy," Cancer Gene Ther. 10:30-39 (2003).

Staffa et al., Identification of positive and negative splicing regulatory elements within the terminal tat-rev exon of human immunodeficiency virus type 1. Mol. Cell Biol. 15:4597-4605 (1995).

Stuhlmann et al., "Construction and properties of replication-competent murine retroviral vectors encoding methotrexate resistance," Mol. Cell. Biol. 9:100-108 (1989).

Subramanian et al., "Temperature-sensitive replication-competent adenovirus shRNA vectors to study cellular genes in virus-induced apoptosis," Methods in Molecular Medicine 130:125-134 (2007).

Sun et al., "Chronic gene delivery of interferon-inducible protein 10 through replication competent retrovirus vectors suppresses tumor growth," Cancer Gene Ther. 12:900-912 (2005).

(56) References Cited

OTHER PUBLICATIONS

Svarovskaia et al., Retroviral mutation rates and reverse transcriptase fidelity, Front. Biosci. 8:d117-d134 (2003).
Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.
Tai et al., "Antibody-Mediated Targeting of Replication-Competent Retroviral Vectors," Human Gene Therapy 14:789-802 (2003).
Tai et al., "Single-Shot, Multicycle Suicide Gene Therapy by Replication-Competent Retrovirus Vectors Achieves Long-Term Survival Benefit in Experimental Glioma", Molecular Therapy, vol. 12, No. 5, Nov. 2005, pp. 842-851.
Tai et al., "Replication-competent retrovirus vectors for cancer gene therapy," Frontiers in Bioscience 13:3083-95 (2008).
Takeuchi et al., "Type C retrovirus inactivation by human complement is determined by both the viral genome and the producer cell," J. Virol. 68: 8001-8007 (1994).
Trubetskoy et al., "R region sequences in the long terminal repeat of a murine retrovirus specifically increase expression of unspliced RNAs," J. Virol. 73:3477-3483 (1999).
Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).
Van Santen et al., "mRNA precursor splicing in vivo: sequence requirements determined by deletion analysis of an intervening sequence," Proc. Natl Acad. Sci. USA 82:2885-2889 (1985).
Vermes et al., "An accelerated stability study of 5-flucytosine in intravenous solution", Pharm World Sci., 1999, 21(1):35-39.
Vermes et al., "Flucytosine: Correlation between Toxicity and Pharmacokinetic Parameters" Chemotherapy, 2000, 46:86-94.
Vermes et al., "Prediction of Flucytosine-Induced Thrombocytopenia Using Creatinine Clearance", Chemotherapy, 2000, 46:335-341.
Vermes et al., "An in vitro Study on the Active Conversion of Flucytosine to Fluorouracil by Microorganisms in the Human Intestinal Microflora", Chemotherapy, 2003, 49:17-23.
Wang et al., "Highly Efficient and Tumor-Restricted Gene Transfer to Malignant Gliomas by Replication-Competent Retroviral Vectors", Human Gene Therapy, 14:117-127 (Jan. 20, 2003).
Wang et al., "A murine leukemia virus with Cre-LoxP excisible coding sequences allowing superinfection, transgene delivery, and generation of host genomic deletions," Retrovirology 1(5) (2004).
Warmann et al., "Adenovirus-Mediated Cytosine Deaminase/5-Fluorocytosine Suicide Gene Therapy of Human Hepatoblastoma In Vitro", Pediatr. Blood Cancer, 2009, 53:145-151.
Xie et al., "Adenovirus-mediated tissue-targeted expression of a caspase-9-based artificial death switch for the treatment of prostate cancer," Cancer Res. 61:6795-6804 (2001).
Xie et al., "Enhanced Retinal Ganglion Cell Differentiation by atb5 an NSCL1 Coexpression", Investigative Ophthalmology & Visual Science, Sep. 2004, vol. 45, No. 9, pp. 2922-2928.
Yamashita et al., "The Cell Cycle Independence of HIV Infections is Not Determined by Known Karyophilic Viral Elements", PLoS Pathog. 1:e18 (2005).
Yap et al., "Trim5alpha protein restricts both HIV-1 and murine leukemia virus," Proc. Natl. Acad. Sci. USA 101:10786-10791 (2004).
Yi, et al., "Retroviral gene therapy: safety issues and possible solutions," Curr. Gene Ther. 5:25-35 (2005).
Yin et al., "Insertion of sequences into the 3' untranslated region of a replication-competent spleen necrosis virus vector disrupts env gene expression," Arch Virol (1999) 144:73-87.
Young et al., "Chimeric Retroviral Helper Virus and Picornavirus IRES Sequence to Eliminate DNA Methylation for Improved Retroviral Packaging Cells," J. Virol. 74(11):5242-5249 (2000).
Young, Lee W., International Search Report and Written Opinion, PCT/US09/49322, dated Sep. 2, 2009.
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Horn et al., "Highly efficient gene transfer into baboon marrow repopulating cells using GALV-pseudotype oncoretroviral vectors produced by human packaging cells," Blood 100:3960-3967 (2002).
Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).
Hughes, Stephen H., "The RCAS Vector System," Folia Biologica (Praha) 50(3-4):107019 (2004).
Jespersen et al., "Epression of hterologous genes from an IRES translational cassette in replication competent murine leukemia virus vectors," Gene 239(2):227-235 (1999).
Johann et al., "Definition of a domain of GLVR1 which is necessary for infection by gibbon ape leukemia virus and which is highly polymorphic between species," J. Virol. 67:6733-6736 (1993).
Kaliberov et al., "Mutation of *Escherichia coli* cytosine deaminase significantly enhances molecular chemotherapy of human glioma," Gene Ther. 14(14):1111-9; Epub May 10, 2007.
Kaliberova et al., "Molecular chemotherapy of pancreatic cancer using novel mutant bacterial cytosine deaminase gene," 7(9):2845-54 (2008).
Kasahara et al., "Viral vectors", U.S. Publication No. 20080008685A1, Sequence 1, Three Different Score Results.
Kawasaki et al., "Replication-competent retrovirus vector-mediated prodrug activator gene therapy in experimental models of human malignant mesothelioma," Cancer Gene Therapy 18:571-578 (2011).
Kikuchi et al., "Highly Efficient Gene Delivery for Bladder Cancers by Intravesically Administered Replication-Competent Retroviral Vectors," Clin. Cancer Res. 13:4511-4518 (2007).
Klein et al., "Rapid identification of viable retrovirus-transduced cells using the green fluorescent protein as a marker," Gene Ther. 4:1256-1260 (1997).
Kornblihtt et al., "Multiple links between transcription and splicing," RNA 10:1489-1498 (2004).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lazo et al., "Splice acceptor site for the env message of Moloney murine leukemia virus," J. Virol. 61:2038-2041 (1987).
Lewis, Russell E., "Pharmacodynamic implications of use of antifungal agents", Current Opinion in Pharmacology, 2007, 7:491-497.
Lipinski et al., "Optimization of a synthetic beta-catenin-dependent promoter for tumor-specific cancer gene therapy," Mol. Ther. 10:150-161 (2004).
Liu et al., "Tumor-specific therapeutic effect induced by an oncolytic adenoviral vector containing heat shock protein 70 and prodrug activation genes," 13(16):1235-43; Epub Apr. 13, 2006.
Liu et al. "Engineering conditionally replication-competent adenoviral vectors carrying the cytosine deaminase gene increase the infectivity and therapeutic effect for breast cancer gene therapy," 13(4):346-56 (2006).
Liu et al., "The receptors for gibbon ape leukemia virus and amphotropic murine leukemia virus are not downregulated in productively infected cells," Retrovirology 8:53 (2011).
Logg et al., "A Uniquely Stable Replication-Competent Retrovirus Vector Achieves Efficient Gene Delivery in Vitro and in Solid Tumors," Human Gene Therapy 12:921-932 (2001).

(56) References Cited

OTHER PUBLICATIONS

Logg et al., "Genomic Stability of Murine Leukemia Viruses Containing Insertions at the Env-3' Untranslated Region Boundary," Journal of Virology 75(15):6989-6998 (2001).
Logg et al., "Tissue-Specific Transcriptional Targeting of a Replication-Competent Retroviral Vector," Journal of Virology 76(24):12783-12791 (2002).
Logg et al., "Retrovirus-Mediated Gene Transfer to Tumors," Methods in Molecular Biology 246:499-525 (2004).
Logg et al., "Adaptive Evolution of a Tagged Chimeric Gammaretrovirus: Identification of Novel cis-Acting Elements that Modulate Splicing", J. Mol. Biol., (2007), 369, 1214-1229.
Lu et al., "Highly efficient gene transfer to solid tumors in vivo by tumor-selective replicating retrovirus vectors," Int. J. Mol. Med. 25(5):769-75 (2010).
Maguire, Simon. Examination Report. New Zealand Application No. 592070. dated May 24, 2011.
Malim et al., "The HIV-1 rev trans-activator acts through a structured target sequence to activate nuclear export of unspliced viral mRNA," Nature 338:254-257 (1989).
Marzio et al., "In vitro evolution of a highly replicating, doxycycline-dependent HIV for applications in vaccine studies," Proc. Natl Acad. Sci. USA 98:6342-6347 (2001).
Marvich, Maria, Notice of Allowance issued in U.S. Appl. No. 13/072,705, United States Patent and Trademark Office, dated Feb. 18, 2014.
Metzl et al., "Tissue- and Tumor-Specific Targeting of Murine Leukemia Virus-Based Replication-Competent Retroviral Vectors," Journal of Virology 80(14):7070-7078 (2006).
Mild et al., "Frequent intrapatient recombination between human immunodeficiency virus type 1 R5 and X4 envelopes: implications for coreceptor switch," J. Virol. 81:3369-3376 (2007).
Miller et al., "Gene transfer by retrovirus vectors occurs only in cells that are actively replicating at the time of infection," Mol. Cell. Biol. 10:4239-4242 (1990).
Miller et al., "Construction and properties of retrovirus packaging cells based on gibbon ape leukemia virus," J. Virol. 65:2220-2224 (1991).
Miller et al., "Intratumurol 5-Fluorouracil Produced by Cytosine Deaminase/5-Fluorocytosine Gene Therapy is Effective for Experimental Human Glioblastomas," Cancer Res. 62:773 (2002).
Morgan et al., "Retroviral vectors containing putative internal ribosome entry sites: development of a polycistronic gene transfer system and applications to human gene therapy," Nucleic Acids Research 20(6):1293-1299 (1992).
Mullen et al., "Transfer of the bacterial gene for cytosine deaminase to mammalian cells confers lethal sensitivity to 5-fluorocytosine: a negative selection system," PNAS 89(1):33-37 (1992).
Murakami et al., "High-level expression of exogenous genes by replication-competent retrovirus vectors with an internal ribosomal entry site," Gene 202:23-29 (1997).
Nack et al., "Replacement of the murine leukemia virus (MLV) envelope gene with a truncated HIV envelope gene in MLV generates a virus with impaired replication capacity," Virology 315:209-216 (2003).
Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.
Naldini et al., "Efficient transfer, integration, and sustained long-term expression of the transgene in adult rat brains injected with a lentiviral vector," Proc. Natl. Acad. Sci. USA 93:11382-11388 (1996).
Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).
Nogues et al., "Transcriptional activators differ in their abilities to control alternative splicing," J. Biol. Chem. 277:43110-43114 (2002).
Nyati et al., "High and Selective Expression of Yeast Cytosine Deaminase Under a Carcinoembryonic Antigen Promoter-Enhancer," Cancer Res. 62:2337-2342 (2002).
O'Reilly et al., "Second-site changes affect viability of amphotropic/ecotropic chimeric enveloped murine leukemia viruses," J. Virol. 74:899-913 (2000).
Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).
Owens et al., "Human and simian immunodeficiency virus capsid proteins are major viral determinants of early, postentry replication blocks in simian cells," J. Virol. 77:726-731 (2003).
Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).
Aagaard et al., "Fv1-like restriction of N-tropic replication-competent murine leukaemia viruses in mCAT-1-expressing human cells," Journal of General Virology 83:439-442 (2002).
Addison et al., "Comparison of the human versus murine cytomegalovirus immediate early gene promoters for transgene expression by adenoviral vectors," J. Gen. Virol. 78:1653-1661 (1997).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Attar et al., "New transgenic non-human mammal expressing a reporter nucleic acid under the regulation of androgen response elements, useful as models for identifying and developing selective androgen receptor modulators for treating cancer", ADJ25523, May 20, 2004, Patent No. WO2004007753A2.
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick et al., "Splicing mediates the activity of four putative cellular internal ribosome entry sites," PNAS 105 (12):4733-4738 (2008).
Barsov et al., "Adaptation of chimeric retroviruses in vitro and in vivo: isolation of avian retroviral vectors with extended host range," J. Virol. 75:4973-4983 (2001).
Beijer, Gijsbertus. International Preliminary Report on Patentability. International Application No. PCT/US2009/058510. dated Apr. 7, 2011.
Beijer, Gijsbertus. International Preliminary Report on Patentability. International Application No. PCT/US2009/058512. dated Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).

(56) References Cited

OTHER PUBLICATIONS

Bourbeau et al., "Improvement of antitumor activity by gene amplification with a replicating but nondisseminating adenovirus," 67(7):3387-95 (2007).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56, (1999).
Chang et al., "A Replication-Competent Feline Leukemia Virus, Subgroup A (FELV-A), Tagged with Green Fluorescent Protein Reporter Exhibits In Vitro Biological Properties Similar to Those of the Parental FeIV-A," Journal of Virology 75(18):8837-8841 (2001).
Chaszczewska-Markowska et al., "Liposomal formulation of 5-flurocytosine in suicide gene therapy with cytosine deaminase-for colorectal cancer", Cancer Letters, 262 (2008) 164-172.
Cherry et al., "Retroviral Expression in Embryonic Stem Cells and Hematopoietic Stem Cells," Molecular and Cellular Biology 20(20):7419-7426 (2000).
Chio, Jun Ho. International Search Report and Written Opinion. International Application No. PCT/US2009/058510. Date of mailing of the International Search Report dated Jul. 6, 2010.
Cho, Jeong Han. International Search Report and Written Opinion. International Application No. PCT/US2009/058512. Date of mailing of the Report: dated May 11, 2011.
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-region sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.
Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, xenotropic, and amphotropic murine leukemia viruses," J. Virol. 64: 6176-6183 (1990).
Ferrick et al., "Vector for screening for modulators of IgE synthesis, secretion and switch rearrangement," Score Result, AR756992, Sequence 5 from U.S. Pat. No. 6,953,688, Dec. 8, 2005.
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.
Freytag et al., "Phase I Study of Replication-competent Adenovirus-mediated Double Suicide Gene Therapy for the Treatment of Locally Recurrent Prostate Cancer," Cancer Res. 62:4968 (2002).
Friedmann et al., "MoMLV retrovirus gag gene", ABS57189, U.S. Pat. No. 6,451,304, Sep. 17, 2002.
Garton et al., "Efficient Expression of Exogenous Genes in Primary Vascular Cells Using IRES-Based Retroviral Vectors," Biotechniques 32:830-843 (2002).
Giffo-Schmitt, Beate. International Preliminary Report on Patentability. International Application No. PCT/US2009/049322. Date of Issuance of Report: dated Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Khatri, Aparajita et al., "Combination of cytosine deaminase with uracil phosphoribosyl transferase leads to local and distant bystander effects against RM1 prostate cancer in mice," The Journal of Gene Medicine, Sep. 1, 2006, vol. 8, No. 9, pp. 1086-1096.
Korkegian, A. et al., "Computational Thermostabilization of an Enzyme", Science, vol. 308; May 6, 2005; 857-860.
Korkegian, A, Gene-Bank-Y1SB_A; Chain A, Yeast Cytosine Deaminase Triple Mutant; pp. 1-2; http://www.ncbi.nlm.nih.gov/protein/1ySB_A.
Kubo et al., "Highly efficient tumor transduction and antitumor efficacy in experimental human malignant mesothelioma using replicating gibbon ape leukemia virus," Canc. Gene Ther., 20:671-677, 2013.
Kuriyama, Shigeki et al., "Tissue-Specific Expression of HSV-tk Gene Can Induce Efficient Antitumor Effect and Protective Immunity to Wild-Type Hepatocellular Carcinoma", Int. J. Cancer, 1997, 71:470-475.
Lesk, Arthur M. et al., "Prediction of Protein Function from Protein Sequence and Structure", pp. 27 and 28, Abstract, downloaded Sep. 16, 2007.
Logg, Christopher R. et al., "Retroviral Replicating Vectors in Cancer", Methods in Enzymology, 2012, vol. 607, pp. 199-228.
Lowenstein, Pedro Ricardo et al., "Recent advances in the pharmacology of neurological gene therapy," Review, Current Opinion in Pharmacology, 2004, 4:91-97.
Lun, Xueqing et al., "Myxoma Virus Virotherapy for Glioma in Immunocompetent Routes and Synergy with Rapamycin", Cancer Research, Jan. 2010, vol. 70, No. 2.
Luqmani, YA, "Mechanisms of drug resistance in cancer chemotherapy," Med Princ Pract, 2005, 14 Suppl, 1:35-48, Abstract.
Mahan, S. et al., "Random mutagenesis and selection of *Escherichia coli* cytosine deaminase for cancer gene therapy", Protein Engineering, Design & Selection, 2004, vol. 17, No. 8, pp. 625-633.
Mahan, S. et al., "Alanine-Scanning Mutagenesis Reveals a Cytosine Deaminase Mutant with Altered Substrate Preference", Biochemistry, 2004, 43, 8957-8964.

(56) References Cited

OTHER PUBLICATIONS

Maio et al., "Large Randomized Study of 1-7 Thymosin 1, Interferon Alpha, or Both in Combination with Dacarbazine in Patients with Metastatic Melanoma", Journal of Clinical Oncology, vol. 28, No. 10, 2010.
Martin, Joseph B., "Gene therapy and pharmacological treatment of inherited neurological disorders," TIBTECH, 1995, 13:28-35.
Martin, Jill D., International Preliminary Report on Patentability, PCT/US99/23016, dated Jan. 22, 2001.
Martuza, Robert L., "Art locally, think globally," Nature Medicine, 1997, 3:1323.
Mastrangelo, Michael J. et al., "Gene Therapy for Human Cancer: An Essay for Clinicians", Seminars in Oncology, 1996, 23, 1:4-21.
Matthews, Thomas et al., "Antiviral Activity and Mechanism of Action of Ganciclovir", Reviews of Infectious Diseases, Jul.-Aug. 1988, vol. 10, Supp. 3.
Mechold, Undine et al., "Codon optimization of the BirA enzyme gene leads to higher expression and an improved efficiency of biotinylation of target proteins in mammalian cells", Journal of Biotechnology, 2005, 116:245-249.
Meng, Raymond D. et al., "Tumor Suppressor Genes as Targets for Cancer Gene Therapy," 1999, Chapter 1, pp. 3-20.
Meyer, F. et al., "Gene Therapy: Progress and Challenges", Review, Cell Mol. Biol., 2001, 47:1277-1294.
Miller et al., "Targeted vectors for gene therapy", FASEB Journal, vol. 9, Feb. 1995, pp. 190-199.
Miller, Nicholas et al., "Progress in Transcriptionally Targeted and Regulatable Vectors for Genetic Therapy," Human Gene Therapy, May 1, 1997, 8:803-815.
Mukesh et al., "High and Selective Expression of Yeast Cytosine Deaminase Under a Carcinoembryonic Antigen Promoter-Enhancer", Cancer Res., 62:2337-2342 (Apr. 2002).
National Institutes of Health, Recombinant DNA Advisory Committee (RAC), Office of Biotechnology Activities, Jun. 17, 2009, video available at http://videocast.nih.gov/launch.asp?15212 (last visited Oct. 18, 2013).
Naylor, Paul H. et al., "Immunopharmacology of Thymosin α 1 and Cytokine Surgery," Ann NY Acad. Sci., Jun. 13, 2007, 112:235-44.
Nishiyama, T. et al., "Antineoplastic Effects in Rats of 5-Fluorocytosine in Combination with Cytosine Deaminase Capsules". Cancer Res, 1985, 45:1753-1761.
Orkin et al., Report and Recommendations of the Panel to Access the NIH Investment in Research on Gene Therapy, www.NIH.gov, Dec. 1995.
Ostertag et al., "Brain tumor eradication and prolonged survival from intratumoral conversion of 5-fluorocytosine to 5-fluorouracil using a nonlytic retroviral replicating vector", Neuro-Oncology, Feb. 2012, vol. 14, No. 2, pp. 145-159.
Otsuki, Akihiro et al., "Histone deacetylase inhibitors augment antitumor efficacy of herpes-based oncolytic viruses", Molecular Therapy: The Journal of the American Society of Gene Therapy, Sep. 9, 2008, vol. 16, No. 9.
Perez et al., "Design and selection of toca 511 for clinical use: modified retroviral replicating vector with improved stability and gene expression", Molecular Therapy, 2012, vol. 20, No. 9, May 1, 2012, 1689-1698.
Pluta, Krzysztof et al., "Use of HIV as a gene transfer vector", Acta Biochimica Polonica, 2009, vol. 56, No. 4, pp. 531-595.
Poltoratsky, V., "Recombinogenic Phenotype of Human Activation-Induced Cytosine Deaminas", J Immunol., 2004, 172:4308-4313.
Portsmouth et al., "Suicide genes for cancer therapy," Molecular Aspects of Medicine, Mar. 1, 2007, vol. 28, No. 1, pp. 4-41.
Ram, Zvi et al., "In Situ Retroviral-mediated Gene Transfer for the Treatment of Brain Tumors in Rats," Cancer Research, Jan. 1, 1993, 53:83-88.
Romano Gaetano et al., "Latest Developments in Gene Transfer Technology: Achievements, Perspectives, and Controversies over Therapeutic Applications," Stem Cells, 2000, 18:19-39.
Saito, Kengo et al., "Oncolytic virotherapy for oral squamous cell carcinoma using replication-competent viruses", Oral Oncology, 2009, vol. 45, No. 12, pp. 1021-1027.
Schmidt, M. et al., "Replicating Foamy Virus-Based Vectors Directing High Level Expression of Foreign Genes", Virology, vol. 210, 1995, pp. 167-178.
Schulz, Regine, Communication Pursuant to Article 94(30 EPC, European Patent Application No. 09816967.5, dated Oct. 17, 2014.
Shen, H. et al., "Targeting of the Activation-Induced Cytosine Deaminase is Strongly Influenced by the Sequence and Structure of the Targeted DNA", Molecular and Cellular Biology, Dec. 2005, vol. 25, No. 24, pp. 10815-10821.
Silecchia, Gianfranco et al., "Efficacy of repeated cycles of chemo-immunotherapy with Thymosin α1 and Interleukin-2 after intraperitoneal 5-fluorouracil delivery", Cancer Immunol. Immunother., 1999, 48:172-178.
Sjogren, Maria H., "Thymalfasin: an immune system enhancer for the treatment of liver disease," Journal of Gastroenterology and Hepatology, 2004, vol. 19:S69-S72.
Solodushko, V. et al., "Dexamethasone and mifepristone increase retroviral infectivity through different mechanisms," Am. J. Physiol. Lung Cell Mol. Physiol., 2009, vol. 297, pp. L538-L545.
Sotos, G. et al., "Preclinical and clinical aspects of biomodulation of 5-fluorouracil", Cancer Treatment Reviews, 1994, 20:11-49.
Springer, Caroline J. et al., "Prodrug-activating systems in suicide gene therapy," J. Clin. Invest, 2000, 105:1161-1167.
Sterman, Daniel H. et al., "A pilot study of systemic corticosteroid administration in conjunction with intrapleural vector administration in patients with malignant pleural mesothelioma", Cancer Gene Therapy, 2000, vol. 7, No. 12, pp. 1511-1518.
Stewart et al., "Lentivirus-delivered gene stable gene silencing by RNAi in primary cells", RNA, 2003, vol. 9, No. 4, 493-501.
Stolworthy, T., et al., "Yeast Cytosine Deaminase Mutants with Increased Thermostability Impart Sensitivity to 5-Fluorocytosine", J Mol Biol., Mar. 28, 2008; 377(3):854-869.
Strauss, Bryan E. et al., "A novel gene transfer strategy that combines promoter and transgene activities for improved tumor cell inhibition", Cancer Gene Therapy, 2005, 12:935-946.
Stuhlmann et al., "Transfer of a mutant dihydrofolate reductase gene into pre- and postimplantation mouse embryos by a replication-competent retrovirus vector", Journal of Virology, Nov. 1, 1989, vol. 63, No. 11, pp. 4857-4865.
Aghi et al., "Synergistic Anticancer Effects of Ganciclovir/Thymidine Kinase and 5-Fluorocytoseine/Cytosine Deaminase Gene Therapies", J. Natl. Cancer Inst., 90(5):370-380 (Mar. 1998).
Akimoto, M. et al., "A new delivery system for 5-fluorouracil using prodrug and converting enzyme", Laboratory Science, Br J Ophthalmol, 2002, 86:581-586.
Altaner, Cestmir, "Prodrug cancer gene therapy", Cancer Letters, 2008, vol. 270, No. 2, pp. 191-201.
Amar, Lahouari et al., "Control of small inhibitory RNA levels and RNA interference by doxycycline induced activation of a minimal RNA polymerase III promoter", Nucleic Acids Research, 2006, vol. 34, No. 5, e37, pp. 1-7.
Anderson, W. French, "Human Gene Therapy," Nature, Apr. 1998, vol. 392, pp. 25-30.
Bestor, Timothy H ., "Gene silencing as a threat to the success of gene therapy," Clin. Invest., 2000, 105:409-411.
Bhattacharyya et al., "Gene therapy developments for pancreatic cancer", Best Practice & Research Clinical Gastroenterology, Apr. 1, 2006, vol. 20, No. 2, pp. 285-298.
Borisy, Alexis A. et al., "Systematic discovery of multicomponent therapeutics," Proc. Natl. Acad. Sci. USA, 2003, 100:7977-7982.
Brown, B.D. et al., "In vivo administration of lentiviral vectors triggers a type I interferon response that restricts hepatocyte gene transfer and promotes vector clearance", Blood, 2007, 109:2797-2805.
Bushman et al., "Sequence Requirements for Integration of Moloney Murine Leukemia Virus DNA In Vitro", J Virol, 1990, 64: 5645-5648.
Carbone, Michele et al., "Multistep and multifactorial carcinogenesis: when does a contributing factor become a carcinogen?", Seminars in Cancer Biology, 2004, 14:399-405.

(56) References Cited

OTHER PUBLICATIONS

Cavazzana-Calvo, M. et al., "Gene Therapy of Human Severe Combined Immunodeficiency (SCID)-X1 Disease," Science, 2000, 288(5466):669-672.
Cepko et al., "Transduction of Genes Using Retrovirus Vectors", Current Protocols in Molecular Biology, 1996, Chapter 9: Unit 9.9; 9.91-9.916.
Chang et al., "Human Immunodeficiency Viruses Containing Heterologous Enhancer/Promoters Are Replication Competent and Exhibit Different Lymphocyte Tropisms", Journal of Virology, Feb. 1993, vol. 67, No. 3, pp. 743-752.
Chen et al., "Inhibition of Marek's disease virus replication by retroviral vector-based RNA interference," Virology, 2008, vol. 377, No. 2, 265-272.
Clark, Deborah J., Search Report, PCT/US99/23016, dated Mar. 15, 2000.
Clark, Deborah J., Written Opinion, PCT/US99/23016, dated Sep. 14, 2000.
Coffin, John M. et al., "Retroviruses—Development and Applications of Retroviral Vectors—Principles of Retroviral Vector Design", 1997, Cold Spring Harbor Laboratory Press.
Coffin, John M. et al., "Retroviruses—Development and Applications of Retroviral Vectors—Principles of Retroviral Vector Design", 1997, www.ncbi.nlm.nih.gov/books/bv.fcgi?rid=rv.fggrp.4358, figure 1.
Copenheaver, Blaine R., International Search Report and Written Opinion, PCT/US2014/049831, U.S. Patent Office, dated Dec. 29, 2014.
Douar, AM et al., "Effect of amniotic fluid on cationic lipid mediated transfection and retroviral infection," Gene Therapy, 1996, 3:789-796, Abstract.
El-Need, Anas, "Current Strategies in cancer gene therapy," European Jouranl of Pharmacology, 2004, 498:1-8.
El-Need, Anas, "An overview of current delivery systems in cancer gene therapy", Journal of Controlled Release, 2004, 94:1-14.
Elroy-Stein, Orna et al., "Cap-independent translation of mRNA conferred by encephalomyocarditis virus 5' sequence improves the performance of the vaccinia virus/bacteriophage T7 hybrid expression system", Proc. Natl. Acad. Sci. USA, Aug. 1989, vol. 86, pp. 6126-6130.
Erbs, P., et al., "Characterization of the *Saccharomyces cerevisiae* FCY1 gene encoding cytosine deaminase and is homologue FCA1 of Candida albicans", Curr Genet, 1997, 31:1-6.
Fassati et al., "Insertion of two independent enhancers in the long terminal repeat of a self-inactivating vector results in high-titer retroviral vectors with tissue-specific expression," Human Gene Therapy, 1998, vol. 9, pp. 2459-2468.
Faustinella et al., "A New Family of Murine Retroviral Vectors with Extended Multiple Cloning Sites for Gene Insertion", Human Gene Therapy, 1994, vol. 5, pp. 307-312.
Fillat, C. et al., "Suicide Gene Therapy Mediated by the Herpes Simplex Virus Thymidine Kinase Gene/Ganciclovir System: Fifteen Years of Application", Current Gene Therapy, 2003, 3:13-26.
Friedmann et al., "Producing replication-incompetent retrovirus vectors, by transfecting cells with a provirus plasmid that encodes gag, a provirus plasmid that encodes pol, and an envelope protein encoding construct," Score Result to Friedmann et al., downloaded Jan. 14, 2013.
Fu et al., Viral sequences enable efficient and tissue-specific expression of transgenes in Xenopus, Nature Biotechnology, vol. 6, Mar. 1988, pp. 253-257.
Fulci, Giulia et al., "Cyclophosphamide enchances glioma virotherapy by inhibiting innate immune responses", PNAS, 2006, vol. 103, No. 34, pp. 12873-12878.
Garaci et al., "Combination therapy with BRMs in Cancer and Infectious Disease", Mechanisms of Ageing and Development, 96 (1997) 103-116.
Gardlik, Roman et al., "Vectors and delivery systems in gene therapy," Review, Med. Sci. Monit., 2005, 11: RA110-121.
Gomez-Navarro, J. et al., "Gene Therapy for Cancer", European J. of Cancer, 1999, vol. 35, No. 6, pp. 867-885.
Gromeier, Matthias, "Viruses for Treating Cancer", ASM News, 2002, vol. 68, pp. 438-445.
Guo et al., "Protein tolerance to random amino acid change," PNAS, 2004, vol. 101, 25:9205-9210.
Gupta, "Project Report Codon Optimization", Arizona State University, Plant and Molecular Biology Department, May 2003, 13 pages.
Gustafsson et al., "Codon bias and heterologous protein expression", TRENDS in Biotechnology, Jul. 2004, vol. 22(7):346-353.
Huang, Ling et al., "Empirical study to treatment of peritoneal carcinomstosis with a combination of adenoviral p53 gene therapy and thymosin a1", Cancer Research and Clinic, Oct. 2006, vol. 18, No. 10.
Ianni, Di M. et al., "Retroviral Transfer of Herpes Simplex Virus-Thymidine Kinase and Beta-Galactosidase Genes into U937 Cells with Bicistronic Vector", Leukemia Research, vol. 21, No. 10, 1997, pp. 951-959.
Ionnou et al., "Prothymosin alpha: a ubiquitous polypeptide with potential use in cancer diagnosis and therapy", Cancer Immunol., (2012) 61:599-614.
Ireton, G. et al., "The Structure of *Escherichia coli* Cytosine Deaminase", J. Mol. Biol., 2002, 315, 687-697.
Ireton, G. et al., "The 1.14A° Crystal Structure of Yeast Cytosine Deaminase: Evolution of Nucleotide Salvage Enzymes and Implications for Genetic Chemotherapy": Structure, Aug. 2003, vol. 11, 961-972.
Jolly, Douglas, "Viral vector systems for gene therapy," Cancer Gene Therapy, vol. 1, 1994, pp. 51-64.
Jolly, Douglas, "Tocagen Presentation to the RAC", Slides 1-38, Jun. 17, 2009.
Kaminski et al., "The polypyrimidine tract binding protein (PTB) requirement for internal initiation of translation of cardiovirus RNAs is conditional rather than absolute," RNA, Jun. 1, 1998, vol. 4, No. 6, pp. 626-638.
Kasahara, Noriyuki et al., "Tissue-Specific Targeting of Retroviral Vectors Through Ligand-Receptor Interactions", Science, 1994, 226:1373-1376.
Kasahara et al., "Viroreplicative Gene Therapy Targeted to Prostate Cancer," U.S. Army Medical Research and Material Command, Grant No. W81WH-08-1-510, covering Aug. 1, 2008 to Jul. 31, 2010, published Aug. 2010.
Kern, L et al., "The FUR1 gene of *Sacckaromyces ceret*, isiae: cloning, structure and expression of wild-type and mutant alleles", Gene, 1990, 88:149-157.
Tait, David L. et al., "Ovarian Cancer BRCA1 Gene Therapy: Phase I and II Trial Differences in Immune Response and Vector Stability", Clinical Cancer Research, Jul. 1999, vol. 5, pp. 1708-1714.
Terwilliger E.F. et al., "Construction and Use of a Replication-Competent Human Immunodeficiency Virus HIV-1 that Expresses the Chloramphenicol Acetyltransferase Enzyme," PNAS, vol. 86, No. 10, 1989, pp. 3857-3861.
Thompson, M.R. et al., "Pattern recognition receptors and the innate immune response to viral infection", Viruses, 2011, vol. 3, pp. 920-940.
Touchefu, Y et al., "Review article: gene therapy, recent developments and future prospects in gastrointestinal oncology", Alimentary Pharmacology & Therapeutics, Aug. 15, 2010, vol. 32, No. 8.
Tuszynski, Mark H., "Gene therapy for neurological disease," Gene Therapy, 2003, 3:815-828.
Umeda, Yukio et al., "Thymosin α1 Restores NK-Cell Activity and Prevents Tumor Progression in Mice Immunosuppressed by Cytostatics or X-Rays", Cancer Immunol. Immunother., 1983, 15:78-83.
Vassaux, G. et al., "Use of suicide genes for cancer gene therapy: study of the different approaches", Expert Opin. Biol. Ther., 2004, 4:519-530.
Verma et al., "Gene Therapy—promises, problems, and prospects," Nature, vol. 389, Sep. 1997, pp. 239-242.
Vile, Richard G. et al., "Tissue-Specific Gene Expression from Mo-MLV Retroviral Vectors with Hybrid LTRs Containing the Murine Tyrosinase Enhancer/Promoter", Virology, 214, 307-313 (1995).

(56) References Cited

OTHER PUBLICATIONS

Vile, Richard G. et al., "Strategies for achieving multiple layers of selectivity in gene therapy", Molecular Medicine Today, Feb. 1998, vol. 4 2:84-92.

Wallace, P. et al., "Intratumoral Generation of 5-Fluorouracil Mediated by an Antibody-Cytosine Deaminase Conjugate in Combination with 5-Fluorocytosine", Cancer Res., 1994, 54:2719-2723.

Wang, W. et al., "Use of replication-competent retroviral vectors in an immunocompetent intracranial glioma model", Neurosurg. Focus, Apr. 2006, vol. 20, pp. 1-9.

Wimmer, G., European Search Report, EP99969648.7, dated Oct. 18, 2002.

Wittman-Regis, Agnes, International Preliminary Report on Patentability and Written Opinion, PCT/US2014/049831, The International Bureau of WIPO, dated Feb. 18, 2016.

Yan, Y. et al., "Large Fragment of the Probasin Promoter Targets High Levels of Transgene Expression to the Prostate of Trangenic Mice", The Prostate, 1997, 32:129-139.

Yanez RJ et al., "REVIEW Therapeutic gene targeting," Gene Therapy, 1998, 5, pp. 149-159.

Yoshida, Kayoko, Office Action, Japanese Patent Application No. 2013-502771, Japanese Patent Office, dated Feb. 24, 2015.

Zhang, Yu et al., "MicroRNA-128 inhibits glioma cells proliferation by targeting transcription factor E2F3a", J. Mol. Med., 2009, 87:43-51.

Zhang, J., et al., A Novel Oncolytic Adenovirus Expressing *Escherichia coli* Cytosine Deaminase Exhibits Potent Antitumor Effect on Human Solid Tumors, Cancer Biotherapy and Radiopharmaceuticals, 2010, vol. 25, No. 4, pp. 487-495.

Zlokovic, Berislav et al., "Cellular and Molecular Neurosurgery: Pathways from Concept to Reality—Part II: Vector Systems and Delivery Methodologies for Gene Therapy and of the Central Nervous System", Neurosurgery, 1997, 40:805-813.

Kim, S. et al., "Nucleotide sequence changes in thymidine kinase gene of herpes simplex virus type 2 clones from an isolete of a patient treated with acyclovir", Antimicrob. Agents Chemother. 31 (10), 1483-1490 (1987), GenBank Accession No. M29940, NCBI, HS2TK1A, [retrieved on Jun. 23, 2017], URL, https://www.ncbi.nlm.nih.gov/nucleotide/M29940.1.

Hukuma, Nobuko, Office Action, Japanese Patent Office, Application No. 2015-539817, dated Jul. 4, 2017.

NCBI, HS2TK1A, Accession No. M29940, Aug. 2, 1993, URL, https://www.ncbi.nlm.nih.gov/nucleotide/M299940.1, [retrieved on Jun. 23, 2017].

Pending Claims for Japanese patent application JP2018-128726, dated Nov. 25, 2019, 8 pages.

Final Rejection for Japanese patent application JP2018-128726, dated Apr. 14, 2020, 5 pages with extra 4 pages of English language equivalent or summary.

Grief, Gabriela, Extended European Search Report, European Patent Application No. EP13849839.9, European Patent Office, dated Jun. 8, 2016.

Juven-Gershon Tamar et al., "Rational design of a super core promoter that enhances gene expression", Nature, vol. 3, No. 11, Nov. 1, 2006, pp. 917-922.

Mukherjee et al., "A HIV-2-based self-inactivating vector for enhanced gene transduction", Journal of Biotechnology, vol. 127, No. 4, Dec. 22, 2006, pp. 745-747.

Zhao-Emonet, Jing Chao et al., "T Cell-Specific Expression from MO-MLV Retroviral Vectors Containing a CD4 Mini-Promoter/Enhancer", Journal of Gene Medicine, vol. 2, No. 6, Nov. 1, 2000, pp. 416-425.

* cited by examiner

SEQUENCE LISTING

```
<160> NUMBER OF SEQ ID NOS: 86

<210> SEQ ID NO 1
<211> LENGTH: 477
<212> TYPE: DNA
<213> ORGANISM: Saccharomyces cerevisiae
<220> FEATURE:
<221> NAME/KEY: CDS
<222> LOCATION: (1)..(477)

<400> SEQUENCE: 1

atg gtg aca ggg gga atg gca agc aag tgg gat cag aag ggt atg gac       48
Met Val Thr Gly Gly Met Ala Ser Lys Trp Asp Gln Lys Gly Met Asp
1               5                   10                  15

att gcc tat gag gag gcg gcc tta ggt tac aaa gag ggt ggt gtt cct       96
Ile Ala Tyr Glu Glu Ala Ala Leu Gly Tyr Lys Glu Gly Gly Val Pro
            20                  25                  30

att ggc gga tgt ctt atc aat aac aaa gac gga agt gtt ctc ggt cgt      144
Ile Gly Gly Cys Leu Ile Asn Asn Lys Asp Gly Ser Val Leu Gly Arg
        35                  40                  45

ggt cac aac atg aga ttt caa aag gga tcc gcc aca cta cat ggt gag      192
Gly His Asn Met Arg Phe Gln Lys Gly Ser Ala Thr Leu His Gly Glu
    50                  55                  60

atc tcc act ttg gaa aac tgt ggg aga tta gag ggc aaa gtg tac aaa      240
Ile Ser Thr Leu Glu Asn Cys Gly Arg Leu Glu Gly Lys Val Tyr Lys
65                  70                  75                  80
```

```
gat acc act ttg tat acg acg ctg tct cca tgc gac atg tgt aca ggt      288
Asp Thr Thr Leu Tyr Thr Thr Leu Ser Pro Cys Asp Met Cys Thr Gly
                85                  90                  95

gcc atc atc atg tat ggt att cca cgc tgt gtt gtc ggt gag aac gtt      336
Ala Ile Ile Met Tyr Gly Ile Pro Arg Cys Val Val Gly Glu Asn Val
            100                 105                 110

aat ttc aaa agt aag ggc gag aaa tat tta caa act aga ggt cac gag      384
Asn Phe Lys Ser Lys Gly Glu Lys Tyr Leu Gln Thr Arg Gly His Glu
        115                 120                 125

gtt gtt gtt gtt gac gat gag agg tgt aaa aag atc atg aaa caa ttt      432
Val Val Val Val Asp Asp Glu Arg Cys Lys Lys Ile Met Lys Gln Phe
    130                 135                 140

atc gat gaa aga cct cag gat tgg ttt gaa gat att ggt gag tag          477
Ile Asp Glu Arg Pro Gln Asp Trp Phe Glu Asp Ile Gly Glu
145                 150                 155


<210> SEQ ID NO 2
<211> LENGTH: 158
<212> TYPE: PRT
<213> ORGANISM: Saccharomyces cerevisiae

<400> SEQUENCE: 2

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155


<210> SEQ ID NO 3
<211> LENGTH: 477
<212> TYPE: DNA
<213> ORGANISM: Artificial Sequence
<220> FEATURE:
<223> OTHER INFORMATION: Engineered cytosine deaminase
<220> FEATURE:
<221> NAME/KEY: CDS
<222> LOCATION: (1)..(477)

<400> SEQUENCE: 3

atg gtg aca ggg gga atg gca agc aag tgg gat cag aag ggt atg gac       48
Met Val Thr Gly Gly Met Ala Ser Lys Trp Asp Gln Lys Gly Met Asp
1               5                   10                  15

att gcc tat gag gag gcg tta tta ggt tac aaa gag ggt ggt gtt cct       96
Ile Ala Tyr Glu Glu Ala Leu Leu Gly Tyr Lys Glu Gly Gly Val Pro
            20                  25                  30
```

```
att ggc gga tgt ctt atc aat aac aaa gac gga agt gtt ctc ggt cgt      144
Ile Gly Gly Cys Leu Ile Asn Asn Lys Asp Gly Ser Val Leu Gly Arg
        35                  40                  45

ggt cac aac atg aga ttt caa aag gga tcc gcc aca cta cat ggt gag      192
Gly His Asn Met Arg Phe Gln Lys Gly Ser Ala Thr Leu His Gly Glu
    50                  55                  60

atc tcc act ttg gaa aac tgt ggg aga tta gag ggc aaa gtg tac aaa      240
Ile Ser Thr Leu Glu Asn Cys Gly Arg Leu Glu Gly Lys Val Tyr Lys
65                  70                  75                  80

gat acc act ttg tat acg acg ctg tct cca tgc gac atg tgt aca ggt      288
Asp Thr Thr Leu Tyr Thr Thr Leu Ser Pro Cys Asp Met Cys Thr Gly
                85                  90                  95

gcc atc atc atg tat ggt att cca cgc tgt gtc atc ggt gag aac gtt      336
Ala Ile Ile Met Tyr Gly Ile Pro Arg Cys Val Ile Gly Glu Asn Val
            100                 105                 110

aat ttc aaa agt aag ggc gag aaa tat tta caa act aga ggt cac gag      384
Asn Phe Lys Ser Lys Gly Glu Lys Tyr Leu Gln Thr Arg Gly His Glu
        115                 120                 125

gtt gtt gtt gtt gac gat gag agg tgt aaa aag tta atg aaa caa ttt      432
Val Val Val Val Asp Asp Glu Arg Cys Lys Lys Leu Met Lys Gln Phe
    130                 135                 140

atc gat gaa aga cct cag gat tgg ttt gaa gat att ggt gag tag          477
Ile Asp Glu Arg Pro Gln Asp Trp Phe Glu Asp Ile Gly Glu
145                 150                 155


<210> SEQ ID NO 4
<211> LENGTH: 158
<212> TYPE: PRT
<213> ORGANISM: Artificial Sequence
<220> FEATURE:
<223> OTHER INFORMATION: Synthetic Construct

<400> SEQUENCE: 4

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu
145                 150                 155


<210> SEQ ID NO 5
<211> LENGTH: 480
<212> TYPE: DNA
<213> ORGANISM: Artificial Sequence
<220> FEATURE:
```

```
<223> OTHER INFORMATION: Human codon optimized cytosine deaminase
<220> FEATURE:
<221> NAME/KEY: CDS
<222> LOCATION: (1)..(480)

<400> SEQUENCE: 5

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc gca ctg ggc tac aag gag ggc ggc gtg cct       96
Ile Ala Tyr Glu Glu Ala Ala Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg gtc ggc gag aac gtg      336
Ala Ile Ile Met Tyr Gly Ile Pro Arg Cys Val Val Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag atc atg aag cag ttc      432
Val Val Val Val Asp Asp Glu Arg Cys Lys Lys Ile Met Lys Gln Phe
    130                 135                 140

atc gac gag agg cct cag gac tgg ttc gag gat atc ggc gag tga taa      480
Ile Asp Glu Arg Pro Gln Asp Trp Phe Glu Asp Ile Gly Glu
145                 150                 155


<210> SEQ ID NO 6
<211> LENGTH: 158
<212> TYPE: PRT
<213> ORGANISM: Artificial Sequence
<220> FEATURE:
<223> OTHER INFORMATION: Synthetic Construct

<400> SEQUENCE: 6

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
```

-continued

```
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155


<210> SEQ ID NO 7
<211> LENGTH: 756
<212> TYPE: DNA
<213> ORGANISM: Saccharomyces cerevisiae
<220> FEATURE:
<221> NAME/KEY: CDS
<222> LOCATION: (1)..(756)

<400> SEQUENCE: 7

atg aac ccg tta ttc ttt ttg gct tct cca ttc ttg tac ctt aca tat       48
Met Asn Pro Leu Phe Phe Leu Ala Ser Pro Phe Leu Tyr Leu Thr Tyr
1               5                   10                  15

ctt ata tat tat cca aac aaa ggg tct ttc gtt agc aaa cct aga aat       96
Leu Ile Tyr Tyr Pro Asn Lys Gly Ser Phe Val Ser Lys Pro Arg Asn
            20                  25                  30

ctg caa aaa atg tct tcg gaa cca ttt aag aac gtc tac ttg cta cct      144
Leu Gln Lys Met Ser Ser Glu Pro Phe Lys Asn Val Tyr Leu Leu Pro
        35                  40                  45

caa aca aac caa ttg ctg ggt ttg tac acc atc atc aga aat aag aat      192
Gln Thr Asn Gln Leu Leu Gly Leu Tyr Thr Ile Ile Arg Asn Lys Asn
    50                  55                  60

aca act aga cct gat ttc att ttc tac tcc gat aga atc atc aga ttg      240
Thr Thr Arg Pro Asp Phe Ile Phe Tyr Ser Asp Arg Ile Ile Arg Leu
65                  70                  75                  80

ttg gtt gaa gaa ggt ttg aac cat cta cct gtg caa aag caa att gtg      288
Leu Val Glu Glu Gly Leu Asn His Leu Pro Val Gln Lys Gln Ile Val
                85                  90                  95

gaa act gac acc aac gaa aac ttc gaa ggt gtc tca ttc atg ggt aaa      336
Glu Thr Asp Thr Asn Glu Asn Phe Glu Gly Val Ser Phe Met Gly Lys
            100                 105                 110

atc tgt ggt gtt tcc att gtc aga gct ggt gaa tcg atg gag caa gga      384
Ile Cys Gly Val Ser Ile Val Arg Ala Gly Glu Ser Met Glu Gln Gly
        115                 120                 125

tta aga gac tgt tgt agg tct gtg cgt atc ggt aaa att tta att caa      432
Leu Arg Asp Cys Cys Arg Ser Val Arg Ile Gly Lys Ile Leu Ile Gln
    130                 135                 140

agg gac gag gag act gct tta cca aag tta ttc tac gaa aaa tta cca      480
Arg Asp Glu Glu Thr Ala Leu Pro Lys Leu Phe Tyr Glu Lys Leu Pro
145                 150                 155                 160

gag gat ata tct gaa agg tat gtc ttc cta tta gac cca atg ctg gcc      528
Glu Asp Ile Ser Glu Arg Tyr Val Phe Leu Leu Asp Pro Met Leu Ala
                165                 170                 175

acc ggt ggt agt gct atc atg gct aca gaa gtc ttg att aag aga ggt      576
Thr Gly Gly Ser Ala Ile Met Ala Thr Glu Val Leu Ile Lys Arg Gly
            180                 185                 190

gtt aag cca gag aga att tac ttc tta aac cta atc tgt agt aag gaa      624
Val Lys Pro Glu Arg Ile Tyr Phe Leu Asn Leu Ile Cys Ser Lys Glu
        195                 200                 205

ggg att gaa aaa tac cat gcc gcc ttc cca gag gtc aga att gtt act      672
Gly Ile Glu Lys Tyr His Ala Ala Phe Pro Glu Val Arg Ile Val Thr
    210                 215                 220

ggt gcc ctc gac aga ggt cta gat gaa aac aag tat cta gtt cca ggg      720
Gly Ala Leu Asp Arg Gly Leu Asp Glu Asn Lys Tyr Leu Val Pro Gly
225                 230                 235                 240
```

-continued

```
ttg ggt gac ttt ggt gac aga tac tac tgt gtt taa                        756
Leu Gly Asp Phe Gly Asp Arg Tyr Tyr Cys Val
                245                 250


<210> SEQ ID NO 8
<211> LENGTH: 251
<212> TYPE: PRT
<213> ORGANISM: Saccharomyces cerevisiae

<400> SEQUENCE: 8

Met Asn Pro Leu Phe Phe Leu Ala Ser Pro Phe Leu Tyr Leu Thr Tyr
1               5                   10                  15

Leu Ile Tyr Tyr Pro Asn Lys Gly Ser Phe Val Ser Lys Pro Arg Asn
            20                  25                  30

Leu Gln Lys Met Ser Ser Glu Pro Phe Lys Asn Val Tyr Leu Leu Pro
        35                  40                  45

Gln Thr Asn Gln Leu Leu Gly Leu Tyr Thr Ile Ile Arg Asn Lys Asn
    50                  55                  60

Thr Thr Arg Pro Asp Phe Ile Phe Tyr Ser Asp Arg Ile Ile Arg Leu
65                  70                  75                  80

Leu Val Glu Glu Gly Leu Asn His Leu Pro Val Gln Lys Gln Ile Val
                85                  90                  95

Glu Thr Asp Thr Asn Glu Asn Phe Glu Gly Val Ser Phe Met Gly Lys
            100                 105                 110

Ile Cys Gly Val Ser Ile Val Arg Ala Gly Glu Ser Met Glu Gln Gly
        115                 120                 125

Leu Arg Asp Cys Cys Arg Ser Val Arg Ile Gly Lys Ile Leu Ile Gln
    130                 135                 140

Arg Asp Glu Glu Thr Ala Leu Pro Lys Leu Phe Tyr Glu Lys Leu Pro
145                 150                 155                 160

Glu Asp Ile Ser Glu Arg Tyr Val Phe Leu Leu Asp Pro Met Leu Ala
                165                 170                 175

Thr Gly Gly Ser Ala Ile Met Ala Thr Glu Val Leu Ile Lys Arg Gly
            180                 185                 190

Val Lys Pro Glu Arg Ile Tyr Phe Leu Asn Leu Ile Cys Ser Lys Glu
        195                 200                 205

Gly Ile Glu Lys Tyr His Ala Ala Phe Pro Glu Val Arg Ile Val Thr
    210                 215                 220

Gly Ala Leu Asp Arg Gly Leu Asp Glu Asn Lys Tyr Leu Val Pro Gly
225                 230                 235                 240

Leu Gly Asp Phe Gly Asp Arg Tyr Tyr Cys Val
                245                 250


<210> SEQ ID NO 9
<211> LENGTH: 1443
<212> TYPE: DNA
<213> ORGANISM: homo sapiens
<220> FEATURE:
<221> NAME/KEY: CDS
<222> LOCATION: (1)..(1443)

<400> SEQUENCE: 9

atg gct gtt gct cgt gct gct ctt ggt cct ctt gtt act ggt ctt tat         48
Met Ala Val Ala Arg Ala Ala Leu Gly Pro Leu Val Thr Gly Leu Tyr
1               5                   10                  15

gat gtt caa gct ttt aaa ttt ggt gat ttt gtt ctt aaa tct ggt ctt         96
Asp Val Gln Ala Phe Lys Phe Gly Asp Phe Val Leu Lys Ser Gly Leu
            20                  25                  30
```

-continued

```
tct tct cct att tat att gat ctt cgt ggt att gtt tct cgt cct cgt      144
Ser Ser Pro Ile Tyr Ile Asp Leu Arg Gly Ile Val Ser Arg Pro Arg
        35                  40                  45

ctt ctt tct caa gtt gct gat att ctt ttt caa act gct caa aat gct      192
Leu Leu Ser Gln Val Ala Asp Ile Leu Phe Gln Thr Ala Gln Asn Ala
    50                  55                  60

ggt att tct ttt gat act gtt tgt ggt gtt cct tat act gct ctt cct      240
Gly Ile Ser Phe Asp Thr Val Cys Gly Val Pro Tyr Thr Ala Leu Pro
65                  70                  75                  80

ctt gct act gtt att tgt tct act aat caa att cct atg ctt att cgt      288
Leu Ala Thr Val Ile Cys Ser Thr Asn Gln Ile Pro Met Leu Ile Arg
                85                  90                  95

cgt aaa gaa act aaa gat tat ggt act aaa cgt ctt gtt gaa ggt act      336
Arg Lys Glu Thr Lys Asp Tyr Gly Thr Lys Arg Leu Val Glu Gly Thr
            100                 105                 110

att aat cct ggt gaa act tgt ctt att att gaa gat gtt gtt act tct      384
Ile Asn Pro Gly Glu Thr Cys Leu Ile Ile Glu Asp Val Val Thr Ser
        115                 120                 125

ggt tct tct gtt ctt gaa act gtt gaa gtt ctt caa aaa gaa ggt ctt      432
Gly Ser Ser Val Leu Glu Thr Val Glu Val Leu Gln Lys Glu Gly Leu
    130                 135                 140

aaa gtt act gat gct att gtt ctt ctt gat cgt gaa caa ggt ggt aaa      480
Lys Val Thr Asp Ala Ile Val Leu Leu Asp Arg Glu Gln Gly Gly Lys
145                 150                 155                 160

gat aaa ctt caa gct cat ggt att cgt ctt cat tct gtt tgt act ctt      528
Asp Lys Leu Gln Ala His Gly Ile Arg Leu His Ser Val Cys Thr Leu
                165                 170                 175

tct aaa atg ctt gaa att ctt gaa caa caa aaa aaa gtt gat gct gaa      576
Ser Lys Met Leu Glu Ile Leu Glu Gln Gln Lys Lys Val Asp Ala Glu
            180                 185                 190

act gtt ggt cgt gtt aaa cgt ttt att caa gaa aat gtt ttt gtt gct      624
Thr Val Gly Arg Val Lys Arg Phe Ile Gln Glu Asn Val Phe Val Ala
        195                 200                 205

gct aat cat aat ggt tct cct ctt tct att aaa gaa gct cct aaa gaa      672
Ala Asn His Asn Gly Ser Pro Leu Ser Ile Lys Glu Ala Pro Lys Glu
    210                 215                 220

ctt tct ttt ggt gct cgt gct gaa ctt cct cgt att cat cct gtt gct      720
Leu Ser Phe Gly Ala Arg Ala Glu Leu Pro Arg Ile His Pro Val Ala
225                 230                 235                 240

tct aaa ctt ctt cgt ctt atg caa aaa aaa gaa act aat ctt tgt ctt      768
Ser Lys Leu Leu Arg Leu Met Gln Lys Lys Glu Thr Asn Leu Cys Leu
                245                 250                 255

tct gct gat gtt tct ctt gct cgt gaa ctt ctt caa ctt gct gat gct      816
Ser Ala Asp Val Ser Leu Ala Arg Glu Leu Leu Gln Leu Ala Asp Ala
            260                 265                 270

ctt ggt cct tct att tgt atg ctt aaa act cat gtt gat att ctt aat      864
Leu Gly Pro Ser Ile Cys Met Leu Lys Thr His Val Asp Ile Leu Asn
        275                 280                 285

gat ttt act ctt gat gtt atg aaa gaa ctt att act ctt gct aaa tgt      912
Asp Phe Thr Leu Asp Val Met Lys Glu Leu Ile Thr Leu Ala Lys Cys
    290                 295                 300

cat gaa ttt ctt att ttt gaa gat cgt aaa ttt gct gat att ggt aat      960
His Glu Phe Leu Ile Phe Glu Asp Arg Lys Phe Ala Asp Ile Gly Asn
305                 310                 315                 320

act gtt aaa aaa caa tat gaa ggt ggt att ttt aaa att gct tct tgg     1008
Thr Val Lys Lys Gln Tyr Glu Gly Gly Ile Phe Lys Ile Ala Ser Trp
                325                 330                 335

gct gat ctt gtt aat gct cat gtt gtt cct ggt tct ggt gtt gtt aaa     1056
Ala Asp Leu Val Asn Ala His Val Val Pro Gly Ser Gly Val Val Lys
            340                 345                 350
```

-continued

```
ggt ctt caa gaa gtt ggt ctt cct ctt cat cgt ggt tgt ctt ctt att      1104
Gly Leu Gln Glu Val Gly Leu Pro Leu His Arg Gly Cys Leu Leu Ile
        355                 360                 365

gct gaa atg tct tct act ggt tct ctt gct act ggt gat tat act cgt      1152
Ala Glu Met Ser Ser Thr Gly Ser Leu Ala Thr Gly Asp Tyr Thr Arg
    370                 375                 380

gct gct gtt cgt atg gct gaa gaa cat tct gaa ttt gtt gtt ggt ttt      1200
Ala Ala Val Arg Met Ala Glu Glu His Ser Glu Phe Val Val Gly Phe
385                 390                 395                 400

att tct ggt tct cgt gtt tct atg aaa cct gaa ttt ctt cat ctt act      1248
Ile Ser Gly Ser Arg Val Ser Met Lys Pro Glu Phe Leu His Leu Thr
                405                 410                 415

cct ggt gtt caa ctt gaa gct ggt ggt gat aat ctt ggt caa caa tat      1296
Pro Gly Val Gln Leu Glu Ala Gly Gly Asp Asn Leu Gly Gln Gln Tyr
            420                 425                 430

aat tct cct caa gaa gtt att ggt aaa cgt ggt tct gat att att att      1344
Asn Ser Pro Gln Glu Val Ile Gly Lys Arg Gly Ser Asp Ile Ile Ile
        435                 440                 445

gtt ggt cgt ggt att att tct gct gct gat cgt ctt gaa gct gct gaa      1392
Val Gly Arg Gly Ile Ile Ser Ala Ala Asp Arg Leu Glu Ala Ala Glu
    450                 455                 460

atg tat cgt aaa gct gct tgg gaa gct tat ctt tct cgt ctt ggt gtt      1440
Met Tyr Arg Lys Ala Ala Trp Glu Ala Tyr Leu Ser Arg Leu Gly Val
465                 470                 475                 480

taa                                                                  1443


<210> SEQ ID NO 10
<211> LENGTH: 480
<212> TYPE: PRT
<213> ORGANISM: homo sapiens

<400> SEQUENCE: 10

Met Ala Val Ala Arg Ala Ala Leu Gly Pro Leu Val Thr Gly Leu Tyr
1               5                   10                  15

Asp Val Gln Ala Phe Lys Phe Gly Asp Phe Val Leu Lys Ser Gly Leu
            20                  25                  30

Ser Ser Pro Ile Tyr Ile Asp Leu Arg Gly Ile Val Ser Arg Pro Arg
        35                  40                  45

Leu Leu Ser Gln Val Ala Asp Ile Leu Phe Gln Thr Ala Gln Asn Ala
    50                  55                  60

Gly Ile Ser Phe Asp Thr Val Cys Gly Val Pro Tyr Thr Ala Leu Pro
65                  70                  75                  80

Leu Ala Thr Val Ile Cys Ser Thr Asn Gln Ile Pro Met Leu Ile Arg
                85                  90                  95

Arg Lys Glu Thr Lys Asp Tyr Gly Thr Lys Arg Leu Val Glu Gly Thr
            100                 105                 110

Ile Asn Pro Gly Glu Thr Cys Leu Ile Ile Glu Asp Val Val Thr Ser
        115                 120                 125

Gly Ser Ser Val Leu Glu Thr Val Glu Val Leu Gln Lys Glu Gly Leu
    130                 135                 140

Lys Val Thr Asp Ala Ile Val Leu Leu Asp Arg Glu Gln Gly Gly Lys
145                 150                 155                 160

Asp Lys Leu Gln Ala His Gly Ile Arg Leu His Ser Val Cys Thr Leu
                165                 170                 175

Ser Lys Met Leu Glu Ile Leu Glu Gln Gln Lys Lys Val Asp Ala Glu
            180                 185                 190
```

```
Thr Val Gly Arg Val Lys Arg Phe Ile Gln Glu Asn Val Phe Val Ala
        195                 200                 205

Ala Asn His Asn Gly Ser Pro Leu Ser Ile Lys Glu Ala Pro Lys Glu
    210                 215                 220

Leu Ser Phe Gly Ala Arg Ala Glu Leu Pro Arg Ile His Pro Val Ala
225                 230                 235                 240

Ser Lys Leu Leu Arg Leu Met Gln Lys Lys Glu Thr Asn Leu Cys Leu
                245                 250                 255

Ser Ala Asp Val Ser Leu Ala Arg Glu Leu Leu Gln Leu Ala Asp Ala
            260                 265                 270

Leu Gly Pro Ser Ile Cys Met Leu Lys Thr His Val Asp Ile Leu Asn
        275                 280                 285

Asp Phe Thr Leu Asp Val Met Lys Glu Leu Ile Thr Leu Ala Lys Cys
    290                 295                 300

His Glu Phe Leu Ile Phe Glu Asp Arg Lys Phe Ala Asp Ile Gly Asn
305                 310                 315                 320

Thr Val Lys Lys Gln Tyr Glu Gly Gly Ile Phe Lys Ile Ala Ser Trp
                325                 330                 335

Ala Asp Leu Val Asn Ala His Val Val Pro Gly Ser Gly Val Val Lys
            340                 345                 350

Gly Leu Gln Glu Val Gly Leu Pro Leu His Arg Gly Cys Leu Leu Ile
        355                 360                 365

Ala Glu Met Ser Ser Thr Gly Ser Leu Ala Thr Gly Asp Tyr Thr Arg
    370                 375                 380

Ala Ala Val Arg Met Ala Glu Glu His Ser Glu Phe Val Val Gly Phe
385                 390                 395                 400

Ile Ser Gly Ser Arg Val Ser Met Lys Pro Glu Phe Leu His Leu Thr
                405                 410                 415

Pro Gly Val Gln Leu Glu Ala Gly Gly Asp Asn Leu Gly Gln Gln Tyr
            420                 425                 430

Asn Ser Pro Gln Glu Val Ile Gly Lys Arg Gly Ser Asp Ile Ile Ile
        435                 440                 445

Val Gly Arg Gly Ile Ile Ser Ala Ala Asp Arg Leu Glu Ala Ala Glu
    450                 455                 460

Met Tyr Arg Lys Ala Ala Trp Glu Ala Tyr Leu Ser Arg Leu Gly Val
465                 470                 475                 480


<210> SEQ ID NO 11
<211> LENGTH: 1227
<212> TYPE: DNA
<213> ORGANISM: Artificial Sequence
<220> FEATURE:
<223> OTHER INFORMATION: Fusion construct CDopt-UPRT
<220> FEATURE:
<221> NAME/KEY: CDS
<222> LOCATION: (1)..(1227)

<400> SEQUENCE: 11

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45
```

-continued

```
ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag aac ccg      480
Ile Asp Glu Arg Pro Gln Asp Trp Phe Glu Asp Ile Gly Glu Asn Pro
145                 150                 155                 160

tta ttc ttt ttg gct tct cca ttc ttg tac ctt aca tat ctt ata tat      528
Leu Phe Phe Leu Ala Ser Pro Phe Leu Tyr Leu Thr Tyr Leu Ile Tyr
                165                 170                 175

tat cca aac aaa ggg tct ttc gtt agc aaa cct aga aat ctg caa aaa      576
Tyr Pro Asn Lys Gly Ser Phe Val Ser Lys Pro Arg Asn Leu Gln Lys
            180                 185                 190

atg tct tcg gaa cca ttt aag aac gtc tac ttg cta cct caa aca aac      624
Met Ser Ser Glu Pro Phe Lys Asn Val Tyr Leu Leu Pro Gln Thr Asn
        195                 200                 205

caa ttg ctg ggt ttg tac acc atc atc aga aat aag aat aca act aga      672
Gln Leu Leu Gly Leu Tyr Thr Ile Ile Arg Asn Lys Asn Thr Thr Arg
    210                 215                 220

cct gat ttc att ttc tac tcc gat aga atc atc aga ttg ttg gtt gaa      720
Pro Asp Phe Ile Phe Tyr Ser Asp Arg Ile Ile Arg Leu Leu Val Glu
225                 230                 235                 240

gaa ggt ttg aac cat cta cct gtg caa aag caa att gtg gaa act gac      768
Glu Gly Leu Asn His Leu Pro Val Gln Lys Gln Ile Val Glu Thr Asp
                245                 250                 255

acc aac gaa aac ttc gaa ggt gtc tca ttc atg ggt aaa atc tgt ggt      816
Thr Asn Glu Asn Phe Glu Gly Val Ser Phe Met Gly Lys Ile Cys Gly
            260                 265                 270

gtt tcc att gtc aga gct ggt gaa tcg atg gag caa gga tta aga gac      864
Val Ser Ile Val Arg Ala Gly Glu Ser Met Glu Gln Gly Leu Arg Asp
        275                 280                 285

tgt tgt agg tct gtg cgt atc ggt aaa att tta att caa agg gac gag      912
Cys Cys Arg Ser Val Arg Ile Gly Lys Ile Leu Ile Gln Arg Asp Glu
    290                 295                 300

gag act gct tta cca aag tta ttc tac gaa aaa tta cca gag gat ata      960
Glu Thr Ala Leu Pro Lys Leu Phe Tyr Glu Lys Leu Pro Glu Asp Ile
305                 310                 315                 320

tct gaa agg tat gtc ttc cta tta gac cca atg ctg gcc acc ggt ggt     1008
Ser Glu Arg Tyr Val Phe Leu Leu Asp Pro Met Leu Ala Thr Gly Gly
                325                 330                 335

agt gct atc atg gct aca gaa gtc ttg att aag aga ggt gtt aag cca     1056
Ser Ala Ile Met Ala Thr Glu Val Leu Ile Lys Arg Gly Val Lys Pro
            340                 345                 350

gag aga att tac ttc tta aac cta atc tgt agt aag gaa ggg att gaa     1104
Glu Arg Ile Tyr Phe Leu Asn Leu Ile Cys Ser Lys Glu Gly Ile Glu
        355                 360                 365
```

```
aaa tac cat gcc gcc ttc cca gag gtc aga att gtt act ggt gcc ctc     1152
Lys Tyr His Ala Ala Phe Pro Glu Val Arg Ile Val Thr Gly Ala Leu
    370                 375                 380

gac aga ggt cta gat gaa aac aag tat cta gtt cca ggg ttg ggt gac     1200
Asp Arg Gly Leu Asp Glu Asn Lys Tyr Leu Val Pro Gly Leu Gly Asp
385                 390                 395                 400

ttt ggt gac aga tac tac tgt gtt taa                                 1227
Phe Gly Asp Arg Tyr Tyr Cys Val
                405


<210> SEQ ID NO 12
<211> LENGTH: 408
<212> TYPE: PRT
<213> ORGANISM: Artificial Sequence
<220> FEATURE:
<223> OTHER INFORMATION: Synthetic Construct

<400> SEQUENCE: 12

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Asn Pro
145                 150                 155                 160

Leu Phe Phe Leu Ala Ser Pro Phe Leu Tyr Leu Thr Tyr Leu Ile Tyr
                165                 170                 175

Tyr Pro Asn Lys Gly Ser Phe Val Ser Lys Pro Arg Asn Leu Gln Lys
            180                 185                 190

Met Ser Ser Glu Pro Phe Lys Asn Val Tyr Leu Leu Pro Gln Thr Asn
        195                 200                 205

Gln Leu Leu Gly Leu Tyr Thr Ile Ile Arg Asn Lys Asn Thr Thr Arg
    210                 215                 220

Pro Asp Phe Ile Phe Tyr Ser Asp Arg Ile Ile Arg Leu Leu Val Glu
225                 230                 235                 240

Glu Gly Leu Asn His Leu Pro Val Gln Lys Gln Ile Val Glu Thr Asp
                245                 250                 255

Thr Asn Glu Asn Phe Glu Gly Val Ser Phe Met Gly Lys Ile Cys Gly
            260                 265                 270

Val Ser Ile Val Arg Ala Gly Glu Ser Met Glu Gln Gly Leu Arg Asp
        275                 280                 285

Cys Cys Arg Ser Val Arg Ile Gly Lys Ile Leu Ile Gln Arg Asp Glu
    290                 295                 300
```

```
Glu Thr Ala Leu Pro Lys Leu Phe Tyr Glu Lys Leu Pro Glu Asp Ile
305                 310                 315                 320

Ser Glu Arg Tyr Val Phe Leu Leu Asp Pro Met Leu Ala Thr Gly Gly
                325                 330                 335

Ser Ala Ile Met Ala Thr Glu Val Leu Ile Lys Arg Gly Val Lys Pro
            340                 345                 350

Glu Arg Ile Tyr Phe Leu Asn Leu Ile Cys Ser Lys Glu Gly Ile Glu
        355                 360                 365

Lys Tyr His Ala Ala Phe Pro Glu Val Arg Ile Val Thr Gly Ala Leu
    370                 375                 380

Asp Arg Gly Leu Asp Glu Asn Lys Tyr Leu Val Pro Gly Leu Gly Asp
385                 390                 395                 400

Phe Gly Asp Arg Tyr Tyr Cys Val
                405


<210> SEQ ID NO 13
<211> LENGTH: 1287
<212> TYPE: DNA
<213> ORGANISM: Artificial Sequence
<220> FEATURE:
<223> OTHER INFORMATION: Fusion construction - CDopt - linker - UPRT
<220> FEATURE:
<221> NAME/KEY: CDS
<222> LOCATION: (1)..(1287)

<400> SEQUENCE: 13

atg gtg acc ggc ggc atg gcc tcc aag tgg gat caa aag ggc atg gat        48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct        96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg       144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag       192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag       240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc       288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg       336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag       384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc       432
Val Val Val Val Asp Asp Glu Arg Cys Lys Lys Leu Met Lys Gln Phe
    130                 135                 140

atc gac gag agg cct cag gac tgg ttc gag gat atc ggc gag tcc ggc       480
Ile Asp Glu Arg Pro Gln Asp Trp Phe Glu Asp Ile Gly Glu Ser Gly
145                 150                 155                 160

ggc ggc gcc tcc ggc ggc ggc gcc tcc ggc ggc ggc gcc tcc ggc ggc       528
Gly Gly Ala Ser Gly Gly Gly Ala Ser Gly Gly Gly Ala Ser Gly Gly
                165                 170                 175
```

-continued

```
ggc gcc aac ccg tta ttc ttt ttg gct tct cca ttc ttg tac ctt aca      576
Gly Ala Asn Pro Leu Phe Phe Leu Ala Ser Pro Phe Leu Tyr Leu Thr
            180                 185                 190

tat ctt ata tat tat cca aac aaa ggg tct ttc gtt agc aaa cct aga      624
Tyr Leu Ile Tyr Tyr Pro Asn Lys Gly Ser Phe Val Ser Lys Pro Arg
        195                 200                 205

aat ctg caa aaa atg tct tcg gaa cca ttt aag aac gtc tac ttg cta      672
Asn Leu Gln Lys Met Ser Ser Glu Pro Phe Lys Asn Val Tyr Leu Leu
    210                 215                 220

cct caa aca aac caa ttg ctg ggt ttg tac acc atc atc aga aat aag      720
Pro Gln Thr Asn Gln Leu Leu Gly Leu Tyr Thr Ile Ile Arg Asn Lys
225                 230                 235                 240

aat aca act aga cct gat ttc att ttc tac tcc gat aga atc atc aga      768
Asn Thr Thr Arg Pro Asp Phe Ile Phe Tyr Ser Asp Arg Ile Ile Arg
                245                 250                 255

ttg ttg gtt gaa gaa ggt ttg aac cat cta cct gtg caa aag caa att      816
Leu Leu Val Glu Glu Gly Leu Asn His Leu Pro Val Gln Lys Gln Ile
            260                 265                 270

gtg gaa act gac acc aac gaa aac ttc gaa ggt gtc tca ttc atg ggt      864
Val Glu Thr Asp Thr Asn Glu Asn Phe Glu Gly Val Ser Phe Met Gly
        275                 280                 285

aaa atc tgt ggt gtt tcc att gtc aga gct ggt gaa tcg atg gag caa      912
Lys Ile Cys Gly Val Ser Ile Val Arg Ala Gly Glu Ser Met Glu Gln
    290                 295                 300

gga tta aga gac tgt tgt agg tct gtg cgt atc ggt aaa att tta att      960
Gly Leu Arg Asp Cys Cys Arg Ser Val Arg Ile Gly Lys Ile Leu Ile
305                 310                 315                 320

caa agg gac gag gag act gct tta cca aag tta ttc tac gaa aaa tta     1008
Gln Arg Asp Glu Glu Thr Ala Leu Pro Lys Leu Phe Tyr Glu Lys Leu
                325                 330                 335

cca gag gat ata tct gaa agg tat gtc ttc cta tta gac cca atg ctg     1056
Pro Glu Asp Ile Ser Glu Arg Tyr Val Phe Leu Leu Asp Pro Met Leu
            340                 345                 350

gcc acc ggt ggt agt gct atc atg gct aca gaa gtc ttg att aag aga     1104
Ala Thr Gly Gly Ser Ala Ile Met Ala Thr Glu Val Leu Ile Lys Arg
        355                 360                 365

ggt gtt aag cca gag aga att tac ttc tta aac cta atc tgt agt aag     1152
Gly Val Lys Pro Glu Arg Ile Tyr Phe Leu Asn Leu Ile Cys Ser Lys
    370                 375                 380

gaa ggg att gaa aaa tac cat gcc gcc ttc cca gag gtc aga att gtt     1200
Glu Gly Ile Glu Lys Tyr His Ala Ala Phe Pro Glu Val Arg Ile Val
385                 390                 395                 400

act ggt gcc ctc gac aga ggt cta gat gaa aac aag tat cta gtt cca     1248
Thr Gly Ala Leu Asp Arg Gly Leu Asp Glu Asn Lys Tyr Leu Val Pro
                405                 410                 415

ggg ttg ggt gac ttt ggt gac aga tac tac tgt gtt taa                 1287
Gly Leu Gly Asp Phe Gly Asp Arg Tyr Tyr Cys Val
            420                 425
```

<210> SEQ ID NO 14
<211> LENGTH: 428
<212> TYPE: PRT
<213> ORGANISM: Artificial Sequence
<220> FEATURE:
<223> OTHER INFORMATION: Synthetic Construct

<400> SEQUENCE: 14

```
Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30
```

```
Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Gly Ala Ser Gly Gly
                165                 170                 175

Gly Ala Asn Pro Leu Phe Phe Leu Ala Ser Pro Phe Leu Tyr Leu Thr
            180                 185                 190

Tyr Leu Ile Tyr Tyr Pro Asn Lys Gly Ser Phe Val Ser Lys Pro Arg
        195                 200                 205

Asn Leu Gln Lys Met Ser Ser Glu Pro Phe Lys Asn Val Tyr Leu Leu
    210                 215                 220

Pro Gln Thr Asn Gln Leu Leu Gly Leu Tyr Thr Ile Ile Arg Asn Lys
225                 230                 235                 240

Asn Thr Thr Arg Pro Asp Phe Ile Phe Tyr Ser Asp Arg Ile Ile Arg
                245                 250                 255

Leu Leu Val Glu Glu Gly Leu Asn His Leu Pro Val Gln Lys Gln Ile
            260                 265                 270

Val Glu Thr Asp Thr Asn Glu Asn Phe Glu Gly Val Ser Phe Met Gly
        275                 280                 285

Lys Ile Cys Gly Val Ser Ile Val Arg Ala Gly Glu Ser Met Glu Gln
    290                 295                 300

Gly Leu Arg Asp Cys Cys Arg Ser Val Arg Ile Gly Lys Ile Leu Ile
305                 310                 315                 320

Gln Arg Asp Glu Glu Thr Ala Leu Pro Lys Leu Phe Tyr Glu Lys Leu
                325                 330                 335

Pro Glu Asp Ile Ser Glu Arg Tyr Val Phe Leu Leu Asp Pro Met Leu
            340                 345                 350

Ala Thr Gly Gly Ser Ala Ile Met Ala Thr Glu Val Leu Ile Lys Arg
        355                 360                 365

Gly Val Lys Pro Glu Arg Ile Tyr Phe Leu Asn Leu Ile Cys Ser Lys
    370                 375                 380

Glu Gly Ile Glu Lys Tyr His Ala Ala Phe Pro Glu Val Arg Ile Val
385                 390                 395                 400

Thr Gly Ala Leu Asp Arg Gly Leu Asp Glu Asn Lys Tyr Leu Val Pro
                405                 410                 415

Gly Leu Gly Asp Phe Gly Asp Arg Tyr Tyr Cys Val
            420                 425
```

<210> SEQ ID NO 15
<211> LENGTH: 1200

-continued

```
<212> TYPE: DNA
<213> ORGANISM: Artificial Sequence
<220> FEATURE:
<223> OTHER INFORMATION: Fusion Construct - CDopt3 - OPRT
<220> FEATURE:
<221> NAME/KEY: CDS
<222> LOCATION: (1)..(1200)

<400> SEQUENCE: 15

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag gcg gtc      480
Ile Asp Glu Arg Pro Gln Asp Trp Phe Glu Asp Ile Gly Glu Ala Val
145                 150                 155                 160

gct cgt gca gct ttg ggg cca ttg gtg acg ggt ctg tac gac gtg cag      528
Ala Arg Ala Ala Leu Gly Pro Leu Val Thr Gly Leu Tyr Asp Val Gln
                165                 170                 175

gct ttc aag ttt ggg gac ttc gtg ctg aag agc ggg ctt tcc tcc ccc      576
Ala Phe Lys Phe Gly Asp Phe Val Leu Lys Ser Gly Leu Ser Ser Pro
            180                 185                 190

atc tac atc gat ctg cgg ggc atc gtg tct cga ccg cgt ctt ctg agt      624
Ile Tyr Ile Asp Leu Arg Gly Ile Val Ser Arg Pro Arg Leu Leu Ser
        195                 200                 205

cag gtt gca gat att tta ttc caa act gcc caa aat gca ggc atc agt      672
Gln Val Ala Asp Ile Leu Phe Gln Thr Ala Gln Asn Ala Gly Ile Ser
    210                 215                 220

ttt gac acc gtg tgt gga gtg cct tat aca gct ttg cca ttg gct aca      720
Phe Asp Thr Val Cys Gly Val Pro Tyr Thr Ala Leu Pro Leu Ala Thr
225                 230                 235                 240

gtt atc tgt tca acc aat caa att cca atg ctt att aga agg aaa gaa      768
Val Ile Cys Ser Thr Asn Gln Ile Pro Met Leu Ile Arg Arg Lys Glu
                245                 250                 255

aca aag gat tat gga act aag cgt ctt gta gaa gga act att aat cca      816
Thr Lys Asp Tyr Gly Thr Lys Arg Leu Val Glu Gly Thr Ile Asn Pro
            260                 265                 270

gga gaa acc tgt tta atc att gaa gat gtt gtc acc agt gga tct agt      864
```

-continued

```
Gly Glu Thr Cys Leu Ile Ile Glu Asp Val Val Thr Ser Gly Ser Ser
        275                 280                 285

gtt ttg gaa act gtt gag gtt ctt cag aag gag ggc ttg aag gtc act      912
Val Leu Glu Thr Val Glu Val Leu Gln Lys Glu Gly Leu Lys Val Thr
    290                 295                 300

gat gcc ata gtg ctg ttg gac aga gag cag gga ggc aag gac aag ttg      960
Asp Ala Ile Val Leu Leu Asp Arg Glu Gln Gly Gly Lys Asp Lys Leu
305                 310                 315                 320

cag gcg cac ggg atc cgc ctc cac tca gtg tgt aca ttg tcc aaa atg     1008
Gln Ala His Gly Ile Arg Leu His Ser Val Cys Thr Leu Ser Lys Met
                325                 330                 335

ctg gag att ctc gag cag cag aaa aaa gtt gat gct gag aca gtt ggg     1056
Leu Glu Ile Leu Glu Gln Gln Lys Lys Val Asp Ala Glu Thr Val Gly
            340                 345                 350

aga gtg aag agg ttt att cag gag aat gtc ttt gtg gca gcg aat cat     1104
Arg Val Lys Arg Phe Ile Gln Glu Asn Val Phe Val Ala Ala Asn His
        355                 360                 365

aat ggt tct ccc ctt tct ata aag gaa gca ccc aaa gaa ctc agc ttc     1152
Asn Gly Ser Pro Leu Ser Ile Lys Glu Ala Pro Lys Glu Leu Ser Phe
    370                 375                 380

ggt gca cgt gca gag ctg ccc agg atc cac cca gtt gca tcg aag taa     1200
Gly Ala Arg Ala Glu Leu Pro Arg Ile His Pro Val Ala Ser Lys
385                 390                 395


<210> SEQ ID NO 16
<211> LENGTH: 399
<212> TYPE: PRT
<213> ORGANISM: Artificial Sequence
<220> FEATURE:
<223> OTHER INFORMATION: Synthetic Construct

<400> SEQUENCE: 16

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ala Val
145                 150                 155                 160

Ala Arg Ala Ala Leu Gly Pro Leu Val Thr Gly Leu Tyr Asp Val Gln
                165                 170                 175

Ala Phe Lys Phe Gly Asp Phe Val Leu Lys Ser Gly Leu Ser Ser Pro
            180                 185                 190

Ile Tyr Ile Asp Leu Arg Gly Ile Val Ser Arg Pro Arg Leu Leu Ser
        195                 200                 205
```

```
Gln Val Ala Asp Ile Leu Phe Gln Thr Ala Gln Asn Ala Gly Ile Ser
    210                 215                 220

Phe Asp Thr Val Cys Gly Val Pro Tyr Thr Ala Leu Pro Leu Ala Thr
225                 230                 235                 240

Val Ile Cys Ser Thr Asn Gln Ile Pro Met Leu Ile Arg Arg Lys Glu
                245                 250                 255

Thr Lys Asp Tyr Gly Thr Lys Arg Leu Val Glu Gly Thr Ile Asn Pro
            260                 265                 270

Gly Glu Thr Cys Leu Ile Ile Glu Asp Val Val Thr Ser Gly Ser Ser
        275                 280                 285

Val Leu Glu Thr Val Glu Val Leu Gln Lys Glu Gly Leu Lys Val Thr
    290                 295                 300

Asp Ala Ile Val Leu Leu Asp Arg Glu Gln Gly Gly Lys Asp Lys Leu
305                 310                 315                 320

Gln Ala His Gly Ile Arg Leu His Ser Val Cys Thr Leu Ser Lys Met
                325                 330                 335

Leu Glu Ile Leu Glu Gln Gln Lys Lys Val Asp Ala Glu Thr Val Gly
            340                 345                 350

Arg Val Lys Arg Phe Ile Gln Glu Asn Val Phe Val Ala Ala Asn His
        355                 360                 365

Asn Gly Ser Pro Leu Ser Ile Lys Glu Ala Pro Lys Glu Leu Ser Phe
    370                 375                 380

Gly Ala Arg Ala Glu Leu Pro Arg Ile His Pro Val Ala Ser Lys
385                 390                 395


<210> SEQ ID NO 17
<211> LENGTH: 1260
<212> TYPE: DNA
<213> ORGANISM: Artificial Sequence
<220> FEATURE:
<223> OTHER INFORMATION: Fusion Construct - CDopt3 - linker - OPRT
<220> FEATURE:
<221> NAME/KEY: CDS
<222> LOCATION: (1)..(1260)

<400> SEQUENCE: 17

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
```

-continued

```
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag tcc ggc      480
Ile Asp Glu Arg Pro Gln Asp Trp Phe Glu Asp Ile Gly Glu Ser Gly
145                 150                 155                 160

ggc ggc gcc tcc ggc ggc ggc gcc tcc ggc ggc ggc gcc tcc ggc ggc      528
Gly Gly Ala Ser Gly Gly Gly Ala Ser Gly Gly Gly Ala Ser Gly Gly
                165                 170                 175

ggc gcc gcg gtc gct cgt gca gct ttg ggg cca ttg gtg acg ggt ctg      576
Gly Ala Ala Val Ala Arg Ala Ala Leu Gly Pro Leu Val Thr Gly Leu
            180                 185                 190

tac gac gtg cag gct ttc aag ttt ggg gac ttc gtg ctg aag agc ggg      624
Tyr Asp Val Gln Ala Phe Lys Phe Gly Asp Phe Val Leu Lys Ser Gly
        195                 200                 205

ctt tcc tcc ccc atc tac atc gat ctg cgg ggc atc gtg tct cga ccg      672
Leu Ser Ser Pro Ile Tyr Ile Asp Leu Arg Gly Ile Val Ser Arg Pro
    210                 215                 220

cgt ctt ctg agt cag gtt gca gat att tta ttc caa act gcc caa aat      720
Arg Leu Leu Ser Gln Val Ala Asp Ile Leu Phe Gln Thr Ala Gln Asn
225                 230                 235                 240

gca ggc atc agt ttt gac acc gtg tgt gga gtg cct tat aca gct ttg      768
Ala Gly Ile Ser Phe Asp Thr Val Cys Gly Val Pro Tyr Thr Ala Leu
                245                 250                 255

cca ttg gct aca gtt atc tgt tca acc aat caa att cca atg ctt att      816
Pro Leu Ala Thr Val Ile Cys Ser Thr Asn Gln Ile Pro Met Leu Ile
            260                 265                 270

aga agg aaa gaa aca aag gat tat gga act aag cgt ctt gta gaa gga      864
Arg Arg Lys Glu Thr Lys Asp Tyr Gly Thr Lys Arg Leu Val Glu Gly
        275                 280                 285

act att aat cca gga gaa acc tgt tta atc att gaa gat gtt gtc acc      912
Thr Ile Asn Pro Gly Glu Thr Cys Leu Ile Ile Glu Asp Val Val Thr
    290                 295                 300

agt gga tct agt gtt ttg gaa act gtt gag gtt ctt cag aag gag ggc      960
Ser Gly Ser Ser Val Leu Glu Thr Val Glu Val Leu Gln Lys Glu Gly
305                 310                 315                 320

ttg aag gtc act gat gcc ata gtg ctg ttg gac aga gag cag gga ggc     1008
Leu Lys Val Thr Asp Ala Ile Val Leu Leu Asp Arg Glu Gln Gly Gly
                325                 330                 335

aag gac aag ttg cag gcg cac ggg atc cgc ctc cac tca gtg tgt aca     1056
Lys Asp Lys Leu Gln Ala His Gly Ile Arg Leu His Ser Val Cys Thr
            340                 345                 350

ttg tcc aaa atg ctg gag att ctc gag cag cag aaa aaa gtt gat gct     1104
Leu Ser Lys Met Leu Glu Ile Leu Glu Gln Gln Lys Lys Val Asp Ala
        355                 360                 365

gag aca gtt ggg aga gtg aag agg ttt att cag gag aat gtc ttt gtg     1152
Glu Thr Val Gly Arg Val Lys Arg Phe Ile Gln Glu Asn Val Phe Val
    370                 375                 380

gca gcg aat cat aat ggt tct ccc ctt tct ata aag gaa gca ccc aaa     1200
Ala Ala Asn His Asn Gly Ser Pro Leu Ser Ile Lys Glu Ala Pro Lys
385                 390                 395                 400

gaa ctc agc ttc ggt gca cgt gca gag ctg ccc agg atc cac cca gtt     1248
Glu Leu Ser Phe Gly Ala Arg Ala Glu Leu Pro Arg Ile His Pro Val
                405                 410                 415

gca tcg aag taa                                                     1260
Ala Ser Lys
```

-continued

```
<210> SEQ ID NO 18
<211> LENGTH: 419
<212> TYPE: PRT
<213> ORGANISM: Artificial Sequence
<220> FEATURE:
<223> OTHER INFORMATION: Synthetic Construct

<400> SEQUENCE: 18

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Gly Ala Ser Gly Gly
                165                 170                 175

Gly Ala Ala Val Ala Arg Ala Ala Leu Gly Pro Leu Val Thr Gly Leu
            180                 185                 190

Tyr Asp Val Gln Ala Phe Lys Phe Gly Asp Phe Val Leu Lys Ser Gly
        195                 200                 205

Leu Ser Ser Pro Ile Tyr Ile Asp Leu Arg Gly Ile Val Ser Arg Pro
    210                 215                 220

Arg Leu Leu Ser Gln Val Ala Asp Ile Leu Phe Gln Thr Ala Gln Asn
225                 230                 235                 240

Ala Gly Ile Ser Phe Asp Thr Val Cys Gly Val Pro Tyr Thr Ala Leu
                245                 250                 255

Pro Leu Ala Thr Val Ile Cys Ser Thr Asn Gln Ile Pro Met Leu Ile
            260                 265                 270

Arg Arg Lys Glu Thr Lys Asp Tyr Gly Thr Lys Arg Leu Val Glu Gly
        275                 280                 285

Thr Ile Asn Pro Gly Glu Thr Cys Leu Ile Ile Glu Asp Val Val Thr
    290                 295                 300

Ser Gly Ser Ser Val Leu Glu Thr Val Glu Val Leu Gln Lys Glu Gly
305                 310                 315                 320

Leu Lys Val Thr Asp Ala Ile Val Leu Leu Asp Arg Glu Gln Gly Gly
                325                 330                 335

Lys Asp Lys Leu Gln Ala His Gly Ile Arg Leu His Ser Val Cys Thr
            340                 345                 350

Leu Ser Lys Met Leu Glu Ile Leu Glu Gln Gln Lys Lys Val Asp Ala
        355                 360                 365

Glu Thr Val Gly Arg Val Lys Arg Phe Ile Gln Glu Asn Val Phe Val
```

```
    370                 375                 380

Ala Ala Asn His Asn Gly Ser Pro Leu Ser Ile Lys Glu Ala Pro Lys
385                 390                 395                 400

Glu Leu Ser Phe Gly Ala Arg Ala Glu Leu Pro Arg Ile His Pro Val
                405                 410                 415

Ala Ser Lys
```

<210> SEQ ID NO 19
<211> LENGTH: 11428
<212> TYPE: DNA
<213> ORGANISM: Artificial Sequence
<220> FEATURE:
<223> OTHER INFORMATION: RCR Vector - pAC3-C1.yCD2

<400> SEQUENCE: 19

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440

tcccctacat cgtgacctgg gaagccttgg cttttgaccc ccctccctgg gtcaagccct   1500

ttgtacaccc taagcctccg cctcctcttc ctccatccgc cccgtctctc ccccttgaac   1560

ctcctcgttc gaccccgcct cgatcctccc tttatccagc cctcactcct tctctaggcg   1620

ccaaacctaa acctcaagtt ctttctgaca gtggggggcc gctcatcgac ctacttacag   1680

aagacccccc gccttatagg gacccaagac caccccctte cgacagggac ggaaatggtg   1740

gagaagcgac ccctgcggga gaggcaccgg acccctcccc aatggcatct cgcctacgtg   1800
```

-continued

```
ggagacggga gccccctgtg gccgactcca ctacctcgca ggcattcccc ctccgcgcag   1860

gaggaaacgg acagcttcaa tactggccgt tctcctcttc tgacctttac aactggaaaa   1920

ataataaccc ttctttttct gaagatccag gtaaactgac agctctgatc gagtctgtcc   1980

tcatcaccca tcagcccacc tgggacgact gtcagcagct gttggggact ctgctgaccg   2040

gagaagaaaa acaacgggtg ctcttagagg ctagaaaggc ggtgcggggc gatgatgggc   2100

gccccactca actgcccaat gaagtcgatg ccgcttttcc cctcgagcgc ccagactggg   2160

attacaccac ccaggcaggt aggaaccacc tagtccacta tcgccagttg ctcctagcgg   2220

gtctccaaaa cgcgggcaga agccccacca atttggccaa ggtaaaagga ataacacaag   2280

ggcccaatga gtctccctcg gccttcctag agagacttaa ggaagcctat cgcaggtaca   2340

ctccttatga ccctgaggac ccagggcaag aaactaatgt gtctatgtct ttcatttggc   2400

agtctgcccc agacattggg agaaagttag agaggttaga agatttaaaa aacaagacgc   2460

ttggagattt ggttagagag gcagaaaaga tctttaataa acgagaaacc ccggaagaaa   2520

gagaggaacg tatcaggaga gaaacagagg aaaaagaaga acgccgtagg acagaggatg   2580

agcagaaaga gaaagaaaga gatcgtagga gacatagaga gatgagcaag ctattggcca   2640

ctgtcgttag tggacagaaa caggatagac agggaggaga acgaaggagg tcccaactcg   2700

atcgcgacca gtgtgcctac tgcaaagaaa aggggcactg ggctaaagat tgtcccaaga   2760

aaccacgagg acctcgggga ccaagacccc agacctccct cctgacccta gatgactagg   2820

gaggtcaggg tcaggagccc ccccctgaac ccaggataac cctcaaagtc ggggggcaac   2880

ccgtcacctt cctggtagat actggggccc aacactccgt gctgacccaa aatcctggac   2940

ccctaagtga taagtctgcc tgggtccaag ggctactgg aggaaagcgg tatcgctgga   3000

ccacggatcg caaagtacat ctagctaccg gtaaggtcac ccactctttc ctccatgtac   3060

cagactgtcc ctatcctctg ttaggaagag atttgctgac taaactaaaa gcccaaatcc   3120

actttgaggg atcaggagcc caggttatgg gaccaatggg gcagcccctg caagtgttga   3180

ccctaaatat agaagatgag tatcggctac atgagacctc aaaagagcca gatgtttctc   3240

tagggtccac atggctgtct gattttcctc aggcctgggc ggaaaccggg ggcatgggac   3300

tggcagttcg ccaagctcct ctgatcatac ctctgaaagc aacctctacc cccgtgtcca   3360

taaaacaata ccccatgtca caagaagcca gactggggat caagccccac atacagagac   3420

tgttggacca gggaatactg gtaccctgcc agtccccctg gaacacgccc ctgctacccg   3480

ttaagaaacc agggactaat gattataggc ctgtccagga tctgagagaa gtcaacaagc   3540

gggtggaaga catccacccc accgtgccca acccttacaa cctcttgagc gggctcccac   3600

cgtcccacca gtggtacact gtgcttgatt taaaggatgc ctttttctgc ctgagactcc   3660

accccaccag tcagcctctc ttcgcctttg agtggagaga tccagagatg ggaatctcag   3720

gacaattgac ctggaccaga ctcccacagg gtttcaaaaa cagtcccacc ctgtttgatg   3780

aggcactgca cagagaccta gcagacttcc ggatccagca cccagacttg atcctgctac   3840

agtacgtgga tgacttactg ctggccgcca cttctgagct agactgccaa caaggtactc   3900

gggccctgtt acaaacccta gggaacctcg ggtatcgggc ctcggccaag aaagcccaaa   3960

tttgccagaa acaggtcaag tatctggggt atcttctaaa agagggtcag agatggctga   4020

ctgaggccag aaaagagact gtgatggggc agcctactcc gaagacccct cgacaactaa   4080

gggagttcct agggacggca ggcttctgtc gcctctggat ccctgggttt gcagaaatgg   4140
```

-continued cagccccctt gtaccctctc accaaaacgg ggactctgtt taattggggc ccagaccaac 4200
aaaaggccta tcaagaaatc aagcaagctc ttctaactgc cccagccctg gggttgccag 4260
atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tggggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac ccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc ccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagccccct caataccagt taccccctt ccactaccag 7200
tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgtg aggtctatat 8340
aagcagagct cgtttagtga accgtcagat cgcctggaga cgccatccac gctgttttga 8400
cctccgttaa catggtgacc ggcggcatgg cctccaagtg ggatcaaaag ggcatggata 8460
tcgcttacga ggaggccctg ctgggctaca aggagggcgg cgtgcctatc ggcggctgtc 8520
tgatcaacaa caaggacggc agtgtgctgg gcaggggcca caacatgagg ttccagaagg 8580
gctccgccac cctgcacggc gagatctcca ccctggagaa ctgtggcagg ctggagggca 8640
aggtgtacaa ggacaccacc ctgtacacca ccctgtcccc ttgtgacatg tgtaccggcg 8700
ctatcatcat gtacggcatc cctaggtgtg tgatcggcga gaacgtgaac ttcaagtcca 8760
agggcgagaa gtacctgcaa accaggggcc acgaggtggt ggttgttgac gatgagaggt 8820
gtaagaagct gatgaagcag ttcatcgacg agaggcctca ggactggttc gaggatatcg 8880
gcgagtaagc ggccgcagat aaaataaaag attttattta gtctccagaa aaagggggga 8940
atgaaagacc ccacctgtag gtttggcaag ctagcttaag taacgccatt ttgcaaggca 9000
tggaaaaata cataactgag aatagagaag ttcagatcaa ggtcaggaac agatggaaca 9060
gctgaatatg ggccaaacag gatatctgtg gtaagcagtt cctgccccgg ctcagggcca 9120
agaacagatg gaacagctga atatgggcca aacaggatat ctgtggtaag cagttcctgc 9180
cccggctcag ggccaagaac agatggtccc cagatgcggt ccagccctca gcagtttcta 9240
gagaaccatc agatgtttcc agggtgcccc aaggacctga aatgaccctg tgccttattt 9300
gaactaacca atcagttcgc ttctcgcttc tgttcgcgcg cttctgctcc ccgagctcaa 9360
taaaagagcc cacaacccct cactcggggc gccagtcctc cgattgactg agtcgcccgg 9420
gtacccgtgt atccaataaa ccctcttgca gttgcatccg acttgtggtc tcgctgttcc 9480
ttgggagggt ctcctctgag tgattgacta cccgtcagcg ggggtctttc attacatgtg 9540
agcaaaaggc cagcaaaagg ccaggaaccg taaaaaggcc gcgttgctgg cgtttttcca 9600
taggctccgc ccccctgacg agcatcacaa aaatcgacgc tcaagtcaga ggtggcgaaa 9660
cccgacagga ctataaagat accaggcgtt tccccctgga agctccctcg tgcgctctcc 9720
tgttccgacc ctgccgctta ccggatacct gtccgccttt ctcccttcgg gaagcgtggc 9780
gctttctcat agctcacgct gtaggtatct cagttcggtg taggtcgttc gctccaagct 9840
gggctgtgtg cacgaacccc ccgttcagcc cgaccgctgc gccttatccg gtaactatcg 9900
tcttgagtcc aacccggtaa gacacgactt atcgccactg gcagcagcca ctggtaacag 9960
gattagcaga gcgaggtatg taggcggtgc tacagagttc ttgaagtggt ggcctaacta 10020
cggctacact agaaggacag tatttggtat ctgcgctctg ctgaagccag ttaccttcgg 10080
aaaaagagtt ggtagctctt gatccggcaa acaaaccacc gctggtagcg gtggtttttt 10140
tgtttgcaag cagcagatta cgcgcagaaa aaaaggatct caagaagatc ctttgatctt 10200
ttctacgggg tctgacgctc agtggaacga aaactcacgt taagggattt tggtcatgag 10260
attatcaaaa aggatcttca cctagatcct tttaaattaa aaatgaagtt ttaaatcaat 10320
ctaaagtata tatgagtaaa cttggtctga cagttaccaa tgcttaatca gtgaggcacc 10380
tatctcagcg atctgtctat ttcgttcatc catagttgcc tgactccccg tcgtgtagat 10440
aactacgata cgggagggct taccatctgg ccccagtgct gcaatgatac cgcgagaccc 10500
acgctcaccg gctccagatt tatcagcaat aaaccagcca gccggaaggg ccgagcgcag 10560
aagtggtcct gcaactttat ccgcctccat ccagtctatt aattgttgcc gggaagctag 10620
agtaagtagt tcgccagtta atagtttgcg caacgttgtt gccattgctg caggcatcgt 10680
ggtgtcacgc tcgtcgtttg gtatggcttc attcagctcc ggttcccaac gatcaaggcg 10740
agttacatga tcccccatgt tgtgcaaaaa agcggttagc tccttcggtc ctccgatcgt 10800
tgtcagaagt aagttggccg cagtgttatc actcatggtt atggcagcac tgcataattc 10860
tcttactgtc atgccatccg taagatgctt ttctgtgact ggtgagtact caaccaagtc 10920
attctgagaa tagtgtatgc ggcgaccgag ttgctcttgc ccggcgtcaa cacgggataa 10980
taccgcgcca catagcagaa ctttaaaagt gctcatcatt ggaaaacgtt cttcggggcg 11040
aaaactctca aggatcttac cgctgttgag atccagttcg atgtaaccca ctcgtgcacc 11100
caactgatct tcagcatctt ttactttcac cagcgtttct gggtgagcaa aaacaggaag 11160
gcaaaatgcc gcaaaaaagg gaataagggc gacacggaaa tgttgaatac tcatactctt 11220
ccttttttcaa tattattgaa gcatttatca gggttattgt ctcatgagcg gatacatatt 11280

```
tgaatgtatt tagaaaaata aacaaatagg ggttccgcgc acatttcccc gaaaagtgcc  11340

acctgacgtc taagaaacca ttattatcat gacattaacc tataaaaata ggcgtatcac  11400

gaggcccttt cgtcttcaag aattccat                                     11428
```

```
<210> SEQ ID NO 20
<211> LENGTH: 11384
<212> TYPE: DNA
<213> ORGANISM: Artificial Sequence
<220> FEATURE:
<223> OTHER INFORMATION: RCR Vector - pAC3-S1.hGMCSF

<400> SEQUENCE: 20

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440

tcccctacat cgtgacctgg gaagccttgg cttttgaccc ccctccctgg gtcaagccct   1500

ttgtacaccc taagcctccg cctcctcttc ctccatccgc cccgtctctc cccccttgaac  1560

ctcctcgttc gaccccgcct cgatcctccc tttatccagc cctcactcct tctctaggcg   1620

ccaaacctaa acctcaagtt ctttctgaca gtggggggcc gctcatcgac ctacttacag   1680

aagacccccc gccttatagg gacccaagac cacccccttc cgacagggac ggaaatggtg   1740

gagaagcgac ccctgcggga gaggcaccgg accccctcccc aatggcatct cgcctacgtg  1800

ggagacggga gccccctgtg gccgactcca ctacctcgca ggcattcccc ctccgcgcag   1860
```

-continued gaggaaacgg acagcttcaa tactggccgt tctcctcttc tgacctttac aactggaaaa 1920
ataataaccc ttctttttct gaagatccag gtaaactgac agctctgatc gagtctgtcc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160
attacaccac ccaggcaggt aggaaccacc tagtccacta tcgccagttg ctcctagcgg 2220
gtctccaaaa cgcgggcaga agccccacca atttggccaa ggtaaaagga ataacacaag 2280
ggcccaatga gtctccctcg gccttcctag agagacttaa ggaagcctat cgcaggtaca 2340
ctccttatga ccctgaggac ccagggcaag aaactaatgt gtctatgtct ttcatttggc 2400
agtctgcccc agacattggg agaaagttag agaggttaga agatttaaaa aacaagacgc 2460
ttggagattt ggttagagag gcagaaaaga tctttaataa acgagaaacc ccggaagaaa 2520
gagaggaacg tatcaggaga gaaacagagg aaaaagaaga acgccgtagg acagaggatg 2580
agcagaaaga gaaagaaaga gatcgtagga gacatagaga gatgagcaag ctattggcca 2640
ctgtcgttag tggacagaaa caggatagac agggaggaga acgaaggagg tcccaactcg 2700
atcgcgacca gtgtgcctac tgcaaagaaa aggggcactg ggctaaagat tgtcccaaga 2760
aaccacgagg acctcgggga ccaagacccc agacctccct cctgacccta gatgactagg 2820
gaggtcaggg tcaggagccc ccccctgaac ccaggataac cctcaaagtc ggggggcaac 2880
ccgtcacctt cctggtagat actggggccc aacactccgt gctgacccaa aatcctggac 2940
ccctaagtga taagtctgcc tgggtccaag ggctactgg aggaaagcgg tatcgctgga 3000
ccacggatcg caaagtacat ctagctaccg gtaaggtcac ccactctttc ctccatgtac 3060
cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag tatcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc cccagccctg ggttgccag 4260

-continued

```
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
```

-continued gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccct caataccagt tacccccctt ccactaccag 7200
tacaccctca acctccccta caagtccaag tgtcccacag ccaccccag gaactggaga 7260 tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgta cttatataag 8340
ggggtggggg cgcgttcgtc ctcagtcgcg atcgaacact cgagccgagc agacgtgcct 8400
acggttaaca tgtggctgca gagcctgctg ctcttgggca ctgtggcctg cagcatctct 8460
gcacccgccc gctcgcccag ccccagcacg cagccctggg agcatgtgaa tgccatccag 8520
gaggcccggc gtctcctgaa cctgagtaga gacactgctg ctgagatgaa tgaaacagta 8580
gaagtcatct cagaaatgtt tgacctccag gagccgacct gcctacagac ccgcctggag 8640
ctgtacaagc agggcctgcg gggcagcctc accaagctca agggcccctt gaccatgatg 8700
gccagccact acaagcagca ctgccctcca accccggaaa cttcctgtgc aacccagatt 8760
atcacctttg aaagtttcaa agagaacctg aaggactttc tgcttgtcat ccccttttgac 8820 tgctgggagc cagtccagga gtgagcggcc gcagataaaa taaaagattt tatttagtct 8880
ccagaaaaag gggggaatga aagaccccac ctgtaggttt ggcaagctag cttaagtaac 8940
gccattttgc aaggcatgga aaaatacata actgagaata gagaagttca gatcaaggtc 9000

```
aggaacagat ggaacagctg aatatgggcc aaacaggata tctgtggtaa gcagttcctg   9060
ccccggctca gggccaagaa cagatggaac agctgaatat gggccaaaca ggatatctgt   9120
ggtaagcagt tcctgccccg gctcagggcc aagaacagat ggtccccaga tgcggtccag   9180
ccctcagcag tttctagaga accatcagat gtttccaggg tgccccaagg acctgaaatg   9240
accctgtgcc ttatttgaac taaccaatca gttcgcttct cgcttctgtt cgcgcgcttc   9300
tgctccccga gctcaataaa agagcccaca acccctcact cggggcgcca gtcctccgat   9360
tgactgagtc gcccgggtac ccgtgtatcc aataaaccct cttgcagttg catccgactt   9420
gtggtctcgc tgttccttgg gagggtctcc tctgagtgat tgactacccg tcagcggggg   9480
tctttcatta catgtgagca aaaggccagc aaaaggccag gaaccgtaaa aaggccgcgt   9540
tgctggcgtt tttccatagg ctccgccccc ctgacgagca tcacaaaaat cgacgctcaa   9600
gtcagaggtg gcgaaacccg acaggactat aaagatacca ggcgtttccc cctggaagct   9660
ccctcgtgcg ctctcctgtt ccgaccctgc cgcttaccgg atacctgtcc gcctttctcc   9720
cttcgggaag cgtggcgctt tctcatagct cacgctgtag gtatctcagt tcggtgtagg   9780
tcgttcgctc caagctgggc tgtgtgcacg aaccccccgt tcagcccgac cgctgcgcct   9840
tatccggtaa ctatcgtctt gagtccaacc cggtaagaca cgacttatcg ccactggcag   9900
cagccactgg taacaggatt agcagagcga ggtatgtagg cggtgctaca gagttcttga   9960
agtggtggcc taactacggc tacactagaa ggacagtatt tggtatctgc gctctgctga  10020
agccagttac cttcggaaaa agagttggta gctcttgatc cggcaaacaa accaccgctg  10080
gtagcggtgg tttttttgtt tgcaagcagc agattacgcg cagaaaaaaa ggatctcaag  10140
aagatccttt gatcttttct acggggtctg acgctcagtg gaacgaaaac tcacgttaag  10200
ggattttggt catgagatta tcaaaaagga tcttcaccta gatcctttta aattaaaaat  10260
gaagttttaa atcaatctaa agtatatatg agtaaacttg gtctgacagt taccaatgct  10320
taatcagtga ggcacctatc tcagcgatct gtctatttcg ttcatccata gttgcctgac  10380
tccccgtcgt gtagataact acgatacggg agggcttacc atctggcccc agtgctgcaa  10440
tgataccgcg agacccacgc tcaccggctc cagatttatc agcaataaac cagccagccg  10500
gaagggccga gcgcagaagt ggtcctgcaa ctttatccgc ctccatccag tctattaatt  10560
gttgccggga agctagagta agtagttcgc cagttaatag tttgcgcaac gttgttgcca  10620
ttgctgcagg catcgtggtg tcacgctcgt cgtttggtat ggcttcattc agctccggtt  10680
cccaacgatc aaggcgagtt acatgatccc ccatgttgtg caaaaaagcg gttagctcct  10740
tcggtcctcc gatcgttgtc agaagtaagt tggccgcagt gttatcactc atggttatgg  10800
cagcactgca taattctctt actgtcatgc catccgtaag atgcttttct gtgactggtg  10860
agtactcaac caagtcattc tgagaatagt gtatgcggcg accgagttgc tcttgcccgg  10920
cgtcaacacg ggataatacc gcgccacata gcagaacttt aaaagtgctc atcattggaa  10980
aacgttcttc ggggcgaaaa ctctcaagga tcttaccgct gttgagatcc agttcgatgt  11040
aacccactcg tgcacccaac tgatcttcag catcttttac tttcaccagc gtttctgggt  11100
gagcaaaaac aggaaggcaa aatgccgcaa aaaagggaat aagggcgaca cggaaatgtt  11160
gaatactcat actcttcctt tttcaatatt attgaagcat ttatcagggt tattgtctca  11220
tgagcggata catatttgaa tgtatttaga aaaataaaca aataggggtt ccgcgcacat  11280
ttccccgaaa agtgccacct gacgtctaag aaaccattat tatcatgaca ttaacctata  11340
```

aaaataggcg tatcacgagg ccctttcgtc ttcaagaatt ccat 11384

<210> SEQ ID NO 21
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 21
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaga 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc cccc ttgaac 1560 ctcctcgttc gaccccgcct cgatcctccc tttatccagc cctcactcct tctctaggcg 1620
ccaaacctaa acctcaagtt ctttctgaca gtgggggggcc gctcatcgac ctacttacag 1680
aagacccccc gccttatagg gacccaagac cacccccttc cgacagggac ggaaatggtg 1740
gagaagcgac ccctgcggga gaggcaccgg acccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgttc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160
attacaccac ccaggcaggt aggaaccacc tagtccacta tcgccagttg ctcctagcgg 2220
gtctccaaaa cgcgggcaga agccccacca atttggccaa ggtaaaagga ataacacaag 2280
ggcccaatga gtctccctcg gccttcctag agagacttaa ggaagcctat cgcaggtaca 2340
ctccttatga ccctgaggac ccagggcaag aaactaatgt gtctatgtct ttcatttggc 2400
agtctgcccc agacattggg agaaagttag agaggttaga agatttaaaa aacaagacgc 2460
ttggagattt ggttagagag gcagaaaaga tctttaataa acgagaaacc ccggaagaaa 2520
gagaggaacg tatcaggaga gaaacagagg aaaaagaaga acgccgtagg acagaggatg 2580
agcagaaaga gaaagaaaga gatcgtagga gacatagaga gatgagcaag ctattggcca 2640
ctgtcgttag tggacagaaa caggatagac agggaggaga acgaaggagg tcccaactcg 2700
atcgcgacca gtgtgcctac tgcaaagaaa aggggcactg ggctaaagat tgtcccaaga 2760
aaccacgagg acctcgggga ccaagacccc agacctccct cctgacccta gatgactagg 2820
gaggtcaggg tcaggagccc ccccctgaac ccaggataac cctcaaagtc ggggggcaac 2880
ccgtcacctt cctggtagat actggggccc aacactccgt gctgacccaa aatcctggac 2940
ccctaagtga taagtctgcc tgggtccaag gggctactgg aggaaagcgg tatcgctgga 3000
ccacggatcg caaagtacat ctagctaccg gtaaggtcac ccactctttc ctccatgtac 3060
cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag catcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc cccagccctg ggggttgccag 4260
atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380

-continued

```
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
```

ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccct caataccagt taccccctt ccactaccag 7200
tacaccctca acctcccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgatta gtccaatttg ttaaagacag gatatcagtg gtccaggctc tagttttgac 8280
tcaacaatat caccagctga agcctataga gtacgagcca tgacgtacgt tactggccga 8340
agccgcttgg aataaggccg gtgtgcgttt gtctatatgt tattttccac catattgccg 8400
tcttttggca atgtgagggc ccggaaacct ggccctgtct tcttgacgag cattcctagg 8460
ggtctttccc ctctcgccaa aggaatgcaa ggtctgttga atgtcgtgaa ggaagcagtt 8520
cctctggaag cttcttgaag acaaacaacg tctgtagcga ccctttgcag gcagcggaac 8580
cccccacctg gcgacaggtg cctctgcggc caaaagccac gtgtataaga tacacctgca 8640
aaggcggcac aaccccagtg ccacgttgtg agttggatag ttgtggaaag agtcaaatgg 8700
ctctcctcaa gcgtattcaa caaggggctg aaggatgccc agaaggtacc ccattgtatg 8760
ggatctgatc tggggcctcg gtgcacatgc tttacatgtg tttagtcgag gttaaaaaaa 8820
cgtctaggcc ccccgaacca cggggacgtg gttttccttt gaaaaacacg ataataccat 8880
ggtgacaggg ggaatggcaa gcaagtggga tcagaagggt atggacattg cctatgagga 8940
ggcggcctta ggttacaaag agggtggtgt tcctattggc ggatgtctta tcaataacaa 9000
agacggaagt gttctcggtc gtggtcacaa catgagattt caaaagggat ccgccacact 9060
acatggtgag atctccactt tggaaaactg tgggagatta gagggcaaag tgtacaaaga 9120

-continued

```
taccactttg tatacgacgc tgtctccatg cgacatgtgt acaggtgcca tcatcatgta   9180
tggtattcca cgctgtgttg tcggtgagaa cgttaatttc aaaagtaagg gcgagaaata   9240
tttacaaact agaggtcacg aggttgttgt tgttgacgat gagaggtgta aaaagatcat   9300
gaaacaattt atcgatgaaa gacctcagga ttggtttgaa gatattggtg agtaggcggc   9360
cgcgccatag ataaaataaa agattttatt tagtctccag aaaaaggggg gaatgaaaga   9420
ccccacctgt aggtttggca agctagctta agtaacgcca ttttgcaagg catggaaaaa   9480
tacataactg agaatagaga agttcagatc aaggtcagga acagatggaa cagctgaata   9540
tgggccaaac aggatatctg tggtaagcag ttcctgcccc ggctcagggc caagaacaga   9600
tggaacagct gaatatgggc caaacaggat atctgtggta agcagttcct gccccggctc   9660
agggccaaga acagatggtc cccagatgcg gtccagccct cagcagtttc tagagaacca   9720
tcagatgttt ccagggtgcc ccaaggacct gaaatgaccc tgtgccttgt ttaaactaac   9780
caatcagttc gcttctcgct tctgttcgcg cgcttctgct ccccgagctc aataaaagag   9840
cccacaaccc ctcactcggg gcgccagtcc tccgattgac tgagtcgccc gggtacccgt   9900
gtatccaata aaccctcttg cagttgcatc cgacttgtgg tctcgctgtt ccttgggagg   9960
gtctcctctg agtgattgac tacccgtcag cgggggtctt tcatttgggg gctcgtccgg  10020
gatcgggaga cccctgccca gggaccaccg acccaccacc gggaggtaag ctggctgcct  10080
cgcgcgtttc ggtgatgacg gtgaaaacct ctgacatgtg agcaaaaggc cagcaaaagg  10140
ccaggaaccg taaaaaggcc gcgttgctgg cgtttttcca taggctccgc ccccctgacg  10200
agcatcacaa aaatcgacgc tcaagtcaga ggtggcgaaa cccgacagga ctataaagat  10260
accaggcgtt tccccctgga agctccctcg tgcgctctcc tgttccgacc ctgccgctta  10320
ccggatacct gtccgccttt ctcccttcgg gaagcgtggc gctttctcaa tgctcacgct  10380
gtaggtatct cagttcggtg taggtcgttc gctccaagct gggctgtgtg cacgaacccc  10440
ccgttcagcc cgaccgctgc gccttatccg gtaactatcg tcttgagtcc aacccggtaa  10500
gacacgactt atcgccactg gcagcagcca ctggtaacag gattagcaga gcgaggtatg  10560
taggcggtgc tacagagttc ttgaagtggt ggcctaacta cggctacact agaaggacag  10620
tatttggtat ctgcgctctg ctgaagccag ttaccttcgg aaaaagagtt ggtagctctt  10680
gatccggcaa acaaaccacc gctggtagcg gtggtttttt tgtttgcaag cagcagatta  10740
cgcgcagaaa aaaaggatct caagaagatc ctttgatctt ttctacgggg tctgacgctc  10800
agtggaacga aaactcacgt taagggattt tggtcatgag attatcaaaa aggatcttca  10860
cctagatcct tttaaattaa aaatgaagtt ttaaatcaat ctaaagtata tatgagtaaa  10920
cttggtctga cagttaccaa tgcttaatca gtgaggcacc tatctcagcg atctgtctat  10980
ttcgttcatc catagttgcc tgactccccg tcgtgtagat aactacgata cgggagggct  11040
taccatctgg ccccagtgct gcaatgatac cgcgagaccc acgctcaccg gctccagatt  11100
tatcagcaat aaaccagcca gccggaaggg ccgagcgcag aagtggtcct gcaactttat  11160
ccgcctccat ccagtctatt aattgttgcc gggaagctag agtaagtagt tcgccagtta  11220
atagtttgcg caacgttgtt gccattgctg caggcatcgt ggtgtcacgc tcgtcgtttg  11280
gtatggcttc attcagctcc ggttcccaac gatcaaggcg agttacatga tcccccatgt  11340
tgtgcaaaaa agcggttagc tccttcggtc ctccgatcgt tgtcagaagt aagttggccg  11400
cagtgttatc actcatggtt atggcagcac tgcataattc tcttactgtc atgccatccg  11460
taagatgctt ttctgtgact ggtgagtact caaccaagtc attctgagaa tagtgtatgc  11520
```

ggcgaccgag ttgctcttgc ccggcgtcaa cacgggataa taccgcgcca catagcagaa 11580
ctttaaaagt gctcatcatt ggaaaacgtt cttcggggcg aaaactctca aggatcttac 11640
cgctgttgag atccagttcg atgtaaccca ctcgtgcacc caactgatct tcagcatctt 11700
ttactttcac cagcgtttct gggtgagcaa aaacaggaag gcaaaatgcc gcaaaaaagg 11760
gaataagggc gacacggaaa tgttgaatac tcatactctt cctttttcaa tattattgaa 11820
gcatttatca gggttattgt ctcatgagcg gatacatatt tgaatgtatt tagaaaaata 11880
aacaaatagg ggttccgcgc acatttcccc gaaaagtgcc acctgacgtc taagaaacca 11940
ttattatcat gacattaacc tataaaaata ggcgtatcac gaggcccttt cgtcttcaag 12000
aattcat 12007

<210> SEQ ID NO 22
<211> LENGTH: 11375
<212> TYPE: DNA
<213> ORGANISM: Artificial Sequence
<220> FEATURE:
<223> OTHER INFORMATION: RCR Vector - pAC3-S1.mGMCSF

<400> SEQUENCE: 22
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500

-continued

```
ttgtacaccc taagcctccg cctcctcttc ctccatccgc cccgtctctc cccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc cccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
```

-continued

```
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag    4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
```

-continued

```
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca cccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccatacggg cccaacccag tattacccga ccaaagactc ccttcctcac caatagagat   7140
tgtaccggct ccacagccac ctagcccccct caataccagt taccccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta cttatataag   8340
gggtgggggg cgcgttcgtc ctcagtcgcg atcgaacact cgagccgagc agacgtgcct   8400
acggttaaca tgtggctgca gaatttactt ttcctgggca ttgtggtcta cagcctctca   8460
gcacccaccc gctcacccat cactgtcacc cggccttgga agcatgtaga ggccatcaaa   8520
gaagccctga acctcctgga tgacatgcct gtcacgttga atgaagaggt agaagtcgtc   8580
tctaacgagt tctccttcaa gaagctaaca tgtgtgcaga cccgcctgaa gatattcgag   8640
```

```
cagggtctac ggggcaattt caccaaactc aagggcgcct tgaacatgac agccagctac   8700
taccagacat actgccccc aactccggaa acggactgtg aaacacaagt taccacctat   8760
gcggatttca tagacagcct taaaaccttt ctgactgata tcccctttga atgcaaaaaa   8820
ccaggccaaa aatgagcggc cgcagataaa ataaaagatt ttatttagtc tccagaaaaa   8880
ggggggaatg aaagacccca cctgtaggtt tggcaagcta gcttaagtaa cgccattttg   8940
caaggcatgg aaaaatacat aactgagaat agagaagttc agatcaaggt caggaacaga   9000
tggaacagct gaatatgggc caaacaggat atctgtggta agcagttcct gccccggctc   9060
agggccaaga acagatggaa cagctgaata tgggccaaac aggatatctg tggtaagcag   9120
ttcctgcccc ggctcagggc caagaacaga tggtccccag atgcggtcca gccctcagca   9180
gtttctagag aaccatcaga tgtttccagg gtgccccaag gacctgaaat gaccctgtgc   9240
cttatttgaa ctaaccaatc agttcgcttc tcgcttctgt tcgcgcgctt ctgctccccg   9300
agctcaataa aagagcccac aacccctcac tcggggcgcc agtcctccga ttgactgagt   9360
cgcccgggta cccgtgtatc caataaaccc tcttgcagtt gcatccgact tgtggtctcg   9420
ctgttccttg ggagggtctc ctctgagtga ttgactaccc gtcagcgggg gtctttcatt   9480
acatgtgagc aaaaggccag caaaaggcca ggaaccgtaa aaaggccgcg ttgctggcgt   9540
ttttccatag gctccgcccc cctgacgagc atcacaaaaa tcgacgctca agtcagaggt   9600
ggcgaaaccc gacaggacta taaagatacc aggcgtttcc ccctggaagc tccctcgtgc   9660
gctctcctgt tccgaccctg ccgcttaccg gatacctgtc cgcctttctc ccttcgggaa   9720
gcgtggcgct ttctcatagc tcacgctgta ggtatctcag ttcggtgtag gtcgttcgct   9780
ccaagctggg ctgtgtgcac gaaccccccg ttcagcccga ccgctgcgcc ttatccggta   9840
actatcgtct tgagtccaac ccggtaagac acgacttatc gccactggca gcagccactg   9900
gtaacaggat tagcagagcg aggtatgtag gcggtgctac agagttcttg aagtggtggc   9960
ctaactacgg ctacactaga aggacagtat ttggtatctg cgctctgctg aagccagtta  10020
ccttcggaaa aagagttggt agctcttgat ccggcaaaca aaccaccgct ggtagcggtg  10080
gtttttttgt ttgcaagcag cagattacgc gcagaaaaaa aggatctcaa gaagatcctt  10140
tgatcttttc tacggggtct gacgctcagt ggaacgaaaa ctcacgttaa gggattttgg  10200
tcatgagatt atcaaaaagg atcttcacct agatcctttt aaattaaaaa tgaagtttta  10260
aatcaatcta aagtatatat gagtaaactt ggtctgacag ttaccaatgc ttaatcagtg  10320
aggcacctat ctcagcgatc tgtctatttc gttcatccat agttgcctga ctccccgtcg  10380
tgtagataac tacgatacgg gagggcttac catctggccc cagtgctgca atgataccgc  10440
gagacccacg ctcaccggct ccagatttat cagcaataaa ccagccagcc ggaagggccg  10500
agcgcagaag tggtcctgca actttatccg cctccatcca gtctattaat tgttgccggg  10560
aagctagagt aagtagttcg ccagttaata gtttgcgcaa cgttgttgcc attgctgcag  10620
gcatcgtggt gtcacgctcg tcgtttggta tggcttcatt cagctccggt tcccaacgat  10680
caaggcgagt tacatgatcc cccatgttgt gcaaaaaagc ggttagctcc ttcggtcctc  10740
cgatcgttgt cagaagtaag ttggccgcag tgttatcact catggttatg gcagcactgc  10800
ataattctct tactgtcatg ccatccgtaa gatgcttttc tgtgactggt gagtactcaa  10860
ccaagtcatt ctgagaatag tgtatgcggc gaccgagttg ctcttgcccg gcgtcaacac  10920
gggataatac cgcgccacat agcagaactt taaaagtgct catcattgga aaacgttctt  10980
```

```
cggggcgaaa actctcaagg atcttaccgc tgttgagatc cagttcgatg taacccactc  11040

gtgcacccaa ctgatcttca gcatctttta ctttcaccag cgtttctggg tgagcaaaaa  11100

caggaaggca aaatgccgca aaaaagggaa taagggcgac acggaaatgt tgaatactca  11160

tactcttcct ttttcaatat tattgaagca tttatcaggg ttattgtctc atgagcggat  11220

acatatttga atgtatttag aaaaataaac aaataggggt tccgcgcaca tttccccgaa  11280

aagtgccacc tgacgtctaa gaaaccatta ttatcatgac attaacctat aaaaataggc  11340

gtatcacgag gccctttcgt cttcaagaat tccat                             11375


<210> SEQ ID NO 23
<211> LENGTH: 4473
<212> TYPE: DNA
<213> ORGANISM: Homo sapiens
<220> FEATURE:
<221> NAME/KEY: CDS
<222> LOCATION: (175)..(3942)

<400> SEQUENCE: 23

aaggggaggt aaccctggcc cctttggtcg gggccccggg cagccgcgcg ccccttccca     60

cggggccctt tactgcgccg cgcgcccggc ccccacccct cgcagcaccc cgcgccccgc    120

gccctcccag ccgggtccag ccggagccat ggggccggag ccgcagtgag cacc atg      177
                                                            Met
                                                            1

gag ctg gcg gcc ttg tgc cgc tgg ggg ctc ctc ctc gcc ctc ttg ccc      225
Glu Leu Ala Ala Leu Cys Arg Trp Gly Leu Leu Leu Ala Leu Leu Pro
            5                   10                  15

ccc gga gcc gcg agc acc caa gtg tgc acc ggc aca gac atg aag ctg      273
Pro Gly Ala Ala Ser Thr Gln Val Cys Thr Gly Thr Asp Met Lys Leu
        20                  25                  30

cgg ctc cct gcc agt ccc gag acc cac ctg gac atg ctc cgc cac ctc      321
Arg Leu Pro Ala Ser Pro Glu Thr His Leu Asp Met Leu Arg His Leu
    35                  40                  45

tac cag ggc tgc cag gtg gtg cag gga aac ctg gaa ctc acc tac ctg      369
Tyr Gln Gly Cys Gln Val Val Gln Gly Asn Leu Glu Leu Thr Tyr Leu
50                  55                  60                  65

ccc acc aat gcc agc ctg tcc ttc ctg cag gat atc cag gag gtg cag      417
Pro Thr Asn Ala Ser Leu Ser Phe Leu Gln Asp Ile Gln Glu Val Gln
                70                  75                  80

ggc tac gtg ctc atc gct cac aac caa gtg agg cag gtc cca ctg cag      465
Gly Tyr Val Leu Ile Ala His Asn Gln Val Arg Gln Val Pro Leu Gln
            85                  90                  95

agg ctg cgg att gtg cga ggc acc cag ctc ttt gag gac aac tat gcc      513
Arg Leu Arg Ile Val Arg Gly Thr Gln Leu Phe Glu Asp Asn Tyr Ala
        100                 105                 110

ctg gcc gtg cta gac aat gga gac ccg ctg aac aat acc acc cct gtc      561
Leu Ala Val Leu Asp Asn Gly Asp Pro Leu Asn Asn Thr Thr Pro Val
    115                 120                 125

aca ggg gcc tcc cca gga ggc ctg cgg gag ctg cag ctt cga agc ctc      609
Thr Gly Ala Ser Pro Gly Gly Leu Arg Glu Leu Gln Leu Arg Ser Leu
130                 135                 140                 145

aca gag atc ttg aaa gga ggg gtc ttg atc cag cgg aac ccc cag ctc      657
Thr Glu Ile Leu Lys Gly Gly Val Leu Ile Gln Arg Asn Pro Gln Leu
                150                 155                 160

tgc tac cag gac acg att ttg tgg aag gac atc ttc cac aag aac aac      705
Cys Tyr Gln Asp Thr Ile Leu Trp Lys Asp Ile Phe His Lys Asn Asn
            165                 170                 175

cag ctg gct ctc aca ctg ata gac acc aac cgc tct cgg gcc tgc cac      753
Gln Leu Ala Leu Thr Leu Ile Asp Thr Asn Arg Ser Arg Ala Cys His
```

```
        180                 185                 190

ccc tgt tct ccg atg tgt aag ggc tcc cgc tgc tgg gga gag agt tct      801
Pro Cys Ser Pro Met Cys Lys Gly Ser Arg Cys Trp Gly Glu Ser Ser
    195                 200                 205

gag gat tgt cag agc ctg acg cgc act gtc tgt gcc ggt ggc tgt gcc      849
Glu Asp Cys Gln Ser Leu Thr Arg Thr Val Cys Ala Gly Gly Cys Ala
210                 215                 220                 225

cgc tgc aag ggg cca ctg ccc act gac tgc tgc cat gag cag tgt gct      897
Arg Cys Lys Gly Pro Leu Pro Thr Asp Cys Cys His Glu Gln Cys Ala
            230                 235                 240

gcc ggc tgc acg ggc ccc aag cac tct gac tgc ctg gcc tgc ctc cac      945
Ala Gly Cys Thr Gly Pro Lys His Ser Asp Cys Leu Ala Cys Leu His
            245                 250                 255

ttc aac cac agt ggc atc tgt gag ctg cac tgc cca gcc ctg gtc acc      993
Phe Asn His Ser Gly Ile Cys Glu Leu His Cys Pro Ala Leu Val Thr
        260                 265                 270

tac aac aca gac acg ttt gag tcc atg ccc aat ccc gag ggc cgg tat     1041
Tyr Asn Thr Asp Thr Phe Glu Ser Met Pro Asn Pro Glu Gly Arg Tyr
    275                 280                 285

aca ttc ggc gcc agc tgt gtg act gcc tgt ccc tac aac tac ctt tct     1089
Thr Phe Gly Ala Ser Cys Val Thr Ala Cys Pro Tyr Asn Tyr Leu Ser
290                 295                 300                 305

acg gac gtg gga tcc tgc acc ctc gtc tgc ccc ctg cac aac caa gag     1137
Thr Asp Val Gly Ser Cys Thr Leu Val Cys Pro Leu His Asn Gln Glu
            310                 315                 320

gtg aca gca gag gat gga aca cag cgg tgt gag aag tgc agc aag ccc     1185
Val Thr Ala Glu Asp Gly Thr Gln Arg Cys Glu Lys Cys Ser Lys Pro
            325                 330                 335

tgt gcc cga gtg tgc tat ggt ctg ggc atg gag cac ttg cga gag gtg     1233
Cys Ala Arg Val Cys Tyr Gly Leu Gly Met Glu His Leu Arg Glu Val
        340                 345                 350

agg gca gtt acc agt gcc aat atc cag gag ttt gct ggc tgc aag aag     1281
Arg Ala Val Thr Ser Ala Asn Ile Gln Glu Phe Ala Gly Cys Lys Lys
    355                 360                 365

atc ttt ggg agc ctg gca ttt ctg ccg gag agc ttt gat ggg gac cca     1329
Ile Phe Gly Ser Leu Ala Phe Leu Pro Glu Ser Phe Asp Gly Asp Pro
370                 375                 380                 385

gcc tcc aac act gcc ccg ctc cag cca gag cag ctc caa gtg ttt gag     1377
Ala Ser Asn Thr Ala Pro Leu Gln Pro Glu Gln Leu Gln Val Phe Glu
            390                 395                 400

act ctg gaa gag atc aca ggt tac cta tac atc tca gca tgg ccg gac     1425
Thr Leu Glu Glu Ile Thr Gly Tyr Leu Tyr Ile Ser Ala Trp Pro Asp
            405                 410                 415

agc ctg cct gac ctc agc gtc ttc cag aac ctg caa gta atc cgg gga     1473
Ser Leu Pro Asp Leu Ser Val Phe Gln Asn Leu Gln Val Ile Arg Gly
        420                 425                 430

cga att ctg cac aat ggc gcc tac tcg ctg acc ctg caa ggg ctg ggc     1521
Arg Ile Leu His Asn Gly Ala Tyr Ser Leu Thr Leu Gln Gly Leu Gly
    435                 440                 445

atc agc tgg ctg ggg ctg cgc tca ctg agg gaa ctg ggc agt gga ctg     1569
Ile Ser Trp Leu Gly Leu Arg Ser Leu Arg Glu Leu Gly Ser Gly Leu
450                 455                 460                 465

gcc ctc atc cac cat aac acc cac ctc tgc ttc gtg cac acg gtg ccc     1617
Ala Leu Ile His His Asn Thr His Leu Cys Phe Val His Thr Val Pro
            470                 475                 480

tgg gac cag ctc ttt cgg aac ccg cac caa gct ctg ctc cac act gcc     1665
Trp Asp Gln Leu Phe Arg Asn Pro His Gln Ala Leu Leu His Thr Ala
            485                 490                 495

aac cgg cca gag gac gag tgt gtg ggc gag ggc ctg gcc tgc cac cag     1713
```

-continued

```
Asn Arg Pro Glu Asp Glu Cys Val Gly Glu Gly Leu Ala Cys His Gln
        500                 505                 510

ctg tgc gcc cga ggg cac tgc tgg ggt cca ggg ccc acc cag tgt gtc      1761
Leu Cys Ala Arg Gly His Cys Trp Gly Pro Gly Pro Thr Gln Cys Val
    515                 520                 525

aac tgc agc cag ttc ctt cgg ggc cag gag tgc gtg gag gaa tgc cga      1809
Asn Cys Ser Gln Phe Leu Arg Gly Gln Glu Cys Val Glu Glu Cys Arg
530                 535                 540                 545

gta ctg cag ggg ctc ccc agg gag tat gtg aat gcc agg cac tgt ttg      1857
Val Leu Gln Gly Leu Pro Arg Glu Tyr Val Asn Ala Arg His Cys Leu
                550                 555                 560

ccg tgc cac cct gag tgt cag ccc cag aat ggc tca gtg acc tgt ttt      1905
Pro Cys His Pro Glu Cys Gln Pro Gln Asn Gly Ser Val Thr Cys Phe
            565                 570                 575

gga ccg gag gct gac cag tgt gtg gcc tgt gcc cac tat aag gac cct      1953
Gly Pro Glu Ala Asp Gln Cys Val Ala Cys Ala His Tyr Lys Asp Pro
        580                 585                 590

ccc ttc tgc gtg gcc cgc tgc ccc agc ggt gtg aaa cct gac ctc tcc      2001
Pro Phe Cys Val Ala Arg Cys Pro Ser Gly Val Lys Pro Asp Leu Ser
    595                 600                 605

tac atg ccc atc tgg aag ttt cca gat gag gag ggc gca tgc cag cct      2049
Tyr Met Pro Ile Trp Lys Phe Pro Asp Glu Glu Gly Ala Cys Gln Pro
610                 615                 620                 625

tgc ccc atc aac tgc acc cac tcc tgt gtg gac ctg gat gac aag ggc      2097
Cys Pro Ile Asn Cys Thr His Ser Cys Val Asp Leu Asp Asp Lys Gly
                630                 635                 640

tgc ccc gcc gag cag aga gcc agc cct ctg acg tcc atc atc tct gcg      2145
Cys Pro Ala Glu Gln Arg Ala Ser Pro Leu Thr Ser Ile Ile Ser Ala
            645                 650                 655

gtg gtt ggc att ctg ctg gtc gtg gtc ttg ggg gtg gtc ttt ggg atc      2193
Val Val Gly Ile Leu Leu Val Val Val Leu Gly Val Val Phe Gly Ile
        660                 665                 670

ctc atc aag cga cgg cag cag aag atc cgg aag tac acg atg cgg aga      2241
Leu Ile Lys Arg Arg Gln Gln Lys Ile Arg Lys Tyr Thr Met Arg Arg
    675                 680                 685

ctg ctg cag gaa acg gag ctg gtg gag ccg ctg aca cct agc gga gcg      2289
Leu Leu Gln Glu Thr Glu Leu Val Glu Pro Leu Thr Pro Ser Gly Ala
690                 695                 700                 705

atg ccc aac cag gcg cag atg cgg atc ctg aaa gag acg gag ctg agg      2337
Met Pro Asn Gln Ala Gln Met Arg Ile Leu Lys Glu Thr Glu Leu Arg
                710                 715                 720

aag gtg aag gtg ctt gga tct ggc gct ttt ggc aca gtc tac aag ggc      2385
Lys Val Lys Val Leu Gly Ser Gly Ala Phe Gly Thr Val Tyr Lys Gly
            725                 730                 735

atc tgg atc cct gat ggg gag aat gtg aaa att cca gtg gcc atc aaa      2433
Ile Trp Ile Pro Asp Gly Glu Asn Val Lys Ile Pro Val Ala Ile Lys
        740                 745                 750

gtg ttg agg gaa aac aca tcc ccc aaa gcc aac aaa gaa atc tta gac      2481
Val Leu Arg Glu Asn Thr Ser Pro Lys Ala Asn Lys Glu Ile Leu Asp
    755                 760                 765

gaa gca tac gtg atg gct ggt gtg ggc tcc cca tat gtc tcc cgc ctt      2529
Glu Ala Tyr Val Met Ala Gly Val Gly Ser Pro Tyr Val Ser Arg Leu
770                 775                 780                 785

ctg ggc atc tgc ctg aca tcc acg gtg cag ctg gtg aca cag ctt atg      2577
Leu Gly Ile Cys Leu Thr Ser Thr Val Gln Leu Val Thr Gln Leu Met
                790                 795                 800

ccc tat ggc tgc ctc tta gac cat gtc cgg gaa aac cgc gga cgc ctg      2625
Pro Tyr Gly Cys Leu Leu Asp His Val Arg Glu Asn Arg Gly Arg Leu
            805                 810                 815
```

```
ggc tcc cag gac ctg ctg aac tgg tgt atg cag att gcc aag ggg atg     2673
Gly Ser Gln Asp Leu Leu Asn Trp Cys Met Gln Ile Ala Lys Gly Met
        820                 825                 830

agc tac ctg gag gat gtg cgg ctc gta cac agg gac ttg gcc gct cgg     2721
Ser Tyr Leu Glu Asp Val Arg Leu Val His Arg Asp Leu Ala Ala Arg
    835                 840                 845

aac gtg ctg gtc aag agt ccc aac cat gtc aaa att aca gac ttc ggg     2769
Asn Val Leu Val Lys Ser Pro Asn His Val Lys Ile Thr Asp Phe Gly
850                 855                 860                 865

ctg gct cgg ctg ctg gac att gac gag aca gag tac cat gca gat ggg     2817
Leu Ala Arg Leu Leu Asp Ile Asp Glu Thr Glu Tyr His Ala Asp Gly
                870                 875                 880

ggc aag gtg ccc atc aag tgg atg gcg ctg gag tcc att ctc cgc cgg     2865
Gly Lys Val Pro Ile Lys Trp Met Ala Leu Glu Ser Ile Leu Arg Arg
            885                 890                 895

cgg ttc acc cac cag agt gat gtg tgg agt tat ggt gtg act gtg tgg     2913
Arg Phe Thr His Gln Ser Asp Val Trp Ser Tyr Gly Val Thr Val Trp
        900                 905                 910

gag ctg atg act ttt ggg gcc aaa cct tac gat ggg atc cca gcc cgg     2961
Glu Leu Met Thr Phe Gly Ala Lys Pro Tyr Asp Gly Ile Pro Ala Arg
    915                 920                 925

gag atc cct gac ctg ctg gaa aag ggg gag cgg ctg ccc cag ccc ccc     3009
Glu Ile Pro Asp Leu Leu Glu Lys Gly Glu Arg Leu Pro Gln Pro Pro
930                 935                 940                 945

atc tgc acc att gat gtc tac atg atc atg gtc aaa tgt tgg atg att     3057
Ile Cys Thr Ile Asp Val Tyr Met Ile Met Val Lys Cys Trp Met Ile
                950                 955                 960

gac tct gaa tgt cgg cca aga ttc cgg gag ttg gtg tct gaa ttc tcc     3105
Asp Ser Glu Cys Arg Pro Arg Phe Arg Glu Leu Val Ser Glu Phe Ser
            965                 970                 975

cgc atg gcc agg gac ccc cag cgc ttt gtg gtc atc cag aat gag gac     3153
Arg Met Ala Arg Asp Pro Gln Arg Phe Val Val Ile Gln Asn Glu Asp
        980                 985                 990

ttg ggc cca gcc agt ccc ttg  gac agc acc ttc tac  cgc tca ctg ctg   3201
Leu Gly Pro Ala Ser Pro Leu  Asp Ser Thr Phe Tyr  Arg Ser Leu Leu
    995                 1000                 1005

gag  gac gat gac atg ggg  gac ctg gtg gat gct  gag gag tat ctg      3246
Glu  Asp Asp Asp Met Gly  Asp Leu Val Asp Ala  Glu Glu Tyr Leu
1010                 1015                 1020

gta  ccc cag cag ggc ttc  ttc tgt cca gac cct  gcc ccg ggc gct      3291
Val  Pro Gln Gln Gly Phe  Phe Cys Pro Asp Pro  Ala Pro Gly Ala
1025                 1030                 1035

ggg  ggc atg gtc cac cac  agg cac cgc agc tca  tct acc agg agt      3336
Gly  Gly Met Val His His  Arg His Arg Ser Ser  Ser Thr Arg Ser
1040                 1045                 1050

ggc  ggt ggg gac ctg aca  cta ggg ctg gag ccc  tct gaa gag gag      3381
Gly  Gly Gly Asp Leu Thr  Leu Gly Leu Glu Pro  Ser Glu Glu Glu
1055                 1060                 1065

gcc  ccc agg tct cca ctg  gca ccc tcc gaa ggg  gct ggc tcc gat      3426
Ala  Pro Arg Ser Pro Leu  Ala Pro Ser Glu Gly  Ala Gly Ser Asp
1070                 1075                 1080

gta  ttt gat ggt gac ctg  gga atg ggg gca gcc  aag ggg ctg caa      3471
Val  Phe Asp Gly Asp Leu  Gly Met Gly Ala Ala  Lys Gly Leu Gln
1085                 1090                 1095

agc  ctc ccc aca cat gac  ccc agc cct cta cag  cgg tac agt gag      3516
Ser  Leu Pro Thr His Asp  Pro Ser Pro Leu Gln  Arg Tyr Ser Glu
1100                 1105                 1110

gac  ccc aca gta ccc ctg  ccc tct gag act gat  ggc tac gtt gcc      3561
Asp  Pro Thr Val Pro Leu  Pro Ser Glu Thr Asp  Gly Tyr Val Ala
1115                 1120                 1125
```

```
ccc  ctg acc tgc agc ccc  cag cct gaa tat gtg  aac cag cca gat      3606
Pro  Leu Thr Cys Ser Pro  Gln Pro Glu Tyr Val  Asn Gln Pro Asp
1130                 1135                 1140

gtt  cgg ccc cag ccc cct  tcg ccc cga gag ggc  cct ctg cct gct      3651
Val  Arg Pro Gln Pro Pro  Ser Pro Arg Glu Gly  Pro Leu Pro Ala
1145                 1150                 1155

gcc  cga cct gct ggt gcc  act ctg gaa agg ccc  aag act ctc tcc      3696
Ala  Arg Pro Ala Gly Ala  Thr Leu Glu Arg Pro  Lys Thr Leu Ser
1160                 1165                 1170

cca  ggg aag aat ggg gtc  gtc aaa gac gtt ttt  gcc ttt ggg ggt      3741
Pro  Gly Lys Asn Gly Val  Val Lys Asp Val Phe  Ala Phe Gly Gly
1175                 1180                 1185

gcc  gtg gag aac ccc gag  tac ttg aca ccc cag  gga gga gct gcc      3786
Ala  Val Glu Asn Pro Glu  Tyr Leu Thr Pro Gln  Gly Gly Ala Ala
1190                 1195                 1200

cct  cag ccc cac cct cct  cct gcc ttc agc cca  gcc ttc gac aac      3831
Pro  Gln Pro His Pro Pro  Pro Ala Phe Ser Pro  Ala Phe Asp Asn
1205                 1210                 1215

ctc  tat tac tgg gac cag  gac cca cca gag cgg  ggg gct cca ccc      3876
Leu  Tyr Tyr Trp Asp Gln  Asp Pro Pro Glu Arg  Gly Ala Pro Pro
1220                 1225                 1230

agc  acc ttc aaa ggg aca  cct acg gca gag aac  cca gag tac ctg      3921
Ser  Thr Phe Lys Gly Thr  Pro Thr Ala Glu Asn  Pro Glu Tyr Leu
1235                 1240                 1245

ggt  ctg gac gtg cca gtg  tga accagaaggc caagtccgca gaagccctga     3972
Gly  Leu Asp Val Pro Val
1250                 1255

tgtgtcctca gggagcaggg aaggcctgac ttctgctggc atcaagaggt gggagggccc   4032

tccgaccact tccaggggaa cctgccatgc caggaacctg tcctaaggaa ccttccttcc   4092

tgcttgagtt cccagatggc tggaaggggt ccagcctcgt tggaagagga acagcactgg   4152

ggagtctttg tggattctga ggccctgccc aatgagactc tagggtccag tggatgccac   4212

agcccagctt ggccctttcc ttccagatcc tgggtactga aagccttagg gaagctggcc   4272

tgagagggga agcggcccta agggagtgtc taagaacaaa agcgacccat tcagagactg   4332

tccctgaaac ctagtactgc cccccatgag gaaggaacag caatggtgtc agtatccagg   4392

ctttgtacag agtgcttttc tgtttagttt ttactttttt tgttttgttt ttttaaagat   4452

gaaataaaga cccaggggga g                                             4473


<210> SEQ ID NO 24
<211> LENGTH: 1255
<212> TYPE: PRT
<213> ORGANISM: Homo sapiens

<400> SEQUENCE: 24

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
```

-continued

```
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510
```

Gln Leu Cys Ala Arg Gly His Cys Trp Gly Pro Gly Pro Thr Gln Cys
515 520 525

Val Asn Cys Ser Gln Phe Leu Arg Gly Gln Glu Cys Val Glu Glu Cys
530 535 540

Arg Val Leu Gln Gly Leu Pro Arg Glu Tyr Val Asn Ala Arg His Cys
545 550 555 560

Leu Pro Cys His Pro Glu Cys Gln Pro Gln Asn Gly Ser Val Thr Cys
565 570 575

Phe Gly Pro Glu Ala Asp Gln Cys Val Ala Cys Ala His Tyr Lys Asp
580 585 590

Pro Pro Phe Cys Val Ala Arg Cys Pro Ser Gly Val Lys Pro Asp Leu
595 600 605

Ser Tyr Met Pro Ile Trp Lys Phe Pro Asp Glu Glu Gly Ala Cys Gln
610 615 620

Pro Cys Pro Ile Asn Cys Thr His Ser Cys Val Asp Leu Asp Asp Lys
625 630 635 640

Gly Cys Pro Ala Glu Gln Arg Ala Ser Pro Leu Thr Ser Ile Ile Ser
645 650 655

Ala Val Val Gly Ile Leu Leu Val Val Val Leu Gly Val Val Phe Gly
660 665 670

Ile Leu Ile Lys Arg Arg Gln Gln Lys Ile Arg Lys Tyr Thr Met Arg
675 680 685

Arg Leu Leu Gln Glu Thr Glu Leu Val Glu Pro Leu Thr Pro Ser Gly
690 695 700

Ala Met Pro Asn Gln Ala Gln Met Arg Ile Leu Lys Glu Thr Glu Leu
705 710 715 720

Arg Lys Val Lys Val Leu Gly Ser Gly Ala Phe Gly Thr Val Tyr Lys
725 730 735

Gly Ile Trp Ile Pro Asp Gly Glu Asn Val Lys Ile Pro Val Ala Ile
740 745 750

Lys Val Leu Arg Glu Asn Thr Ser Pro Lys Ala Asn Lys Glu Ile Leu
755 760 765

Asp Glu Ala Tyr Val Met Ala Gly Val Gly Ser Pro Tyr Val Ser Arg
770 775 780

Leu Leu Gly Ile Cys Leu Thr Ser Thr Val Gln Leu Val Thr Gln Leu
785 790 795 800

Met Pro Tyr Gly Cys Leu Leu Asp His Val Arg Glu Asn Arg Gly Arg
805 810 815

Leu Gly Ser Gln Asp Leu Leu Asn Trp Cys Met Gln Ile Ala Lys Gly
820 825 830

Met Ser Tyr Leu Glu Asp Val Arg Leu Val His Arg Asp Leu Ala Ala
835 840 845

Arg Asn Val Leu Val Lys Ser Pro Asn His Val Lys Ile Thr Asp Phe
850 855 860

Gly Leu Ala Arg Leu Leu Asp Ile Asp Glu Thr Glu Tyr His Ala Asp
865 870 875 880

Gly Gly Lys Val Pro Ile Lys Trp Met Ala Leu Glu Ser Ile Leu Arg
885 890 895

Arg Arg Phe Thr His Gln Ser Asp Val Trp Ser Tyr Gly Val Thr Val
900 905 910

Trp Glu Leu Met Thr Phe Gly Ala Lys Pro Tyr Asp Gly Ile Pro Ala
915 920 925

-continued

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                 1015                 1020

Leu Val  Pro Gln Gln Gly Phe  Phe Cys Pro Asp Pro  Ala Pro Gly
    1025                 1030                 1035

Ala Gly  Gly Met Val His His  Arg His Arg Ser Ser  Ser Thr Arg
    1040                 1045                 1050

Ser Gly  Gly Gly Asp Leu Thr  Leu Gly Leu Glu Pro  Ser Glu Glu
    1055                 1060                 1065

Glu Ala  Pro Arg Ser Pro Leu  Ala Pro Ser Glu Gly  Ala Gly Ser
    1070                 1075                 1080

Asp Val  Phe Asp Gly Asp Leu  Gly Met Gly Ala Ala  Lys Gly Leu
    1085                 1090                 1095

Gln Ser  Leu Pro Thr His Asp  Pro Ser Pro Leu Gln  Arg Tyr Ser
    1100                 1105                 1110

Glu Asp  Pro Thr Val Pro Leu  Pro Ser Glu Thr Asp  Gly Tyr Val
    1115                 1120                 1125

Ala Pro  Leu Thr Cys Ser Pro  Gln Pro Glu Tyr Val  Asn Gln Pro
    1130                 1135                 1140

Asp Val  Arg Pro Gln Pro Pro  Ser Pro Arg Glu Gly  Pro Leu Pro
    1145                 1150                 1155

Ala Ala  Arg Pro Ala Gly Ala  Thr Leu Glu Arg Pro  Lys Thr Leu
    1160                 1165                 1170

Ser Pro  Gly Lys Asn Gly Val  Val Lys Asp Val Phe  Ala Phe Gly
    1175                 1180                 1185

Gly Ala  Val Glu Asn Pro Glu  Tyr Leu Thr Pro Gln  Gly Gly Ala
    1190                 1195                 1200

Ala Pro  Gln Pro His Pro Pro  Pro Ala Phe Ser Pro  Ala Phe Asp
    1205                 1210                 1215

Asn Leu  Tyr Tyr Trp Asp Gln  Asp Pro Pro Glu Arg  Gly Ala Pro
    1220                 1225                 1230

Pro Ser  Thr Phe Lys Gly Thr  Pro Thr Ala Glu Asn  Pro Glu Tyr
    1235                 1240                 1245

Leu Gly  Leu Asp Val Pro Val
    1250                 1255


<210> SEQ ID NO 25
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 25

atg aca gcc atc atc aaa gag atc gtt agc aga aac aaa agg aga tat       48
Met Thr Ala Ile Ile Lys Glu Ile Val Ser Arg Asn Lys Arg Arg Tyr
```

-continued

```
1               5                   10                  15

caa gag gat gga ttc gac tta gac ttg acc tat att tat cca aac att        96
Gln Glu Asp Gly Phe Asp Leu Asp Leu Thr Tyr Ile Tyr Pro Asn Ile
            20                  25                  30

att gct atg gga ttt cct gca gaa aga ctt gaa ggc gta tac agg aac       144
Ile Ala Met Gly Phe Pro Ala Glu Arg Leu Glu Gly Val Tyr Arg Asn
        35                  40                  45

aat att gat gat gta gta agg ttt ttg gat tca aag cat aaa aac cat       192
Asn Ile Asp Asp Val Val Arg Phe Leu Asp Ser Lys His Lys Asn His
    50                  55                  60

tac aag ata tac aat ctt tgt gct gaa aga cat tat gac acc gcc aaa       240
Tyr Lys Ile Tyr Asn Leu Cys Ala Glu Arg His Tyr Asp Thr Ala Lys
65                  70                  75                  80

ttt aat tgc aga gtt gca caa tat cct ttt gaa gac cat aac cca cca       288
Phe Asn Cys Arg Val Ala Gln Tyr Pro Phe Glu Asp His Asn Pro Pro
                85                  90                  95

cag cta gaa ctt atc aaa ccc ttt tgt gaa gat ctt gac caa tgg cta       336
Gln Leu Glu Leu Ile Lys Pro Phe Cys Glu Asp Leu Asp Gln Trp Leu
            100                 105                 110

agt gaa gat gac aat cat gtt gca gca att cac tgt aaa gct gga aag       384
Ser Glu Asp Asp Asn His Val Ala Ala Ile His Cys Lys Ala Gly Lys
        115                 120                 125

gga cga act ggt gta atg ata tgt gca tat tta tta cat cgg ggc aaa       432
Gly Arg Thr Gly Val Met Ile Cys Ala Tyr Leu Leu His Arg Gly Lys
    130                 135                 140

ttt tta aag gca caa gag gcc cta gat ttc tat ggg gaa gta agg acc       480
Phe Leu Lys Ala Gln Glu Ala Leu Asp Phe Tyr Gly Glu Val Arg Thr
145                 150                 155                 160

aga gac aaa aag gga gta act att ccc agt cag agg cgc tat gtg tat       528
Arg Asp Lys Lys Gly Val Thr Ile Pro Ser Gln Arg Arg Tyr Val Tyr
                165                 170                 175

tat tat agc tac ctg tta aag aat cat ctg gat tat aga cca gtg gca       576
Tyr Tyr Ser Tyr Leu Leu Lys Asn His Leu Asp Tyr Arg Pro Val Ala
            180                 185                 190

ctg ttg ttt cac aag atg atg ttt gaa act att cca atg ttc agt ggc       624
Leu Leu Phe His Lys Met Met Phe Glu Thr Ile Pro Met Phe Ser Gly
        195                 200                 205

gga act tgc aat cct cag ttt gtg gtc tgc cag cta aag gtg aag ata       672
Gly Thr Cys Asn Pro Gln Phe Val Val Cys Gln Leu Lys Val Lys Ile
    210                 215                 220

tat tcc tcc aat tca gga ccc aca cga cgg gaa gac aag ttc atg tac       720
Tyr Ser Ser Asn Ser Gly Pro Thr Arg Arg Glu Asp Lys Phe Met Tyr
225                 230                 235                 240

ttt gag ttc cct cag ccg tta cct gtg tgt ggt gat atc aaa gta gag       768
Phe Glu Phe Pro Gln Pro Leu Pro Val Cys Gly Asp Ile Lys Val Glu
                245                 250                 255

ttc ttc cac aaa cag aac aag atg cta aaa aag gac aaa atg ttt cac       816
Phe Phe His Lys Gln Asn Lys Met Leu Lys Lys Asp Lys Met Phe His
            260                 265                 270

ttt tgg gta aat aca ttc ttc ata cca gga cca gag gaa acc tca gaa       864
Phe Trp Val Asn Thr Phe Phe Ile Pro Gly Pro Glu Glu Thr Ser Glu
        275                 280                 285

aaa gta gaa aat gga agt cta tgt gat caa gaa atc gat agc att tgc       912
Lys Val Glu Asn Gly Ser Leu Cys Asp Gln Glu Ile Asp Ser Ile Cys
    290                 295                 300

agt ata gag cgt gca gat aat gac aag gaa tat cta gta ctt act tta       960
Ser Ile Glu Arg Ala Asp Asn Asp Lys Glu Tyr Leu Val Leu Thr Leu
305                 310                 315                 320

aca aaa aat gat ctt gac aaa gca aat aaa gac aaa gcc aac cga tac      1008
```

```
Thr Lys Asn Asp Leu Asp Lys Ala Asn Lys Asp Lys Ala Asn Arg Tyr
            325                 330                 335

ttt tct cca aat ttt aag gtg aag ctg tac ttc aca aaa aca gta gag      1056
Phe Ser Pro Asn Phe Lys Val Lys Leu Tyr Phe Thr Lys Thr Val Glu
            340                 345                 350

gag ccg tca aat cca gag gct agc agt tca act tct gta aca cca gat      1104
Glu Pro Ser Asn Pro Glu Ala Ser Ser Ser Thr Ser Val Thr Pro Asp
        355                 360                 365

gtt agt gac aat gaa cct gat cat tat aga tat tct gac acc act gac      1152
Val Ser Asp Asn Glu Pro Asp His Tyr Arg Tyr Ser Asp Thr Thr Asp
    370                 375                 380

tct gat cca gag aat gaa cct ttt gat gaa gat cag cat aca caa att      1200
Ser Asp Pro Glu Asn Glu Pro Phe Asp Glu Asp Gln His Thr Gln Ile
385                 390                 395                 400

aca aaa gtc tga                                                      1212
Thr Lys Val


<210> SEQ ID NO 26
<211> LENGTH: 403
<212> TYPE: PRT
<213> ORGANISM: Homo sapiens

<400> SEQUENCE: 26

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
```

```
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val


<210> SEQ ID NO 27
<211> LENGTH: 597
<212> TYPE: DNA
<213> ORGANISM: Homo sapiens
<220> FEATURE:
<221> NAME/KEY: CDS
<222> LOCATION: (1)..(597)

<400> SEQUENCE: 27

atg tca aac gtg cga gtg tct aac ggg agc cct agc ctg gag cgg atg       48
Met Ser Asn Val Arg Val Ser Asn Gly Ser Pro Ser Leu Glu Arg Met
1               5                   10                  15

gac gcc agg cag gcg gag cac ccc aag ccc tcg gcc tgc agg aac ctc       96
Asp Ala Arg Gln Ala Glu His Pro Lys Pro Ser Ala Cys Arg Asn Leu
            20                  25                  30

ttc ggc ccg gtg gac cac gaa gag tta acc cgg gac ttg gag aag cac      144
Phe Gly Pro Val Asp His Glu Glu Leu Thr Arg Asp Leu Glu Lys His
        35                  40                  45

tgc aga gac atg gaa gag gcg agc cag cgc aag tgg aat ttc gat ttt      192
Cys Arg Asp Met Glu Glu Ala Ser Gln Arg Lys Trp Asn Phe Asp Phe
    50                  55                  60

cag aat cac aaa ccc cta gag ggc aag tac gag tgg caa gag gtg gag      240
Gln Asn His Lys Pro Leu Glu Gly Lys Tyr Glu Trp Gln Glu Val Glu
65                  70                  75                  80

aag ggc agc ttg ccc gag ttc tac tac aga ccc ccg cgg ccc ccc aaa      288
Lys Gly Ser Leu Pro Glu Phe Tyr Tyr Arg Pro Pro Arg Pro Pro Lys
                85                  90                  95

ggt gcc tgc aag gtg ccg gcg cag gag agc cag gat gtc agc ggg agc      336
Gly Ala Cys Lys Val Pro Ala Gln Glu Ser Gln Asp Val Ser Gly Ser
            100                 105                 110

cgc ccg gcg gcg cct tta att ggg gct ccg gct aac tct gag gac acg      384
Arg Pro Ala Ala Pro Leu Ile Gly Ala Pro Ala Asn Ser Glu Asp Thr
        115                 120                 125

cat ttg gtg gac cca aag act gat ccg tcg gac agc cag acg ggg tta      432
His Leu Val Asp Pro Lys Thr Asp Pro Ser Asp Ser Gln Thr Gly Leu
    130                 135                 140

gcg gag caa tgc gca gga ata agg aag cga cct gca acc gac gat tct      480
Ala Glu Gln Cys Ala Gly Ile Arg Lys Arg Pro Ala Thr Asp Asp Ser
145                 150                 155                 160
```

```
tct act caa aac aaa aga gcc aac aga aca gaa gaa aat gtt tca gac      528
Ser Thr Gln Asn Lys Arg Ala Asn Arg Thr Glu Glu Asn Val Ser Asp
                165                 170                 175

ggt tcc cca aat gcc ggt tct gtg gag cag acg ccc aag aag cct ggc      576
Gly Ser Pro Asn Ala Gly Ser Val Glu Gln Thr Pro Lys Lys Pro Gly
            180                 185                 190

ctc aga aga cgt caa acg taa                                          597
Leu Arg Arg Arg Gln Thr
        195


<210> SEQ ID NO 28
<211> LENGTH: 198
<212> TYPE: PRT
<213> ORGANISM: Homo sapiens

<400> SEQUENCE: 28

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195


<210> SEQ ID NO 29
<211> LENGTH: 894
<212> TYPE: DNA
<213> ORGANISM: Homo sapiens
<220> FEATURE:
<221> NAME/KEY: CDS
<222> LOCATION: (1)..(894)

<400> SEQUENCE: 29

atg aca aca ccc aga aat tca gta aat ggg act ttc ccg gca gag cca       48
Met Thr Thr Pro Arg Asn Ser Val Asn Gly Thr Phe Pro Ala Glu Pro
1               5                   10                  15

atg aaa ggc cct att gct atg caa tct ggt cca aaa cca ctc ttc agg       96
Met Lys Gly Pro Ile Ala Met Gln Ser Gly Pro Lys Pro Leu Phe Arg
            20                  25                  30

agg atg tct tca ctg gtg ggc ccc acg caa agc ttc ttc atg agg gaa      144
```

```
Arg Met Ser Ser Leu Val Gly Pro Thr Gln Ser Phe Phe Met Arg Glu
        35                  40                  45

tct aag act ttg ggg gct gtc cag att atg aat ggg ctc ttc cac att      192
Ser Lys Thr Leu Gly Ala Val Gln Ile Met Asn Gly Leu Phe His Ile
    50                  55                  60

gcc ctg ggg ggt ctt ctg atg atc cca gca ggg atc tat gca ccc atc      240
Ala Leu Gly Gly Leu Leu Met Ile Pro Ala Gly Ile Tyr Ala Pro Ile
65                  70                  75                  80

tgt gtg act gtg tgg tac cct ctc tgg gga ggc att atg tat att att      288
Cys Val Thr Val Trp Tyr Pro Leu Trp Gly Gly Ile Met Tyr Ile Ile
                85                  90                  95

tcc gga tca ctc ttg gca gca acg gag aaa aac tct agg aag tgt ttg      336
Ser Gly Ser Leu Leu Ala Ala Thr Glu Lys Asn Ser Arg Lys Cys Leu
            100                 105                 110

gtc aaa gga aaa atg ata atg aat tca ttg agc ctc ttt gct gcc att      384
Val Lys Gly Lys Met Ile Met Asn Ser Leu Ser Leu Phe Ala Ala Ile
        115                 120                 125

tct gga atg att ctt tca atc atg gac ata ctt aat att aaa att tcc      432
Ser Gly Met Ile Leu Ser Ile Met Asp Ile Leu Asn Ile Lys Ile Ser
    130                 135                 140

cat ttt tta aaa atg gag agt ctg aat ttt att aga gct cac aca cca      480
His Phe Leu Lys Met Glu Ser Leu Asn Phe Ile Arg Ala His Thr Pro
145                 150                 155                 160

tat att aac ata tac aac tgt gaa cca gct aat ccc tct gag aaa aac      528
Tyr Ile Asn Ile Tyr Asn Cys Glu Pro Ala Asn Pro Ser Glu Lys Asn
                165                 170                 175

tcc cca tct acc caa tac tgt tac agc ata caa tct ctg ttc ttg ggc      576
Ser Pro Ser Thr Gln Tyr Cys Tyr Ser Ile Gln Ser Leu Phe Leu Gly
            180                 185                 190

att ttg tca gtg atg ctg atc ttt gcc ttc ttc cag gaa ctt gta ata      624
Ile Leu Ser Val Met Leu Ile Phe Ala Phe Phe Gln Glu Leu Val Ile
        195                 200                 205

gct ggc atc gtt gag aat gaa tgg aaa aga acg tgc tcc aga ccc aaa      672
Ala Gly Ile Val Glu Asn Glu Trp Lys Arg Thr Cys Ser Arg Pro Lys
    210                 215                 220

tct aac ata gtt ctc ctg tca gca gaa gaa aaa aaa gaa cag act att      720
Ser Asn Ile Val Leu Leu Ser Ala Glu Glu Lys Lys Glu Gln Thr Ile
225                 230                 235                 240

gaa ata aaa gaa gaa gtg gtt ggg cta act gaa aca tct tcc caa cca      768
Glu Ile Lys Glu Glu Val Val Gly Leu Thr Glu Thr Ser Ser Gln Pro
                245                 250                 255

aag aat gaa gaa gac att gaa att att cca atc caa gaa gag gaa gaa      816
Lys Asn Glu Glu Asp Ile Glu Ile Ile Pro Ile Gln Glu Glu Glu Glu
            260                 265                 270

gaa gaa aca gag acg aac ttt cca gaa cct ccc caa gat cag gaa tcc      864
Glu Glu Thr Glu Thr Asn Phe Pro Glu Pro Pro Gln Asp Gln Glu Ser
        275                 280                 285

tca cca ata gaa aat gac agc tct cct taa                              894
Ser Pro Ile Glu Asn Asp Ser Ser Pro
    290                 295


<210> SEQ ID NO 30
<211> LENGTH: 297
<212> TYPE: PRT
<213> ORGANISM: Homo sapiens

<400> SEQUENCE: 30

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
```

-continued

```
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 31
<211> LENGTH: 596
<212> TYPE: DNA
<213> ORGANISM: homo sapiens

<400> SEQUENCE: 31

```
acgcgtactg gagtcaatga aagcaactat ttcaaaagat cagattactt accagtttca     60

ctaataaaga tttattactt taaaccttta tcataaaatg tatgctttga atactgtgaa    120

gtacactgca tataaggagt gtggtatagt ataaagaaac tttctgcagg tagtaattat    180

agtgaagatt ttaggtttac aaagccctag ctgttttctg tgtagctttt attattctta    240

tgactcttga caagtttgta gcttcaccat atacatttaa tattttgcaa taattggcct    300

tgttcctgag ctgttggatt cggggccgta gcactgtctg agaggtttac atttctcaca    360

gtgaaccggt ctctttttca gctgcttcct ggcttctttt tactcaggtt tccactgctt    420

ttttgctttt tttaatgctg tatgaaggtg ttaacatttg tttatatttt tcattaattg    480

taatacttt aaatcatgca tcatactcag aaatagggat tagaatttaa gtgacatctt    540
```

tggcctaata taatttacct gttaaaaatt tgtgaaagct attgcttagc ggccgc 596

<210> SEQ ID NO 32
<211> LENGTH: 511
<212> TYPE: DNA
<213> ORGANISM: Homo sapiens

<400> SEQUENCE: 32
acgcgtccat gtccgtacct ttctagttca taccttcttt taattttttt tttcttttca 60
atttgaagag agtgcttcct ctgttcttaa ggctagggaa ccaaattagg ttgtttcaat 120
atcgtgctaa aagatactgc ctttagaaga aggctattga caatccagcg tgtctcggtg 180
gaactctgac tccatggttc actttcatga tggccacatg cctcctgccc agagcccggc 240
agccactgtg cagtgggaag gggggccgat acactgtacg agagtgagta gcaggtctca 300
cagtgaaccg gtctctttcc ctactgtgtc acactcctaa tggaatgccg ttatccaaag 360
agcagcacga acccgacagg gctgagtggc ttgtgctagg gagaggtttg tgtcattcct 420
gctgaccaaa ctgcaggaaa aactgctaat tgtcatgctg aagactgcct gacggggaga 480
ctctgccttc tgtaagtagg tcagcggccg c 511

<210> SEQ ID NO 33
<211> LENGTH: 203
<212> TYPE: DNA
<213> ORGANISM: Homo sapiens

<400> SEQUENCE: 33
acgcgtaatt catatttgca tgtcgctatg tgttctggga aatcaccata aacgtgaaat 60
gtctttggat ttgggaatct tataagttct gtatgagacc actcggatga gctgttggat 120
tcggggccgt agcactgtct gagaggttta catttctcac agtgaaccgg tctctttttc 180
agctgcttct tttttgcggc cgc 203

<210> SEQ ID NO 34
<211> LENGTH: 205
<212> TYPE: DNA
<213> ORGANISM: Homo sapiens

<400> SEQUENCE: 34
gcggccgcaa ttcatatttg catgtcgcta tgtgttctgg gaaatcacca taaacgtgaa 60
atgtctttgg atttgggaat cttataagtt ctgtatgaga ccactcggat gagctgttgg 120
attcggggcc gtagcactgt ctgagaggtt tacatttctc acagtgaacc ggtctctttt 180
tcagctgctt cttttttgcg gccgc 205

<210> SEQ ID NO 35
<211> LENGTH: 1131
<212> TYPE: DNA
<213> ORGANISM: herpes simplex virus 1

<400> SEQUENCE: 35
atggcttcgt accccggcca tcagcacgcg tctgcgttcg accaggctgc gcgttctcgc 60
ggccatagca accgacgtac ggcgttgcgc cctcgccggc agcaagaagc cacggaagtc 120
cgcccggagc agaaaatgcc cacgctactg cgggtttata tagacggtcc ccacgggatg 180
gggaaaacca ccaccacgca actgctggtg gccctgggtt cgcgcgacga tatcgtctac 240
gtacccgagc cgatgactta ctggcaggtg ctgggggctt ccgagacaat cgcgaacatc 300
tacaccacac aacaccgcct cgaccagggt gagatatcgg ccggggacgc ggcggtggta 360

-continued

```
atgacaagcg cccagataac aatgggcatg ccttatgccg tgaccgacgc cgttctggct    420

cctcatatcg ggggggaggc tgggagctca catgccccgc ccccggccct caccctcatc    480

ttcgaccgcc atcccatcgc cgccctcctg tgttacccgg ccgcgcgata ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gcgagcggct tgacctggct atgctggccg cgattcgccg cgtttacgag    720

ctgcttgcca atacggtgcg gtatctgcag ggcggcgggt cgtggcggga ggattgggga    780

cagctttcgg ggacggccgt gccgccccag ggtgccgagc cccagagcaa cgcgggccca    840

cgaccccata tcggggacac gttatttacc ctgtttcggg cccccgagtt gctggccccc    900

aacggcgacc tgtataacgt gtttgcctgg gccttggacg tcttggccaa acgcctccgt    960

cccatgcacg tctttatcct ggattacgac caatcgcccg ccggctaccg ggacgccctg   1020

ctgcaactta cctccgggat ggtccagacc cacgtcacca cccccggctc cataccgacg   1080

atctgcgacc tggcgcgcac gtttgcccgg gagatggggg aggctaacta a            1131
```

<210> SEQ ID NO 36
<211> LENGTH: 499
<212> TYPE: DNA
<213> ORGANISM: Homo sapiens

<400> SEQUENCE: 36

```
atgaaatata caagttatat cttggctttt cagctctgca tcgttttggg ttctcttggc     60

tgttactgcc aggaccatat gtaaaagaag cagaaaacct taagaaatat tttaatgcag    120

gtcattcaga tgtagcggat aatggaactc ttttcttagg cattttgaag aattggaaag    180

aggagagtga cagaaaaata atgcagagcc aaattgtctc cttttacttc aaactttta     240

aaaactttaa agatgaccag agcatccaaa agagtgtgga gaccatcaag gaagacatga    300

atgtaagttt ttcaatagca acaaaaagaa acgagatgac ttcgaaaagc tgactaatta    360

ttcggtaact gacttgaatg tccaacgcaa agcaatacat gaactcatcc aagtgatggc    420

tgaactgtcg ccagcagcta aaacagggaa gcgaaaaagg agtcagatgc tgtttcgagg    480

tcgaagagca tcccagtaa                                                 499
```

<210> SEQ ID NO 37
<211> LENGTH: 468
<212> TYPE: DNA
<213> ORGANISM: Mus musculus

<400> SEQUENCE: 37

```
atgaacgcta cacactgcat cttggctttg cagctcttcc tcatggctgt ttctggctgt     60

tactgccacg gcacagtcat tgaaagccta gaaagtctga ataactattt taactcaagt    120

ggcatagatg tggaagaaaa gagtctcttc ttggatatct ggaggaactg gcaaaaggat    180

ggtgacatga aaatcctgca gagccagatt atctctttct acctcagact ctttgaagtc    240

ttgaaagaca atcaggccat cagcaacaac ataagcgtca ttgaatcaca cctgattact    300

accttcttca gcaacagcaa ggcgaaaaag gatgcattca tgagtattgc caagtttgag    360

gtcaacaacc cacaggtcca gcgccaagca ttcaatgagc tcatccgagt ggtccaccag    420

ctgttgccgg aatccagcct caggaagcgg aaaaggagtc gctgctga                 468
```

<210> SEQ ID NO 38

<211> LENGTH: 462
<212> TYPE: DNA
<213> ORGANISM: Homo sapiens

<400> SEQUENCE: 38
atgtacagga tgcaactcct gtcttgcatt gcactaagtc ttgcacttgt cacaaacagt 60
gcacctactt caagttctac aaagaaaaca cagctacaac tggagcattt actgctggat 120
ttacagatga ttttgaatgg aattaataat tacaagaatc ccaaactcac caggatgctc 180
acatttaagt tttacatgcc caagaaggcc acagaactga aacatcttca gtgtctagaa 240
gaagaactca aacctctgga ggaagtgcta aatttagctc aaagcaaaaa ctttcactta 300
agacccaggg acttaatcag caatatcaac gtaatagttc tggaactaaa gggatctgaa 360
acaacattca tgtgtgaata tgctgatgag acagcaacca ttgtagaatt tctgaacaga 420
tggattacct tttgtcaaag catcatctca acactgactt ga 462

<210> SEQ ID NO 39
<211> LENGTH: 11426
<212> TYPE: DNA
<213> ORGANISM: Artificial Sequence
<220> FEATURE:
<223> OTHER INFORMATION: pAC3-S1.yCD2

<400> SEQUENCE: 39
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc cccctttgaac 1560
ctcctcgttc gaccccgcct cgatcctccc tttatccagc cctcactcct tctctaggcg 1620
ccaaacctaa acctcaagtt ctttctgaca gtggggggcc gctcatcgac ctacttacag 1680
aagacccccc gccttatagg gacccaagac cacccccttc cgacagggac ggaaatggtg 1740
gagaagcgac ccctgcggga gaggcaccgg acccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgtcc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160
attacaccac ccaggcaggt aggaaccacc tagtccacta tcgccagttg ctcctagcgg 2220
gtctccaaaa cgcgggcaga agccccacca atttggccaa ggtaaaagga ataacacaag 2280
ggcccaatga gtctccctcg gccttcctag agagacttaa ggaagcctat cgcaggtaca 2340
ctccttatga ccctgaggac ccagggcaag aaactaatgt gtctatgtct ttcatttggc 2400
agtctgcccc agacattggg agaaagttag agaggttaga agatttaaaa aacaagacgc 2460
ttggagattt ggttagagag gcagaaaaga tctttaataa acgagaaacc ccggaagaaa 2520
gagaggaacg tatcaggaga gaaacagagg aaaaagaaga acgccgtagg acagaggatg 2580
agcagaaaga gaaagaaaga gatcgtagga gacatagaga gatgagcaag ctattggcca 2640
ctgtcgttag tggacagaaa caggatagac agggaggaga acgaaggagg tcccaactcg 2700
atcgcgacca gtgtgcctac tgcaaagaaa aggggcactg ggctaaagat tgtcccaaga 2760
aaccacgagg acctcgggga ccaagacccc agacctccct cctgacccta gatgactagg 2820
gaggtcaggg tcaggagccc ccccctgaac ccaggataac cctcaaagtc ggggggcaac 2880
ccgtcacctt cctggtagat actggggccc aacactccgt gctgacccaa aatcctggac 2940
ccctaagtga taagtctgcc tgggtccaag ggctactgg aggaaagcgg tatcgctgga 3000
ccacggatcg caaagtacat ctagctaccg gtaaggtcac ccactctttc ctccatgtac 3060
cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag tatcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780

-continued

```
aggcactgca cagagaccta gcagacttcc ggatccagca cccagacttg atcctgctac   3840

agtacgtgga tgacttactg ctggccgcca cttctgagct agactgccaa caaggtactc   3900

gggccctgtt acaaaccta gggaacctcg ggtatcgggc ctcggccaag aaagcccaaa    3960

tttgccagaa acaggtcaag tatctggggt atcttctaaa agagggtcag agatggctga   4020

ctgaggccag aaaagagact gtgatggggc agcctactcc gaagacccct cgacaactaa   4080

gggagttcct agggacggca ggcttctgtc gcctctggat ccctgggttt gcagaaatgg   4140

cagcccccctt gtaccctctc accaaaacgg ggactctgtt taattggggc ccagaccaac  4200

aaaaggccta tcaagaaatc aagcaagctc ttctaactgc cccagccctg ggggttgccag   4260

atttgactaa gccctttgaa ctctttgtcg acgagaagca gggctacgcc aaaggtgtcc   4320

taacgcaaaa actgggacct tggcgtcggc cggtggccta cctgtccaaa aagctagacc   4380

cagtagcagc tgggtggccc ccttgcctac ggatggtagc agccattgcc gtactgacaa   4440

aggatgcagg caagctaacc atgggacagc cactagtcat tctggccccc catgcagtag   4500

aggcactagt caaacaaccc cccgaccgct ggctttccaa cgcccggatg actcactatc   4560

aggccttgct tttggacacg gaccgggtcc agttcggacc ggtggtagcc ctgaacccgg   4620

ctacgctgct cccactgcct gaggaagggc tgcaacacaa ctgccttgat atcctggccg   4680

aagcccacgg aacccgaccc gacctaacgg accagccgct cccagacgcc gaccacacct   4740

ggtacacgga tggaagcagt ctcttacaag agggacagcg taaggcggga gctgcggtga   4800

ccaccgagac cgaggtaatc tgggctaaag ccctgccagc cgggacatcc gctcagcggg   4860

ctgaactgat agcactcacc caggccctaa agatggcaga aggtaagaag ctaaatgttt   4920

atactgatag ccgttatgct tttgctactg cccatatcca tggagaaata tacagaaggc   4980

gtgggttgct cacatcagaa ggcaaagaga tcaaaaataa agacgagatc ttggccctac   5040

taaaagccct ctttctgccc aaaagactta gcataatcca ttgtccagga catcaaaagg   5100

gacacagcgc cgaggctaga ggcaaccgga tggctgacca agcggcccga aaggcagcca   5160

tcacagagac tccagacacc tctaccctcc tcatagaaaa ttcatcaccc tacacctcag   5220

aacattttca ttacacagtg actgatataa aggacctaac caagttgggg gccatttatg   5280

ataaaacaaa gaagtattgg gtctaccaag gaaaacctgt gatgcctgac cagtttactt   5340

ttgaattatt agactttctt catcagctga ctcacctcag cttctcaaaa atgaaggctc   5400

tcctagagag aagccacagt ccctactaca tgctgaaccg ggatcgaaca ctcaaaaata   5460

tcactgagac ctgcaaagct tgtgcacaag tcaacgccag caagtctgcc gttaaacagg   5520

gaactagggt ccgcgggcat cggcccggca ctcattggga gatcgatttc accgagataa   5580

agcccggatt gtatggctat aaatatcttc tagtttttat agataccttt tctggctgga   5640

tagaagcctt cccaaccaag aaagaaaccg ccaaggtcgt aaccaagaag ctactagagg   5700

agatcttccc caggttcggc atgcctcagg tattgggaac tgacaatggg cctgccttcg   5760

tctccaaggt gagtcagaca gtggccgatc tgttggggat tgattggaaa ttacattgtg   5820

catacagacc ccaaagctca ggccaggtag aaagaatgaa tagaaccatc aaggagactt   5880

taactaaatt aacgcttgca actggctcta gagactgggt gctcctactc cccttagccc   5940

tgtaccgagc ccgcaacacg ccgggccccc atggcctcac cccatatgag atcttatatg   6000

gggcaccccc gccccttgta aacttccctg accctgacat gacaagagtt actaacagcc   6060

cctctctcca agctcactta caggctctct acttagtcca gcacgaagtc tggagacctc   6120

tggcggcagc ctaccaagaa caactggacc gaccggtggt acctcaccct taccgagtcg   6180
```

gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc cccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccct caataccagt tacccccctt ccactaccag 7200
tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgta cttatataag 8340
ggggtggggg cgcgttcgtc ctcagtcgcg atcgaacact cgagccgagc agacgtgcct 8400
acggttaaca tggtgaccgg cggcatggcc tccaagtggg atcaaaaggg catggatatc 8460
gcttacgagg aggccctgct gggctacaag gagggcggcg tgcctatcgg cggctgtctg 8520
atcaacaaca aggacggcag tgtgctgggc aggggccaca acatgaggtt ccagaagggc 8580
tccgccaccc tgcacggcga gatctccacc ctggagaact gtggcaggct ggagggcaag 8640
gtgtacaagg acaccaccct gtacaccacc ctgtcccctt gtgacatgtg taccggcgct 8700
atcatcatgt acggcatccc taggtgtgtg atcggcgaga acgtgaactt caagtccaag 8760
ggcgagaagt acctgcaaac caggggccac gaggtggtgg ttgttgacga tgagaggtgt 8820
aagaagctga tgaagcagtt catcgacgag aggcctcagg actggttcga ggatatcggc 8880
gagtaagcgg ccgcagataa aataaaagat tttatttagt ctccagaaaa aggggggaat 8940
gaaagacccc acctgtaggt ttggcaagct agcttaagta acgccatttt gcaaggcatg 9000
gaaaaataca taactgagaa tagagaagtt cagatcaagg tcaggaacag atggaacagc 9060
tgaatatggg ccaaacagga tatctgtggt aagcagttcc tgccccggct cagggccaag 9120
aacagatgga acagctgaat atgggccaaa caggatatct gtggtaagca gttcctgccc 9180
cggctcaggg ccaagaacag atggtcccca gatgcggtcc agccctcagc agtttctaga 9240
gaaccatcag atgtttccag ggtgccccaa ggacctgaaa tgaccctgtg ccttatttga 9300
actaaccaat cagttcgctt ctcgcttctg ttcgcgcgct tctgctcccc gagctcaata 9360
aaagagccca caacccctca ctcggggcgc cagtcctccg attgactgag tcgcccgggt 9420
acccgtgtat ccaataaacc ctcttgcagt tgcatccgac ttgtggtctc gctgttcctt 9480
gggagggtct cctctgagtg attgactacc cgtcagcggg ggtctttcat tacatgtgag 9540
caaaaggcca gcaaaaggcc aggaaccgta aaaaggccgc gttgctggcg tttttccata 9600
ggctccgccc ccctgacgag catcacaaaa atcgacgctc aagtcagagg tggcgaaacc 9660
cgacaggact ataaagatac caggcgtttc cccctggaag ctccctcgtg cgctctcctg 9720
ttccgaccct gccgcttacc ggatacctgt ccgcctttct cccttcggga agcgtggcgc 9780
tttctcatag ctcacgctgt aggtatctca gttcggtgta ggtcgttcgc tccaagctgg 9840
gctgtgtgca cgaacccccc gttcagcccg accgctgcgc cttatccggt aactatcgtc 9900
ttgagtccaa cccggtaaga cacgacttat cgccactggc agcagccact ggtaacagga 9960
ttagcagagc gaggtatgta ggcggtgcta cagagttctt gaagtggtgg cctaactacg 10020
gctacactag aaggacagta tttggtatct gcgctctgct gaagccagtt accttcggaa 10080
aaagagttgg tagctcttga tccggcaaac aaaccaccgc tggtagcggt ggtttttttg 10140
tttgcaagca gcagattacg cgcagaaaaa aaggatctca agaagatcct ttgatctttt 10200
ctacggggtc tgacgctcag tggaacgaaa actcacgtta agggattttg gtcatgagat 10260
tatcaaaaag gatcttcacc tagatccttt taaattaaaa atgaagtttt aaatcaatct 10320
aaagtatata tgagtaaact tggtctgaca gttaccaatg cttaatcagt gaggcaccta 10380
tctcagcgat ctgtctattt cgttcatcca tagttgcctg actccccgtc gtgtagataa 10440
ctacgatacg ggagggctta ccatctggcc ccagtgctgc aatgataccg cgagacccac 10500
gctcaccggc tccagattta tcagcaataa accagccagc cggaagggcc gagcgcagaa 10560
gtggtcctgc aactttatcc gcctccatcc agtctattaa ttgttgccgg gaagctagag 10620
taagtagttc gccagttaat agtttgcgca acgttgttgc cattgctgca ggcatcgtgg 10680
tgtcacgctc gtcgtttggt atggcttcat tcagctccgg ttcccaacga tcaaggcgag 10740
ttacatgatc ccccatgttg tgcaaaaaag cggttagctc cttcggtcct ccgatcgttg 10800
tcagaagtaa gttggccgca gtgttatcac tcatggttat ggcagcactg cataattctc 10860
ttactgtcat gccatccgta agatgctttt ctgtgactgg tgagtactca accaagtcat 10920
tctgagaata gtgtatgcgg cgaccgagtt gctcttgccc ggcgtcaaca cgggataata 10980
ccgcgccaca tagcagaact ttaaaagtgc tcatcattgg aaaacgttct tcggggcgaa 11040
aactctcaag gatcttaccg ctgttgagat ccagttcgat gtaacccact cgtgcaccca 11100
actgatcttc agcatctttt actttcacca gcgtttctgg gtgagcaaaa acaggaaggc 11160
aaaatgccgc aaaaaaggga ataagggcga cacggaaatg ttgaatactc atactcttcc 11220
tttttcaata ttattgaagc atttatcagg gttattgtct catgagcgga tacatatttg 11280
aatgtattta gaaaaataaa caaatagggg ttccgcgcac atttccccga aaagtgccac 11340
ctgacgtcta agaaaccatt attatcatga cattaaccta taaaaatagg cgtatcacga 11400
ggccctttcg tcttcaagaa ttccat 11426

<210> SEQ ID NO 40
<211> LENGTH: 11671
<212> TYPE: DNA
<213> ORGANISM: Artificial Sequence
<220> FEATURE:
<223> OTHER INFORMATION: pAC3-C1.GFP

<400> SEQUENCE: 40
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500

-continued

```
ttgtacaccc taagcctccg cctcctcttc ctccatccgc cccgtctctc cccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac caccccccttc cgacagggac ggaaatggtg   1740
gagaagcgac ccctgcggga gaggcaccgg acccctcccc aatggcatct cgcctacgtg   1800
ggagacggga gcccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggggcaac   2880
ccgtcacctt cctggtagat actggggccc aacactccgt gctgacccaa aatcctggac   2940
ccctaagtga taagtctgcc tgggtccaag ggggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
```

-continued

```
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
```

-continued cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aacccccctca agataagatt aacccgtgga agcccttaat 6420
agtcatggga gtcctgttag gagtagggat ggcagagagc cccatcagg tctttaatgt 6480 aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca cccccctggga 6840 cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccccct caataccagt taccccccctt ccactaccag 7200 tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgtg aggtctatat 8340
aagcagagct cgtttagtga accgtcagat cgcctggaga cgccatccac gctgttttga 8400
cctccgttaa catggccagc aagggcgagg agctgttcac cggggtggtg cccatcctgg 8460
tcgagctgga cggcgacgta aacggccaca agttcagcgt gtccggcgag ggcgagggcg 8520
atgccaccta cggcaagctg accctgaagt tcatctgcac caccggcaag ctgcccgtgc 8580
cctggcccac cctcgtgacc accttgacct acggcgtgca gtgcttcgcc cgctaccccg 8640

-continued

```
accacatgaa gcagcacgac ttcttcaagt ccgccatgcc cgaaggctac gtccaggagc   8700
gcaccatctt cttcaaggac gacggcaact acaagacccg cgccgaggtg aagttcgagg   8760
gcgacaccct ggtgaaccgc atcgagctga agggcatcga cttcaaggag gacggcaaca   8820
tcctggggca caagctggag tacaactaca acagccacaa ggtctatatc accgccgaca   8880
agcagaagaa cggcatcaag gtgaacttca agacccgcca caacatcgag gacggcagcg   8940
tgcagctcgc cgaccactac cagcagaaca cccccatcgg cgacggcccc gtgctgctgc   9000
ccgacaacca ctacctgagc acccagtccg ccctgagcaa agaccccaac gagaagcgcg   9060
atcacatggt cctgctggag ttcgtgaccg ccgccgggat cactctcggc atggacgagc   9120
tgtacaagtg agcggccgca gataaaataa aagattttat ttagtctcca gaaaaagggg   9180
ggaatgaaag accccacctg taggtttggc aagctagctt aagtaacgcc attttgcaag   9240
gcatggaaaa atacataact gagaatagag aagttcagat caaggtcagg aacagatgga   9300
acagctgaat atgggccaaa caggatatct gtggtaagca gttcctgccc cggctcaggg   9360
ccaagaacag atggaacagc tgaatatggg ccaaacagga tatctgtggt aagcagttcc   9420
tgccccggct cagggccaag aacagatggt ccccagatgc ggtccagccc tcagcagttt   9480
ctagagaacc atcagatgtt tccagggtgc cccaaggacc tgaaatgacc ctgtgcctta   9540
tttgaactaa ccaatcagtt cgcttctcgc ttctgttcgc gcgcttctgc tccccgagct   9600
caataaaaga gcccacaacc cctcactcgg ggcgccagtc ctccgattga ctgagtcgcc   9660
cgggtacccg tgtatccaat aaaccctctt gcagttgcat ccgacttgtg gtctcgctgt   9720
tccttgggag ggtctcctct gagtgattga ctacccgtca gcgggggtct ttcattacat   9780
gtgagcaaaa ggccagcaaa aggccaggaa ccgtaaaaag gccgcgttgc tggcgttttt   9840
ccataggctc cgcccccctg acgagcatca caaaaatcga cgctcaagtc agaggtggcg   9900
aaacccgaca ggactataaa gataccaggc gtttccccct ggaagctccc tcgtgcgctc   9960
tcctgttccg accctgccgc ttaccggata cctgtccgcc tttctccctt cgggaagcgt  10020
ggcgctttct catagctcac gctgtaggta tctcagttcg gtgtaggtcg ttcgctccaa  10080
gctgggctgt gtgcacgaac cccccgttca gcccgaccgc tgcgccttat ccggtaacta  10140
tcgtcttgag tccaacccgg taagacacga cttatcgcca ctggcagcag ccactggtaa  10200
caggattagc agagcgaggt atgtaggcgg tgctacagag ttcttgaagt ggtggcctaa  10260
ctacggctac actagaagga cagtatttgg tatctgcgct ctgctgaagc cagttacctt  10320
cggaaaaaga gttggtagct cttgatccgg caaacaaacc accgctggta gcggtggttt  10380
ttttgtttgc aagcagcaga ttacgcgcag aaaaaaagga tctcaagaag atcctttgat  10440
cttttctacg gggtctgacg ctcagtggaa cgaaaactca cgttaaggga ttttggtcat  10500
gagattatca aaaaggatct tcacctagat ccttttaaat taaaaatgaa gttttaaatc  10560
aatctaaagt atatatgagt aaacttggtc tgacagttac caatgcttaa tcagtgaggc  10620
acctatctca gcgatctgtc tatttcgttc atccatagtt gcctgactcc ccgtcgtgta  10680
gataactacg atacgggagg gcttaccatc tggccccagt gctgcaatga taccgcgaga  10740
cccacgctca ccggctccag atttatcagc aataaaccag ccagccggaa gggccgagcg  10800
cagaagtggt cctgcaactt tatccgcctc catccagtct attaattgtt gccgggaagc  10860
tagagtaagt agttcgccag ttaatagttt gcgcaacgtt gttgccattg ctgcaggcat  10920
cgtggtgtca cgctcgtcgt ttggtatggc ttcattcagc tccggttccc aacgatcaag  10980
```

-continued gcgagttaca tgatccccca tgttgtgcaa aaaagcggtt agctccttcg gtcctccgat 11040
cgttgtcaga agtaagttgg ccgcagtgtt atcactcatg gttatggcag cactgcataa 11100
ttctcttact gtcatgccat ccgtaagatg cttttctgtg actggtgagt actcaaccaa 11160
gtcattctga gaatagtgta tgcggcgacc gagttgctct tgcccggcgt caacacggga 11220
taataccgcg ccacatagca gaactttaaa agtgctcatc attggaaaac gttcttcggg 11280
gcgaaaactc tcaaggatct taccgctgtt gagatccagt tcgatgtaac ccactcgtgc 11340
acccaactga tcttcagcat cttttacttt caccagcgtt tctgggtgag caaaaacagg 11400
aaggcaaaat gccgcaaaaa agggaataag ggcgacacgg aaatgttgaa tactcatact 11460
cttccttttt caatattatt gaagcattta tcagggttat tgtctcatga gcggatacat 11520
atttgaatgt atttagaaaa ataaacaaat aggggttccg cgcacatttc cccgaaaagt 11580
gccacctgac gtctaagaaa ccattattat catgacatta acctataaaa ataggcgtat 11640
cacgaggccc tttcgtcttc aagaattcca t 11671

<210> SEQ ID NO 41
<211> LENGTH: 11669
<212> TYPE: DNA
<213> ORGANISM: Artificial Sequence
<220> FEATURE:
<223> OTHER INFORMATION: pAC3-S1.GFP

<400> SEQUENCE: 41
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380

-continued

```
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg accccctccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
```

-continued

```
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
```

-continued

```
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccccct caataccagt taccccccctt ccactaccag   7200
tacaccctca acctccccta caagtccaag tgtcccacag ccaccccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta cttatataag   8340
gggtgggggg cgcgttcgtc ctcagtcgcg atcgaacact cgagccgagc agacgtgcct   8400
acggttaaca tggccagcaa gggcgaggag ctgttcaccg ggtggtgcc catcctggtc   8460
```

gagctggacg gcgacgtaaa cggccacaag ttcagcgtgt ccggcgaggg cgagggcgat 8520
gccacctacg gcaagctgac cctgaagttc atctgcacca ccggcaagct gcccgtgccc 8580
tggcccaccc tcgtgaccac cttgacctac ggcgtgcagt gcttcgcccg ctaccccgac 8640
cacatgaagc agcacgactt cttcaagtcc gccatgcccg aaggctacgt ccaggagcgc 8700
accatcttct tcaaggacga cggcaactac aagacccgcg ccgaggtgaa gttcgagggc 8760
gacaccctgg tgaaccgcat cgagctgaag ggcatcgact tcaaggagga cggcaacatc 8820
ctggggcaca agctggagta caactacaac agccacaagg tctatatcac cgccgacaag 8880
cagaagaacg gcatcaaggt gaacttcaag acccgccaca acatcgagga cggcagcgtg 8940
cagctcgccg accactacca gcagaacacc cccatcggcg acggccccgt gctgctgccc 9000
gacaaccact acctgagcac ccagtccgcc ctgagcaaag accccaacga gaagcgcgat 9060
cacatggtcc tgctggagtt cgtgaccgcc gccgggatca ctctcggcat ggacgagctg 9120
tacaagtgag cggccgcaga taaaataaaa gattttattt agtctccaga aaaagggggg 9180
aatgaaagac cccacctgta ggtttggcaa gctagcttaa gtaacgccat tttgcaaggc 9240
atggaaaaat acataactga gaatagagaa gttcagatca aggtcaggaa cagatggaac 9300
agctgaatat gggccaaaca ggatatctgt ggtaagcagt tcctgccccg gctcagggcc 9360
aagaacagat ggaacagctg aatatgggcc aaacaggata tctgtggtaa gcagttcctg 9420
ccccggctca gggccaagaa cagatggtcc ccagatgcgg tccagccctc agcagtttct 9480
agagaaccat cagatgtttc cagggtgccc caaggacctg aaatgaccct gtgccttatt 9540
tgaactaacc aatcagttcg cttctcgctt ctgttcgcgc gcttctgctc cccgagctca 9600
ataaaagagc ccacaacccc tcactcgggg cgccagtcct ccgattgact gagtcgcccg 9660
ggtacccgtg tatccaataa accctcttgc agttgcatcc gacttgtggt ctcgctgttc 9720
cttgggaggg tctcctctga gtgattgact acccgtcagc gggggtcttt cattacatgt 9780
gagcaaaagg ccagcaaaag gccaggaacc gtaaaaaggc cgcgttgctg gcgtttttcc 9840
ataggctccg cccccctgac gagcatcaca aaaatcgacg ctcaagtcag aggtggcgaa 9900
acccgacagg actataaaga taccaggcgt ttccccctgg aagctccctc gtgcgctctc 9960
ctgttccgac cctgccgctt accggatacc tgtccgcctt tctcccttcg ggaagcgtgg 10020
cgctttctca tagctcacgc tgtaggtatc tcagttcggt gtaggtcgtt cgctccaagc 10080
tgggctgtgt gcacgaaccc cccgttcagc ccgaccgctg cgccttatcc ggtaactatc 10140
gtcttgagtc caacccggta agacacgact tatcgccact ggcagcagcc actggtaaca 10200
ggattagcag agcgaggtat gtaggcggtg ctacagagtt cttgaagtgg tggcctaact 10260
acggctacac tagaaggaca gtatttggta tctgcgctct gctgaagcca gttaccttcg 10320
gaaaaagagt tggtagctct tgatccggca aacaaaccac cgctggtagc ggtggttttt 10380
ttgtttgcaa gcagcagatt acgcgcagaa aaaaaggatc tcaagaagat cctttgatct 10440
tttctacggg gtctgacgct cagtggaacg aaaactcacg ttaagggatt ttggtcatga 10500
gattatcaaa aaggatcttc acctagatcc ttttaaatta aaaatgaagt tttaaatcaa 10560
tctaaagtat atatgagtaa acttggtctg acagttacca atgcttaatc agtgaggcac 10620
ctatctcagc gatctgtcta tttcgttcat ccatagttgc ctgactcccc gtcgtgtaga 10680
taactacgat acgggagggc ttaccatctg gccccagtgc tgcaatgata ccgcgagacc 10740
cacgctcacc ggctccagat ttatcagcaa taaaccagcc agccggaagg gccgagcgca 10800
gaagtggtcc tgcaacttta tccgcctcca tccagtctat taattgttgc cgggaagcta 10860
gagtaagtag ttcgccagtt aatagtttgc gcaacgttgt tgccattgct gcaggcatcg 10920
tggtgtcacg ctcgtcgttt ggtatggctt cattcagctc cggttcccaa cgatcaaggc 10980
gagttacatg atcccccatg ttgtgcaaaa aagcggttag ctccttcggt cctccgatcg 11040
ttgtcagaag taagttggcc gcagtgttat cactcatggt tatggcagca ctgcataatt 11100
ctcttactgt catgccatcc gtaagatgct tttctgtgac tggtgagtac tcaaccaagt 11160
cattctgaga atagtgtatg cggcgaccga gttgctcttg cccggcgtca acacgggata 11220
ataccgcgcc acatagcaga actttaaaag tgctcatcat tggaaaacgt tcttcggggc 11280
gaaaactctc aaggatctta ccgctgttga gatccagttc gatgtaaccc actcgtgcac 11340
ccaactgatc ttcagcatct tttactttca ccagcgtttc tgggtgagca aaaacaggaa 11400
ggcaaaatgc cgcaaaaaag ggaataaggg cgacacggaa atgttgaata ctcatactct 11460
tcctttttca atattattga agcatttatc agggttattg tctcatgagc ggatacatat 11520
ttgaatgtat ttagaaaaat aaacaaatag gggttccgcg cacatttccc cgaaaagtgc 11580
cacctgacgt ctaagaaacc attattatca tgacattaac ctataaaaat aggcgtatca 11640
cgaggccctt tcgtcttcaa gaattccat 11669

<210> SEQ ID NO 42
<211> LENGTH: 13
<212> TYPE: DNA
<213> ORGANISM: Artificial Sequence
<220> FEATURE:
<223> OTHER INFORMATION: HBV X core promoter fragment

<400> SEQUENCE: 42
ccccgttgcc cgg 13

<210> SEQ ID NO 43
<211> LENGTH: 8
<212> TYPE: DNA
<213> ORGANISM: Artificial Sequence
<220> FEATURE:
<223> OTHER INFORMATION: AP-1 Motif

<400> SEQUENCE: 43 tgtctcag 8

<210> SEQ ID NO 44
<211> LENGTH: 10
<212> TYPE: DNA
<213> ORGANISM: Artificial Sequence
<220> FEATURE:
<223> OTHER INFORMATION: CarG Motif

<400> SEQUENCE: 44
ccatataagg 10

<210> SEQ ID NO 45
<211> LENGTH: 10
<212> TYPE: DNA
<213> ORGANISM: Artificial Sequence
<220> FEATURE:
<223> OTHER INFORMATION: NF-kB1 Motif

<400> SEQUENCE: 45
ggaaatcccc 10

<210> SEQ ID NO 46

<211> LENGTH: 11
<212> TYPE: DNA
<213> ORGANISM: Artificial Sequence
<220> FEATURE:
<223> OTHER INFORMATION: NF-kB2 Motif

<400> SEQUENCE: 46
ggaaagtccc c 11

<210> SEQ ID NO 47
<211> LENGTH: 9
<212> TYPE: DNA
<213> ORGANISM: Artificial Sequence
<220> FEATURE:
<223> OTHER INFORMATION: NF-kB3 Motif

<400> SEQUENCE: 47 ggagttccc 9

<210> SEQ ID NO 48
<211> LENGTH: 7
<212> TYPE: DNA
<213> ORGANISM: Artificial Sequence
<220> FEATURE:
<223> OTHER INFORMATION: NF-Y Motif

<400> SEQUENCE: 48 cattggg 7

<210> SEQ ID NO 49
<211> LENGTH: 8
<212> TYPE: DNA
<213> ORGANISM: Artificial Sequence
<220> FEATURE:
<223> OTHER INFORMATION: CRE1 Motif

<400> SEQUENCE: 49 ttacgtaa 8

<210> SEQ ID NO 50
<211> LENGTH: 8
<212> TYPE: DNA
<213> ORGANISM: Artificial Sequence
<220> FEATURE:
<223> OTHER INFORMATION: CRE2

<400> SEQUENCE: 50 ttgcatca 8

<210> SEQ ID NO 51
<211> LENGTH: 7
<212> TYPE: DNA
<213> ORGANISM: Artificial Sequence
<220> FEATURE:
<223> OTHER INFORMATION: Kozak Sequence
<220> FEATURE:
<221> NAME/KEY: misc_feature
<222> LOCATION: (1)..(1)
<223> OTHER INFORMATION: R at position 1 is A or G

<400> SEQUENCE: 51 rccatgg 7

<210> SEQ ID NO 52
<211> LENGTH: 68
<212> TYPE: DNA
<213> ORGANISM: Artificial Sequence
<220> FEATURE:
<223> OTHER INFORMATION: Omega Kozak sequence from Tobacco Mosaic Virus

<400> SEQUENCE: 52
ttatttttac aaaattacca acaacaacaa acaacaaaca attacaatta ctatttacaa 60
ttacaatg 68

<210> SEQ ID NO 53
<211> LENGTH: 21
<212> TYPE: DNA
<213> ORGANISM: Artificial Sequence
<220> FEATURE:
<223> OTHER INFORMATION: L21 Kozak sequence

<400> SEQUENCE: 53
aactcctaaa aaaccgccac c 21

<210> SEQ ID NO 54
<211> LENGTH: 23
<212> TYPE: DNA
<213> ORGANISM: Artificial Sequene
<220> FEATURE:
<223> OTHER INFORMATION: Oligonucleotide Primer IRES-F

<400> SEQUENCE: 54
ctgatcttac tctttggacc ttg 23

<210> SEQ ID NO 55
<211> LENGTH: 24
<212> TYPE: DNA
<213> ORGANISM: Artificial Sequence
<220> FEATURE:
<223> OTHER INFORMATION: Oligonucleotide primer IRES-R

<400> SEQUENCE: 55
cccctttttc tggagactaa ataa 24

<210> SEQ ID NO 56
<211> LENGTH: 625
<212> TYPE: DNA
<213> ORGANISM: Artificial Sequence
<220> FEATURE:
<223> OTHER INFORMATION: Synthetic fragment Heme Oxygenase 1 promoter
fused with Kozak and yCD2

<400> SEQUENCE: 56
acgcgtgggg cgggctgggc gcgggcccct gcgggtgttg caacgcccgg ccagaaagtg 60
ggcatcagct gttccgcctg gcccacgtga cccgccgagc ataaatgtga ccggccgcgg 120
ctccggcagt caacgccacc atggtgaccg gcggcatggc ctccaagtgg gatcaaaagg 180
gcatggatat cgcttacgag gaggccctgc tgggctacaa ggagggcggc gtgcctatcg 240
gcggctgtct gatcaacaac aaggacggca gtgtgctggg caggggccac aacatgaggt 300
tccagaaggg ctccgccacc ctgcacggcg agatctccac cctggagaac tgtggcaggc 360
tggagggcaa ggtgtacaag gacaccaccc tgtacaccac cctgtcccct tgtgacatgt 420
gtaccggcgc tatcatcatg tacggcatcc ctaggtgtgt gatcggcgag aacgtgaact 480
tcaagtccaa gggcgagaag tacctgcaaa ccaggggcca cgaggtggtg gttgttgacg 540
atgagaggtg taagaagctg atgaagcagt tcatcgacga gaggcctcag gactggttcg 600
aggatatcgg cgagtgagcg gccgc 625

<210> SEQ ID NO 57
<211> LENGTH: 180
<212> TYPE: DNA
<213> ORGANISM: Artificial Sequence
<220> FEATURE:
<223> OTHER INFORMATION: Thymidine Kinase cryptic promoter

<400> SEQUENCE: 57
atggcttcgt acccctgcca tcaacacgcg tctgcgttcg accaggctgc gcgttctcgc 60
ggccatagca accgacgtac ggcgttgcgc cctcgccggc agcaagaagc cacggaagtc 120
cgcctggagc agaaaatgcc cacgctactg cgggtttata tagacggtcc tcacgggatg 180

<210> SEQ ID NO 58
<211> LENGTH: 72
<212> TYPE: DNA
<213> ORGANISM: Artificial Sequence
<220> FEATURE:
<223> OTHER INFORMATION: SV40 enhancer

<400> SEQUENCE: 58
tggttgctga ctaattgaga tgcatgcttt gcatacttct gcctgctggg gagcctgggg 60
actttccaca cc 72

<210> SEQ ID NO 59
<211> LENGTH: 266
<212> TYPE: DNA
<213> ORGANISM: Artificial Sequence
<220> FEATURE:
<223> OTHER INFORMATION: Human U6 promoter

<400> SEQUENCE: 59
aaggtcgggc aggaagaggg cctatttccc atgattcctt catatttgca tatacgatac 60
aaggctgtta gagagataat tagaattaat ttgactgtaa acacaaagat attagtacaa 120
aatacgtgac gtagaaagta ataatttctt gggtagtttg cagtttttaa aattatgttt 180
taaaatggac tatcatatgc ttaccgtaac ttgaaagtat ttcgatttct tggctttata 240
tatcttgtgg aaaggacgaa acaccg 266

<210> SEQ ID NO 60
<211> LENGTH: 129
<212> TYPE: DNA
<213> ORGANISM: Artificial Sequence
<220> FEATURE:
<223> OTHER INFORMATION: pre-miR30

<400> SEQUENCE: 60
ttgtttgaat gaggcttcag tactttacag aatcgttgcc tgcacatctt ggaaacactt 60
gctgggatta cttcttcagg ttaacccaac agaaggctcg agaaggtata ttgctgttga 120
cagtgagcg 129

<210> SEQ ID NO 61
<211> LENGTH: 19
<212> TYPE: DNA
<213> ORGANISM: Artificial Sequene
<220> FEATURE:
<223> OTHER INFORMATION: 19 nucleotide loop sequence

<400> SEQUENCE: 61
tagtgaagcc acagatgta 19

<210> SEQ ID NO 62

<211> LENGTH: 164
<212> TYPE: DNA
<213> ORGANISM: Artificial Sequence
<220> FEATURE:
<223> OTHER INFORMATION: pre-miR30 with U6 termination sequence

<400> SEQUENCE: 62
tgcctactgc ctcggaattc aaggggctac tttaggagca attatcttgt ttactaaaac 60
tgaatacctt gctatctctt tgatacattt ttacaaagct gaattaaaat ggtataaatt 120
aaatcacttt tttcaattgg aagactaatg cggcggccgc gatc 164

<210> SEQ ID NO 63
<211> LENGTH: 49
<212> TYPE: DNA
<213> ORGANISM: Artificial Sequence
<220> FEATURE:
<223> OTHER INFORMATION: Undefined flanking sequence downstream of U6

<400> SEQUENCE: 63
tgctcgcttc ggcagcacat atactagtcg actagggata acagggtaa 49

<210> SEQ ID NO 64
<211> LENGTH: 81
<212> TYPE: DNA
<213> ORGANISM: Artificial Sequence
<220> FEATURE:
<223> OTHER INFORMATION: S1 sequence

<400> SEQUENCE: 64
gtacttatat aagggggtgg gggcgcgttc gtcctcagtc gcgatcgaac actcgagccg 60
agcagacgtg cctacggacc g 81

<210> SEQ ID NO 65
<211> LENGTH: 85
<212> TYPE: DNA
<213> ORGANISM: Artificial Sequence
<220> FEATURE:
<223> OTHER INFORMATION: S1-Kozak sequence

<400> SEQUENCE: 65
gtacttatat aagggggtgg gggcgcgttc gtcctcagtc gcgatcgaac actcgagccg 60
agcagacgtg cctacggacc gcacc 85

<210> SEQ ID NO 66
<211> LENGTH: 81
<212> TYPE: DNA
<213> ORGANISM: Artificial Sequence
<220> FEATURE:
<223> OTHER INFORMATION: S2 promoter sequence

<400> SEQUENCE: 66
aggtctatat aagcagagct cgtttagtga accgtcagat cgcctggaga cgtcgagccg 60
agtggttgtg cctccataga a 81

<210> SEQ ID NO 67
<211> LENGTH: 85
<212> TYPE: DNA
<213> ORGANISM: Artificial Sequence
<220> FEATURE:
<223> OTHER INFORMATION: S2-Kozak sequences

<400> SEQUENCE: 67
aggtctatat aagcagagct cgtttagtga accgtcagat cgcctggaga cgtcgagccg 60
agtggttgtg cctccataga acacc 85

<210> SEQ ID NO 68
<211> LENGTH: 325
<212> TYPE: DNA
<213> ORGANISM: Artificial Sequences
<220> FEATURE:
<223> OTHER INFORMATION: SV40 promoter

<400> SEQUENCE: 68
ccagcaggca gaagtatgca aagcatgcat ctcaattagt cagcaaccag gtgtggaaag 60
tccccaggct ccccagcagg cagaagtatg caaagcatgc atctcaatta gtcagcaacc 120
atagtcccgc ccctaactcc gcccatcccg cccctaactc cgcccagttc cgcccattct 180
ccgccccatg gctgactaat tttttttatt tatgcagagg ccgaggccgc ctctgcctct 240
gagctattcc agaagtagtg aggaggcttt tttggaggcc taggcttttg caaaaagctc 300
ccgggagctt gtatatccat tttcg 325

<210> SEQ ID NO 69
<211> LENGTH: 262
<212> TYPE: DNA
<213> ORGANISM: Artificial Sequence
<220> FEATURE:
<223> OTHER INFORMATION: RSV promoter

<400> SEQUENCE: 69
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
ccgcattgca gagatattgt atttaagtgc ctagctcgat acaataaacg ccatttgacc 240
attcaccaca ttggtgtgca cc 262

<210> SEQ ID NO 70
<211> LENGTH: 102
<212> TYPE: DNA
<213> ORGANISM: Artificial Sequence
<220> FEATURE:
<223> OTHER INFORMATION: CRE Enhancer sequence

<400> SEQUENCE: 70
gaattgacgc atatattgac gcatattgac gcaaattgac gcaaatgaca gcaagattga 60
cgcaaattga gcgcaaattg acgcaaatta attgacgcat gt 102

<210> SEQ ID NO 71
<211> LENGTH: 181
<212> TYPE: DNA
<213> ORGANISM: Artificial Sequence
<220> FEATURE:
<223> OTHER INFORMATION: ES1 synthetic promoter

<400> SEQUENCE: 71
gaattgacgc atatattgac gcatattgac gcaaattgac gcaaatgaca gcaagattga 60
cgcaaattga gcgcaaattg acgcaaatta attgacgcat gtacttatat aagggggtgg 120
gggcgcgttc gtcctcagtc gcgatcgaac actcgagccg agcagacgtg cctacggacc 180
g 181

<210> SEQ ID NO 72

<211> LENGTH: 107
<212> TYPE: DNA
<213> ORGANISM: Artificial Sequence
<220> FEATURE:
<223> OTHER INFORMATION: Human ASK gene mini-promoter

<400> SEQUENCE: 72
aaggcaggca cgaggggcga gcgcgaggcg gggcacggcg cgtggcgtga gacggggcgg 60
ggcgcgcgta tcggcgccgc ggccgcgtga cgcgttttca aatcttc 107

<210> SEQ ID NO 73
<211> LENGTH: 145
<212> TYPE: DNA
<213> ORGANISM: Artificial Sequence
<220> FEATURE:
<223> OTHER INFORMATION: Human ASK gene mini-promoter

<400> SEQUENCE: 73
aggacggcgg cgtgaggggg cggggcgcgc agcgcgagaa ggcaggcacg aggggcgagc 60
gcgaggcggg gcacggcgcg tggcgtgaga cggggcgggg cgcgcgtatc ggcgccgcgg 120
ccgcgtgacg cgttttcaaa tcttc 145

<210> SEQ ID NO 74
<211> LENGTH: 380
<212> TYPE: DNA
<213> ORGANISM: Artificial Sequence
<220> FEATURE:
<223> OTHER INFORMATION: Human ASK gene mini-promoter

<400> SEQUENCE: 74
aggacggcgg cgtgaggggg cggggcgcgc agcgcgagaa ggcaggcacg aggggcgagc 60
gcgaggcggg gcacggcgcg tggcgtgaga cggggcgggg cgcgcgtatc ggcgccgcgg 120
ccgcgtgacg cgttttcaaa tcttcaaccg ccgcagccca ctcgtttgtg ctttgcgcct 180
tcctcctccg cgccttggag ccggatccgg ccccggaaac ccgacctgca gacgcggtac 240
ctctactgcg tagaggccgt agctggcgga aggagagagg cggccgtcct gtcaacaggc 300
cgggggaagc cgtgctttcg cgggtgcccg gtgcgacact ttctccggac ccagcatgta 360
ggtgccgggc gactgccatg 380

<210> SEQ ID NO 75
<211> LENGTH: 1131
<212> TYPE: DNA
<213> ORGANISM: Artificial Sequence
<220> FEATURE:
<223> OTHER INFORMATION: Human Codon Optimized Thymidine Kinase
<220> FEATURE:
<221> NAME/KEY: CDS
<222> LOCATION: (1)..(1131)

<400> SEQUENCE: 75 atg gct tca tat cct tgc cac caa cat gct tcc gct ttc gac caa gcc 48
Met Ala Ser Tyr Pro Cys His Gln His Ala Ser Ala Phe Asp Gln Ala
1 5 10 15 gca cgg tct agg ggc cac aat aat cgc cgg act gcc ctg cgg cct cgg 96
Ala Arg Ser Arg Gly His Asn Asn Arg Arg Thr Ala Leu Arg Pro Arg
20 25 30 aga cag cag aag gca acc gaa gtc agg ctc gag caa aag atg cca acc 144
Arg Gln Gln Lys Ala Thr Glu Val Arg Leu Glu Gln Lys Met Pro Thr
35 40 45 ctc ctg cgg gtc tat atc gat gga ccc cat gga atg ggg aag acc act 192
Leu Leu Arg Val Tyr Ile Asp Gly Pro His Gly Met Gly Lys Thr Thr

```
    50                  55                  60

acc aca caa ctc ctg gtg gca ctc ggt agc cgg gac gac atc gtc tac      240
Thr Thr Gln Leu Leu Val Ala Leu Gly Ser Arg Asp Asp Ile Val Tyr
65                  70                  75                  80

gtg ccc gaa ccc atg act tac tgg cgg gtt ctc ggt gct tcc gag aca      288
Val Pro Glu Pro Met Thr Tyr Trp Arg Val Leu Gly Ala Ser Glu Thr
                85                  90                  95

atc gcc aat atc tac aca acc caa cac cgc ctc gat caa gga gaa att      336
Ile Ala Asn Ile Tyr Thr Thr Gln His Arg Leu Asp Gln Gly Glu Ile
            100                 105                 110

agc gca ggg gac gct gcc gtg gtg atg aca tca gcc caa atc acc atg      384
Ser Ala Gly Asp Ala Ala Val Val Met Thr Ser Ala Gln Ile Thr Met
        115                 120                 125

gga atg ccc tac gcc gtc acc gat gct gtc ctg gca cca cac att ggc      432
Gly Met Pro Tyr Ala Val Thr Asp Ala Val Leu Ala Pro His Ile Gly
    130                 135                 140

gga gag gcc ggg tca agt cat gca cca cca cca gcc ctg act atc ttt      480
Gly Glu Ala Gly Ser Ser His Ala Pro Pro Pro Ala Leu Thr Ile Phe
145                 150                 155                 160

ctc gac cgg cat cca att gca ttc atg ctg tgc tat cct gcc gca cgc      528
Leu Asp Arg His Pro Ile Ala Phe Met Leu Cys Tyr Pro Ala Ala Arg
                165                 170                 175

tac ctg atg gga agt atg aca cca cag gcc gtc ctc gcc ttc gtt gct      576
Tyr Leu Met Gly Ser Met Thr Pro Gln Ala Val Leu Ala Phe Val Ala
            180                 185                 190

ctg atc cct cca acc ctg cct ggc act aac atc gtt ctc ggc gca ctc      624
Leu Ile Pro Pro Thr Leu Pro Gly Thr Asn Ile Val Leu Gly Ala Leu
        195                 200                 205

ccc gaa gac aga cac att gat cgg ctg gcc aag agg caa cgg cct ggc      672
Pro Glu Asp Arg His Ile Asp Arg Leu Ala Lys Arg Gln Arg Pro Gly
    210                 215                 220

gag aga ctc gat ctg gct atg ctg gct gct att agg aga gtg tac ggg      720
Glu Arg Leu Asp Leu Ala Met Leu Ala Ala Ile Arg Arg Val Tyr Gly
225                 230                 235                 240

ctg ctg gcc aat act gtg aga tac ctc caa ggg gga gga agc tgg cgc      768
Leu Leu Ala Asn Thr Val Arg Tyr Leu Gln Gly Gly Gly Ser Trp Arg
                245                 250                 255

gag gat tgg ggc caa ctg tct ggc gct gct gtg cca cct caa ggc gcc      816
Glu Asp Trp Gly Gln Leu Ser Gly Ala Ala Val Pro Pro Gln Gly Ala
            260                 265                 270

gag cca cag tca aat gct ggt cct agg ccc cac atc ggc gat act ctc      864
Glu Pro Gln Ser Asn Ala Gly Pro Arg Pro His Ile Gly Asp Thr Leu
        275                 280                 285

ttt aca ctg ttc cgg gca cca gag ctg ctc gca cct aat gga gat ctg      912
Phe Thr Leu Phe Arg Ala Pro Glu Leu Leu Ala Pro Asn Gly Asp Leu
    290                 295                 300

tac aat gtt ttc gct tgg gcc ctc gat gtc ctg gct aag cgg ctc cgg      960
Tyr Asn Val Phe Ala Trp Ala Leu Asp Val Leu Ala Lys Arg Leu Arg
305                 310                 315                 320

cct atg cac gtg ttc atc ctc gac tac gac cag agc cca gct ggt tgt     1008
Pro Met His Val Phe Ile Leu Asp Tyr Asp Gln Ser Pro Ala Gly Cys
                325                 330                 335

cgg gat gct ctc ctg caa ctg acc agc ggg atg gtg cag aca cac gtt     1056
Arg Asp Ala Leu Leu Gln Leu Thr Ser Gly Met Val Gln Thr His Val
            340                 345                 350

act act ccc ggc tcc atc ccc act atc tgt gac ctc gcc cgg aca ttt     1104
Thr Thr Pro Gly Ser Ile Pro Thr Ile Cys Asp Leu Ala Arg Thr Phe
        355                 360                 365

gcc cgg gaa atg ggc gaa gcc aac tga                                 1131
```

```
Ala Arg Glu Met Gly Glu Ala Asn
    370                 375


<210> SEQ ID NO 76
<211> LENGTH: 376
<212> TYPE: PRT
<213> ORGANISM: Artificial Sequence
<220> FEATURE:
<223> OTHER INFORMATION: Synthetic Construct

<400> SEQUENCE: 76

Met Ala Ser Tyr Pro Cys His Gln His Ala Ser Ala Phe Asp Gln Ala
1               5                   10                  15

Ala Arg Ser Arg Gly His Asn Asn Arg Arg Thr Ala Leu Arg Pro Arg
            20                  25                  30

Arg Gln Gln Lys Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Ile Phe
145                 150                 155                 160

Leu Asp Arg His Pro Ile Ala Phe Met Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Ala Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350
```

-continued

```
Thr Thr Pro Gly Ser Ile Pro Thr Ile Cys Asp Leu Ala Arg Thr Phe
        355                 360                 365

Ala Arg Glu Met Gly Glu Ala Asn
    370                 375


<210> SEQ ID NO 77
<211> LENGTH: 11429
<212> TYPE: DNA
<213> ORGANISM: Artificial Sequence
<220> FEATURE:
<223> OTHER INFORMATION: pAC3-S1K-yCD2

<400> SEQUENCE: 77

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600

actgagtcgc ccgggtaccc gtgtatccaa taaaccctct tgcagttgca tccgacttgt    660

ggtctcgctg ttccttggga gggtctcctc tgagtgattg actacccgtc agcgggggtc    720

tttcatttgg gggctcgtcc gggatcggga gacccctgcc cagggaccac cgacccacca    780

ccgggaggta agctggccag caacttatct gtgtctgtcc gattgtctag tgtctatgac    840

tgattttatg cgcctgcgtc ggtactagtt agctaactag ctctgtatct ggcggacccg    900

tggtggaact gacgagttcg gaacacccgg ccgcaaccct gggagacgtc ccagggactt    960

cgggggccgt ttttgtggcc cgacctgagt ccaaaaatcc cgatcgtttt ggactctttg   1020

gtgcaccccc cttagaggag ggatatgtgg ttctggtagg agacgagaac ctaaaacagt   1080

tcccgcctcc gtctgaattt ttgctttcgg tttgggaccg aagccgcgcc gcgcgtcttg   1140

tctgctgcag catcgttctg tgttgtctct gtctgactgt gtttctgtat ttgtctgaaa   1200

atatgggcca gactgttacc actcccttaa gtttgacctt aggtcactgg aaagatgtcg   1260

agcggatcgc tcacaaccag tcggtagatg tcaagaagag acgttgggtt accttctgct   1320

ctgcagaatg gccaaccttt aacgtcggat ggccgcgaga cggcaccttt aaccgagacc   1380

tcatcaccca ggttaagatc aaggtctttt cacctggccc gcatggacac ccagaccagg   1440

tcccctacat cgtgacctgg gaagccttgg cttttgaccc ccctccctgg gtcaagccct   1500

ttgtacaccc taagcctccg cctcctcttc ctccatccgc cccgtctctc ccccttgaac   1560

ctcctcgttc gaccccgcct cgatcctccc tttatccagc cctcactcct tctctaggcg   1620

ccaaacctaa acctcaagtt ctttctgaca gtgggggggcc gctcatcgac ctacttacag   1680

aagacccccc gccttatagg gacccaagac cacccccttc cgacagggac ggaaatggtg   1740

gagaagcgac ccctgcggga gaggcaccgg acccctcccc aatggcatct cgcctacgtg   1800

ggagacggga gccccctgtg gccgactcca ctacctcgca ggcattcccc ctccgcgcag   1860

gaggaaacgg acagcttcaa tactggccgt tctcctcttc tgacctttac aactggaaaa   1920
```

```
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
```

-continued

```
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tggggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac ccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
```

```
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt taccccctt ccactaccag   7200
tacaccctca acctcccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta cttatataag   8340
ggggtggggg cgcgttcgtc ctcagtcgcg atcgaacact cgagccgagc agacgtgcct   8400
acggaccgca ccatggtgac cggcggcatg gcctccaagt gggatcaaaa gggcatggat   8460
atcgcttacg aggaggccct gctgggctac aaggagggcg gcgtgcctat cggcggctgt   8520
ctgatcaaca acaaggacgg cagtgtgctg ggcaggggcc acaacatgag gttccagaag   8580
ggctccgcca ccctgcacgg cgagatctcc accctggaga actgtggcag gctggagggc   8640
aaggtgtaca aggacaccac cctgtacacc accctgtccc cttgtgacat gtgtaccggc   8700
gctatcatca tgtacggcat ccctaggtgt gtgatcggcg agaacgtgaa cttcaagtcc   8760
aagggcgaga agtacctgca aaccaggggc cacgaggtgg tggttgttga cgatgagagg   8820
tgtaagaagc tgatgaagca gttcatcgac gagaggcctc aggactggtt cgaggatatc   8880
ggcgagtaag cggccgcaga taaaataaaa gattttattt agtctccaga aaaagggggg   8940
aatgaaagac cccacctgta ggtttggcaa gctagcttaa gtaacgccat tttgcaaggc   9000
```

-continued

```
atggaaaaat acataactga gaatagagaa gttcagatca aggtcaggaa cagatggaac   9060
agctgaatat gggccaaaca ggatatctgt ggtaagcagt tcctgccccg gctcagggcc   9120
aagaacagat ggaacagctg aatatgggcc aaacaggata tctgtggtaa gcagttcctg   9180
ccccggctca gggccaagaa cagatggtcc ccagatgcgg tccagccctc agcagtttct   9240
agagaaccat cagatgtttc cagggtgccc caaggacctg aaatgaccct gtgccttatt   9300
tgaactaacc aatcagttcg cttctcgctt ctgttcgcgc gcttctgctc cccgagctca   9360
ataaaagagc ccacaacccc tcactcgggg cgccagtcct ccgattgact gagtcgcccg   9420
ggtacccgtg tatccaataa accctcttgc agttgcatcc gacttgtggt ctcgctgttc   9480
cttgggaggg tctcctctga gtgattgact acccgtcagc gggggtcttt cattacatgt   9540
gagcaaaagg ccagcaaaag gccaggaacc gtaaaaaggc cgcgttgctg gcgtttttcc   9600
ataggctccg cccccctgac gagcatcaca aaaatcgacg ctcaagtcag aggtggcgaa   9660
acccgacagg actataaaga taccaggcgt ttccccctgg aagctccctc gtgcgctctc   9720
ctgttccgac cctgccgctt accggatacc tgtccgcctt tctcccttcg ggaagcgtgg   9780
cgctttctca tagctcacgc tgtaggtatc tcagttcggt gtaggtcgtt cgctccaagc   9840
tgggctgtgt gcacgaaccc cccgttcagc ccgaccgctg cgccttatcc ggtaactatc   9900
gtcttgagtc caacccggta agacacgact tatcgccact ggcagcagcc actggtaaca   9960
ggattagcag agcgaggtat gtaggcggtg ctacagagtt cttgaagtgg tggcctaact  10020
acggctacac tagaaggaca gtatttggta tctgcgctct gctgaagcca gttaccttcg  10080
gaaaaagagt tggtagctct tgatccggca aacaaaccac cgctggtagc ggtggttttt  10140
ttgtttgcaa gcagcagatt acgcgcagaa aaaaaggatc tcaagaagat cctttgatct  10200
tttctacggg gtctgacgct cagtggaacg aaaactcacg ttaagggatt ttggtcatga  10260
gattatcaaa aaggatcttc acctagatcc ttttaaatta aaaatgaagt tttaaatcaa  10320
tctaaagtat atatgagtaa acttggtctg acagttacca atgcttaatc agtgaggcac  10380
ctatctcagc gatctgtcta tttcgttcat ccatagttgc ctgactcccc gtcgtgtaga  10440
taactacgat acgggagggc ttaccatctg gccccagtgc tgcaatgata ccgcgagacc  10500
cacgctcacc ggctccagat ttatcagcaa taaaccagcc agccggaagg gccgagcgca  10560
gaagtggtcc tgcaacttta tccgcctcca tccagtctat taattgttgc cgggaagcta  10620
gagtaagtag ttcgccagtt aatagtttgc gcaacgttgt tgccattgct gcaggcatcg  10680
tggtgtcacg ctcgtcgttt ggtatggctt cattcagctc cggttcccaa cgatcaaggc  10740
gagttacatg atcccccatg ttgtgcaaaa aagcggttag ctccttcggt cctccgatcg  10800
ttgtcagaag taagttggcc gcagtgttat cactcatggt tatggcagca ctgcataatt  10860
ctcttactgt catgccatcc gtaagatgct tttctgtgac tggtgagtac tcaaccaagt  10920
cattctgaga atagtgtatg cggcgaccga gttgctcttg cccggcgtca acacgggata  10980
ataccgcgcc acatagcaga actttaaaag tgctcatcat tggaaaacgt tcttcggggc  11040
gaaaactctc aaggatctta ccgctgttga gatccagttc gatgtaaccc actcgtgcac  11100
ccaactgatc ttcagcatct tttactttca ccagcgtttc tgggtgagca aaaacaggaa  11160
ggcaaaatgc cgcaaaaaag ggaataaggg cgacacggaa atgttgaata ctcatactct  11220
tcctttttca atattattga agcatttatc agggttattg tctcatgagc ggatacatat  11280
ttgaatgtat ttagaaaaat aaacaaatag gggttccgcg cacatttccc cgaaaagtgc  11340
cacctgacgt ctaagaaacc attattatca tgacattaac ctataaaaat aggcgtatca  11400
```

cgaggccctt tcgtcttcaa gaattccat 11429

<210> SEQ ID NO 78
<211> LENGTH: 11427
<212> TYPE: DNA
<213> ORGANISM: Artificial Sequence
<220> FEATURE:
<223> OTHER INFORMATION: pAC3-S2-yCD2

<400> SEQUENCE: 78
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtggggggcc gctcatcgac ctacttacag 1680
aagacccccc gccttatagg gacccaagac cacccccttc cgacagggac ggaaatggtg 1740
gagaagcgac ccctgcggga gaggcaccgg accccctccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgtcc 1980

-continued tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160
attacaccac ccaggcaggt aggaaccacc tagtccacta tcgccagttg ctcctagcgg 2220
gtctccaaaa cgcgggcaga agccccacca atttggccaa ggtaaaagga ataacacaag 2280
ggcccaatga gtctccctcg gccttcctag agagacttaa ggaagcctat cgcaggtaca 2340
ctccttatga ccctgaggac ccagggcaag aaactaatgt gtctatgtct ttcatttggc 2400
agtctgcccc agacattggg agaaagttag agaggttaga agatttaaaa aacaagacgc 2460
ttggagattt ggttagagag gcagaaaaga tctttaataa acgagaaacc ccggaagaaa 2520
gagaggaacg tatcaggaga gaaacagagg aaaaagaaga acgccgtagg acagaggatg 2580
agcagaaaga gaaagaaaga gatcgtagga gacatagaga gatgagcaag ctattggcca 2640
ctgtcgttag tggacagaaa caggatagac agggaggaga acgaaggagg tcccaactcg 2700
atcgcgacca gtgtgcctac tgcaaagaaa aggggcactg ggctaaagat tgtcccaaga 2760
aaccacgagg acctcgggga ccaagacccc agacctccct cctgacccta gatgactagg 2820
gaggtcaggg tcaggagccc ccccctgaac ccaggataac cctcaaagtc ggggggcaac 2880
ccgtcacctt cctggtagat actggggccc aacactccgt gctgacccaa aatcctggac 2940
ccctaagtga taagtctgcc tgggtccaag ggctactgg aggaaagcgg tatcgctgga 3000
ccacggatcg caaagtacat ctagctaccg gtaaggtcac ccactctttc ctccatgtac 3060
cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag tatcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc cccagccctg ggttgccag 4260 atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tgggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aacccccctca agataagatt aacccgtgga agcccttaat 6420
agtcatggga gtcctgttag gagtagggat ggcagagagc cccccatcagg tctttaatgt 6480 aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720

-continued

```
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta ggtctatata   8340
agcagagctc gtttagtgaa ccgtcagatc gcctggagac gtcgagccga gtggttgtgc   8400
ctccatagaa atggtgaccg gcggcatggc ctccaagtgg gatcaaaagg gcatggatat   8460
cgcttacgag gaggccctgc tgggctacaa ggagggcggc gtgcctatcg gcggctgtct   8520
gatcaacaac aaggacggca gtgtgctggg caggggccac aacatgaggt tccagaaggg   8580
ctccgccacc ctgcacggcg agatctccac cctggagaac tgtggcaggc tggagggcaa   8640
ggtgtacaag gacaccaccc tgtacaccac cctgtcccct tgtgacatgt gtaccggcgc   8700
tatcatcatg tacggcatcc ctaggtgtgt gatcggcgag aacgtgaact tcaagtccaa   8760
gggcgagaag tacctgcaaa ccaggggcca cgaggtggtg gttgttgacg atgagaggtg   8820
taagaagctg atgaagcagt tcatcgacga gaggcctcag gactggttcg aggatatcgg   8880
cgagtaagcg gccgcagata aaataaaaga ttttatttag tctccagaaa aaggggggaa   8940
tgaaagaccc cacctgtagg tttggcaagc tagcttaagt aacgccattt tgcaaggcat   9000
ggaaaaatac ataactgaga atagagaagt tcagatcaag gtcaggaaca gatggaacag   9060
ctgaatatgg gccaaacagg atatctgtgg taagcagttc ctgccccggc tcagggccaa   9120
```

```
gaacagatgg aacagctgaa tatgggccaa acaggatatc tgtggtaagc agttcctgcc   9180
ccggctcagg gccaagaaca gatggtcccc agatgcggtc cagccctcag cagtttctag   9240
agaaccatca gatgtttcca gggtgcccca aggacctgaa atgaccctgt gccttatttg   9300
aactaaccaa tcagttcgct tctcgcttct gttcgcgcgc ttctgctccc cgagctcaat   9360
aaaagagccc acaacccctc actcggggcg ccagtcctcc gattgactga gtcgcccggg   9420
tacccgtgta tccaataaac cctcttgcag ttgcatccga cttgtggtct cgctgttcct   9480
tgggagggtc tcctctgagt gattgactac ccgtcagcgg gggtctttca ttacatgtga   9540
gcaaaaggcc agcaaaaggc caggaaccgt aaaaaggccg cgttgctggc gtttttccat   9600
aggctccgcc cccctgacga gcatcacaaa aatcgacgct caagtcagag gtggcgaaac   9660
ccgacaggac tataaagata ccaggcgttt ccccctggaa gctccctcgt gcgctctcct   9720
gttccgaccc tgccgcttac cggatacctg tccgcctttc tcccttcggg aagcgtggcg   9780
ctttctcata gctcacgctg taggtatctc agttcggtgt aggtcgttcg ctccaagctg   9840
ggctgtgtgc acgaaccccc cgttcagccc gaccgctgcg ccttatccgg taactatcgt   9900
cttgagtcca acccggtaag acacgactta tcgccactgg cagcagccac tggtaacagg   9960
attagcagag cgaggtatgt aggcggtgct acagagttct tgaagtggtg gcctaactac  10020
ggctacacta gaaggacagt atttggtatc tgcgctctgc tgaagccagt taccttcgga  10080
aaaagagttg gtagctcttg atccggcaaa caaaccaccg ctggtagcgg tggttttttt  10140
gtttgcaagc agcagattac gcgcagaaaa aaaggatctc aagaagatcc tttgatcttt  10200
tctacggggt ctgacgctca gtggaacgaa aactcacgtt aagggatttt ggtcatgaga  10260
ttatcaaaaa ggatcttcac ctagatcctt ttaaattaaa aatgaagttt taaatcaatc  10320
taaagtatat atgagtaaac ttggtctgac agttaccaat gcttaatcag tgaggcacct  10380
atctcagcga tctgtctatt tcgttcatcc atagttgcct gactccccgt cgtgtagata  10440
actacgatac gggagggctt accatctggc cccagtgctg caatgatacc gcgagaccca  10500
cgctcaccgg ctccagattt atcagcaata aaccagccag ccggaagggc cgagcgcaga  10560
agtggtcctg caactttatc cgcctccatc cagtctatta attgttgccg ggaagctaga  10620
gtaagtagtt cgccagttaa tagtttgcgc aacgttgttg ccattgctgc aggcatcgtg  10680
gtgtcacgct cgtcgtttgg tatggcttca ttcagctccg gttcccaacg atcaaggcga  10740
gttacatgat cccccatgtt gtgcaaaaaa gcggttagct ccttcggtcc tccgatcgtt  10800
gtcagaagta agttggccgc agtgttatca ctcatggtta tggcagcact gcataattct  10860
cttactgtca tgccatccgt aagatgcttt tctgtgactg gtgagtactc aaccaagtca  10920
ttctgagaat agtgtatgcg gcgaccgagt tgctcttgcc cggcgtcaac acgggataat  10980
accgcgccac atagcagaac tttaaaagtg ctcatcattg gaaaacgttc ttcggggcga  11040
aaactctcaa ggatcttacc gctgttgaga tccagttcga tgtaacccac tcgtgcaccc  11100
aactgatctt cagcatcttt tactttcacc agcgtttctg ggtgagcaaa aacaggaagg  11160
caaaatgccg caaaaaaggg aataagggcg acacggaaat gttgaatact catactcttc  11220
ctttttcaat attattgaag catttatcag ggttattgtc tcatgagcgg atacatattt  11280
gaatgtattt agaaaaataa acaaataggg gttccgcgca catttccccg aaaagtgcca  11340
cctgacgtct aagaaaccat tattatcatg acattaacct ataaaaatag gcgtatcacg  11400
aggccctttc gtcttcaaga attccat                                      11427
```

<210> SEQ ID NO 79
<211> LENGTH: 11431
<212> TYPE: DNA
<213> ORGANISM: Artificial Sequence
<220> FEATURE:
<223> OTHER INFORMATION: pAC3-S2K-yCD2

<400> SEQUENCE: 79
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtggggggcc gctcatcgac ctacttacag 1680
aagacccccc gccttatagg gacccaagac cacccccttc cgacagggac ggaaatggtg 1740
gagaagcgac ccctgcggga gaggcaccgg acccctcccc aatggcatct cgcctacgtg 1800
ggagacggga gcccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttcttttttct gaagatccag gtaaactgac agctctgatc gagtctgtcc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100

-continued

```
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtcccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
```

-continued

```
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
```

cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagccccct caataccagt taccccctt ccactaccag 7200 tacaccctca acctccccta caagtccaag tgtcccacag ccaccccag gaactggaga 7260 tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgta ggtctatata 8340
agcagagctc gtttagtgaa ccgtcagatc gcctggagac gtcgagccga gtggttgtgc 8400
ctccatagaa caccatggtg accggcggca tggcctccaa gtgggatcaa aagggcatgg 8460
atatcgctta cgaggaggcc ctgctgggct acaaggaggg cggcgtgcct atcggcggct 8520
gtctgatcaa caacaaggac ggcagtgtgc tgggcagggg ccacaacatg aggttccaga 8580
agggctccgc caccctgcac ggcgagatct ccaccctgga gaactgtggc aggctggagg 8640
gcaaggtgta caaggacacc accctgtaca ccaccctgtc cccttgtgac atgtgtaccg 8700
gcgctatcat catgtacggc atccctaggt gtgtgatcgg cgagaacgtg aacttcaagt 8760
ccaagggcga gaagtacctg caaaccaggg gccacgaggt ggtggttgtt gacgatgaga 8820
ggtgtaagaa gctgatgaag cagttcatcg acgagaggcc tcaggactgg ttcgaggata 8880
tcggcgagta agcggccgca gataaaataa aagattttat ttagtctcca gaaaaagggg 8940
ggaatgaaag accccacctg taggtttggc aagctagctt aagtaacgcc attttgcaag 9000
gcatggaaaa atacataact gagaatagag aagttcagat caaggtcagg aacagatgga 9060
acagctgaat atgggccaaa caggatatct gtggtaagca gttcctgccc cggctcaggg 9120
ccaagaacag atggaacagc tgaatatggg ccaaacagga tatctgtggt aagcagttcc 9180

```
tgccccggct cagggccaag aacagatggt ccccagatgc ggtccagccc tcagcagttt   9240
ctagagaacc atcagatgtt tccagggtgc cccaaggacc tgaaatgacc ctgtgcctta   9300
tttgaactaa ccaatcagtt cgcttctcgc ttctgttcgc gcgcttctgc tccccgagct   9360
caataaaaga gcccacaacc cctcactcgg ggcgccagtc ctccgattga ctgagtcgcc   9420
cgggtacccg tgtatccaat aaaccctctt gcagttgcat ccgacttgtg gtctcgctgt   9480
tccttgggag ggtctcctct gagtgattga ctacccgtca gcgggggtct ttcattacat   9540
gtgagcaaaa ggccagcaaa aggccaggaa ccgtaaaaag gccgcgttgc tggcgttttt   9600
ccataggctc cgcccccctg acgagcatca caaaaatcga cgctcaagtc agaggtggcg   9660
aaacccgaca ggactataaa gataccaggc gtttccccct ggaagctccc tcgtgcgctc   9720
tcctgttccg accctgccgc ttaccggata cctgtccgcc tttctccctt cgggaagcgt   9780
ggcgctttct catagctcac gctgtaggta tctcagttcg gtgtaggtcg ttcgctccaa   9840
gctgggctgt gtgcacgaac cccccgttca gcccgaccgc tgcgccttat ccggtaacta   9900
tcgtcttgag tccaacccgg taagacacga cttatcgcca ctggcagcag ccactggtaa   9960
caggattagc agagcgaggt atgtaggcgg tgctacagag ttcttgaagt ggtggcctaa  10020
ctacggctac actagaagga cagtatttgg tatctgcgct ctgctgaagc cagttacctt  10080
cggaaaaaga gttggtagct cttgatccgg caaacaaacc accgctggta gcggtggttt  10140
ttttgtttgc aagcagcaga ttacgcgcag aaaaaaagga tctcaagaag atcctttgat  10200
cttttctacg gggtctgacg ctcagtggaa cgaaaactca cgttaaggga ttttggtcat  10260
gagattatca aaaaggatct tcacctagat ccttttaaat taaaaatgaa gttttaaatc  10320
aatctaaagt atatatgagt aaacttggtc tgacagttac caatgcttaa tcagtgaggc  10380
acctatctca gcgatctgtc tatttcgttc atccatagtt gcctgactcc ccgtcgtgta  10440
gataactacg atacgggagg gcttaccatc tggccccagt gctgcaatga taccgcgaga  10500
cccacgctca ccggctccag atttatcagc aataaaccag ccagccggaa gggccgagcg  10560
cagaagtggt cctgcaactt tatccgcctc catccagtct attaattgtt gccgggaagc  10620
tagagtaagt agttcgccag ttaatagttt gcgcaacgtt gttgccattg ctgcaggcat  10680
cgtggtgtca cgctcgtcgt ttggtatggc ttcattcagc tccggttccc aacgatcaag  10740
gcgagttaca tgatccccca tgttgtgcaa aaaagcggtt agctccttcg gtcctccgat  10800
cgttgtcaga agtaagttgg ccgcagtgtt atcactcatg gttatggcag cactgcataa  10860
ttctcttact gtcatgccat ccgtaagatg cttttctgtg actggtgagt actcaaccaa  10920
gtcattctga gaatagtgta tgcggcgacc gagttgctct tgcccggcgt caacacggga  10980
taataccgcg ccacatagca gaactttaaa agtgctcatc attggaaaac gttcttcggg  11040
gcgaaaactc tcaaggatct taccgctgtt gagatccagt tcgatgtaac ccactcgtgc  11100
acccaactga tcttcagcat cttttacttt caccagcgtt tctgggtgag caaaaacagg  11160
aaggcaaaat gccgcaaaaa agggaataag ggcgacacgg aaatgttgaa tactcatact  11220
cttccttttt caatattatt gaagcattta tcagggttat tgtctcatga gcggatacat  11280
atttgaatgt atttagaaaa ataaacaaat aggggttccg cgcacatttc cccgaaaagt  11340
gccacctgac gtctaagaaa ccattattat catgacatta acctataaaa ataggcgtat  11400
cacgaggccc tttcgtcttc aagaattcca t                                 11431
```

<210> SEQ ID NO 80
<211> LENGTH: 12190

<212> TYPE: DNA
<213> ORGANISM: Artificial Sequence
<220> FEATURE:
<223> OTHER INFORMATION: pAC3-SV40-GFP-R

<400> SEQUENCE: 80
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtgggggggcc gctcatcgac ctacttacag 1680
aagacccccc gccttatagg gacccaagac cacccccttc cgacagggac ggaaatggtg 1740
gagaagcgac ccctgcggga gaggcaccgg accccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920
ataataaccc ttctttttct gaagatccag gtaaactgac agctctgatc gagtctgtcc 1980
tcatcaccca tcagcccacc tgggacgact gtcagcagct gttggggact ctgctgaccg 2040
gagaagaaaa acaacgggtg ctcttagagg ctagaaaggc ggtgcggggc gatgatgggc 2100
gccccactca actgcccaat gaagtcgatg ccgcttttcc cctcgagcgc ccagactggg 2160

```
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtcccccctg gaacacgccc ctgctacccg  3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag    4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
```

aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tggggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agatacccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac ccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aacccctca agataagatt aacccgtgga agcccttaat 6420
agtcatggga gtcctgttag gagtagggat ggcagagagc cccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900

-continued

```
cttccaaggg gctactcgag ggggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtg cagtgaaaaa   8340
aatgctttat ttgtgaaatt tgtgatgcta ttgctttatt tgtaaccatt ataagctgca   8400
ataaacaagt tggggtgggc gaagaactcc agcatgagat ccccgcgctg gaggatcatc   8460
cagccggcgt cccggaaaac gattccgaag cccaaccttt catagaaggc ggcggtggaa   8520
tcgaaatctc gtgatggcag gttgggcgtc gcttggtcgg tcatttcgat cacttgtaca   8580
gctcgtccat gccgagagtg atcccggcgg cggtcacgaa ctccagcagg accatgtgat   8640
cgcgcttctc gttggggtct ttgctcaggg cggactgggt gctcaggtag tggttgtcgg   8700
gcagcagcac ggggccgtcg ccgatggggg tgttctgctg gtagtggtcg gcgagctgca   8760
cgctgccgtc ctcgatgttg tggcgggtct tgaagttcac cttgatgccg ttcttctgct   8820
tgtcggcggt gatatagacc ttgtggctgt tgtagttgta ctccagcttg tgccccagga   8880
tgttgccgtc ctccttgaag tcgatgccct tcagctcgat gcggttcacc agggtgtcgc   8940
cctcgaactt cacctcggcg cgggtcttgt agttgccgtc gtccttgaag aagatggtgc   9000
gctcctggac gtagccttcg ggcatggcgg acttgaagaa gtcgtgctgc ttcatgtggt   9060
cggggtagcg ggcgaagcac tgcacgccgt aggtcaaggt ggtcacgagg gtgggccagg   9120
gcacgggcag cttgccggtg gtgcagatga acttcagggt cagcttgccg taggtggcat   9180
cgccctcgcc ctcgccggac acgctgaact tgtggccgtt tacgtcgccg tccagctcga   9240
ccaggatggg caccaccccg gtgaacagct cctcgccctt gctggccatg gtggatcccc   9300
```

-continued

```
gggcgagctc gaattccgtg tattccgaaa atggatatac aagctcccgg gagctttttg   9360
caaaagccta ggcctccaaa aaagcctcct cactacttct ggaatagctc agaggcagag   9420
gcggcctcgg cctctgcata aataaaaaaa attagtcagc catggggcgg agaatgggcg   9480
gaactgggcg gagttagggg cgggatgggc ggagttaggg gcgggactat ggttgctgac   9540
taattgagat gcatgctttg catacttctg cctgctgggg agcctgggga ctttccacac   9600
ctggttgctg actaattgag atgcatgctt tgcatacttc tgcctgctgg gcggccgcag   9660
ataaaataaa agattttatt tagtctccag aaaaaggggg gaatgaaaga ccccacctgt   9720
aggtttggca agctagctta agtaacgcca ttttgcaagg catggaaaaa tacataactg   9780
agaatagaga agttcagatc aaggtcagga acagatggaa cagctgaata tgggccaaac   9840
aggatatctg tggtaagcag ttcctgcccc ggctcagggc caagaacaga tggaacagct   9900
gaatatgggc caaacaggat atctgtggta agcagttcct gccccggctc agggccaaga   9960
acagatggtc cccagatgcg gtccagccct cagcagtttc tagagaacca tcagatgttt  10020
ccagggtgcc ccaaggacct gaaatgaccc tgtgccttat ttgaactaac caatcagttc  10080
gcttctcgct tctgttcgcg cgcttctgct ccccgagctc aataaaagag cccacaaccc  10140
ctcactcggg gcgccagtcc tccgattgac tgagtcgccc gggtacccgt gtatccaata  10200
aaccctcttg cagttgcatc cgacttgtgg tctcgctgtt ccttgggagg gtctcctctg  10260
agtgattgac tacccgtcag cgggggtctt tcattacatg tgagcaaaag gccagcaaaa  10320
ggccaggaac cgtaaaaagg ccgcgttgct ggcgtttttc cataggctcc gcccccctga  10380
cgagcatcac aaaaatcgac gctcaagtca gaggtggcga aacccgacag gactataaag  10440
ataccaggcg tttccccctg gaagctccct cgtgcgctct cctgttccga ccctgccgct  10500
taccggatac ctgtccgcct ttctcccttc gggaagcgtg gcgctttctc atagctcacg  10560
ctgtaggtat ctcagttcgg tgtaggtcgt tcgctccaag ctgggctgtg tgcacgaacc  10620
ccccgttcag cccgaccgct gcgccttatc cggtaactat cgtcttgagt ccaacccggt  10680
aagacacgac ttatcgccac tggcagcagc cactggtaac aggattagca gagcgaggta  10740
tgtaggcggt gctacagagt tcttgaagtg gtggcctaac tacggctaca ctagaaggac  10800
agtatttggt atctgcgctc tgctgaagcc agttaccttc ggaaaaagag ttggtagctc  10860
ttgatccggc aaacaaacca ccgctggtag cggtggtttt tttgtttgca agcagcagat  10920
tacgcgcaga aaaaaaggat ctcaagaaga tcctttgatc ttttctacgg ggtctgacgc  10980
tcagtggaac gaaaactcac gttaagggat tttggtcatg agattatcaa aaaggatctt  11040
cacctagatc cttttaaatt aaaaatgaag ttttaaatca atctaaagta tatatgagta  11100
aacttggtct gacagttacc aatgcttaat cagtgaggca cctatctcag cgatctgtct  11160
atttcgttca tccatagttg cctgactccc cgtcgtgtag ataactacga tacgggaggg  11220
cttaccatct ggccccagtg ctgcaatgat accgcgagac ccacgctcac cggctccaga  11280
tttatcagca ataaaccagc cagccggaag ggccgagcgc agaagtggtc ctgcaacttt  11340
atccgcctcc atccagtcta ttaattgttg ccgggaagct agagtaagta gttcgccagt  11400
taatagtttg cgcaacgttg ttgccattgc tgcaggcatc gtggtgtcac gctcgtcgtt  11460
tggtatggct tcattcagct ccggttccca acgatcaagg cgagttacat gatcccccat  11520
gttgtgcaaa aaagcggtta gctccttcgg tcctccgatc gttgtcagaa gtaagttggc  11580
cgcagtgtta tcactcatgg ttatggcagc actgcataat tctcttactg tcatgccatc  11640
```

cgtaagatgc ttttctgtga ctggtgagta ctcaaccaag tcattctgag aatagtgtat 11700
gcggcgaccg agttgctctt gcccggcgtc aacacgggat aataccgcgc cacatagcag 11760
aactttaaaa gtgctcatca ttggaaaacg ttcttcgggg cgaaaactct caaggatctt 11820
accgctgttg agatccagtt cgatgtaacc cactcgtgca cccaactgat cttcagcatc 11880
ttttactttc accagcgttt ctgggtgagc aaaaacagga aggcaaaatg ccgcaaaaaa 11940
gggaataagg gcgacacgga aatgttgaat actcatactc ttcctttttc aatattattg 12000
aagcatttat cagggttatt gtctcatgag cggatacata tttgaatgta tttagaaaaa 12060
taaacaaata ggggttccgc gcacatttcc ccgaaaagtg ccacctgacg tctaagaaac 12120
cattattatc atgacattaa cctataaaaa taggcgtatc acgaggccct ttcgtcttca 12180
agaattccat 12190

<210> SEQ ID NO 81
<211> LENGTH: 11974
<212> TYPE: DNA
<213> ORGANISM: Artificial Sequence
<220> FEATURE:
<223> OTHER INFORMATION: pAC3-Gluc

<400> SEQUENCE: 81
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440
tcccctacat cgtgacctgg gaagccttgg cttttgaccc ccctccctgg gtcaagccct 1500

```
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
```

-continued agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc ccagccctg gggttgccag 4260 atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tgggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240

-continued cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc ccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccccct caataccagt taccccccctt ccactaccag 7200 tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgtt actggccgaa 8340
gccgcttgga ataaggccgg tgtgcgtttg tctatatgtt attttccacc atattgccgt 8400
cttttggcaa tgtgagggcc cggaaacctg gccctgtctt cttgacgagc attcctaggg 8460
gtctttcccc tctcgccaaa ggaatgcaag gtctgttgaa tgtcgtgaag gaagcagttc 8520
ctctggaagc ttcttgaaga caaacaacgt ctgtagcgac cctttgcagg cagcggaacc 8580

-continued

```
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttcctttg aaaaacacga ttataaatgg   8880
gagtcaaagt tctgtttgcc ctgatctgca tcgctgtggc cgaggccaag cccaccgaga   8940
acaacgaaga cttcaacatc gtggccgtgg ccagcaactt cgcgaccacg gatctcgatg   9000
ctgaccgcgg gaagttgccc ggcaagaagc tgccgctgga ggtgctcaaa gagatggaag   9060
ccaatgcccg gaaagctggc tgcaccaggg gctgtctgat ctgcctgtcc cacatcaagt   9120
gcacgcccaa gatgaagaag ttcatcccag gacgctgcca cacctacgaa ggcgacaaag   9180
agtccgcaca gggcggcata ggcgaggcga tcgtcgacat tcctgagatt cctgggttca   9240
aggacttgga gcccatggag cagttcatcg cacaggtcga tctgtgtgtg gactgcacaa   9300
ctggctgcct caaagggctt gccaacgtgc agtgttctga cctgctcaag aagtggctgc   9360
cgcaacgctg tgcgaccttt gccagcaaga tccagggcca ggtggacaag atcaaggggg   9420
ccggtggtga ctaagcggcc gcagataaaa taaaagattt tatttagtct ccagaaaaag   9480
gggggaatga aagaccccac ctgtaggttt ggcaagctag cttaagtaac gccattttgc   9540
aaggcatgga aaaatacata actgagaata gagaagttca gatcaaggtc aggaacagat   9600
ggaacagctg aatatgggcc aaacaggata tctgtggtaa gcagttcctg ccccggctca   9660
gggccaagaa cagatggaac agctgaatat gggccaaaca ggatatctgt ggtaagcagt   9720
tcctgccccg gctcagggcc aagaacagat ggtccccaga tgcggtccag ccctcagcag   9780
tttctagaga accatcagat gtttccaggg tgccccaagg acctgaaatg accctgtgcc   9840
ttatttgaac taaccaatca gttcgcttct cgcttctgtt cgcgcgcttc tgctccccga   9900
gctcaataaa agagcccaca acccctcact cggggcgcca gtcctccgat tgactgagtc   9960
gcccgggtac ccgtgtatcc aataaaccct cttgcagttg catccgactt gtggtctcgc  10020
tgttccttgg gagggtctcc tctgagtgat tgactacccg tcagcggggg tctttcatta  10080
catgtgagca aaaggccagc aaaaggccag gaaccgtaaa aaggccgcgt tgctggcgtt  10140
tttccatagg ctccgccccc ctgacgagca tcacaaaaat cgacgctcaa gtcagaggtg  10200
gcgaaacccg acaggactat aaagatacca ggcgtttccc cctggaagct ccctcgtgcg  10260
ctctcctgtt ccgaccctgc cgcttaccgg atacctgtcc gcctttctcc cttcgggaag  10320
cgtggcgctt tctcatagct cacgctgtag gtatctcagt tcggtgtagg tcgttcgctc  10380
caagctgggc tgtgtgcacg aaccccccgt tcagcccgac cgctgcgcct tatccggtaa  10440
ctatcgtctt gagtccaacc cggtaagaca cgacttatcg ccactggcag cagccactgg  10500
taacaggatt agcagagcga ggtatgtagg cggtgctaca gagttcttga agtggtggcc  10560
taactacggc tacactagaa ggacagtatt tggtatctgc gctctgctga agccagttac  10620
cttcggaaaa agagttggta gctcttgatc cggcaaacaa accaccgctg gtagcggtgg  10680
tttttttgtt tgcaagcagc agattacgcg cagaaaaaaa ggatctcaag aagatccttt  10740
gatcttttct acggggtctg acgctcagtg gaacgaaaac tcacgttaag ggattttggt  10800
catgagatta tcaaaaagga tcttcaccta gatcctttta aattaaaaat gaagttttaa  10860
atcaatctaa agtatatatg agtaaacttg gtctgacagt taccaatgct taatcagtga  10920
ggcacctatc tcagcgatct gtctatttcg ttcatccata gttgcctgac tccccgtcgt  10980
```

-continued gtagataact acgatacggg agggcttacc atctggcccc agtgctgcaa tgataccgcg 11040
agacccacgc tcaccggctc cagatttatc agcaataaac cagccagccg gaagggccga 11100
gcgcagaagt ggtcctgcaa ctttatccgc ctccatccag tctattaatt gttgccggga 11160
agctagagta agtagttcgc cagttaatag tttgcgcaac gttgttgcca ttgctgcagg 11220
catcgtggtg tcacgctcgt cgtttggtat ggcttcattc agctccggtt cccaacgatc 11280
aaggcgagtt acatgatccc ccatgttgtg caaaaaagcg gttagctcct tcggtcctcc 11340
gatcgttgtc agaagtaagt tggccgcagt gttatcactc atggttatgg cagcactgca 11400
taattctctt actgtcatgc catccgtaag atgcttttct gtgactggtg agtactcaac 11460
caagtcattc tgagaatagt gtatgcggcg accgagttgc tcttgcccgg cgtcaacacg 11520
ggataatacc gcgccacata gcagaacttt aaaagtgctc atcattggaa aacgttcttc 11580
ggggcgaaaa ctctcaagga tcttaccgct gttgagatcc agttcgatgt aacccactcg 11640
tgcacccaac tgatcttcag catcttttac tttcaccagc gtttctgggt gagcaaaaac 11700
aggaaggcaa aatgccgcaa aaaagggaat aagggcgaca cggaaatgtt gaatactcat 11760
actcttcctt tttcaatatt attgaagcat ttatcagggt tattgtctca tgagcggata 11820
catatttgaa tgtatttaga aaaataaaca aataggggtt ccgcgcacat ttccccgaaa 11880
agtgccacct gacgtctaag aaaccattat tatcatgaca ttaacctata aaaataggcg 11940
tatcacgagg ccctttcgtc ttcaagaatt ccat 11974

<210> SEQ ID NO 82
<211> LENGTH: 11758
<212> TYPE: DNA
<213> ORGANISM: Artificial Sequence
<220> FEATURE:
<223> OTHER INFORMATION: pAC3-SV40-Gluc

<400> SEQUENCE: 82
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020

-continued

```
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccettgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tggdacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
```

```
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
```

-continued tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc cccccatcagg tctttaatgt 6480 aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag ggggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccccct caataccagt taccccccctt ccactaccag 7200 tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160

-continued

```
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtc cagcaggcag   8340
aagtatgcaa agcatgcatc tcaattagtc agcaaccagg tgtggaaagt ccccaggctc   8400
cccagcaggc agaagtatgc aaagcatgca tctcaattag tcagcaacca tagtcccgcc   8460
cctaactccg cccatcccgc ccctaactcc gcccagttcc gcccattctc cgccccatgg   8520
ctgactaatt ttttttattt atgcagaggc cgaggccgcc tctgcctctg agctattcca   8580
gaagtagtga ggaggctttt ttggaggcct aggcttttgc aaaaagctcc cgggagcttg   8640
tatatccatt ttcgttataa atgggagtca aagttctgtt tgccctgatc tgcatcgctg   8700
tggccgaggc caagcccacc gagaacaacg aagacttcaa catcgtggcc gtggccagca   8760
acttcgcgac cacggatctc gatgctgacc gcgggaagtt gcccggcaag aagctgccgc   8820
tggaggtgct caaagagatg gaagccaatg cccggaaagc tggctgcacc aggggctgtc   8880
tgatctgcct gtcccacatc aagtgcacgc ccaagatgaa gaagttcatc ccaggacgct   8940
gccacaccta cgaaggcgac aaagagtccg cacagggcgg cataggcgag gcgatcgtcg   9000
acattcctga gattcctggg ttcaaggact tggagcccat ggagcagttc atcgcacagg   9060
tcgatctgtg tgtggactgc acaactggct gcctcaaagg gcttgccaac gtgcagtgtt   9120
ctgacctgct caagaagtgg ctgccgcaac gctgtgcgac ctttgccagc aagatccagg   9180
gccaggtgga caagatcaag gggggccggtg gtgactaagc ggccgcagat aaaataaaag   9240
attttattta gtctccagaa aaagggggga atgaaagacc ccacctgtag gtttggcaag   9300
ctagcttaag taacgccatt ttgcaaggca tggaaaaata cataactgag aatagagaag   9360
ttcagatcaa ggtcaggaac agatggaaca gctgaatatg ggccaaacag gatatctgtg   9420
gtaagcagtt cctgccccgg ctcagggcca agaacagatg gaacagctga atatgggcca   9480
aacaggatat ctgtggtaag cagttcctgc cccggctcag ggccaagaac agatggtccc   9540
cagatgcggt ccagccctca gcagtttcta gagaaccatc agatgtttcc agggtgcccc   9600
aaggacctga aatgaccctg tgccttattt gaactaacca atcagttcgc ttctcgcttc   9660
tgttcgcgcg cttctgctcc ccgagctcaa taaaagagcc cacaacccct cactcggggc   9720
gccagtcctc cgattgactg agtcgcccgg gtacccgtgt atccaataaa ccctcttgca   9780
gttgcatccg acttgtggtc tcgctgttcc ttgggagggt ctcctctgag tgattgacta   9840
cccgtcagcg ggggtctttc attacatgtg agcaaaaggc cagcaaaagg ccaggaaccg   9900
taaaaaggcc gcgttgctgg cgtttttcca taggctccgc ccccctgacg agcatcacaa   9960
aaatcgacgc tcaagtcaga ggtggcgaaa cccgacagga ctataaagat accaggcgtt  10020
tccccctgga agctccctcg tgcgctctcc tgttccgacc ctgccgctta ccggatacct  10080
gtccgccttt ctcccttcgg gaagcgtggc gctttctcat agctcacgct gtaggtatct  10140
cagttcggtg taggtcgttc gctccaagct gggctgtgtg cacgaacccc ccgttcagcc  10200
cgaccgctgc gccttatccg gtaactatcg tcttgagtcc aacccggtaa gacacgactt  10260
atcgccactg gcagcagcca ctggtaacag gattagcaga gcgaggtatg taggcggtgc  10320
tacagagttc ttgaagtggt ggcctaacta cggctacact agaaggacag tatttggtat  10380
ctgcgctctg ctgaagccag ttaccttcgg aaaaagagtt ggtagctctt gatccggcaa  10440
acaaaccacc gctggtagcg gtggtttttt tgtttgcaag cagcagatta cgcgcagaaa  10500
```

```
aaaaggatct caagaagatc ctttgatctt ttctacgggg tctgacgctc agtggaacga  10560
aaactcacgt taagggattt tggtcatgag attatcaaaa aggatcttca cctagatcct  10620
tttaaattaa aaatgaagtt ttaaatcaat ctaaagtata tatgagtaaa cttggtctga  10680
cagttaccaa tgcttaatca gtgaggcacc tatctcagcg atctgtctat ttcgttcatc  10740
catagttgcc tgactccccg tcgtgtagat aactacgata cgggagggct taccatctgg  10800
ccccagtgct gcaatgatac cgcgagaccc acgctcaccg gctccagatt tatcagcaat  10860
aaaccagcca gccggaaggg ccgagcgcag aagtggtcct gcaactttat ccgcctccat  10920
ccagtctatt aattgttgcc gggaagctag agtaagtagt tcgccagtta atagtttgcg  10980
caacgttgtt gccattgctg caggcatcgt ggtgtcacgc tcgtcgtttg gtatggcttc  11040
attcagctcc ggttcccaac gatcaaggcg agttacatga tcccccatgt tgtgcaaaaa  11100
agcggttagc tccttcggtc ctccgatcgt tgtcagaagt aagttggccg cagtgttatc  11160
actcatggtt atggcagcac tgcataattc tcttactgtc atgccatccg taagatgctt  11220
ttctgtgact ggtgagtact caaccaagtc attctgagaa tagtgtatgc ggcgaccgag  11280
ttgctcttgc ccggcgtcaa cacgggataa taccgcgcca catagcagaa ctttaaaagt  11340
gctcatcatt ggaaaacgtt cttcggggcg aaaactctca aggatcttac cgctgttgag  11400
atccagttcg atgtaaccca ctcgtgcacc caactgatct tcagcatctt ttactttcac  11460
cagcgtttct gggtgagcaa aaacaggaag gcaaaatgcc gcaaaaaagg gaataagggc  11520
gacacggaaa tgttgaatac tcatactctt cctttttcaa tattattgaa gcatttatca  11580
gggttattgt ctcatgagcg gatacatatt tgaatgtatt tagaaaaata aacaaatagg  11640
ggttccgcgc acatttcccc gaaaagtgcc acctgacgtc taagaaacca ttattatcat  11700
gacattaacc tataaaaata ggcgtatcac gaggcccttt cgtcttcaag aattccat    11758
```

<210> SEQ ID NO 83
<211> LENGTH: 11695
<212> TYPE: DNA
<213> ORGANISM: Artificial Sequence
<220> FEATURE:
<223> OTHER INFORMATION: pAC3-RSV-Gluc

<400> SEQUENCE: 83

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
```

```
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccctgaac    1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
```

-continued ccctaaatat agaagatgag tatcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc cccagccctg ggttgccag 4260
atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tgggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580

-continued agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc cccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccct caataccagt tacccccctt ccactaccag 7200
tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920

-continued

```
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgta atgtagtctt   8340
atgcaatact cttgtagtct tgcaacatgg taacgatgag ttagcaacat gccttacaag   8400
gagagaaaaa gcaccgtgca tgccgattgg tggaagtaag gtggtacgat cgtgccttat   8460
taggaaggca acagacgggt ctgacatgga ttggacgaac cactgaattc cgcattgcag   8520
agatattgta tttaagtgcc tagctcgata caataaacgc catttgacca ttcaccacat   8580
tggtgtgcac cttataaatg ggagtcaaag ttctgtttgc cctgatctgc atcgctgtgg   8640
ccgaggccaa gcccaccgag aacaacgaag acttcaacat cgtggccgtg gccagcaact   8700
tcgcgaccac ggatctcgat gctgaccgcg ggaagttgcc cggcaagaag ctgccgctgg   8760
aggtgctcaa agagatggaa gccaatgccc ggaaagctgg ctgcaccagg ggctgtctga   8820
tctgcctgtc ccacatcaag tgcacgccca agatgaagaa gttcatccca ggacgctgcc   8880
acacctacga aggcgacaaa gagtccgcac agggcggcat aggcgaggcg atcgtcgaca   8940
ttcctgagat tcctgggttc aaggacttgg agcccatgga gcagttcatc gcacaggtcg   9000
atctgtgtgt ggactgcaca actggctgcc tcaaagggct tgccaacgtg cagtgttctg   9060
acctgctcaa gaagtggctg ccgcaacgct gtgcgacctt tgccagcaag atccagggcc   9120
aggtggacaa gatcaagggg gccggtggtg actaagcggc cgcagataaa ataaaagatt   9180
ttatttagtc tccagaaaaa ggggggaatg aaagacccca cctgtaggtt tggcaagcta   9240
gcttaagtaa cgccattttg caaggcatgg aaaaatacat aactgagaat agagaagttc   9300
agatcaaggt caggaacaga tggaacagct gaatatgggc caaacaggat atctgtggta   9360
agcagttcct gccccggctc agggccaaga acagatggaa cagctgaata tgggccaaac   9420
aggatatctg tggtaagcag ttcctgcccc ggctcagggc caagaacaga tggtccccag   9480
atgcggtcca gccctcagca gtttctagag aaccatcaga tgtttccagg gtgccccaag   9540
gacctgaaat gaccctgtgc cttatttgaa ctaaccaatc agttcgcttc tcgcttctgt   9600
tcgcgcgctt ctgctccccg agctcaataa aagagcccac aacccctcac tcggggcgcc   9660
agtcctccga ttgactgagt cgcccgggta cccgtgtatc caataaaccc tcttgcagtt   9720
gcatccgact tgtggtctcg ctgttccttg ggagggtctc ctctgagtga ttgactaccc   9780
gtcagcgggg gtctttcatt acatgtgagc aaaaggccag caaaaggcca ggaaccgtaa   9840
aaaggccgcg ttgctggcgt ttttccatag gctccgcccc cctgacgagc atcacaaaaa   9900
tcgacgctca agtcagaggt ggcgaaaccc gacaggacta taaagatacc aggcgtttcc   9960
ccctggaagc tccctcgtgc gctctcctgt tccgaccctg ccgcttaccg gatacctgtc  10020
cgcctttctc ccttcgggaa gcgtggcgct ttctcatagc tcacgctgta ggtatctcag  10080
ttcggtgtag gtcgttcgct ccaagctggg ctgtgtgcac gaaccccccg ttcagcccga  10140
ccgctgcgcc ttatccggta actatcgtct tgagtccaac ccggtaagac acgacttatc  10200
gccactggca gcagccactg gtaacaggat tagcagagcg aggtatgtag gcggtgctac  10260
agagttcttg aagtggtggc ctaactacgg ctacactaga aggacagtat ttggtatctg  10320
```

cgctctgctg aagccagtta ccttcggaaa aagagttggt agctcttgat ccggcaaaca 10380
aaccaccgct ggtagcggtg gtttttttgt ttgcaagcag cagattacgc gcagaaaaaa 10440
aggatctcaa gaagatcctt tgatcttttc tacggggtct gacgctcagt ggaacgaaaa 10500
ctcacgttaa gggattttgg tcatgagatt atcaaaaagg atcttcacct agatcctttt 10560
aaattaaaaa tgaagtttta aatcaatcta aagtatatat gagtaaactt ggtctgacag 10620
ttaccaatgc ttaatcagtg aggcacctat ctcagcgatc tgtctatttc gttcatccat 10680
agttgcctga ctccccgtcg tgtagataac tacgatacgg gagggcttac catctggccc 10740
cagtgctgca atgataccgc gagacccacg ctcaccggct ccagatttat cagcaataaa 10800
ccagccagcc ggaagggccg agcgcagaag tggtcctgca actttatccg cctccatcca 10860
gtctattaat tgttgccggg aagctagagt aagtagttcg ccagttaata gtttgcgcaa 10920
cgttgttgcc attgctgcag gcatcgtggt gtcacgctcg tcgtttggta tggcttcatt 10980
cagctccggt tcccaacgat caaggcgagt tacatgatcc cccatgttgt gcaaaaaagc 11040
ggttagctcc ttcggtcctc cgatcgttgt cagaagtaag ttggccgcag tgttatcact 11100
catggttatg gcagcactgc ataattctct tactgtcatg ccatccgtaa gatgcttttc 11160
tgtgactggt gagtactcaa ccaagtcatt ctgagaatag tgtatgcggc gaccgagttg 11220
ctcttgcccg gcgtcaacac gggataatac cgcgccacat agcagaactt taaaagtgct 11280
catcattgga aaacgttctt cggggcgaaa actctcaagg atcttaccgc tgttgagatc 11340
cagttcgatg taacccactc gtgcacccaa ctgatcttca gcatctttta ctttcaccag 11400
cgtttctggg tgagcaaaaa caggaaggca aaatgccgca aaaaagggaa taagggcgac 11460
acggaaatgt tgaatactca tactcttcct ttttcaatat tattgaagca tttatcaggg 11520
ttattgtctc atgagcggat acatatttga atgtatttag aaaaataaac aaataggggt 11580
tccgcgcaca tttccccgaa aagtgccacc tgacgtctaa gaaaccatta ttatcatgac 11640
attaacctat aaaaataggc gtatcacgag gccctttcgt cttcaagaat tccat 11695

<210> SEQ ID NO 84
<211> LENGTH: 11515
<212> TYPE: DNA
<213> ORGANISM: Artificial Sequence
<220> FEATURE:
<223> OTHER INFORMATION: pAC3-S1-Gluc

<400> SEQUENCE: 84
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660

-continued

```
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccccttgaac   1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
```

-continued cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag tatcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtcccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140
cagccccctt gtaccctctc accaaaacgg ggactctgtt taattggggc ccagaccaac 4200
aaaaggccta tcaagaaatc aagcaagctc ttctaactgc cccagccctg ggttgccag 4260
atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800
ccaccgagac cgaggtaatc tgggctaaag ccctgccagc cgggacatcc gctcagcggg 4860
ctgaactgat agcactcacc caggccctaa agatggcaga aggtaagaag ctaaatgttt 4920
atactgatag ccgttatgct tttgctactg cccatatcca tggagaaata tacagaaggc 4980
gtgggttgct cacatcagaa ggcaaagaga tcaaaaataa agacgagatc ttggccctac 5040
taaaagccct ctttctgccc aaaagactta gcataatcca ttgtccagga catcaaaagg 5100
gacacagcgc cgaggctaga ggcaaccgga tggctgacca agcggcccga aaggcagcca 5160
tcacagagac tccagacacc tctaccctcc tcatagaaaa ttcatcaccc tacacctcag 5220
aacattttca ttacacagtg actgatataa aggacctaac caagttgggg gccatttatg 5280
ataaaacaaa gaagtattgg gtctaccaag gaaaacctgt gatgcctgac cagtttactt 5340
ttgaattatt agactttctt catcagctga ctcacctcag cttctcaaaa atgaaggctc 5400

-continued

```
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc    6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt tacccccctt ccactaccag   7200
tacaccctca acctccccta caagtccaag tgtcccacag ccaccccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
```

-continued

```
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtg taccttatat   8340
aagggggtgg gggcgcgttc gtcctcagtc gcgatcgaac actcgagccg agcagacgtg   8400
cctacggacc gttataaatg ggagtcaaag ttctgtttgc cctgatctgc atcgctgtgg   8460
ccgaggccaa gcccaccgag aacaacgaag acttcaacat cgtggccgtg gccagcaact   8520
tcgcgaccac ggatctcgat gctgaccgcg ggaagttgcc cggcaagaag ctgccgctgg   8580
aggtgctcaa agagatggaa gccaatgccc ggaaagctgg ctgcaccagg ggctgtctga   8640
tctgcctgtc ccacatcaag tgcacgccca agatgaagaa gttcatccca ggacgctgcc   8700
acacctacga aggcgacaaa gagtccgcac agggcggcat aggcgaggcg atcgtcgaca   8760
ttcctgagat tcctgggttc aaggacttgg agcccatgga gcagttcatc gcacaggtcg   8820
atctgtgtgt ggactgcaca actggctgcc tcaaagggct tgccaacgtg cagtgttctg   8880
acctgctcaa gaagtggctg ccgcaacgct gtgcgacctt tgccagcaag atccagggcc   8940
aggtggacaa gatcaagggg gccggtggtg actaagcggc cgcagataaa ataaaagatt   9000
ttatttagtc tccagaaaaa ggggggaatg aaagacccca cctgtaggtt tggcaagcta   9060
gcttaagtaa cgccattttg caaggcatgg aaaaatacat aactgagaat agagaagttc   9120
agatcaaggt caggaacaga tggaacagct gaatatgggc caaacaggat atctgtggta   9180
agcagttcct gccccggctc agggccaaga acagatggaa cagctgaata tgggccaaac   9240
aggatatctg tggtaagcag ttcctgcccc ggctcagggc caagaacaga tggtccccag   9300
atgcggtcca gccctcagca gtttctagag aaccatcaga tgtttccagg gtgccccaag   9360
gacctgaaat gaccctgtgc cttatttgaa ctaaccaatc agttcgcttc tcgcttctgt   9420
tcgcgcgctt ctgctccccg agctcaataa aagagcccac aacccctcac tcggggcgcc   9480
agtcctccga ttgactgagt cgcccgggta cccgtgtatc caataaaccc tcttgcagtt   9540
gcatccgact tgtggtctcg ctgttccttg ggagggtctc ctctgagtga ttgactaccc   9600
gtcagcgggg gtctttcatt acatgtgagc aaaaggccag caaaaggcca ggaaccgtaa   9660
aaaggccgcg ttgctggcgt ttttccatag gctccgcccc cctgacgagc atcacaaaaa   9720
tcgacgctca agtcagaggt ggcgaaaccc gacaggacta taaagatacc aggcgtttcc   9780
ccctggaagc tccctcgtgc gctctcctgt tccgaccctg ccgcttaccg gatacctgtc   9840
cgcctttctc ccttcgggaa gcgtggcgct ttctcatagc tcacgctgta ggtatctcag   9900
ttcggtgtag gtcgttcgct ccaagctggg ctgtgtgcac gaaccccccg ttcagcccga   9960
ccgctgcgcc ttatccggta actatcgtct tgagtccaac ccggtaagac acgacttatc  10020
gccactggca gcagccactg gtaacaggat tagcagagcg aggtatgtag gcggtgctac  10080
agagttcttg aagtggtggc ctaactacgg ctacactaga aggacagtat ttggtatctg  10140
```

```
cgctctgctg aagccagtta ccttcggaaa aagagttggt agctcttgat ccggcaaaca  10200
aaccaccgct ggtagcggtg gtttttttgt ttgcaagcag cagattacgc gcagaaaaaa  10260
aggatctcaa gaagatcctt tgatcttttc tacggggtct gacgctcagt ggaacgaaaa  10320
ctcacgttaa gggattttgg tcatgagatt atcaaaaagg atcttcacct agatcctttt  10380
aaattaaaaa tgaagtttta aatcaatcta aagtatatat gagtaaactt ggtctgacag  10440
ttaccaatgc ttaatcagtg aggcacctat ctcagcgatc tgtctatttc gttcatccat  10500
agttgcctga ctccccgtcg tgtagataac tacgatacgg gagggcttac catctggccc  10560
cagtgctgca atgataccgc gagacccacg ctcaccggct ccagatttat cagcaataaa  10620
ccagccagcc ggaagggccg agcgcagaag tggtcctgca actttatccg cctccatcca  10680
gtctattaat tgttgccggg aagctagagt aagtagttcg ccagttaata gtttgcgcaa  10740
cgttgttgcc attgctgcag gcatcgtggt gtcacgctcg tcgtttggta tggcttcatt  10800
cagctccggt tcccaacgat caaggcgagt tacatgatcc cccatgttgt gcaaaaaagc  10860
ggttagctcc ttcggtcctc cgatcgttgt cagaagtaag ttggccgcag tgttatcact  10920
catggttatg gcagcactgc ataattctct tactgtcatg ccatccgtaa gatgcttttc  10980
tgtgactggt gagtactcaa ccaagtcatt ctgagaatag tgtatgcggc gaccgagttg  11040
ctcttgcccg gcgtcaacac gggataatac cgcgccacat agcagaactt taaaagtgct  11100
catcattgga aaacgttctt cggggcgaaa actctcaagg atcttaccgc tgttgagatc  11160
cagttcgatg taacccactc gtgcacccaa ctgatcttca gcatctttta ctttcaccag  11220
cgtttctggg tgagcaaaaa caggaaggca aaatgccgca aaaaagggaa taagggcgac  11280
acggaaatgt tgaatactca tactcttcct ttttcaatat tattgaagca tttatcaggg  11340
ttattgtctc atgagcggat acatatttga atgtatttag aaaaataaac aaataggggt  11400
tccgcgcaca tttccccgaa aagtgccacc tgacgtctaa gaaaccatta ttatcatgac  11460
attaacctat aaaaataggc gtatcacgag gccctttcgt cttcaagaat tccat       11515
```

<210> SEQ ID NO 85
<211> LENGTH: 11614
<212> TYPE: DNA
<213> ORGANISM: Artificial Sequence
<220> FEATURE:
<223> OTHER INFORMATION: pAC3-EC1-Gluc

<400> SEQUENCE: 85

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
```

```
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccttgaac    1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac caccccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
```

```
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
```

tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc ccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca cccccctggga 6840
cacgggatgc tctaaagttg cctgtggccc ctgctacgac ctctccaaag tatccaattc 6900
cttccaaggg gctactcgag gggcagatgg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagccccct caataccagt tacccccctt ccactaccag 7200
tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800

-continued

```
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtg aattgacgca   8340
tatattgacg catattgacg caaattgacg caaatgacag caagattgac gcaaattgag   8400
cgcaaattga cgcaaattaa ttgacgcata ggtctatata agcagagctc gtttagtgaa   8460
ccgtcagatc gcctggagac gccatccacg ctgttttgac ctccatagaa ttataaatgg   8520
gagtcaaagt tctgtttgcc ctgatctgca tcgctgtggc cgaggccaag cccaccgaga   8580
acaacgaaga cttcaacatc gtggccgtgg ccagcaactt cgcgaccacg gatctcgatg   8640
ctgaccgcgg gaagttgccc ggcaagaagc tgccgctgga ggtgctcaaa gagatggaag   8700
ccaatgcccg gaaagctggc tgcaccaggg gctgtctgat ctgcctgtcc cacatcaagt   8760
gcacgcccaa gatgaagaag ttcatcccag gacgctgcca cacctacgaa ggcgacaaag   8820
agtccgcaca gggcggcata ggcgaggcga tcgtcgacat tcctgagatt cctgggttca   8880
aggacttgga gcccatggag cagttcatcg cacaggtcga tctgtgtgtg gactgcacaa   8940
ctggctgcct caaagggctt gccaacgtgc agtgttctga cctgctcaag aagtggctgc   9000
cgcaacgctg tgcgaccttt gccagcaaga tccagggcca ggtggacaag atcaaggggg   9060
ccggtggtga ctaagcggcc gcagataaaa taaaagattt tatttagtct ccagaaaaag   9120
gggggaatga aagaccccac ctgtaggttt ggcaagctag cttaagtaac gccattttgc   9180
aaggcatgga aaaatacata actgagaata gagaagttca gatcaaggtc aggaacagat   9240
ggaacagctg aatatgggcc aaacaggata tctgtggtaa gcagttcctg ccccggctca   9300
gggccaagaa cagatggaac agctgaatat gggccaaaca ggatatctgt ggtaagcagt   9360
tcctgccccg gctcagggcc aagaacagat ggtccccaga tgcggtccag ccctcagcag   9420
tttctagaga accatcagat gtttccaggg tgccccaagg acctgaaatg accctgtgcc   9480
ttatttgaac taaccaatca gttcgcttct cgcttctgtt cgcgcgcttc tgctccccga   9540
gctcaataaa agagcccaca acccctcact cggggcgcca gtcctccgat tgactgagtc   9600
gcccgggtac ccgtgtatcc aataaaccct cttgcagttg catccgactt gtggtctcgc   9660
tgttccttgg gagggtctcc tctgagtgat tgactacccg tcagcggggg tctttcatta   9720
catgtgagca aaaggccagc aaaaggccag gaaccgtaaa aaggccgcgt tgctggcgtt   9780
tttccatagg ctccgccccc ctgacgagca tcacaaaaat cgacgctcaa gtcagaggtg   9840
gcgaaacccg acaggactat aaagatacca ggcgtttccc cctggaagct ccctcgtgcg   9900
ctctcctgtt ccgaccctgc cgcttaccgg atacctgtcc gcctttctcc cttcgggaag   9960
cgtggcgctt tctcatagct cacgctgtag gtatctcagt tcggtgtagg tcgttcgctc  10020
caagctgggc tgtgtgcacg aaccccccgt tcagcccgac cgctgcgcct tatccggtaa  10080
ctatcgtctt gagtccaacc cggtaagaca cgacttatcg ccactggcag cagccactgg  10140
taacaggatt agcagagcga ggtatgtagg cggtgctaca gagttcttga agtggtggcc  10200
```

```
taactacggc tacactagaa ggacagtatt tggtatctgc gctctgctga agccagttac  10260

cttcggaaaa agagttggta gctcttgatc cggcaaacaa accaccgctg gtagcggtgg  10320

tttttttgtt tgcaagcagc agattacgcg cagaaaaaaa ggatctcaag aagatccttt  10380

gatcttttct acggggtctg acgctcagtg gaacgaaaac tcacgttaag ggattttggt  10440

catgagatta tcaaaaagga tcttcaccta gatcctttta aattaaaaat gaagttttaa  10500

atcaatctaa agtatatatg agtaaacttg gtctgacagt taccaatgct taatcagtga  10560

ggcacctatc tcagcgatct gtctatttcg ttcatccata gttgcctgac tccccgtcgt  10620

gtagataact acgatacggg agggcttacc atctggcccc agtgctgcaa tgataccgcg  10680

agacccacgc tcaccggctc cagatttatc agcaataaac cagccagccg gaagggccga  10740

gcgcagaagt ggtcctgcaa ctttatccgc ctccatccag tctattaatt gttgccggga  10800

agctagagta agtagttcgc cagttaatag tttgcgcaac gttgttgcca ttgctgcagg  10860

catcgtggtg tcacgctcgt cgtttggtat ggcttcattc agctccggtt cccaacgatc  10920

aaggcgagtt acatgatccc ccatgttgtg caaaaaagcg gttagctcct tcggtcctcc  10980

gatcgttgtc agaagtaagt tggccgcagt gttatcactc atggttatgg cagcactgca  11040

taattctctt actgtcatgc catccgtaag atgcttttct gtgactggtg agtactcaac  11100

caagtcattc tgagaatagt gtatgcggcg accgagttgc tcttgcccgg cgtcaacacg  11160

ggataatacc gcgccacata gcagaacttt aaaagtgctc atcattggaa aacgttcttc  11220

ggggcgaaaa ctctcaagga tcttaccgct gttgagatcc agttcgatgt aacccactcg  11280

tgcacccaac tgatcttcag catcttttac tttcaccagc gtttctgggt gagcaaaaac  11340

aggaaggcaa aatgccgcaa aaaagggaat aagggcgaca cggaaatgtt gaatactcat  11400

actcttcctt tttcaatatt attgaagcat ttatcagggt tattgtctca tgagcggata  11460

catatttgaa tgtatttaga aaaataaaca aataggggtt ccgcgcacat ttccccgaaa  11520

agtgccacct gacgtctaag aaaccattat tatcatgaca ttaacctata aaaataggcg  11580

tatcacgagg ccctttcgtc ttcaagaatt ccat                              11614
```

<210> SEQ ID NO 86
<211> LENGTH: 11614
<212> TYPE: DNA
<213> ORGANISM: Artificial Sequence
<220> FEATURE:
<223> OTHER INFORMATION: pAC3-ES1-Gluc

<400> SEQUENCE: 86

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cggcgccagt cctccgattg    600
```

```
actgagtcgc ccgggtaccc gtgtatccaa taaaccctct tgcagttgca tccgacttgt     660
ggtctcgctg ttccttggga gggtctcctc tgagtgattg actacccgtc agcgggggtc     720
tttcatttgg gggctcgtcc gggatcggga gacccctgcc cagggaccac cgacccacca     780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc ccagggactt     960
cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaaa    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440
tcccctacat cgtgacctgg gaagccttgg cttttgaccc ccctccctgg gtcaagccct    1500
ttgtacaccc taagcctccg cctcctcttc ctccatccgc cccgtctctc cccccttgaac   1560
ctcctcgttc gaccccgcct cgatcctccc tttatccagc cctcactcct tctctaggcg    1620
ccaaacctaa acctcaagtt ctttctgaca gtgggggggcc gctcatcgac ctacttacag   1680
aagacccccc gccttatagg gacccaagac caccccccttc cgacagggac ggaaatggtg   1740
gagaagcgac ccctgcggga gaggcaccgg accccctcccc aatggcatct cgcctacgtg   1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgtcc   1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc ggggggcaac    2880
ccgtcacctt cctggtagat actggggccc aacactccgt gctgacccaa aatcctggac    2940
ccctaagtga taagtctgcc tgggtccaag ggctactgg aggaaagcgg tatcgctgga     3000
```

```
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
```

ttgaattatt agactttctt catcagctga ctcacctcag cttctcaaaa atgaaggctc 5400
tcctagagag aagccacagt ccctactaca tgctgaaccg ggatcgaaca ctcaaaaata 5460
tcactgagac ctgcaaagct tgtgcacaag tcaacgccag caagtctgcc gttaaacagg 5520
gaactagggt ccgcgggcat cggcccggca ctcattggga gatcgatttc accgagataa 5580
agcccggatt gtatggctat aaatatcttc tagtttttat agataccttt tctggctgga 5640
tagaagcctt cccaaccaag aaagaaaccg ccaaggtcgt aaccaagaag ctactagagg 5700
agatcttccc caggttcggc atgcctcagg tattgggaac tgacaatggg cctgccttcg 5760
tctccaaggt gagtcagaca gtggccgatc tgttggggat tgattggaaa ttacattgtg 5820
catacagacc ccaaagctca ggccaggtag aaagaatgaa tagaaccatc aaggagactt 5880
taactaaatt aacgcttgca actggctcta gagactgggt gctcctactc cccttagccc 5940
tgtaccgagc ccgcaacacg ccgggccccc atggcctcac cccatatgag atcttatatg 6000
gggcaccccc gccccttgta aacttccctg accctgacat gacaagagtt actaacagcc 6060
cctctctcca agctcactta caggctctct acttagtcca gcacgaagtc tggagacctc 6120
tggcggcagc ctaccaagaa caactggacc gaccggtggt acctcaccct taccgagtcg 6180
gcgacacagt gtgggtccgc cgacaccaga ctaagaacct agaacctcgc tggaaaggac 6240
cttacacagt cctgctgacc acccccaccg ccctcaaagt agacggcatc gcagcttgga 6300
tacacgccgc ccacgtgaag gctgccgacc ccgggggtgg accatcctct agactgacat 6360
ggcgcgttca acgctctcaa aaccccctca agataagatt aacccgtgga agcccttaat 6420
agtcatggga gtcctgttag gagtagggat ggcagagagc cccccatcagg tctttaatgt 6480
aacctggaga gtcaccaacc tgatgactgg gcgtaccgcc aatgccacct ccctcctggg 6540
aactgtacaa gatgccttcc caaaattata ttttgatcta tgtgatctgg tcggagagga 6600
gtgggaccct tcagaccagg aaccgtatgt cgggtatggc tgcaagtacc ccgcagggag 6660
acagcggacc cggacttttg acttttacgt gtgccctggg cataccgtaa agtcggggtg 6720
tgggggacca ggagagggct actgtggtaa atgggggtgt gaaaccaccg gacaggctta 6780
ctggaagccc acatcatcgt gggacctaat ctcccttaag cgcggtaaca ccccctggga 6840
cacgggatgc tctaaagttg cctgtggccc ctgctacgac ctctccaaag tatccaattc 6900
cttccaaggg gctactcgag gggcagatg caaccctcta gtcctagaat tcactgatgc 6960
aggaaaaaag gctaactggg acgggcccaa atcgtgggga ctgagactgt accggacagg 7020
aacagatcct attaccatgt tctccctgac ccggcaggtc cttaatgtgg gaccccgagt 7080
ccccataggg cccaacccag tattacccga ccaaagactc ccttcctcac caatagagat 7140
tgtaccggct ccacagccac ctagcccct caataccagt taccccccttt ccactaccag 7200
tacaccctca acctccccta caagtccaag tgtcccacag ccacccccag gaactggaga 7260
tagactacta gctctagtca aaggagccta tcaggcgctt aacctcacca atcccgacaa 7320
gacccaagaa tgttggctgt gcttagtgtc gggacctcct tattacgaag gagtagcggt 7380
cgtgggcact tataccaatc attccaccgc tccggccaac tgtacggcca cttcccaaca 7440
taagcttacc ctatctgaag tgacaggaca gggcctatgc atgggggcag tacctaaaac 7500
tcaccaggcc ttatgtaaca ccacccaaag cgccggctca ggatcctact accttgcagc 7560
acccgccgga acaatgtggg cttgcagcac tggattgact ccctgcttgt ccaccacggt 7620
gctcaatcta accacagatt attgtgtatt agttgaactc tggcccagag taatttacca 7680
ctcccccgat tatatgtatg gtcagcttga acagcgtacc aaatataaaa gagagccagt 7740
atcattgacc ctggcccttc tactaggagg attaaccatg ggagggattg cagctggaat 7800
agggacgggg accactgcct taattaaaac ccagcagttt gagcagcttc atgccgctat 7860
ccagacagac ctcaacgaag tcgaaaagtc aattaccaac ctagaaaagt cactgacctc 7920
gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgtg aattgacgca 8340
tatattgacg catattgacg caaattgacg caaatgacag caagattgac gcaaattgag 8400
cgcaaattga cgcaaattaa ttgacgcatg tacttatata agggggtggg ggcgcgttcg 8460
tcctcagtcg cgatcgaaca ctcgagccga gcagacgtgc ctacggaccg ttataaatgg 8520
gagtcaaagt tctgtttgcc ctgatctgca tcgctgtggc cgaggccaag cccaccgaga 8580
acaacgaaga cttcaacatc gtggccgtgg ccagcaactt cgcgaccacg gatctcgatg 8640
ctgaccgcgg gaagttgccc ggcaagaagc tgccgctgga ggtgctcaaa gagatggaag 8700
ccaatgcccg gaaagctggc tgcaccaggg gctgtctgat ctgcctgtcc cacatcaagt 8760
gcacgcccaa gatgaagaag ttcatcccag gacgctgcca cacctacgaa ggcgacaaag 8820
agtccgcaca gggcggcata ggcgaggcga tcgtcgacat tcctgagatt cctgggttca 8880
aggacttgga gcccatggag cagttcatcg cacaggtcga tctgtgtgtg gactgcacaa 8940
ctggctgcct caaagggctt gccaacgtgc agtgttctga cctgctcaag aagtggctgc 9000
cgcaacgctg tgcgaccttt gccagcaaga tccagggcca ggtggacaag atcaaggggg 9060
ccggtggtga ctaagcggcc gcagataaaa taaaagattt tatttagtct ccagaaaaag 9120
gggggaatga aagaccccac ctgtaggttt ggcaagctag cttaagtaac gccattttgc 9180
aaggcatgga aaaatacata actgagaata gagaagttca gatcaaggtc aggaacagat 9240
ggaacagctg aatatgggcc aaacaggata tctgtggtaa gcagttcctg ccccggctca 9300
gggccaagaa cagatggaac agctgaatat gggccaaaca ggatatctgt ggtaagcagt 9360
tcctgccccg gctcagggcc aagaacagat ggtccccaga tgcggtccag ccctcagcag 9420
tttctagaga accatcagat gtttccaggg tgccccaagg acctgaaatg accctgtgcc 9480
ttatttgaac taaccaatca gttcgcttct cgcttctgtt cgcgcgcttc tgctccccga 9540
gctcaataaa agagcccaca acccctcact cggggcgcca gtcctccgat tgactgagtc 9600
gcccgggtac ccgtgtatcc aataaaccct cttgcagttg catccgactt gtggtctcgc 9660
tgttccttgg gagggtctcc tctgagtgat tgactacccg tcagcggggg tctttcatta 9720
catgtgagca aaaggccagc aaaaggccag gaaccgtaaa aaggccgcgt tgctggcgtt 9780
tttccatagg ctccgccccc ctgacgagca tcacaaaaat cgacgctcaa gtcagaggtg 9840
gcgaaacccg acaggactat aaagatacca ggcgtttccc cctggaagct ccctcgtgcg 9900
ctctcctgtt ccgaccctgc cgcttaccgg atacctgtcc gcctttctcc cttcgggaag 9960
cgtggcgctt tctcatagct cacgctgtag gtatctcagt tcggtgtagg tcgttcgctc 10020
caagctgggc tgtgtgcacg aaccccccgt tcagcccgac cgctgcgcct tatccggtaa 10080

-continued

```
ctatcgtctt gagtccaacc cggtaagaca cgacttatcg ccactggcag cagccactgg  10140

taacaggatt agcagagcga ggtatgtagg cggtgctaca gagttcttga agtggtggcc  10200

taactacggc tacactagaa ggacagtatt tggtatctgc gctctgctga agccagttac  10260

cttcggaaaa agagttggta gctcttgatc cggcaaacaa accaccgctg gtagcggtgg  10320

tttttttgtt tgcaagcagc agattacgcg cagaaaaaaa ggatctcaag aagatccttt  10380

gatcttttct acggggtctg acgctcagtg gaacgaaaac tcacgttaag ggattttggt  10440

catgagatta tcaaaaagga tcttcaccta gatcctttta aattaaaaat gaagttttaa  10500

atcaatctaa agtatatatg agtaaacttg gtctgacagt taccaatgct taatcagtga  10560

ggcacctatc tcagcgatct gtctatttcg ttcatccata gttgcctgac tccccgtcgt  10620

gtagataact acgatacggg agggcttacc atctggcccc agtgctgcaa tgataccgcg  10680

agacccacgc tcaccggctc cagatttatc agcaataaac cagccagccg gaagggccga  10740

gcgcagaagt ggtcctgcaa ctttatccgc ctccatccag tctattaatt gttgccggga  10800

agctagagta agtagttcgc cagttaatag tttgcgcaac gttgttgcca ttgctgcagg  10860

catcgtggtg tcacgctcgt cgtttggtat ggcttcattc agctccggtt cccaacgatc  10920

aaggcgagtt acatgatccc ccatgttgtg caaaaaagcg gttagctcct tcggtcctcc  10980

gatcgttgtc agaagtaagt tggccgcagt gttatcactc atggttatgg cagcactgca  11040

taattctctt actgtcatgc catccgtaag atgcttttct gtgactggtg agtactcaac  11100

caagtcattc tgagaatagt gtatgcggcg accgagttgc tcttgcccgg cgtcaacacg  11160

ggataatacc gcgccacata gcagaacttt aaaagtgctc atcattggaa aacgttcttc  11220

ggggcgaaaa ctctcaagga tcttaccgct gttgagatcc agttcgatgt aacccactcg  11280

tgcacccaac tgatcttcag catcttttac tttcaccagc gtttctgggt gagcaaaaac  11340

aggaaggcaa aatgccgcaa aaaagggaat aagggcgaca cggaaatgtt gaatactcat  11400

actcttcctt tttcaatatt attgaagcat ttatcagggt tattgtctca tgagcggata  11460

catatttgaa tgtatttaga aaaataaaca aataggggtt ccgcgcacat ttccccgaaa  11520

agtgccacct gacgtctaag aaaccattat tatcatgaca ttaacctata aaaataggcg  11580

tatcacgagg ccctttcgtc ttcaagaatt ccat                             11614
```

RETROVIRAL VECTOR WITH MINI-PROMOTER CASSETTE

CROSS REFERENCE TO RELATED APPLICATIONS

This application is a U.S. National Stage Application filed under 35 U.S.C. § 371 and claims priority to International Application No. PCT/US2013/066709, filed Oct. 24, 2013, which application claims priority to U.S. Provisional Application Ser. No. 61/718,610, filed Oct. 25, 2012, the disclosure of which is incorporated herein by reference.

TECHNICAL FIELD

This disclosure relates to retroviral replicating vectors (RRV) for treating cell proliferative. The disclosure further relates to the use of such retroviral replicating vectors for delivery and expression of heterologous nucleic acids.

BACKGROUND

The development of effective methods of delivering genes and heterologous nucleic acids to cells and subjects has been a goal for possible treatments of diseases and disorders.

Replicating retroviral vectors (RRV; a.k.a. replication competent retroviruses) have been used to selectively infect tumors in animal models (Wang et al., Hum. Gene. Ther., 14:117-127, 2003, Tai et al., Mol Ther, 12:842-851, 2005), where replication occurs through the tumor. The conventional strategy for transgene expression has been to use an IRES component to allow internal initiation of translation from the internal ribosome binding site. The IRES component is about 600 bp leaving approximately 900 bp for coding sequence in size-limited vectors. If the vector is equipped with a prodrug-activating gene such as cytosine deaminase or purine nucleotide phosphorylase expressed from an internal IRES sequence, then the tumor can be eliminated or growth/spreading inhibited by subsequent treatment with prodrugs (e.g., 5-fluorocytosine, which is converted in situ by cytosine deaminase to the anti-cancer drug 5-fluorouracil (Tai et al., Mol Ther., 12:117-127, 2005, Ostertag et al., Neuro Oncol., 2012)). Such vectors are now in the clinic for experimental treatment of primary brain cancer (see the World Wide Web at clinicaltrials.gov, NCT01156584). However the genetic stability of such an RRV is significantly reduced when the total insert size exceeds approximately 1.5 kb, so that a number of potentially useful genes or gene combinations are not guaranteed to be stable enough for easy and reliable therapeutic use. A particular example is the commonly used prodrug activating gene from herpes thymidine kinase (HSVtk)(SEQ ID NO:35) that can activate common anti-herpetic drugs such as ganciclovir, acyclovir, valacyclovir (Valtrex™) or other analogues by phosphorylation in situ leading to cell killing. The HSVtk gene has a coding sequence of just over 1.1 kb and when combined with an IRES used in some expression constructs results in an insert of greater than about 1.6 kb. This size is not sufficiently stable for clinical use. Another example is the combination of the cytosine deamine gene (SEQ ID NO:1 or 3) with the UPRT gene (SEQ ID NO:7) or OPRT gene (WO2010036986, Perez et al., Mol. Ther., 2005), where these fusion genes are about 1200 bp. When combined with an IRES the size exceeds about 1.8 kb and showed undesirable instability although expression, before deletions occurred, was satisfactory.

Logg et al. (PNAS, 105(12):4733-4738, 2008) tried various shorter sequences of IRES constructs to improve the size of the heterologous gene incorporated into the RRV with limited success. Specifically, Logg et al. demonstrated the expression could be obtained, however, stability was reduced due to the nature of the smaller IRES's having a splice donor/acceptor role.

SUMMARY

This disclosure provides methods and compositions that allow the stable expression in vivo of a gene or multiple genes exceeding a total size of about 0.9 kb in a replicating vector. The disclosure provides vectors comprising at least one mini-promoter cassette capable of expressing heterologous gene(s) that can be greater than 1.2, 1.3, 1.4, 1.5, 1.6, 1.7, 1.8, or 1.9 kb. If one considers a therapeutic cassette to be a plurality of mini-promoter cassettes or a single mini-promoter cassette and a second cassette comprising a polIII promoter or IRES operably linked to a second therapeutic molecule then the overall therapeutic cassette can comprise about 1.2-2.0 kb. For example, where two mini-promoter cassettes are present in a therapeutic cassette, a first mini-cassette can express a first gene or therapeutic molecule, while the second cassette can express a second gene or therapeutic molecule.

Also disclosed are novel minipromoters contructs in a recombinant replication competent retrovirus (RRV) for driving expression of genes that are about 1.2 kb. With the foregoing general concept in mind, the disclosure provides a recombinant replication competent retrovirus (RRV) comprising: a retroviral GAG protein; a retroviral POL protein; a retroviral envelope (ENV); a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a therapeutic cassette comprising at least one mini-promoter operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell. In one embodiment, the therapeutic cassette comprises a least one core- or mini-promoter and enhancer operably linked to a heterologous polynucleotide. In one embodiment, the retroviral polynucleotide sequence is derived from a gamma retrovirus, such as murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In another embodiment, the MLV is an amphotropic MLV or an ecotropic MLV with an amphotropic or GALV envelope gene. In yet another embodiment, the retrovirus is an oncoretrovirus or gamma retrovirus. In yet another embodiment, the vector comprises the mini-promoter cassette can infect a mammalian target cell. In another embodiment, the target cell is a cell having aberrant proliferative capacity such as those associated with a cell proliferative disorder. The cell proliferative disorder can be selected from the group consisting of, but is not limited to, neoplasias and autoimmune diseases. In one embodiment, the promoter for transcription of the RRV genome comprises a CMV promoter. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In another embodiment, the gag and pol of the polynucleotide are derived from an oncoretrovirus or gamma retrovirus. In one embodiment, the env domain encodes an amphotropic ENV protein. In yet a further embodiment of any of the foregoing, the therapeutic cassette comprises at least one mini-promoter cassette and can also include an enhancer and which comprises a therapeutic (heterologous) polynucleotide sequence that upon expression codes for a therapeutic protein or a therapeutic nucleic acid (e.g., an siRNA, shRNA, microRNA or the like). In one embodiment, the mini-promoter cassette is a promoter for RNA polymerase II. In another embodiment, the mini-promoter cassette is a promoter for RNA polymerase III (e.g., a U6 promoter). In one embodiment, the therapeutic cassette comprises a single mini-promoter cassette comprising a mini-promoter and enhancer operably linked to a coding sequence for a therapeutic molecule or molecules. In another embodiment, the therapeutic cassette comprises at least one mini-promoter cassette and a second cassette. The second cassette may be a second mini-promoter cassette, an IRES cassette or a polIII promoter cassette. The mini-promoter promotes transcription of an operably linked gene or coding nucleic acid sequence.

A mini-promoter, as the name refers, includes the minimal amount of elements necessary for effective transcription and/or translation of an operably linked coding sequence and has better expression than a core promoter. A mini-promoter can include a core promoter, but also includes additional regulatory domains that promote transcription. A mini-promoter is about 100-600 bp in length while a core promoter is typically less than about 100 bp (e.g., about 70-80 bp). Where a therapeutic cassette comprises a core promoter, a second cassette (e.g., a second mini-promoter cassette, polIII promoter cassette or IRES cassette) will be present or the core promoter will be accompanied by an enhancer. Furthermore, where a core promoter is present, the cassette will typically comprise an enhancer element or another element either upstream or downstream of the core promoter sequence that facilitates expression of an operably linked coding sequence above the expression levels of the core promoter alone.

Accordingly, the disclosure provides small regulatory promoter domains (e.g., modified core promoters) derived from either cellular elements as determined for "core promoter" elements (<100, <200, <400 or <600 bp) that allow ubiquitous expression at significant levels in target cells and are useful for stable incorporation into vectors, in general, and replicating retroviral vectors, in particular, to allow efficient expression of transgenes. Also provided are core promoters plus minimal enhancer sequences to allow better gene expression, that are still under 200, 400 or 600 bp. Such enhanced promoters include modified core promoters, naturally occurring tissue specific promoters, small viral promoters such as the Rous Sarcoma virus derived promoters. In yet other embodiments, the therapeutic cassette comprising at least one mini-promoter cassette will have expression levels that are greater than or about equal to or about 1 fold to 2 fold less than the expression levels of an IRES cassette with the same gene.

The vector can comprise any number of different heterologous polynucleotides operably inked to a core- or mini-promoter. For example, the heterologous polynucleotide can comprise a cytokine gene, an siRNA, microRNA or RNAi molecules, a targeting sequence, a binding domain, a cytotoxic gene, a single chain antibody or any combination thereof. When the heterologous polynucleotide is a non-translated RNA such as siRNA, microRNA or RNAi then no mini-promoter may be necessary, but may be included in combination with a transcribed gene. In yet a further embodiment, the heterologous polynucleotide comprises a polynucleotide having a sequence as set forth in SEQ ID NO: 3 (CDopt-3pt), 5 (CDopt), 11 (CDopt-UPRT), 13 (CDopt-linker-UPRT), 15 (CDopt3-OPRT), 17 (CDopt3-linker-OPRT), or 75 (HSVtkopt). In a further embodiment, the heterologous sequence encodes a polypeptide comprising a sequence as set forth in SEQ ID NO: 4 or 76. In one embodiment, the heterologous nucleic acid is human codon optimized and encodes a polypeptide as set forth in SEQ ID NO:4 or 76.

The disclosure provides an isolated polynucleotide comprising from 5' to 3': a CMV-R-U5 fusion of the immediate early promoter from human cytomegalovirus to an MLV R-U5 region; a PBS, primer binding site for reverse transcriptase; a 5' splice site; ψ packaging signal; a gag coding sequence for MLV group specific antigen; a pol coding sequence for MLV polymerase polyprotein; a 3' splice site; a 4070A env coding sequence for envelope protein of MLV strain 4070A; at least one mini-promoter cassettes operably linked to a therapeutic gene; a polypurine tract; and a U3-R-U5 MLV long terminal repeat. In one embodiment, the 3' LTR is derived from an oncoretrovirus or gamma-retrovirus. In a further embodiment, the 3' LTR comprises a U3-R-U5 domain.

The disclosure provides a method of treating a cell proliferative disorder in a subject comprising contacting the subject or cell with a retrovirus of the disclosure, wherein the heterologous nucleic acid sequence encodes a therapeutic protein that inhibits proliferation of a neoplastic cell. In one embodiment, the retrovirus comprises a polynucleotide encoding a polypeptide having a sequence as set forth in SEQ ID NO: 4, 12, 14, 16, 18 or 76, wherein the polynucleotide is operably linked to a mini-promoter.

The disclosure provides the sequences of certain RRVs having promoter cassettes operably linked to a cytotoxic gene. For example, SEQ ID NO:19 depicts a pAC3-C1.yCD2 vector wherein the vector comprises a gag, pol and env sequence, the env sequence immediately followed by a promoter CMV core promoter and a humanized cytosine deaminase with 3 heat stabilized mutation, which is then followed by the 3' LTR. SEQ ID NO:20 depicts a similar structure however, the cassette comprises an S1 promoter followed by the transgene of human GMCSF. SEQ ID NO:21 shows the sequence of a an RRV vector "pACE-CD". SEQ ID NO:22 shows a sequence similar to SEQ ID NO:19 and 20 except the promoter cassette comprises an S1 promoter operably linked to murine GMCSF. SEQ ID NO:39 shows the sequence of an RRV having an S1-yCD2 cassette. SEQ ID NO:40 shows the sequence of an RRV having a C1-GFP cassette. SEQ ID NO:41 shows the sequence of an RRV having an S1-GFP cassette. Other vectors of the disclosure comprising mini-promoters linked to heterologous nucleic acids are set forth in SEQ ID NOs: 77-85 and 86.

The disclosure provides a vector comprising a recombinant replication competent retrovirus (RRV) and having a mini-promoter cassette, wherein the vector infects a target cell multiple times leading to a mean of 3 or more copies of the retrovirus genome per target cell. The multiple copies provide a "super" infection useful for gene delivery and protein production in vivo and in vitro. In one embodiment, the RRV comprises: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising at least one mini-promoter or core-promoter and enhancer operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RRV maintains higher replication competency after 6 passages compared to a pACE vector (SEQ ID NO:21, i.e., the vector of Logg et al., Hum Gene Ther. 2001 May 20; 12(8):921-32). In one embodiment, the retroviral polynucleotide sequence is derived from murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In another embodiment, the MLV is an amphotropic MLV. In yet another embodiment, the retrovirus is an oncoretrovirus or gamma retrovirus. In yet another embodiment, the target cell is a cell having aberrant cell proliferative capacity such as those associated with a cell proliferative disorder (e.g., a cancer cell). The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, lymphoma, leukemia, rheumatoid arthritis and other autoimmune diseases. In one embodiment, the vector can comprise a promoter to drive transcription of the gag, pol and env such as a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO: 19, 20 or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO: 19, 20 or 22 from about nucleotide 1 to about nucleotide 1202 or sequences that are at least 95% identical to a sequence as set forth in SEQ ID NO: 19, 20 or 22, wherein the polynucleotide promotes transcription of a nucleic acid molecule operably linked thereto. In another embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO: 19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO: 19 or 22 or a sequence having at least 95%, 98%, 99% or 99.8% identity thereto. The mini-promoter of the vector can be any regulatory domain that is smaller than 600 bp (e.g., about 600 bp, 550 bp, 500 bp, 450 bp, 400 bp, 350 bp, 300 bp, 250 bp, 200 bp, 150 bp, 100 bp, about 90 bp, about 80 bp, about 76 bp, about 74 bp or smaller) and allows for transcription of an operably linked coding sequence or non-coding sequence. In one embodiment the mini-promoter comprises a sequence from about nucleotide number 8330 to about nucleotide 8406 of SEQ ID NO: 19 or 22 or a sequence having at least 95%, 98%, or 99% identity thereto. In another embodiment, the mini-promoter comprises a sequence selected from the group consisting of SEQ ID NO:56, 57, 59, 65, 67, 68, 69, 71, 72, 73, and 74.

The details of one or more embodiments of the disclosure are set forth in the accompanying drawings and the description below. Other features, objects, and advantages will be apparent from the description and drawings, and from the claims.

DETAILED DESCRIPTION

Figure 1:
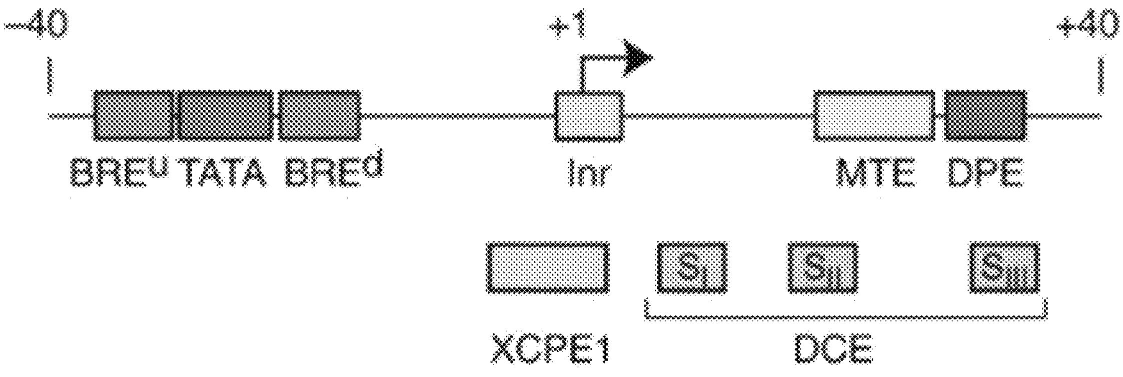
FIG. 1 shows a general structural motif of a core promoter and various elements that can be present (Juven-Gershon & Kadonaga, Developmental Biology 339: 225-229 2010). Typically a core promoter stretches from about −40 bp upstream of the transcription start site to about 40 bp down stream of the start site to initiating translation codon. Abbreviations have the following meanings: BREu—upstream TFIIB Recognition Element; TATA “the tata box”; BREd—downstream TFIIB Recognition Element; Inr—initiator site for transcription; MTE—motif ten element; DPE—downstream promoter element; DCE—downstream core element; XCPE1—X core promoter element 1.

As used herein and in the appended claims, the singular forms "a," "and," and "the" include plural referents unless the context clearly dictates otherwise. Thus, for example, reference to "a cell" includes a plurality of such cells and reference to "the vector" includes reference to one or more vectors and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

General texts and serial volumes, which describe molecular biological techniques useful herein, including the use of vectors, promoters and many other relevant topics, include Methods in Molecular Biology, Series Ed. John M. Walker, Humana Press, ISSN: 1064-3745; Methods in Enzymology, Elsevier Press; company reagent fact sheets and method support publications; scientific networking sites such as Researchgate (world wide web at researchgate.net) and labtests online (e.g., [http://] labtestonline.org/understanding/features/methods/) and individual laboratory sites such as [http://www]cshl.edu.

The publications discussed throughout the text are provided solely for their disclosure prior to the filing date of the present application. Nothing herein is to be construed as an admission that the inventors are not entitled to antedate such disclosure by virtue of prior disclosure.

The disclosure provides methods and compositions useful for gene or protein delivery to a cell or subject. Such methods and compositions can be used to treat various diseases and disorders in a subject including cancer and other cell proliferative diseases and disorders. The disclosure provides retroviral replicating vectors for gene delivery utilizing core-promoter and/or mini-promoter cassettes operably linked to a heterologous polynucleotide to be expressed.

Above a size of about 1.5 kb stability of transgenes in RRV vectors can be variable. The conventional strategy for transgene expression following the successful cloning of an IRES cassette into MLV (Logg et al., supra) has been to use an IRES component to allow internal initiation of translation from the internal ribosome binding site. The IRES component is about 600 bp leaving approximately 900 bp for coding sequence. Accordingly, the size of the polynucleotide linked to the IRES cassette is limited by stability. One alternative to increase the size of the polynucleotide to be expressed or delivered is to use a smaller regulatory sequence that promotes transcription such as a promoter, promoter/enhancer, or other regulatory domains.

Most promoters are rather large; typically over 600 bp for full functionality and the full size of a promoter can be many kilobases. Smaller promoters can be generated that allow reliable expression of transgenes in mammalian cells from vectors such as replicating retroviral vectors (RRVs). For example, one possible solution is to use the "core" promoters described by Kadanaga and collaborators (Juven-Gershon et al., Nature Methods, 11:917-922, 2006). These core promoters are based on the adenovirus major late (AdML) and cytomegalovirus (CMV) major immediate early genes, and the synthetic "super core promoter" SCP1. Other cellular core promoters include, but are not limited to, the human home oxygenase proximal promoter (121 bp; Tyrrell et al., Carcinogenesis, 14: 761-765, 1993), the CTP:phosphocholine cytidylyltransferase (CCT) promoter (240 bp; Zhou et al., Am. J. Respir. Cell Mol. Biol., 30: 61-68, 2004); the Human ASK (for Activator of S phase Kinase, also known as HsDbf4 gene, 63 bp; Yamada et al. J. Biol. Chem., 277: 27668-27681, 2002); and the HSVTK intragenic core (Al-Shawi et al., Mol. Cell. Biol., 11: 4207, 1991; Salamon et al., Mol. Cell. Biol., 15:5322, 1995). Furthermore, these "core" promoters can be used as a starting point for further modifications to improve the activity of the promoter. For example, such modifications including the additional of other domains and sequences to the "core" promoter to improve functionality (e.g., enhancers, Kozak sequences and the like). In one embodiment, such further modifications can includes the addition of enhancers.

The length of these core promoters are approximately 70-80 bp each, thus leaving approximately 1.4 kb of capacity for transgene sequence. The use of such promoters can give useful expression of genes such as the HSVtk gene which is >1.1 kb long. However, such promoters are not always reliable for obtaining levels of expression equivalent to or better than those from the IRES driven expression vectors. Furthermore, there is variability in expression levels from cell to cell and in some cases the levels of expression of the transgene is undetectable. The two CMV and Adenovirus derived core-promoters are even less reliable than the synthetic SCP1 promoter.

The use of core promoters (Juven-Gershon et al., Nat. Methods, 2006; Juven-Gershon and Kadonaga Dev. Biol. 339:225-229, 2010), as described herein, although not as effective as an IRES, allow expression of longer genes, which have therapeutic benefit. Furthermore, using rational design techniques various promoter-components can be used to optimize expression and stability of the RRV. Such optimized core promoters provide a more effective expression and stability of the viral polynucleotide. For example, "designer" promoters can comprise a core promoter that has been further modified to include one or more additional elements suitable for stability and expression.

As described herein, the use of such core promoters either alone or including additional elements for expression can be used in various vectors including replication competent retroviral vectors. The disclosure provides a RRV comprising a therapeutic cassette 3' to the env coding sequence and 5' to the 3' LTR. By "therapeutic cassette" is meant a domain within the RRV that comprises at least one mini-promoter cassette or a core-promoter cassette and one additional cassette (e.g., an IRES, polIII or minipromoter cassette), wherein a therapeutic polynucleotide sequence that upon expression codes for a therapeutic protein (e.g., cytosine deaminse, thymidine kinase and the like) or a therapeutic nucleic acid (e.g., an siRNA, shRNA, microRNA or the like). Accordingly, a "therapeutic cassette" can comprise a single mini-promoter cassette comprising a mini-promoter operably linked to a coding sequence for a therapeutic molecule or molecules, or may include at least one mini-promoter cassette and a second cassette. The second cassette may be a second mini-promoter cassette, a core-promoter cassette, an IRES cassette or a polIII promoter cassette.

As used herein, a "core promoter" refers to a minimal promoter comprising about 50-100 bp and lacks enhancer elements. Such core promoters include, but are not limited to, SCP1, AdML and CMV core promoters. More particularly, where a core-promoter cassette is present a second cassette (e.g., a second mini-promoter cassette, a polIII promoter cassette or IRES cassette) will be present. In some embodiments, a vector comprising a cassette with a core promoter specifically excludes the use of SCP1, AdML and CMV core promoters, but rather utilize designer core promoters as described further herein and below.

Core promoters include certain viral promoters. Viral promoters, as used herein, are promoters that have a core sequence but also usually some further accessory elements. For example, the early promoter for SV40 contains three types of elements: a TATA box, an initiation site and a GC repeat (Barrera-Saldana et al., EMBO J, 4:3839-3849, 1985; Yaniv, Virology, 384:369-374, 2009). The TATA box is located approximately 20 base-pairs upstream from the transcriptional start site. The GC repeat regions is a 21 base-pair repeat containing six GC boxes and is the site that determines the direction of transcription. This core promoter sequence is around 100 bp. Adding an additional 72 base-pair repeats, thus making it a "mini-promoter," is useful as a transcriptional enhancer that increase the functionality of the promoter by a factor of about 10. When the SP1 protein interacts with the 21 bp repeats it binds either the first or the last three GC boxes. Binding of the first three initiates early expression, and binding of the last three initiates late expression. The function of the 72 bp repeats is to enhance the amount of stable RNA and increase the rate of synthesis. This is done by binding (dimerization) with the AP1 (activator protein 1) to give a primary transcript that is 3' polyadenylated and 5' capped. Other viral promoters, such as the Rous Sarcom Virus (RSV), the HBV X gene promoter, and the Herpes Thymidine kinase core promoter can also be used as the basis for selection desired function.

A core promoter typically encompasses −40 to +40 relative to the +1 transcription start site (Juven-Gershon and Kadonaga, Dev. Biol. 339:225-229, 2010), which defines the location at which the RNA polymerase II machinery initiates transcription. Typically, RNA polymerase II interacts with a number of transcription factors that bind to DNA motifs in the promoter. These factors are commonly known as "general" or "basal" transcriptions factors and include, but are not limited to, TFIIA (transcription factor for RNA polymerase IIA), TFIIB, TFIID, TFIIE, TFIIF, and TFIIH. These factors act in a "general" manner with all core promoters; hence they are often referred to as the "basal" transcription factors.

Juven-Gershon et al., 2006 (supra), describe elements of core promoters. For example, the pRC/CMV core promoter consists of a TATA box and is 81 bp in length; the CMV core promoter consists of a TATA box and a initiator site; while the SCP synthetic core promoters (SCP1 and SCP2) consist of a TATA box, an Inr (initiator), an MTE site (Motif Ten Element), and a DPE site (Down stream promoter element) and is about 81 bp in length. The SCP synthetic promoter has improved expression compared to the simple pRC/CMV core promoter.

As used herein a "mini-promoter" or "small promoter" refers to a regulatory domain that promotes transcription of an operably linked gene or coding nucleic acid sequence. The mini-promoter, as the name implies, includes the minimal amount of elements necessary for effective transcription and/or translation of an operably linked coding sequence. A mini-promoter can comprise a "core promoter" in combination with additional regulatory elements or a "modified core promoter". Typically, the mini-promoter or modified core promoter will be about 100-600 bp in length while a core promoter is typically less than about 100 bp (e.g., about 70-80 bp). In other embodiments, where a core promoter is present, the cassette will typically comprise an enhancer element or another element either upstream or downstream of the core promoter sequence that facilitates expression of an operably linked coding sequence above the expression levels of the core promoter alone.

Accordingly, the disclosure provides mini-promoters (e.g., modified core promoters) derived from cellular elements as determined for "core promoter" elements (<100, <200, <400 or <600 bp) that allow ubiquitous expression at significant levels in target cells and are useful for stable incorporation into vectors, in general, and replicating retroviral vectors, in particular, to allow efficient expression of transgenes. Also provided are mini-promoters comprising core promoters plus minimal enhancer sequences and/or Kozak sequences to allow better gene expression compared to a core-promoter lacking such sequences that are still under 200, 400 or 600 bp. Such mini-promoters include modified core promoters and naturally occurring tissue specific promoters such as the elastin promoter (specific for pancreatic acinar cells, (204 bp; Hammer et al., Mol Cell Biol., 7:2956-2967, 1987) and the promoter from the cell cycle dependent ASK gene from mouse and man (63-380 bp; Yamada et al., J. Biol. Chem., 277: 27668-27681, 2002). Ubiquitously expressed small promoters also include viral promoters such as the SV40 early and late promoters (about 340 bp), the RSV LTR promoter (about 270 bp) and the HBV X gene promoter (about 180 bp) (e.g., R Anish et al., PLoS One, 4: 5103, 2009) that has no canonical "TATTAA box" and has a 13 bp core sequence of 5'-CCCCGTTGCCCGG-3' (SEQ ID NO:42). In yet other embodiments, the therapeutic cassette comprising at least one mini-promoter cassette will have expression levels that exceed, are about equal to, or about 1 fold to 2.5 fold less than the expression levels of an IRES cassette present in an RRV.

Transcription from a core- or mini-promoter occurs through the interaction of various elements. In focused transcription, for example, there is either a single major transcription start site or several start sites within a narrow region of several nucleotides. Focused transcription is the predominant mode of transcription in simpler organisms. In dispersed transcription, there are several weak transcription start sites over a broad region of about 50 to 100 nucleotides. Dispersed transcription is the most common mode of transcription in vertebrates. For instance, dispersed transcription is observed in about two-thirds of human genes. In vertebrates, focused transcription tends to be associated with regulated promoters, whereas dispersed transcription is typically observed in constitutive promoters in CpG islands.

A listing and description of some core promoter elements that may be shuffled into a core promoter sequence for both focused and disperse promoter elements is given in Table 1. As mentioned Previously, a mini-promoter used in the compositions of the disclosure can comprise a core promoter that is further modified. Such modifications can include the incorporation of one or more additional elements as set forth in Table 1.

TABLE 1

Binding sites that can contribute to a focused core promoter (almost always with a "TATA box and a single transcription start site (TSS)), or a dispersed promoter without a TATA box, usually with a DPE element (see R. Dickstein, Trasncription, 2(5): 201-206, 2011; Juven-Gershon et al., Nat. Methods, 2006, supra). Symbols for nucleotides follow the international convention (world wide web: chem.qmul.ac.uk/iubmb/misc/naseq.html).

| Transcription factor | Full name | Binding site wrt to transcription start site (TSS +1) |
|---|---|---|
| BREu | TFIIB recognition element, upstream | Upstream of TATA Box, SSRCGCC |
| TATA box | TATA box | T at −31/−30 TATAWAAR, key focused promoter element |
| BREd | TFIIB recognition element, downstream | −23 to −17 RTDKKKK |
| XCPE1 | HBV X core promoter element 1 | −8 to +2 DSGYGGRASM from HBV Xgene |
| XCPE2 | HBV X core promoter element 2 | VCYCRTTRCMY from HBV Xgene |
| Inr | initiator | −2 to +4 YYANWYY |
| DCE SI | Downstream core element site 1 | +6 to +11 CTTC |
| DCE SII | Downstream core element site II | +16 to +21 CTGT |
| DCE SIII | Downstream core element site III | +30 to +34 AGC |
| MTE | Motif ten element | +18 to +27 CSARCSSAAC mostly in *Drosophila* |
| DPE | Downstream promoter element | +28 to +33 RGWYVT common in *Drosophila*, key dispersed promoter element |

Table 2 sets forth oligonucleotides that can be used to construct and clone enhancer elements into core promoter regions. As mentioned above, the modified/optimized core promoters of the disclosure can include a core sequence with the addition of elements from Table 1 and may further include enhancers cloned as set forth in Table 2. In doing so, the size of the core-promoter is increased and can be described as a "mini-promoter". However, the final mini-promoter should not exceed 600 bp and will typically be about 100 bp, 200 bp, 300 bp, 400 bp, 500 bp and any integer there between.

TABLE 2

Oligonucleotides used for constructing enhancer segments.

| No. | Oligo-nucleotide | Motif Sequence (SEQ ID NOs in | Reference |
|---|---|---|---|
| 1 | AP-1 | 5'-TGTCTCAG-3' (43) | Hallahanet al. Int. J. Radiat. Oncol. Biol. Phys. 36:355-360, 1996 |
| 2 | CArG | 5'-CCATATAAGG-3' (44) | Datta et al. Proc. Natl. Acad. Sci. USA 89:10149-10153, 1992 |
| 3 | NF-κB1 | 5'-GGAAATCCCC-3' (45) | Ueda et al. FEBS Lett. 491:40-44, 2001 |
| 4 | NF-κB2 | 5'-GGAAAGTCCCC-3' (46) | Kanno et al. EMBO J. 8:4205-4214, 1989 |
| 5 | NF-κB3 | 5'-GGAGTTCCC-3' (47) | Hong et al. J. Biol. Chem. 275:18022-18028 2000. |
| 6 | NF-Y | 5'-CATTGGG-3' (48) | Hu et al. J. Biol. Chem. 275:2979-2985, 2000. |
| 7 | CRE1 | 5'-TTACGTAA-3' (49) | Theil et al., BMC Mol. Biol., 6:2 1-14, 2005 |
| 8 | CRE2 | 5'-TTGCATCA-3' (50) | Theil et al., BMC Mol. Biol. 6:2 1-14, 2005 |

AP-1, activating protein-1;
NF-κB, nuclear factor κB;
CRE, cAMP response elements.

In addition, most eukaryotic mRNAs contain a short recognition sequence called Kozak sequence (RCCATGG; (SEQ ID NO:51)), where ATG is the translational start site. The presence of a Kozak sequence can greatly facilitates the binding of mRNA to ribosome in the translation machinery. To improve gene expression level, it is advantageous to incorporate Kozak sequence downstream of the core promoter. Although the core promoter has demonstrated useful transcription, efficient protein translation is equally important to confer gene expression. Thus, in one embodiment, the mini-promoter includes regulatory elements (e.g., Kozak sequences) that can improve translation of transcript mRNA. Other "Kozak-like" sequences that can promote efficient translation are known in the art. For example, sequences derived from the 5'-UTR of tobacco mosaic virus mRNA as well as from the lobster tropomyosin gene are able to function in eukaryotic cells to enhance protein translation (Gallei et al., 1989, Gallei et al., 1992 and Gallei et al., 2002; Sano et al., 2002). The length of these sequences varies from 7 to 68 nucleotides (see, e.g., Table 3).

TABLE 3

Known translational enhancer found in 5' UTR of coding genes.

| Enhancer element | Origin | Length | Sequence |
|---|---|---|---|
| Kozak | eukaryotes | 7 nt | RCCATGG (SEQ ID NO: 51) |
| Omega | tobacco mosaic virus | 68 nt | m'pppTTATTTTTACAAAATTACCAA CAACAACAAACAACAAACAATTACA ATTACTATTTACAATTACAATG (SEQ ID NO: 52) |
| L21 | eukaryotes | 21 nt | AACTCCTAAAAAACCGCCACC (SEQ ID NO: 53) |

Particularly, the 5' UTR immediately upstream of the ATG initiation codon have been shown to influence the level of translation initiation. Thus, in one embodiment, the mini-promoter includes regulatory elements (e.g., Kozak sequences) that can improve translation of transcript mRNA. In addition, analysis of the sequence to be expressed and translated (i.e., the sequence to which the mini-promoter is operably linked) can provide insight on modifications useful for better expression. For example, a heat-stabilized, humanized, yeast cytosine deaminase (yCD2) coding sequence (see, e.g., SEQ ID NO:3) has 3 in-frame ATG within the first 15 amino acids in the coding region. The spacing in the 5'UTR and the lack of Kozak sequence flanking the initiation codon in yCD2 mRNA is suboptimal for efficient protein translation initiation. Thus, incorporation of Kozak sequence and/or other translational enhancer element may greatly improve the translation initiation and thus protein production of transgenes.

As mentioned above, the mini-promoters can comprise optimized or modified core promoters that include one or more additional elements that facilitate expression of an operably linked coding sequence. One way of selecting for functional mixtures of these elements is to simply synthesize the various elements or variations of these elements, ligate them together and select functionally for mini-promoters that are able to express in the desired situation. Juven-Gershon et al. describes assays which can be used to determine the expression levels of operably linked genes (e.g., using luciferase report constructs and the like). Using these techniques in combination with elements that bind the transcription factors AP-1, nuclear factor KB (NF-κB), CArG binding factor A (CBF-A) and nuclear factor Y (NF-Y) (see Table 2) one can obtain functional enhancers (Ogawa et al., Biotechniques, 42:628-633, 2007) combined with a cellular core promoter (for example, from the hemoxygenase core) to yield an overall active promoter of approximately 165 bp total. However, other core promoters such as the SCP1 core, optimized core sequences as described here, the TK intragenic core (Al-shawi et al., Mol. Cell. Biol., 11: 4207, 1991; Salamon et al., Mol. Cell. Biol., 15:5322 1995); or the human ASK gene core (Yamada et al.) can be used. Various other genes can be used as positive selectable markers. These include: dyhdrofolate reductase (DHFR; Simonsen et al., Nuc Acid Res., 16:2235-2246, 1988) with methotrexate in conjunction with a nucleotide transport inhibitor such as dipyridamole (Warlick et al., Biochemical Pharmacology, 59: 141-151, 2000) or nitrobenzylmercaptopurine riboside phosphate (Allay et al., Stem Cells, 16(suppl 1):223-233, 1998); Cytosine deaminase using N-(phosphonacetyl)-L-aspartate (PALA) to block de novo synthesis of uracil and anabolically downstream bases and cytosine to supply these through pyrimidine salvage pathways (Wahl et al., J. Biol. Chem., 254:8679; Unger et al., Can. Gene Ther., 14:30-38); and various other selectable markers known to those skilled in the art. In general, higher levels of expression of the selectable marker is indicative of better expression.

In addition, modified or optimized promoters may be obtained through "directed evolution", error prone PCR and the like. For example, rounds of expression and selection can provide for the introduction of errors in a mini-promoter (e.g., a core promoter or modified core promoter) and selection of positive expression profiles using selectable systems such as the DHFR and CD selection schemes described above. In another embodiment, transgenes that are not sufficiently expressed using mini-promoters can be selected for increased expression in the context of an RRV by including a metabolically selectable gene in the RRV and passing the RRV through multiple rounds of replication and selection. The relatively high error rate of the viral reverse transcriptase enzyme allows the incorporation of mutations and advantageous mutations are then selected and become the dominant sequence. Such improved mini-promoters can then be amplified, cloned and used as a more efficient minipromoter. Advantageously, for the use of RRV as anti-cancer agents, the selection can be performed in tumor cell lines of a desired cell type, such as colon, brain, lung, breast or prostate cancers. For example, sequential passage of the RRV encoding the selectable marker driven by a putative minimal promoter in the presence of the selective agent leads to selection for the best expressing minimal promoter. Passage of the RRV in tumor cell lines of the proposed target type can be used if there are tissue specificity issues with a particular combination. In one embodiment, the mini-promoter is synthesized as a single entity and the rate of error accumulation of the RRV reverse transcriptase is relied on to introduce diversity on which selection can be made. In a separate embodiment, the initial promoter is synthesized with programmed random inhomogeneities in the sequence so that when incorporated into the RRV as the promoter for the selectable marker, there is a larger landscape of possible sequences to select from. In another embodiment, the initial viral vector can be supplied with random variants in the promoter sequence and the same type of selection can be used to identify optimal mini-promoter sequences. In another embodiment, Kozak sequence RCCATGG (SEQ ID NO:51) can be incorporated downstream of the mini promoters to facilitate the initial binding of the mRNA to the small subunit of the ribosome, thus improve translation.

Optimized mini-promoters with sufficient expression can be used in any situation where nucleic acid size is limiting (e.g., viral vectors). In one embodiment the optimized mini-promoter is used in a replicating RRV to express one or more genes with an anticancer effect. In one embodiment the mini-promoter is used to express two genes, either as a fusion, a fusion gene separated by a protease cleavage site such as the furin endogenous protease target, or separated by a self-processing sequence like the 2A family (de Felipe et al., Trends Biotech, 24:68-75, 2006) or by the inclusion of two mini-promoters, one for each gene. In another embodiment, the mini-promoter can be used to express a first gene or coding sequence and then a second cassette comprising a polIII promoter can be used to express an siRNA, shRNA or microRNA. Because the mini-promoter cassette is smaller, it can be effectively combined to incorporate other therapeutic coding sequences.

Figure 8A:
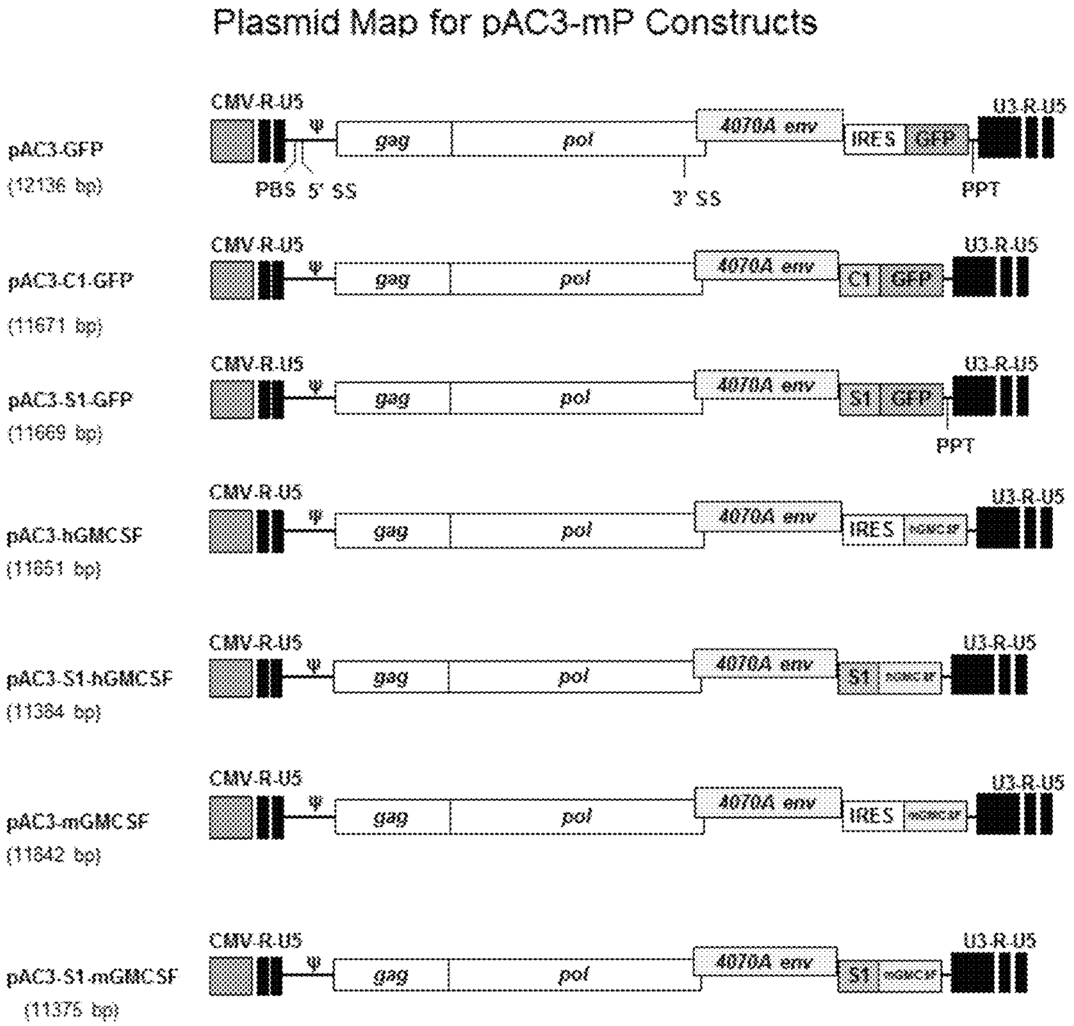
FIG. 8A-B show diagrams of constructs used in the disclosure.
Figure 8B:
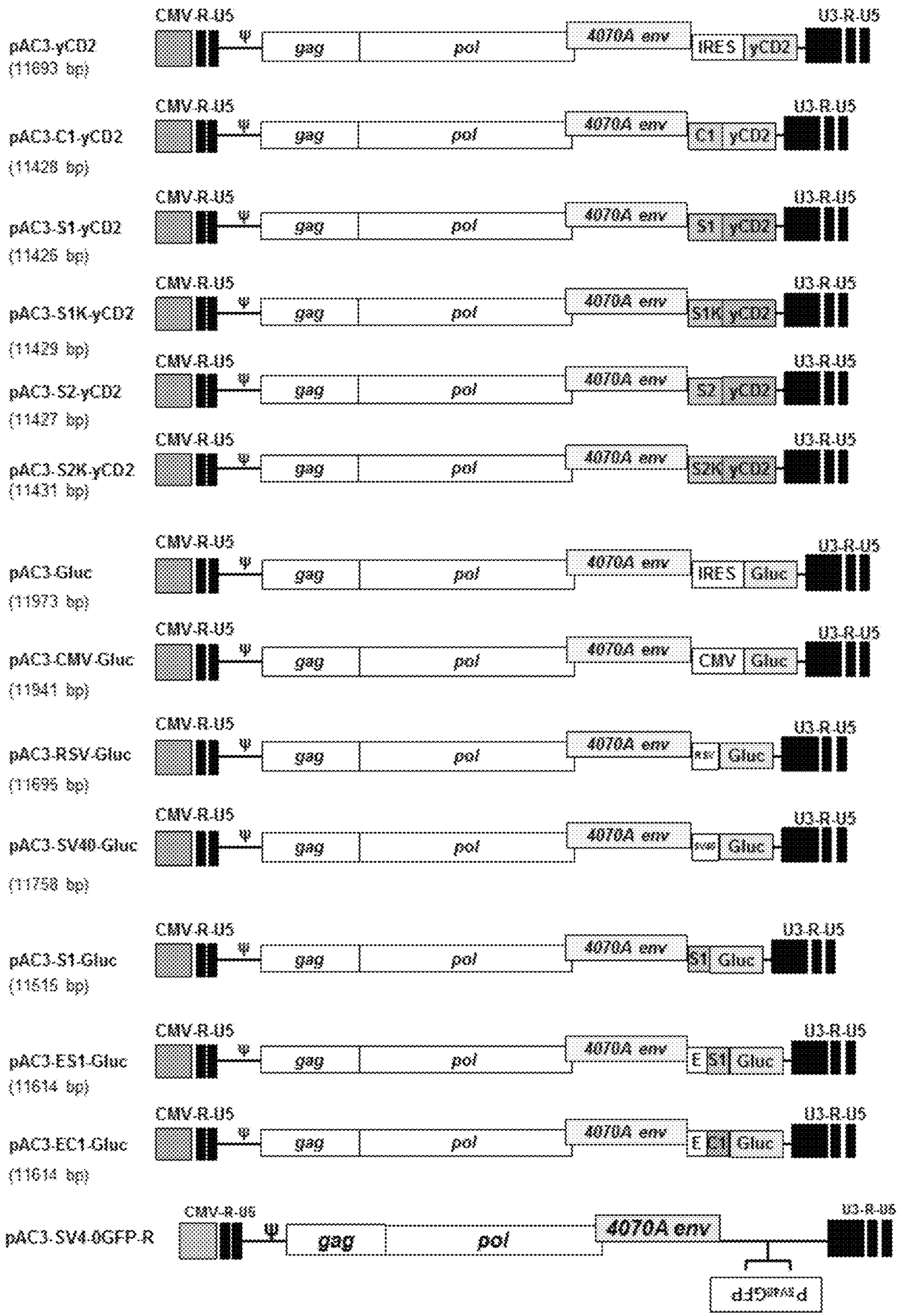

The mini-promoters described herein that are operably linked to a gene or coding sequence to be expressed can be used to drive transcription in a vector. In one embodiment, the disclosure provides vectors comprising from 5' to 3': a CMV-R-U5 fusion of the immediate early promoter from human cytomegalovirus to an MLV R-U5 region; a PBS, primer binding site for reverse transcriptase; a 5' splice site; ψ packaging signal; a gag coding sequence for MLV group specific antigen; a pol coding sequence for MLV polymerase polyprotein; a 3' splice site; a 4070A env coding sequence for envelope protein of MLV strain 4070A; a therapeutic cassette comprising (a) at least one mini-promoter cassettes operably linked to a therapeutic gene or (b) a core-promoter and at least one other cassette selected from the group consisting of a polIII promoter cassette, a second core-promoter cassette, a mini-promoter cassette and an IRES cassette; a polypurine tract; and a U3-R-U5 MLV long terminal repeat. In a further embodiment, each of these various "portion" of the vector (e.g., the gag, pol, env and the like) can comprise well known sequences in the art derived from various gamma retroviral vectors (e.g., MLV, GALV and the like). In some embodiments, the vector is derived from or engineered from an MLV viral sequence. FIGS. 8A and 8B depict various vectors of the disclosure as described in more detail elsewhere herein. For example, the promoter at the 5' end of the vector can comprise a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the vector promoter comprises a sequence as set forth in SEQ ID NO: 19, 20 or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO: 19, 20 or 22 from about nucleotide 1 to about nucleotide 1202 or sequences that are at least 95% identical to a sequence as set forth in SEQ ID NO: 19, 20 or 22 from about nucleotide 1 to about 1202, wherein the polynucleotide promotes transcription of a nucleic acid molecule operably linked thereto. In another embodiment, the gag and pol genes of the vector are derived from an oncoretrovirus or gamma retrovirus. The gag nucleic acid domain can comprise, for example, a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO: 19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO: 19 or 22 or a sequence having at least 95%, 98%, 99% or 99.8% identity thereto.

A therapeutic cassette is located just downstream of the env termination codon. Typically the therapeutic cassette starts immediately after or about 1, 5, 10, 15, 20, 25, 30, 35, 40, 45, 50, or about 100 basepairs downstream of the env stop codon. The beginning of the therapeutic cassette will typically have a minimal distance from the env stop codon so as to optimize the size of the heterologous gene in the cassette. As mentioned above, the therapeutic cassette can comprise one or more mini-promoters each operably linked to a therapeutic coding sequences, or a mini-promoter and a polIII promoter each operably linked to a therapeutic coding sequences, or a mini-promoter and an IRES each operably linked to a therapeutic coding sequences. The mini-promoter of the vector can be any regulatory domain that is smaller than 600 bp (e.g., about 599 bp, 550 bp, 500 bp, 450 bp, 400 bp, 350 bp, 300 bp, 250 bp, 200 bp, 150 bp, 100 bp, about 90 bp, about 80 bp, about 76 bp, about 74 bp or smaller) and allows for transcription of an operably linked coding sequence or non-coding sequence. In one embodiment the cassette comprises a core-promoter such as from about nucleotide number 8330 to about nucleotide 8406 of SEQ ID NO: 19 or 22 or a sequence having at least 95%, 98%, or 99% identity thereto. In another embodiment, the core-promoter set forth in SEQ ID NO:19 or 22 from about 8328 to 8404 can be substituted with any number of other core- or mini-promoters including the promoters having the sequences as set forth in SEQ ID NO:56, 57, 59, 65, 66, 67, 68, 69, 71, 72, 73, and 74 and may further include additional sequences such as enhancer (e.g., SEQ ID NO:58 and 70).

The disclosure provides the sequences of certain RRVs having promoter cassettes operably linked to a cytotoxic gene. For example, SEQ ID NO:19 depicts a pAC3-C1.yCD2 vector wherein the vector comprises a gag, pol and env sequence, the env sequence immediately followed by a CMV core promoter and a humanized cytosine deaminase with 3 heat stabilized mutation, which is then followed by the 3' LTR. SEQ ID NO:20 depicts a similar structure however, the cassette comprises an S1 promoter followed by the transgene of human GMCSF. SEQ ID NO:21 shows the sequence of a prior art RRV vector "pACE-CD". SEQ ID NO:22 shows a sequence similar to SEQ ID NO:19 and 20 expect the promoter cassette comprises an S1 promoter operably linked to murine GMCSF. SEQ ID NO:39 shows the sequence of an RRV having an S1-yCD2 cassette. SEQ ID NO:40 shows the sequence of an RRV having a C1-GFP cassette. SEQ ID NO:41 shows the sequence of an RRV having an S1-GFP cassette.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Although the disclosure describes the use of RRVs comprising a core- or mini-promoter, other "vectors" can includes such core- or mini-promoter constructs to express operably linked genes and sequences. The terms "vector", "vector construct" and "expression vector" mean the vehicle by which a DNA or RNA sequence (e.g., a foreign gene) can be introduced into a host cell, so as to transform the host and promote expression (e.g., transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. However, most vectors have particular size limitations on what can be cloned into the vector (e.g., 12 kb for plasmids, 20 kb for lambda bacteriophage, 30-35 kb for cosmids). This is even more restrictive when one considers retroviral vectors. For example, the genome of a typical replication-competent murine retrovirus is about 8.3 kb, whereas that of the alpha retrovirus RSV, which contains a disposable src sequences in addition to the normal complement of viral genes, is about 9.3 kb. The maximum size for a replication-competent spleen necrosis virus vector is similar, about 10 kb (Gelinas and Temin 1986) (Retroviruses., Coffin J M, Hughes S H, Varmus H E, editors., Cold Spring Harbor (N.Y.): Cold Spring Harbor Laboratory Press; 1997). Presumably, the size limit on the retroviral genome depends on the size of the folded dimeric RNA. Furthermore, "gutted" or replication defective retroviral vectors can incorporate larger sequence than their replication competent counter parts.

The disclosure provides retroviral replicating vectors that contain a heterologous polynucleotide encoding, for example, a polypeptide having cytosine deaminase or mutant thereof; a polypeptide having thymidine kinase activity or mutants thereof; other prodrug activating genes; an microRNA, shRNA or siRNA; a cytokine; an antibody binding domain or combinations thereof that can be delivered to a cell or subject. In addition, to retroviral vectors other viral vector that can be used in the compositions and methods of the disclosure and which can be engineered to contain a core- or mini-promoter cassette include adenoviral vectors, a measles vectors, a herpes vectors, a retroviral vectors (including a lentiviral vector), a rhabdoviral vectors such as a Vesicular Stomatitis viral vectors, a reovirus vectors, a Seneca Valley Virus vectors, a poxvirus vectors (including animal pox or vaccinia derived vectors), a parvovirus vectors (including an AAV vectors), an alphavirus vectors or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000; *Gene Therapy: Therapeutic Mechanism and Strategies*, ed. Nancy Smyth Templetone and Danilo D Lasic, Marcel Dekker, Inc., New York, N.Y., 2004; *Gene and Cell Therapy: Therapeutic Mechanisms and Strategies*, Third Edition, ed. Nancy Smyth Templeton, CRC Press, 2008); the disclosures of which are incorporated herein by reference).

As described herein the disclosure provides modified retroviral vectors. The modified retroviral vectors can be derived from members of the retroviridae family. Retroviruses have been classified in various ways, but the nomenclature has been standardized in the last couple of decades (see ICTVdB—The Universal Virus Database, 2012 release, on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the retroviral replicating vector can comprise an Orthoretrovirus or more typically a gamma retrovirus vector.

In many situations for using a retroviral replicating vector therapeutically, it is advantageous to have high levels of expression of the transgene that is encoded by the retroviral replicating vector. For example, with a prodrug activating gene such as the cytosine deaminase gene it is advantageous to have higher levels of expression of the CD protein in a cell so that the conversion of the prodrug 5-FC to 5-FU is more efficient. Similarly high levels of expression of siRNA or shRNA lead to more efficient suppression of target gene expression. Also for cytokines or single chain antibodies (scAbs) or binding portion of an antibody it is usually advantageous to express high levels of the cytokine or scAb. In addition, in the case that there are mutations in some copies of the vector that inactivate or impair the activity of the vector or transgene, it is advantageous to have multiple copies of the vector in the target cell as this provides a high probability of efficient expression of the intact transgene. The disclosure provides recombinant replication competent retroviruses capable of infecting a target cell or target cell population multiple times resulting in an average number of copies/diploid genome of 3 or greater. The disclosure also provides methods of testing for this property. Also provided are methods of treating a cell proliferative disorder, using a retroviral replicating vector capable of infecting a target cell or target cell population multiple times resulting in an average number of copies/diploid genome of 5 or greater.

In one embodiment, the disclosure provides a recombinant retrovirus capable of infecting a non-dividing call, a dividing cell, or a cell having a cell proliferative disorder. The recombinant replication competent retrovirus of the disclosure comprises a polynucleotide sequence encoding a viral GAG, a viral POL, a viral ENV, a therapeutic cassette comprising at least one heterologous polynucleotide preceded by a core- or mini-promoter, encapsulated within a virion.

The phrase "non-dividing" cell refers to a cell that does not go through mitosis. Non-dividing cells may be blocked at any point in the cell cycle, (e.g., $G_0/G_1$, $G_{1/s}$, $G_{2/M}$), as long as the cell is not actively dividing. For dividing cells ortho- or gamma-retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas, squamous cell cancer, malignant melanoma, sinonasal undifferentiated carcinoma (SNUC), brain (including glioblastomas), blood neoplasia, carcinoma's of the regional lymph nodes, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer (see, e.g., DeVita, Hellman, and Rosenberg's Cancer: Principles and Practice of Oncology $9^{th}$ edition 2011 Wolters Kluwer/Lippincott Williams & Williams for descriptions of these various neoplasia and their current treatments). The cell proliferative disease also includes rheumatoid arthritis (O'Dell NEJM 350:2591 2004) and other auto-immune disorders (Mackay et al NEJM 345:340 2001) that are often characterized by inappropriate proliferation of cells of the immune system.

As described herein, the vector of the disclosure (e.g., an RRV vector) comprises a core- and/or mini-promoter cassette operably linked to a heterologous nucleic acid sequence. As mentioned above, there may be more than one mini-promoter cassettes in a vector of the disclosure. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence.

Depending upon the intended use of the vector of the disclosure, any number of heterologous polynucleotide or nucleic acid sequences may be inserted into the retroviral vector. Additional polynucleotide sequences encoding any desired polypeptide sequence may also be inserted into the vector of the disclosure. Where in vivo delivery of a heterologous nucleic acid sequence is sought both therapeutic and non-therapeutic sequences may be used. For example, the heterologous sequence can encode a therapeutic molecule including an inhibitory nucleic acid molecule (microRNA, shRNA siRNA) or ribozymes directed to a particular gene associated with a cell proliferative disorder or other gene-associated disease or disorder; the heterologous sequence can be a suicide gene (e.g., HSV-tk or PNP or cytosine deaminase; either modified or unmodified), a growth factor or a therapeutic protein (e.g., Factor IX, IL2, GMCSF and the like) and any combination thereof. Other therapeutic proteins or coding sequences applicable to the disclosure are easily identified in the art.

In one embodiment, the heterologous polynucleotide within the vector comprises a cytosine deaminase that has been optimized for expression in a human cell (see, e.g., SEQ ID NO:3 and 5). In a further embodiment, the cytosine deaminase comprises a sequence that has been human codon optimized and comprises mutations that increase the cytosine deaminase's stability (e.g., reduced degradation or increased thermo-stability) compared to a wild-type cytosine deaminase (see, e.g., SEQ ID NO:3). In yet another embodiment, the heterologous polynucleotide encodes a fusion construct comprising a cytosine deaminase (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide of the disclosure (e.g., SEQ ID NO:3, 5, 11, 13, 15, or 17). In yet another embodiment, the heterologous polynucleotide is a human codon optimized sequence encoding a polypeptide having thymidine kinase activity (see, e.g., SEQ ID NO:75).

In another embodiment, a vector of the disclosure (e.g., an RRV) can comprise a heterologous polynucleotide encoding a polypeptide comprising a cytosine deaminase activity and may further comprise a polynucleotide comprising a microRNA or siRNA molecule either as part of the primary transcript from the viral promoter or linked to a promoter, which can be cell-type or tissue specific.

In another embodiment, the disclosure provides a recombinant retroviral replicating vector that contains a heterologous polynucleotide sequence of the human primary precursor miR-128-2 (SEQ ID NO:32) downstream of the env gene. miRNAs that are down-regulated in cancers can be incorporated into the vector for therapeutic gene delivery. For example, let-7, miR-26, miR-124, miR181, MiR181d and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 *BMC Medicine* 6:14 1-17).

The replicating retroviral vectors of the disclosure can be used to treat disease by expressing engineered siRNA, shRNA or miRNA (Dennis, Nature, 418: 122 2002) that switches off or lowers expression of key genes that govern the proliferation or survival of diseased cells including tumor cells. Such targets include genes like Rad 51 a central enzyme in DNA repair, and without which cell growth is drastically restricted. Other targets include many of the signaling pathway molecules that control cell growth (Marquez & McCaffrey Hum Gene Ther. 19:27 2008) or inhibit viral replication (WE Johnson Current Topics in Microbiology and Immunology 371: 123-151, 2013) such as APOBEC3G or tetherin. The siRNA or miRNA may be combined with expression of a cytotoxic gene from the same or different retroviral vector of the disclosure. An example of a suitable cytotoxic gene comprises a cytosine deaminase or modified cytosine deaminase of the disclosure. Examples of siRNA or miRNA that can be expressed from the same vector or a different vector with cytosine deaminase are siRNAs or miRNAs that target thymidilate synthase, dihydropyrimidine dehydrogenase or other nucleic acid anabolic or synthetic enzymes, that can enhance or complement the action of 5-FU produced locally in a tumor or tissue from 5-FC activation by cytosine deaminase. In such instances, the RRV will comprise a therapeutic cassette having a core- or mini-promoter operably linked to a sequence encoding a polypeptide with CD activity and further includes a polIII promoter cassette operably linked to a sequence the encodes an miRNA.

In use, the retroviral vector(s) will replicate through the tumor or other target tissue and before growth inhibition occurs the virus first integrates into the host genome and continues to make virus after growth of that cell is inhibited. Methods for selecting functional miRNA or siRNA sequences are known in the art. A retroviral vector of this disclosure can be made using cells from other species for which the corresponding protein is not significantly targeted. Such cells include dog cell lines or chicken cell line. Alternatively the virus is made by transient transfection on human 293 derived cells or other cell line that allows efficient transient transfection. For this use the siRNA or miRNA sequence can simply be inserted at a convenient site on the viral genome. This site includes the region downstream of the envelope and upstream of the 3'LTR of the replicating retrovirus. Alternatively, polIII transcription units can be inserted in the viral genome with the appropriate siRNA or miRNA, typically downstream of the 3' envelope gene. In one embodiment, the transcription direction will be the same as that of the retroviral replicating vector. Several different siRNA or miRNA sequences can be inserted to ensure efficient down regulation of the target gene or down regulation of more than one gene. Suitable sequences and targets can be obtained from commercial and academic sources known to those skilled in the art (e.g., the MIT/ICBP siRNA Database http:(//)web.mit.edu/sirna/; http:(//)katandin.cshl.org:9331/RNAi_web/scripts/main2.pl RNAi resources, including siRNA and shRNA design tools. (Hannon Lab, Cold Spring Harbor Laboratory); http:(//)www.rnaiweb.com/ General resource; http:(//)genomics.jp/sidirect/; http:(//)[www].rnainterference.org/; http:(//)bioinfo.wistar.upenn.edu/siRNA/siRNA.htm; http:(//)www(.)ambion.com/techlib/misc/siRNA finder.html (Ambion)).

The miRNA target can be inserted 3' to the transgene but before the 3'LTR or upstream of the mini-promoter in the therapeutic cassette but after the 3' end of the envelope. In general the target would not be inserted into protein coding sequences.

In yet further embodiments, the heterologous polynucleotide may comprise a cytokine such as an interleukin, interferon gamma or the like. Cytokines that may expressed from a retroviral vector of the disclosure include, but are not limited to, IL-1alpha, IL-1beta, IL-2 (SEQ ID NO:38), IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21, anti-CD40, CD40L, IFN-gamma (SEQ ID NO:36, 37, 38) and TNF-alpha, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TR10 (International Publication No. WO 98/54202), 312C2 (International Publication No. WO 98/06842), and TR12, and soluble forms CD154, CD70, and CD153. Angiogenic proteins may be useful in some embodiments, particularly for protein production from cell lines. Such angiogenic factors include, but are not limited to, Glioma Derived Growth Factor (GDGF), Platelet Derived Growth Factor-A (PDGF-A), Platelet Derived Growth Factor-B (PDGF-B), Placental Growth Factor (PIGF), Placental Growth Factor-2 (PIGF-2), Vascular Endothelial Growth Factor (VEGF), Vascular Endothelial Growth Factor-A (VEGF-A), Vascular Endothelial Growth Factor-2 (VEGF-2), Vascular Endothelial Growth Factor B (VEGF-3), Vascular Endothelial Growth Factor B-186 (VEGF-B186), Vascular Endothelial Growth Factor-D (VEGF-D), Vascular Endothelial Growth Factor-D (VEGF-D), and Vascular Endothelial Growth Factor-E (VEGF-E). Fibroblast Growth Factors may be delivered by a vector of the disclosure and include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. Hematopoietic growth factors may be delivered using vectors of the disclosure, such growth factors include, but are not limited to, granulocyte macrophage colony stimulating factor (GM-CSF) (sargramostim), granulocyte colony stimulating factor (G-CSF) (filgrastim), macrophage colony stimulating factor (M-CSF, CSF-1) erythropoietin (epoetin alfa), stem cell factor (SCF, c-kit ligand, steel factor), megakaryocyte colony stimulating factor, PIXY321 (a GMCSF/IL-3) fusion protein and the like.

The methods and compositions of the disclosure are useful in combination therapies including therapies with other approved drugs or biologics such as Avastin, Herceptin or various HDAC inhibitors.

The disclosure provides methods for treating cell proliferative disorders such as cancer and neoplasms comprising administering an RRV vector of the disclosure followed by treatment with a chemotherapeutic agent or anti-cancer agent. In one aspect, the RRV vector is administered to a subject for a period of time prior to administration of the chemotherapeutic or anti-cancer agent that allows the RRV to infect and replicate. The subject is then treated with a chemotherapeutic agent or anti-cancer agent for a period of time and dosage to reduce proliferation or kill the cancer cells. In one aspect, if the treatment with the chemotherapeutic or anti-cancer agent reduces, but does not kill the cancer/tumor (e.g., partial remission or temporary remission), the subject may then be treated with a benign therapeutic agent (e.g., 5-FC) that is converted to a toxic therapeutic agent in cells expression a cytotoxic gene (e.g., cytosine deaminase) from the RRV.

Using such methods the RRVs of the disclosure are spread during a replication process of the tumor cells, such cells can then be killed by treatment with an anti-cancer or chemotherapeutic agent and further killing can occur using the RVV treatment process described herein.

In yet another embodiment of the disclosure, the heterologous gene can comprise a coding sequence for a target antigen (e.g., a cancer antigen). In this embodiment, cells comprising a cell proliferative disorder are infected with an RRV comprising a heterologous polynucleotide encoding the target antigen to provide expression of the target antigen (e.g., overexpression of a cancer antigen). An anticancer agent comprising a targeting cognate moiety that specifically interacts with the target antigen is then administered to the subject. The targeting cognate moiety can be operably linked to a cytotoxic agent or can itself be an anticancer agent. Thus, a cancer cell infected by the RRV comprising the targeting antigen coding sequences increases the expression of target on the cancer cell resulting in increased efficiency/efficacy of cytotoxic targeting.

Blocking of interactions between cells of the immune system has been shown to have significant immunological effects, either activating or suppressing (Waldmann Annu Rev Med. 57:65 2006; Callahan & Wolchok J Leukoc Biol. 2013 July; 94(1):41-53. doi: 10.1189/jlb.1212631). Systemic administration of these types of molecules can have undesirable global effects which can at a minimum lead to deleterious side-effects or even death in the case of one CD28 agonist (Suntharalingam et al. NEJM 355 1018 2006). Pfizer has been developing one such anti-CTLA-4 blockading antibody (CP-675,206) as an anticancer reagent but has recently stopped development because of significant side effects. Bristol Meyers Squibb has an approved product Yervoy for late stage melanoma which is a CTLA-4 blocking monoclonal antibody, but this is acknowledged to cause significant toxicity. Local delivery of blockading molecules that are released into the local environment, from the tumor after infection with a replication competent vector encoding such molecules that are released into the extracellular space, provides the immune modulation locally and can avoid these serious side effects. The blockading molecules are antibodies, single chain antibodies, soluble versions of the natural ligand or other peptides that bind such receptors. The blocking targets are various surface molecules that include molecules involved in accessory immune interactions other than CTLA-4, but know to those skilled in the art. Further information on the use of such strategies with RRV with smaller single genes is available in WO2010/036986, WO2010/045002, WO2011/126864 and WO2012/058673 (which are incorporated here by reference) and are similar for the vectors of this disclosure.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Further information on the use of such strategies with RRV with smaller single genes is available in WO2010/036986, WO2010/045002, WO2011/126864 and WO2012/058673 and are similar for the vectors of this disclosure.

For example, and not by way of limitation, a retroviral vector useful in treating a cell proliferative disorder will include an amphotropic ENV protein, GAG, and POL proteins, a promoter sequence in the U3 region retroviral genome, and all cis-acting sequence necessary for replication, packaging and integration of the retroviral genome into the target cell.

As mentioned above and elsewhere herein, a vector of the disclosure can comprise a core- and/or mini-promoter cassette and can further includes an IRES cassette. An internal ribosome entry sites ("IRES"", Pelletier et al., 1988, Mol. Cell. Biol., 8, 1103-1112; Jang et al., J. Virol., 1988, 62, 2636-2643) refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. The disclosure contemplates that the therapeutic cassette can comprise a mini-promoter followed further 3' to the promoter by an IRES.

Additionally, an RRV of the disclosure comprises a promoter region at the 5' end of the retroviral polynucleotide sequence. The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above. Further information on the use of such strategies with RRV with smaller single genes is available in WO2010/036986, WO2010/045002, WO2011/126864 and WO2012/058673 and are similar for the vectors of this disclosure.

In one embodiment, the retroviral genome of the disclosure contains mini-promoter comprising a cloning site downstream of the mini-promoter for insertion of a desired/heterologous polynucleotide in operaly frame to effectuate expression of the heterologous polynucleotide. In one embodiment, at least one mini-promoter is located 3' to the env gene in the retroviral vector, but 5' to the desired heterologous polynucleotide. Accordingly, a heterologous polynucleotide encoding a desired polypeptide may be operably linked to the mini-promoter.

In one embodiment, a recombinant retrovirus of the disclosure is genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, mammary cells, neoplastic cells, glioma cells, neuronal cells and others known in the art) such that the recombinant genome of the retroviral vector is delivered to a target non-dividing, a target dividing cell, or a target cell having a cell proliferative disorder.

In a further related embodiment, the targeting of the vector is achieved using a chimeric env protein comprising a retroviral ENV protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255, 1992; Roux et al., Proc. Natl. Acad. Sci USA 86, 9079-9083, 1989), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376, 1994; Krueger & Albritton, J. Virol., 87:5916-5925, 2013), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995); M. Engelstadter et al. Gene Therapy 8, 1202-1206 (2001)) have reported tissue-specific targeting of spleen necrosis virus (SNV), an avian retrovirus, using envelopes containing single-chain antibodies directed against tumor markers.

In a further related embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Typically, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

Transcription control sequences of the disclosure can also include naturally occurring transcription control sequences naturally associated with a gene encoding a superantigen, a cytokine or a chemokine.

In addition different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV ITR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. The Whey accessory protein (WAP) may be used for breast tissue expression (Andres et al., PNAS 84:1299-1303, 1987).

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

In certain indications, it may be desirable to activate transcription at specific times after administration of the recombinant retroviral replicating vector of the disclosure (RRV). This may be done with promoters that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Further information on the use of controlled or tissue-specific promoter strategies with RRV with smaller single genes is available in WO2010/036986, WO2010/045002, WO2011/126864 and WO2012/058673 and are similar for the vectors of this disclosure.

In addition, this list of promoters should not be construed to be exhaustive or limiting, those of skill in the art will know of other promoters that may be used in conjunction with the promoters and methods disclosed herein.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. For example, promoters that are active in a variety of central nervous system (CNS) neurons may be therapeutically useful in protecting against damage due to stroke, which may affect any of a number of different regions of the brain. Accordingly, the tissue-specific regulatory elements used in the disclosure, have applicability to regulation of the heterologous proteins as well as a applicability as a targeting polynucleotide sequence in the present retroviral vectors.

The retroviral vectors and methods of the disclosure provide a replication competent retrovirus that does not require helper virus or additional nucleic acid sequence or proteins in order to propagate and produce virion. For example, the nucleic acid sequences of the retrovirus of the disclosure encode a group specific antigen and reverse transcriptase, (and integrase and protease-enzymes necessary for maturation and reverse transcription), respectively, as discussed above. The viral gag and pol can be derived from a lentivirus, such as HIV or an oncovirus or gammaretrovirus such as MoMLV. In addition, the nucleic acid genome of the retrovirus of the disclosure includes a sequence encoding a viral envelope (ENV) protein. The env gene can be derived from any retroviruses or other virus. The env may be an amphotropic envelope protein which allows transduction of cells of human and other species, or may be an ecotropic envelope protein, which is able to transduce only mouse and rat cells. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus, and more particularly a mammalian onco-retrovirus. In a further embodiment, the retroviral genome is derived from a gamma retrovirus, and more particularly a mammalian gamma retrovirus. By "derived" is meant that the parent polynucleotide sequence is a wild-type oncovirus which has been modified by insertion or removal of naturally occurring sequences (e.g., insertion of mini-promoter, insertion of a heterologous polynucleotide encoding a polypeptide or inhibitory nucleic acid of interest, swapping of a more effective promoter from a different retrovirus or virus in place of the wild-type promoter and the like).

Unlike recombinant retroviruses produced by standard methods in the art that are defective and require assistance in order to produce infectious vector particles, the disclosure provides a retrovirus that is replication-competent.

In yet another embodiment, the disclosure provides plasmids comprising a recombinant retroviral derived construct. The plasmid can be directly introduced into a target cell or a cell culture such as NIH 3T3 or other tissue culture cells. The resulting cells release the retroviral vector into the culture medium.

In other embodiments, host cells transfected with a retroviral replicating vector of the disclosure are provided. Host cells include eukaryotic cells such as yeast cells, insect cells, or animal cells. Host cells also include prokaryotic cells such as bacterial cells.

Also provided are engineered host cells that are transduced (transformed or transfected) with a vector provided herein (e.g., a retroviral replicating vector). The engineered host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Freshney (1994) Culture of Animal Cells: A Manual of Basic Technique, 3rd ed. (Wiley-Liss, New York) and stem cells of various kinds (world wide web at stembook.org) and the references cited therein. Such host cells can also be used for delivery of RRV by administering the infected cells to an animal or subject (e.g., a patient).

Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc. Typically human cells or cell lines will be used; however, it may be desirable to clone vectors and polynucleotides of the disclosure into non-human host cells for purposes of sequencing, amplification and cloning.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; a therapeutic cassette comprising (a) a core-promoter and at least one addition promoter, each operably linked to a therapeutic polynucleotide sequence or (b) at least one mini-promoter operably linked to a heterologous polynucleotide encoding a marker, therapeutic or diagnostic polypeptide; and a LTR nucleic acid sequence. As described elsewhere herein the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the viral promoter can comprise a CMV promoter having a sequence as set forth in SEQ ID NO:19, 20 or 22 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprises the immediately early promoter from human cytomegalovirus to the MLV R-U5 region. In one embodiment, the CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20, or 22 wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus. In one embodiment the pol domain comprises a sequence from about nucleotide number 2820 to about nucleotide 6358 or a sequence having at least 95%, 98%, 99% or 99.9% (rounded to the nearest $10^{th}$) identity thereto. The env domain of the polynucleotide may be derived from any number of retroviruses, but will typically be derived from an oncoretrovirus or gamma-retrovirus and more particularly from a mammalian oncoretrovirus or gamma-retrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. 3' to the env termination codon is a therapeutic cassette comprising at least one core-promoter cassette and/or a mini-promoter cassette and may further include a polIII promoter cassette and/or an IRES cassette, each operably linked to heterologous domain (e.g., a sequence encoding a therapeutic molecule such as a polypeptide having cytosine deaminase or thymidine kinase activity). The heterologous domain can comprise a cytosine deaminase or thymidine kinase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In another embodiment, the heterologous domain is a human codon optimized sequence comprising SEQ ID NO:75 and encoding a polypeptide having thymidine kinase activity.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a ψ packaging signal; a gag, ORF for MLV group specific antigen; a pol, ORF for MLV polymerase polyprotein; a 3' splice site; a 4070A env, ORF for envelope protein of MLV strain 4070A; a therapeutic cassette comprising at least one mini-promoter operably lined to a heterologous polynucleotide encoding a therapeutic molecule (e.g., a modified cytosine deaminase (thermostabilized and codon optimized)); a PPT, polypurine tract; and a U3-R-U5, MLV long terminal repeat.

In addition, the therapeutic methods (e.g., the gene therapy or gene delivery methods) as described herein can be performed in vivo or ex vivo. It may be preferable to remove the majority of a tumor prior to gene therapy, for example surgically or by radiation. In some aspects, the retroviral therapy may be preceded or followed by surgery, chemotherapy or radiation therapy. In some embodiments, steroids are co-administered with the vector (before, during or immediately after).

The following Examples are intended to illustrate, but not to limit the disclosure. While such Examples are typical of those that might be used, other procedures known to those skilled in the art may alternatively be utilized.

EXAMPLES

Example 1

Vector Stability of emd.GFP and tk Genes

Early passage of a human glioma cell line U87-MG was cultured in complete culture medium. Naïve cells were seeded at 2e5 cell per well in 6-well plates the day prior to infection. Vector from different plasmids was prepared by transient transfection on 293T cells and the supernatant is collected. Titers are measured as described (WO2010036986, Perez et al., Mol. Ther., 2012) typically around 10^6 TU/ml. pAZ based vectors are similar to pAC3 based vectors, but the starting plasmid has an LTR promoter driving the whole viral RNA transcript rather than the hybrid CMV-LTR promoter (FIG. 8. Subsequently the viral particles from both types of plasmid have complete MLV LTRs at both the 5' and 3' ends of the genome. The first cycle of infection is performed at MOI 0.1 according to calculated titers (TU/mL) in the presence of 4 μg/mL polybrene. In subsequent infections, one tenth of the viral supernatant produced by infected cells is used for infecting naïve cells. In each infection cycle, infected cells are passaged at d4 post infection into 6-well plates. Viral supernatant from infected cells at d7 post infection is collected for subsequent infection, and cells are harvested for genomic extraction for assessment of vector stability by IRES-PCR. The primers used for PCR are: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:54). The A1 and S1 promoters in the vectors expressing emd (GFP), derived from pAZ.A1.emd and pAZ.S1.emd appear a little more stable than vector derived from pAZ.C1.emd, but experience has shown that vectors stable to passage 6 in this test are useful, appear stable and, when armed with the appropriate gene, are therapeutic in mouse tumor models (CR. Logg et al., Hum Gene Ther 12:921-932, 2001; Logg & Kasahara in *Methods in Molecular Biology*, vol. 246*: Gene Delivery to Mammalian Cells: Vol. 2: Viral Gene Transfer Techniques* pp499-525. Edited by: W. C. Heiser© Humana Press Inc., Totowa, N.J.). For human use, further stability is preferred (out to 8-12 passages). The stabilities of the pAZ.S1.sr39tk and pAZ.S1.tko derived vectors had increased stability (and hence utility). The sr39tk gene (M. Black et al. *Cancer Res* 2001; 61:3022-3026) is a mutatated functionally optimized version of the Herpes Thymidine Kinase gene and the tko gene is human codon optimized version of the sr39 gene.

Example 2

Construction and Configuration of pAC3 Based Vectors Containing C1 and S1 Core Promoter Driving GFP Expression The retroviral replicating vectors, pAC3-C1.GFP and pAC3-S1.GFP, were derived from the backbone of pAC3-yCD2. The pAC3 backbone was isolated by endonuclease digestion of the pAC3-yCD2 plasmid DNA with Mlu I and Not I. The DNA sequence of C1.GFP and S1.GFP was isolated by endonuclease digestion of the pAZ-C1.GFP and pAZ.S1.GFP plasmid DNA, respectively, with Mlu I and Not I followed by insertion of the isolated DNA fragment to the corresponding restriction enzyme sites in the pAC3 backbone.

Example 3

Construction and Configuration of pAC3 Based Vectors Containing C1, S1 and S2 Core Promoter Driving CD Expression The retroviral replicating vectors, pAC3-C1.yCD2 and pAC3-S1.yCD2, were derived from the backbone of pAC3-yCD2. The pAC3 backbone was isolated by endonuclease digestion of the pAC3-yCD2 plasmid DNA with Mlu I and Not I. The DNA sequence of C1.yCD2, S1.yCD2 and S2.yCD2 was synthesized with Mlu I and Not I restriction enzyme sites present at each end of the DNA fragment for subsequent cloning to the corresponding sites in the pAC3 backbone.

Example 4

Construction and Configuration of pAC3 Based Vectors Containing EMCV IRES and C1 or S1 Core Promoter Driving hGMCSF and mGMCSF Expression The retroviral replicating vectors, pAC3-hGMCSF and pAC3.S1-hGMCSF, pAC3-mGMCSF and pAC3.S1-mGMCSF (see, e.g., FIG. 8), were derived from the backbone of pAC3-yCD2 vector (see, e.g., U.S. Pat. Publ. No. 20110217267A1, incorporated herein by reference). For pAC3-hGMCSF and pAC3-mGMCSF vectors, the pAC3 backbone in the vector was isolated by endonuclease digestion of the pAC3-yCD2 plasmid DNA with Psi I and Not I. The cDNA sequence of human and mouse GMCSF gene, respectively, were synthesized with the Psi I and Not I restriction enzyme sites at each end of the DNA fragment and subsequently cloned into the corresponding site in the pAC3 backbone. For pAC3.S1-hGMCSF and pAC3.S1-mGMCSF vectors, the pAC3 backbone in the vector was isolated by endonuclease digestion of the pAC3-yCD2 plasmid DNA with Mlu I and Not I. The DNA sequence of S1-hGMCSF and S1-mGMCSF, respectively, was synthesized with the Mlu I and Not I restriction enzyme sites at each end of the DNA fragment and subsequently cloned into the corresponding site in the pAC3 backbone.

Example 5

Vector Stability and Transgene Expression of pAC3 Based Vectors Containing C1 and S1 Core Promoter Driving GFP Expression pAC3 based vectors with core promoters driving the expression of emerald GFP (pAC3-C1.emd and pAC3-S1.emd (emd a.k.a. GFP) were constructed as described and compared to pAC3.emd (aka pAC3-GFP, Perez et al., Mol. Ther. 2012), which is the equivalent vector using an internal IRES to drive expression of the emd.GFP gene. Infectious vector was prepared by transient transfection as before. Early passage of a human glioma cell line U87-MG was cultured in complete culture medium. Naïve cells were seeded at 2e5 cell per well in 6-well plates the day prior infection. The first cycle of infection was performed at MOI 0.1 according to calculated titers (TU/mL) in the presence of 4 μg/mL polybrene. In subsequent infections, one tenth of the viral supernatant produced by infected cells was used for infecting naïve cells. In each infection cycle, infected cells were passaged at d4 post infection into 6-well plates. Viral supernatants from infected cells at d7 post infection were collected for subsequent infection, and cells were harvested for genomic extraction for assessment of vector stability by IRES-PCR. The primers used for PCR were: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55).

Figure 2A:
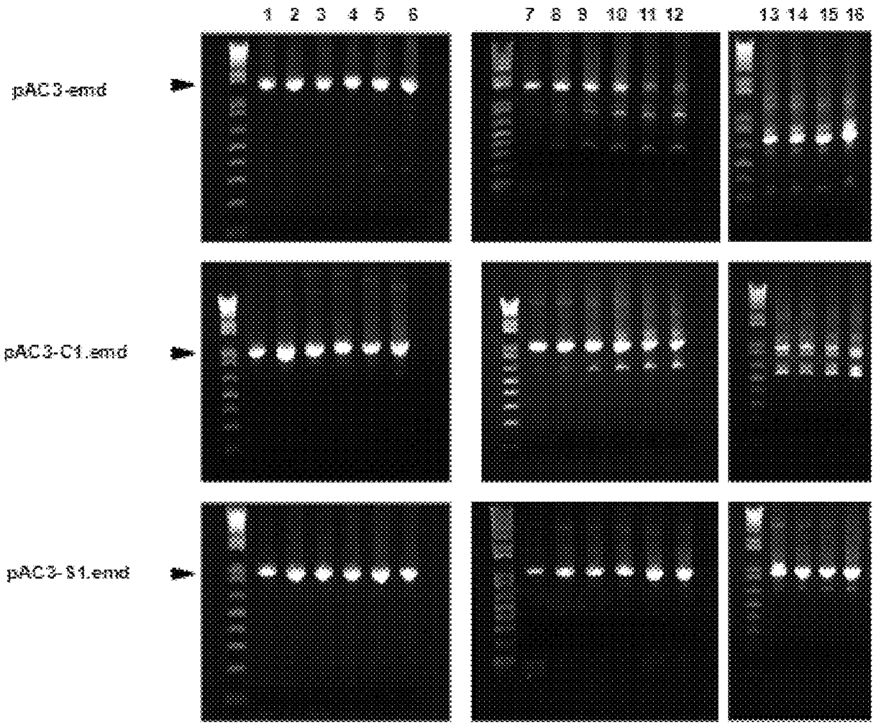
FIG. 2A-B shows vector stability of RRV in pAC backbone containing C1 and S1 core promoter driving transgene (A) GFP and (B) CD expression. The numbers above each lane indicates the number of infection cycle. Arrows indicate expected fragment size.

As can be seen in FIG. 2A the version of the vector with the C1 core promoter (pAC3-C1.emd) has equivalent stability to the IRES driven emd.GFP expression vector (pAC3-emd), whereas the version with the S1 (SCP1) core promoter (pAC3-S1.yCD2) is even more stable.

Figure 4A:
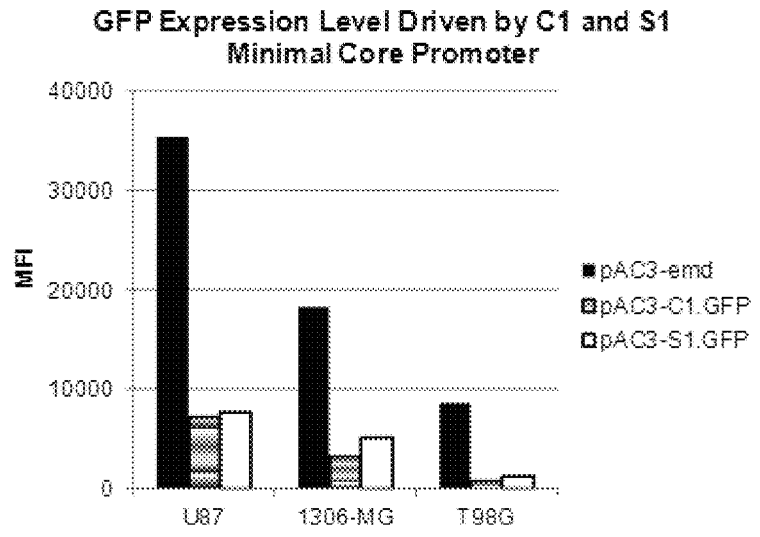
FIG. 4A-H shows (A) GFP protein expression measured by Fluorescent Activated Cell Sorting (FACS) of pAC3-GFP, pAC3.C1-GFP and pAC3.S1-GFP vector in fully infected human tumor cell lines U87, 1306-MG and T98s. MFI—Mean Fluorscent Intensity. (B) Protein expression (Western Blot) of pAC3-yCD2, pAC3.C1-yCD2 and pAC3.S1-yCD2 vector in transiently transfected 293T cells. (C) Protein expression (Western Blot) of pAC3-yCD2, pAC3.C1-yCD2 and pAC3.S1-yCD2 vector in fully infected U87 cells. (D)-(F) GM-CSF protein expression of pAC3-hGMCSF and pAC3.S1-hGMCSF: (D) in transiently transfected 293T; (E) in fully infected U87; (F) in fully infected and PC3 cells. (G)-(H) GM-CSF protein expression of pAC3-mGMCSF and pAC3.S1-mGMCSF: (G) in transiently transfected 293T; (H) in fully infected EMT6 cells.

The level of GFP expression in three human glioblastoma cell lines (U87-MG, 1306-MG and T98G) infected with different vectors was examined by measuring the mean fluorescent intensity by flow cytometry using proper gating of GFP positive cells. Naïve cells were seeded at 2e5 cell per well in 6-well plates the day prior infection. Viral infection was performed at MOI 0.1 according to calculated titers (TU/mL) in the presence of 4 μg/mL polybrene. At d7 post infection, cells were harvested for flow cytometric analysis to measure the percentage of GFP positive cells and Mean Fluorescence Intensity (MFI). FIG. 4A shows the results, demonstrating expression from all these vectors. The IRES dependent expression system showed about 5 fold higher levels of GFP expression in infected cells than the S1 promoter construct for all 3 different glioblastoma cell lines examined here, although absolute levels of expression also varied by a factor of about 5 over the three cell lines.

Example 6

Figure 2B:
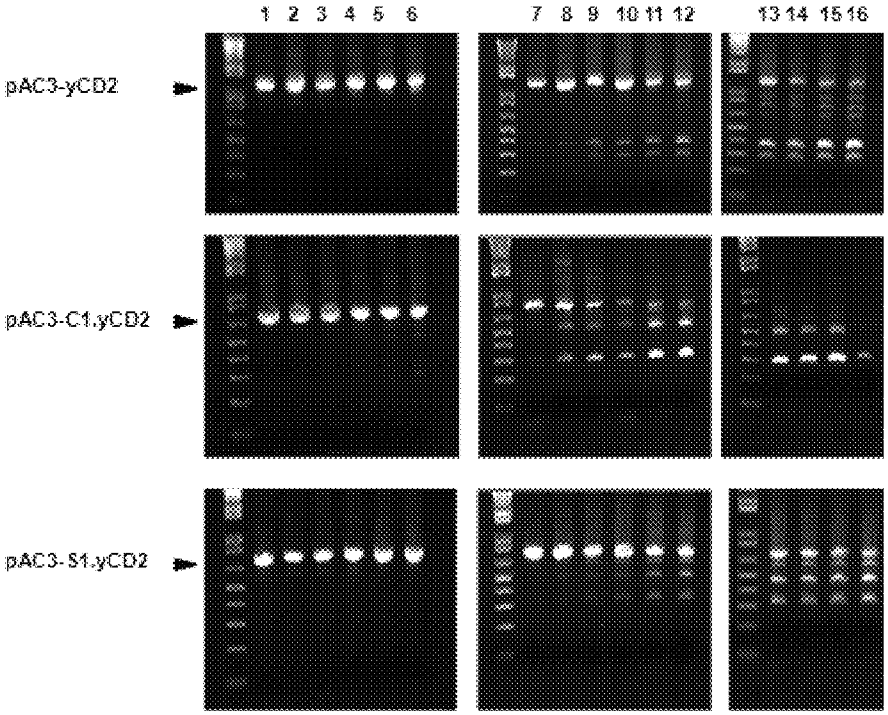

Vector Stability of pAC3-Based Vectors Containing C1 and S1 Core Promoter Driving CD Expression and Comparison to pACE-yCD2 pAC3 based vectors with core promoters driving the expression of CD (pAC3-C1.CD and pAC3-S1.CD) were constructed as described and corresponding infectious vector preparations were compared to vector from pAC3.yCD2 (O.D. Perez et al., Mol. Ther., 2012). Early passage of a human glioma cell line U87-MG was cultured in complete culture medium. Naïve cells were seeded at 2E5 cell per well in 6-well plates the day prior infection. The first cycle of infection was performed at MOI 0.1 according to calculated titers (TU/mL) in the presence of 4 μg/mL polybrene. In subsequent infections, one tenth of the viral supernatant produced by infected cells was used for infecting naïve cells. In each infection cycle, infected cells were passaged at d4 post infection into 6-well plates. Viral supernatant from infected cells at d7 post infection was collected for subsequent infection, and cells were harvested for genomic extraction for assessment of vector stability by IRES-PCR. The primers used for PCR were: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55). The relative stabilities are shown in FIG. 2B and show that the C1.yCD2 vector is less stable than the other two vectors which are roughly equivalent in stability, with the S1.yCD2 vector apparently slightly more stable than the IRES vector (pAC3-yCD2).

Example 7

Figure 4B:
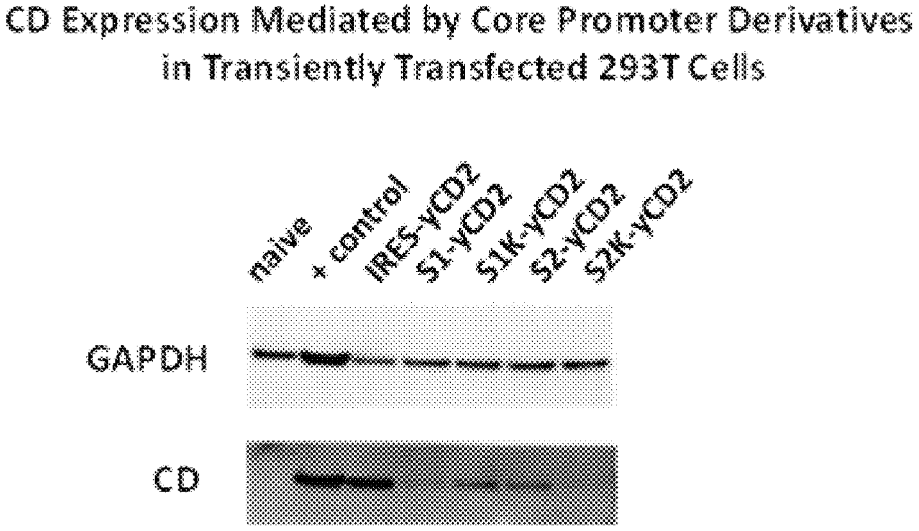
Figure 4C:
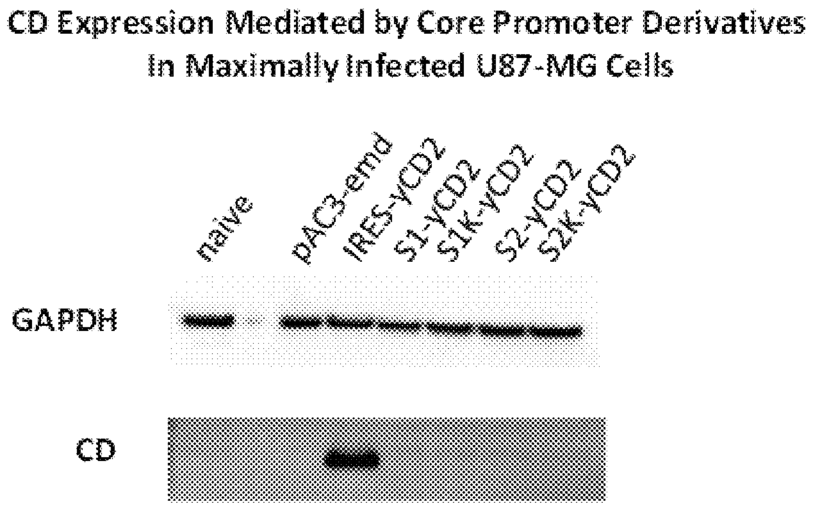

Transgene Expression of pAC3-Based Vectors Containing C1 and S1 Core Promoter Driving CD Expression and Comparison to pAC3-yCD2, after Transfection into 293T Cells The level of CD expression from the vectors after transfection in 293T cells was detected by immunoblotting using an antibody against CD (FIG. 4B). Naïve cells were seeded at 2E6 cell per 10-cm plates the day prior transfection. Transient transfection by calcium phosphate method was performed using plasmid DNA encoding the viral genome of each vector. At 40 h post transfection, cells were harvested and lysed to obtain cell lysates. Protein concentration of cell lysates was determined to allow equal protein loading as indicated by GAPDH. FIG. 4B shows the results demonstrating expression from all these vectors with the IRES system yielding about 15 fold higher levels of expression than the S1 promoter construct. FIG. 4C shows a Western blot of cell extracts from U87 cells fully transduced with vector derived from pAC3-yCD2 in both pAC3-C1.yCD2 and pAC3-S1.yCD2. While the CD protein band is easily detectable for pAC3-yCD2, there was insufficient CD protein from cells infected with pAC3-C1.yCD2 and pAC3-S1.yCD2 to be detected in this assay.

Example 8

Replication Kinetics, Vector Stability and Transgene Expression of pAC3 Based Vectors Containing the IRES or S1 Core Promoter Driving Human and Mouse GM-CSF Expression The replication kinetics of pAC3-IRES.hGMCSF, pAC3-S1.hGMCSF and pAC3-emd were assessed in U87-MG by qRT-PCR. The replication kinetics of pAC3-IRES.mGMCSF, pAC3-S1.mGMCSF and pAC3-emd were assessed in EMT6 (a mouse breast cancer cell line). Naïve cells were seeded at 1E5 cells (U87-MG) or 5E4 cells (EMT6) in E-well plate the day prior infection. Viral infection was performed at MOI 0.1 (U87-MG) or MOI 1 (EMT6) according to calculated titers (TU/mL) in the presence of 4 μg/mL polybrene. Equal number of infected cells were seeded at each passage (every 2 days for U87-MG and 3-4 days for EMT6 cells) during the entire course of infection, and viral supernatant produced from infected cells at various time points is collected and stored in −80° C. freezer. Samples of viral supernatant collected were processed to obtain viral RNA (Maxwell 16 LEV simply RNA Cells Kit, Promega) followed by qRT-PCR. The number of viral RNA copies/ml at each time point is determined from a standard curve included in the qRT-PCR.

Figure 5A:
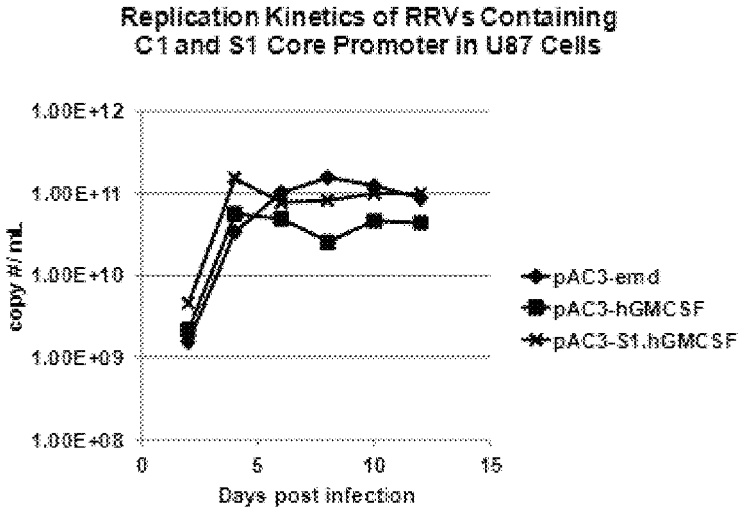
FIG. 5A-B shows (A) Viral replication kinetics of pAC3-emd, pAC3-hGMCSF and pAC3S1-hGMCSF vectors in U87 cells. (B) Viral replication kinetics of pAC3-emd, pAC3-mGMCSF and pAC3.S1-mGMCSF vectors in EMT6 cells.
Figure 5B:
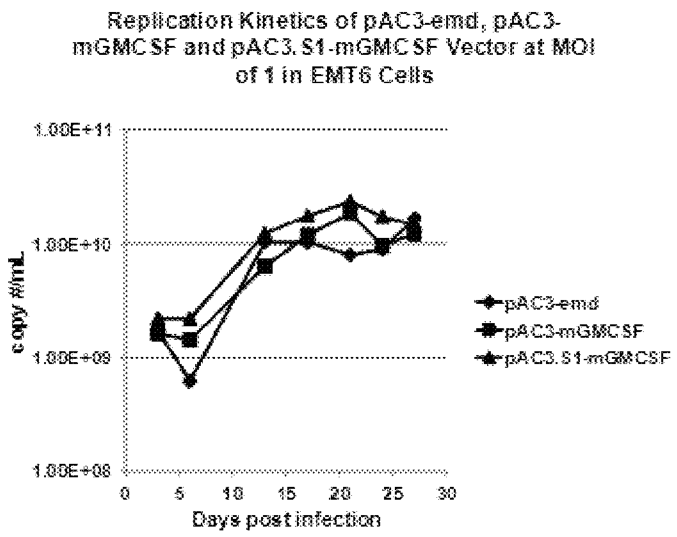

Results of the growth kinetics of the vectors are shown in FIGS. 5A and B, and demonstrate that the vectors all proliferate in target cells with similar kinetics to the archetypal pAC3-emd vector, in human and mouse cells.

Figure 3:
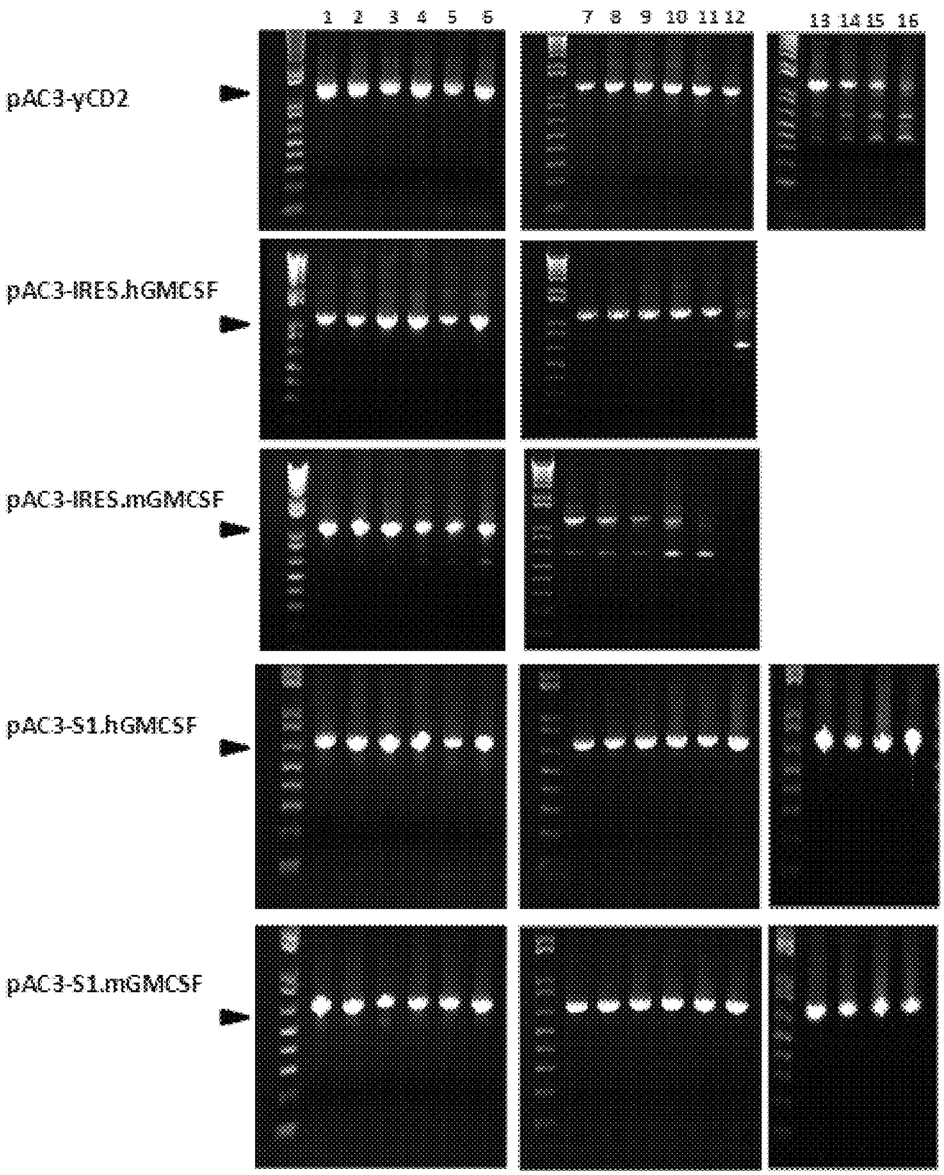
FIG. 3 shows vector stability of RRV in pAC backbone containing IRES element or S1 core promoter driving transgene (human and mouse GM-CSF) expression. The numbers above each lane indicates the number of infection cycle. Arrows indicate expected fragment size.
Figure 4D:
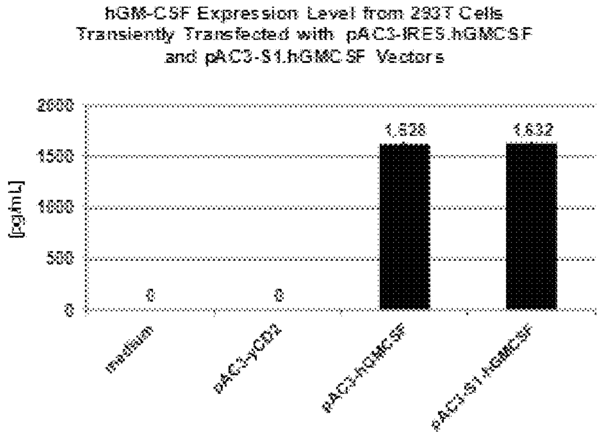
Figure 4E:
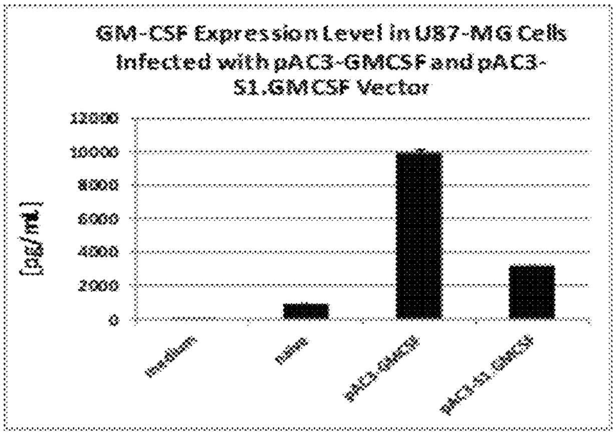
Figure 4F:
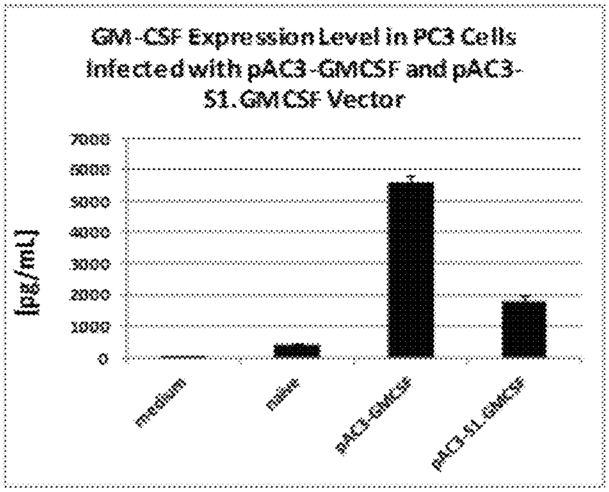
Figure 4G:
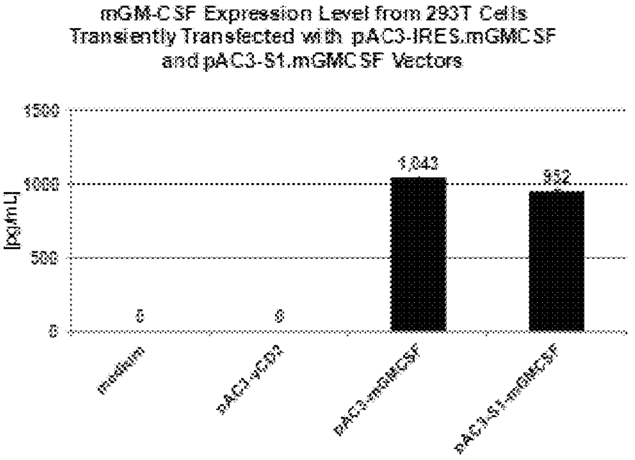
Figure 4H:
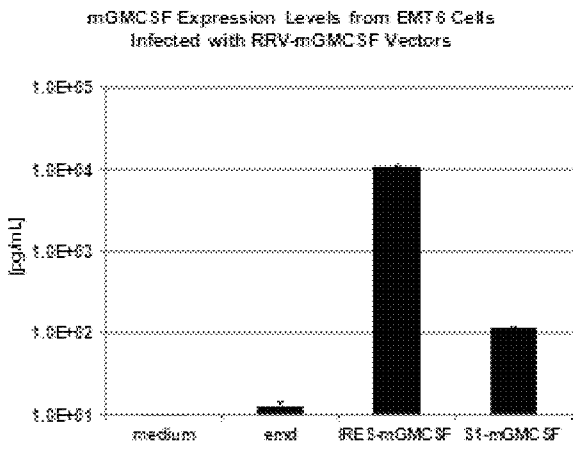

Early passage of a human glioma cell line U87-MG was cultured in complete culture medium. Naïve cells were seeded at 2e5 cell per well in 6-well plates the day prior infection. A first cycle of infection with infectious viral vector from pAC3-hGMCSF, pAC3-S1.hGMCSF and pAC3-emd was performed at MOI 0.1 according to calculated titers (TU/mL) in the presence of 4 μg/mL polybrene. In subsequent infections, one tenth of the viral supernatant produced by infected cells was used for infecting naïve cells. In each infection cycle, infected cells were passaged at d4 post infection into 6-well plates. Viral supernatant from infected cells at d7 post infection was collected for subsequent infection, and cells were harvested for genomic extraction for assessment of vector stability by IRES-PCR. The primers used for PCR are: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55). The stability profiles on serial passage are shown in FIG. 3 and demonstrate that the vector with the S1 promoter is at least as stable as the IRES-hGMCSF vector, while for the mouse GMCSF the S1 vector is more stable than the IRES version.

pAC3 based vectors with a core promoter driving the expression of human and mouse GM-CSF (pAC3-S1.hGMCSF and pAC3-S1.mGMCSF) were constructed and compared to pAC3-IRES.hGMCSF and pAC3-IRES.mGMCSF, respectively. Vector preparations were made from the constructs by transient transfection as described. The vector transfected 293T cells were assayed for production of hGMCSF and mGMCSF and FIGS. 4D and G show that expression of these proteins is observed in transfected cells, and that the transfected cells make about the same levels of human or mouse GMCSF from both the vector using the IRES expression system and the vectors using the S1 core promoter system, respectively. However, FIGS. 4E and F show that hGMCSF expression driven by the S1 promoter is 3 fold less than the IRES configuration, in fully infected U87 and PC3 cells, respectively. Similarly, FIG. 4H shows that in mouse EMT6 cells the S1 promoter is less efficient that the IRES vector in expressing mGMCSF after infection.

Example 9

Poor Transgene Expression of pAC3 Based Vectors Containing C1 and S1 Core Promoters Driving yCD2 Relative to pAC3-yCD2

The levels of CD expression were detected in 293T cells by immunoblotting using an antibody against CD (FIG. 4B). Naïve cells are seeded at 2E6 cell per 10-cm plates the day prior transfection. Transient transfection by calcium phosphate method was performed using plasmid DNA encoding the viral genome of each vector. At 40 h post transfection, cells are harvested and lysed to obtain cell lysates. Protein concentration of cell lysates is determined to allow equal protein loading as indicated by GAPDH. FIG. 4B shows the results demonstrating expression from all these vectors, with the IRES system yielding about 15 fold higher levels of expression than the S1 promoter construct. In addition, FIG. 4C shows expression of CD protein in an immunoblot in fully infected U87-MG cells from cells infected with vector from pAC3-yCD2 (IRES vector) but undetectable expression of yCD2 in both C1. yCD2 and S1.yCD2 vectors.

Example 10

In Vitro Positive Selection Using pAC3-S1.yCD2 Vector in Human Cells to Increase yCD2 Expression Positive selection of fully infected pAC3.S1.yCD2 vector is performed by concurrently giving N-(phosphonacetyl)-L-aspartate (PALA), an inhibitor of pyrimidine de novo synthesis, which leads to pyrimidine depletion-mediated cell death of non-infected cells or cells expression low level of yCD2. With addition of cytosine in culture, it rescues cells expression high level of yCD2 gene via the pyrimidine salvage pathway. The method described below applies to a U87 glioblastoma derived cell line used in the laboratory, but the same procedures can be used with multiple different cell lines derived from different tumor types. In these cases the actual concentrations of reagents and timing of the steps will be determined by the rate of growth of the cells and the initial infection rates of the cell line. Such adjustments can be made as needed by one skilled in the art and will be determined in the course of performing the method. In addition this optimization procedure can be used with any promoter driving a selectable gene in a replicating vector. Also other variations in actual reagent concentrations and timing of selection may be possible.

Figure 6:
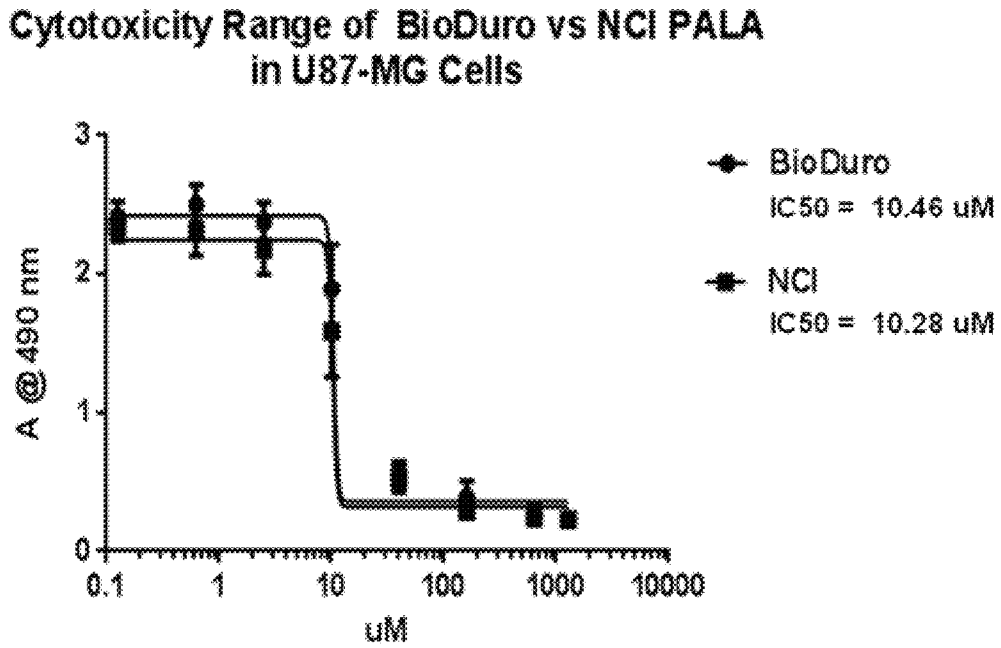
FIG. 6 shows the cell killing curve in U87 cells treated with PALA from two different sources with nearly identical results.

The concentration PALA required to kill naïve U87 cells was first determined, U87 cells infected with pAC3-yCD2 vector and for U87 cells with pAC3.S1-yCD2 vector. Cell were seeded at 3E3 cells in 96-well plates the day before. At 24 hour post cell seeding, PALA at 0.00975, 0.039, 0.156, 0.625, 2.5, 10, 40 and 160 uM were added to the culture for 5 consecutive days followed by an MTS assay to determine the cell viability. FIG. 6 shows that the ICH of PALA ranges between 8-30 uM. A range of cytosine concentrations (0.2, 1, 5 10 mM) in culture was also determined by performing the same experiment described above. This shows that the cells can tolerate cytosine in all concentrations tested.

For positive in vitro selection, naïve U87 cells are seeded at 1e5 cells in 6-well plates the day before. The next day, the cells are infected with pAC3-yCD2 vector (positive control) and separately with pAC3.S1-yCD2 vector, respectively, at MOI of 0.1. At 48 hour post infection (~20% infectivity), PALA at 1 uM and cytosine at 10 mM are added to the culture containing naïve U87 cells (negative control), U87 cells infected with pAC3-yCD2 vector (positive control) and U87 cells with pAC3.S1-yCD2 for 5 consecutive days at which time point, the culture supernatant is collected for a new round of infection with naïve U87 cells. The infection cycle in the presence of PALA and cytosine is repeated for 12 rounds with increasing concentration of PALA cycle 1-2: 1 uM; cycle 3-4: 3.3 uM; cycle 5-6: 10 uM, cycle 7-8: 20 uM and cycle 9-12: 30 uM). At the end of the selection, cells are isolated and expanded in the presence of 30 uM PALA and 10 mM cytosine. MTS assay is performed to demonstrate the increase of cell viability as a result of the positive selection. Cells infected with pAC3.S1.yCD2 vector prior to selection are not able to efficiently utilize the salvage pathway due to low CD expression. In contrast, cells infected with pAC3.S1-yCD2 vector post selection show high cell viability that is comparable to cells infected with pAC3-yCD2 vector.

To confirm that the high cell viability is due to upregulation of CD expression, Western blots are performed to examine CD expression. Cells are harvested and lysed to obtain cell lysates. Protein concentration of cell lysates is determined to allow equal protein loading as indicated by GAPDH in the immunoblot. The data show that the CD expression from cell extracts from U87 cells infected with pAC3.S1-yC2 vector is comparable to that of pAC3-yCD2. The genomic DNA is then isolated from U87 cells infected with pAC3.S1-yCD2 vector and amplified the S1-yCD2 region by PCR using the following primer set. IRES-F: 5'-CTGATCTTACTCTTTGGACCTTG-3' (SEQ ID NO:54) and IRES-R: 5'-CCCCTTTTTCTGGAGACTAAATAA-3'

(SEQ ID NO:55). The resulting PCR products are isolated for PCR cloning for sequencing analysis. The sequencing result show that multiple mutations occur in the S1 core promoter. Subsequently, the S1 promoter with identified mutations is synthesized with Mlu I and Not I site at each end of the DNA fragment for subcloning into pAC3 backbone as described above. The resulting vector with optimized S1 promoter is designated pAC3.mtS1-yCD2.

Infectious pAC3.mtS1-yCD2 vector is prepared by transient transfection in 293T cells as before. Naïve U87 cells are infected with pAC3.mtS1-yCD2 vector at MOI of 0.1. At day 7 post infection, cells are harvested and lysed to obtain cell lysates. Protein concentration of cell lysates is determined to allow equal protein loading as indicated by GAPDH in the immunoblot. The data show that the CD expression of cell extracts from U87 cells infected with pAC3.mtS1-yCD2 vector is comparable to that of pAC3-yCD2 vector driven by the IRES.

To correlate CD expression with 5-FC sensitivity, U87 cells with no vector, with pAC3-yCD2 vector, and pAC3.mtS1-yCD2 vector, respectively, are seeded at 1e3 cells per well in 96-well plates. They are monitored over an eight day period following treatment with various concentrations of 5-FC, which is first added one day after plating and then replenished with whole medium plus 5-FC every two days. Cell viability is assessed every two days by MTS assay. The data show that IC50 value for U87 cells infected with pAC3.mtS1-yCD2 vector is comparable to those infected with pAC3-yCD2 vector (0.5 ug/mL; Perez et al., 2012). Other promoter configurations can be optimized for gene expression using these techniques.

Example 11

Incorporation of Kozak Sequence Downstream of the Core Promoter Increases yCD2 Gene Expression without Altering Vector Stability Most eukaryotic mRNAs contain Kozak sequence which facilitates initiation of protein translation. Incorporation of Kozak sequence downstream of the core promoter increases yCD2 expression in both transiently transfected and fully infected cells. The optimized yeast CD gene, yCD2, has 3 in-frame ATG within the first 15 amino acids in the coding region. The spacing in the 5'UTR and the lack of Kozak sequence flanking the initiation codon in yCD2 mRNA was considered suboptimal for efficient protein translation initiation. Incorporation of Kozak sequence and/or other translational enhancer element may greatly improve the translation initiation and thus protein production of transgenes.

The pAC3.S1-yCD2 vector contains a core promoter without Kozak sequence. Although the core promoter has demonstrated useful transcription, efficient protein translation is equally important to confer gene expression. This improvement can be combined with others in this specification for improved core promoters or other improved minipromoters.

The pAC3-kozakS1.yCD2, (AKA pAC3.S1K-yCD2) and pAC3.kozakS2-yCD2 (AKA pAC3.S2K-yCD2) are derived from the backbone of pAC3-yCD2. The pAC3 backbone is isolated by endonuclease digestion of the pAC3-yCD2 plasmid DNA with Mlu I and Not I. The DNA sequence of kozakS1yCD2 and kozakS2yCd2 are synthesized with Mlu I and Not I restriction enzyme site present at each end of the DNA fragment for subsequent cloning to the corresponding sites in the pAC3 backbone.

Infectious vectors are prepared by transient transfection in 293T cells as before. Naïve U87 cells are infected with vectors at MOI of 0.1. At day 7 post infection, cells are harvested and lysed to obtain cell lysates. Protein concentration of cell lysates is determined to allow equal protein loading as indicated by GAPDH in the immunoblot. FIG. 4B shows that the CD expression of cell extracts from 293T transiently transfected with pAC3.S1K-yCD2 vector is approximately 2-5 higher than pAC3.S1-yCD2 vector. Similarly, CD expression of pAC3.S2K-yCD2 is approximately 2-5 higher than pAC3-S2-yCD2 vector in transiently transfected 293T cells. Moreover, the CD expression is comparable between pAC3-S1K-yCD2 and pAC3-S2K-yCD2 in transiently transfected 293T cells. In contrast, FIG. 4C shows CD expression is undetectable in maximally infected U87 cells with any one of the four vectors.

The data show that the CD expression of cell extracts from U87 cells infected with pAC3-kozakS1.yC2 vector is approximately 2-5 higher than pAC3-S1.yCD2 vector.

To correlate CD expression with 5-FC sensitivity, U87 cells with no vector, with pAC3-yCD2 vector, and pAC3-kozakS1.yCD2 vector, respectively, are seeded at 1E3 cells per well in 96-well plates. They are monitored over an eight day period following treatment with various concentrations of 5-FC, which is first added one day after plating and then replenished with whole medium plus 5-FC every two days. Cell viability is assessed every two days by MTS assay. The data show that $IC_{50}$ value for U87 cells infected with pAC3-kozakS1.yCD2 vector is approximately 5 fold higher than those infected with pAC3-S1.yCD2 vector, and within 10 fold of the pAC3-yCD2 vector (0.5 ug/mL; Perez et al., 2012).

For vector stability, naïve U87 cells are seeded at 2E5 cell per well in 6-well plates the day prior infection. The first cycle of infection is performed at MOI 0.1 according to calculated titers (TU/mL) in the presence of 4 μg/mL polybrene. In subsequent infections, one tenth of the viral supernatant produced by infected cells is used for infecting naïve cells. In each infection cycle, infected cells were passaged at d4 post infection into 6-well plates. Viral supernatants from infected cells at d7 post infection were collected for subsequent infection, and cells were harvested for genomic extraction for assessment of vector stability by IRES-PCR. The primers used for PCR were: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55). The data show that the stability of pAC3.kozakS1-yCD2 vector is comparable to that of pAC3-yCD2 and pAC3.S1-yCD2 vector.

Example 12

Construction and Configuration of pAC3 Based Vectors Containing Optimized S1 Core Promoter Driving yCD2-UPRT The yCD2-UPRT is ~1.2 kb. The mtS1 promoter=optimized S1 promoter (see Example 11). The pAC3-mtS1.yCD2-UPRT vector is derived from the backbone of pAC3-yCD2. The pAC3 backbone is isolated by endonuclease digestion of the pAC3-yCD2 plasmid DNA with Mlu I and Not I. The DNA sequence of mtS1.yCD2-UPRT is synthesized with Mlu I and Not I restriction enzyme site present at each end of the DNA fragment for subsequent cloning to the corresponding sites in the pAC3 backbone.

Example 13

Vector Stability and Transgene Expression of pAC3 Based Vectors Containing Optimized S1 Core Promoter Driving yCD2-UPRT Expression pAC3 based vectors with optimized core promoters driving the expression of yCD2-UPRT are constructed using similar techniques as above and compared to pAC3-yCD2-U (aka T50003, Perez et al., Mol. Ther., 2012, WO2010045002), which is the equivalent vector using an internal IRES to drive expression of the yCD2-UPRT fusion gene.

Infectious pAC3-mtS1.yCD2-UPRT vector is prepared by transient transfection in 293T cells. Naïve U87 cells infected with pAC3kozakS1.yCD2 vector at MOI of 0.1. At day 7 post infection, cells are harvested and lysed to obtain cell lysates. Protein concentration of cell lysates is determined to allow equal protein loading as indicated by GAPDH in the immunoblot. The data show that the CD-UPRT expression (~44KDa) from cell extracts of U87 cells infected with pAC3-mtS1.yCD2-UPRT vector is comparable to pAC3-yCD2-U and pAC3-yCD2 vectors.

To correlate CD expression with 5-FC sensitivity, U87 cells with no vector, with pAC3-yCD2, pAC3-yCD2-U, and pAC3-mtS1.yCD2-UPRT vector, respectively, are seeded at 1E3 cells per well in 96-well plates. They are monitored over an eight day period following treatment with various concentrations of 5-FC, which is first added one day after plating and then replenished with whole medium plus 5-FC every two days. Cell viability is assessed every two days by MTS assay. The data show that ICH value for U87 cells infected with pAC3-mtS1.yCD2-UPRT vector is at least equivalent to those infected with pAC3-yCD2 and pAC3-yCD2-U vectors.

For vector stability, naïve U87 cells are seeded at 2E5 cell per well in 6-well plates the day prior infection. The first cycle of infection is performed at MOI 0.1 according to calculated titers (TU/mL) in the presence of 4 μg/mL polybrene. In subsequent infections, one tenth of the viral supernatant produced by infected cells is used for infecting naïve cells. In each infection cycle, infected cells were passaged at d4 post infection into 6-well plates. Viral supernatants from infected cells at d7 post infection were collected for subsequent infection, and cells were harvested for genomic extraction for assessment of vector stability by IRES-PCR. The primers used for PCR were: IRES-F: 5'-CTGATCTTACTCTTTGGACCTTG-3' (SEQ ID NO:56) and IRES-R: 5'-CCCCTTTTTCTGGAGACTAAATAA-3' (SEQ ID NO:57). The data show that pAC3-S1.yCD2-UPRT vector has significantly better stability than the IRES driven pAC3-yCD2-U vector.

Example 14

Construction and Configuration of pAC3-Based Vectors Containing Optimized S1 Core Promoter Driving yCD2 Expression and Human U6 (Pol III) Promoter Driving shRNA Against TGFb2

The pAC3-S1.yCD2-polIII promoter-shRNATGFb2 vector is derived from the backbone of pAC3-yCD2. The pAC3 backbone is isolated by endonuclease digestion of the pAC3-yCD2 plasmid DNA with Mlu I and Not I. The DNA sequence of mtS1.yCD2 and polIII promoter-shRNATGFb2 is synthesized with Mlu I and Not I restriction enzyme site present at each end of the DNA fragment for subsequent cloning to the corresponding sites in the pAC3 backbone.

Example 15

Vector Stability and Transgene Expression of pAC3 Based Vectors Containing Optimized S1 Core Promoter Driving yCD2 Expression and Human Pol III Promoter Driving shRNA Against TGFb2

Infectious pAC3-mtS1.yCD2-polIII promoter-shRNATGFb2 vector is prepared by transient transfection in 293T cells as before. Naïve U87 cells infected with pAC3-kozakS1.yCD2 vector at MOI of 0.1. At day 7 post infection, one portion of cells are harvested and lysed to obtain cell lysates, and another portion of cells are harvested for total RNA extraction. Protein concentration of cell lysates is determined to allow equal protein loading as indicated by GAPDH in the immunoblot. The data show that the yCD2 expression from cell extracts of U87 cells infected with pAC3-mtS1.yCD2-polIII promoter-shRNATGFb2 vector is comparable to those from pAC3-yCD2 and pAC3-mtS1.yCD2 vectors.

To correlate CD expression with 5-FC sensitivity, U87 cells with no vector, with pAC3-yCD2, and pAC3-mtS1.yCD2-polIII promoter-shRNATGFb2 vector, respectively, are seeded at 1E3 cells per well in 96-well plates. They are monitored over an eight day period following treatment with various concentrations of 5-FC, which is first added one day after plating and then replenished with whole medium plus 5-FC every two days. Cell viability is assessed every two days by MTS assay. The data show that IC50 value for U87 cells infected with pAC3-mtS1.yCD2-polIII promoter-shRNATGFb2 vector is comparable to those infected with pAC3-yCD2 or pAC3-mtS1.yCD2 vectors.

To demonstrate efficient knockdown of TGFb2 in U87 cells infected with pAC3-mtS1.yCD2-polIII promoter-shRNATGFb2 vector, total RNA is extracted from cells harvested at d7 post infection as described above. Gene expression of TGFb2 is measured by qRT-PCR using RNA polIII promoter as an internal control for normalization. The relative expression level of TGFb2 to naïve U87 cells is calculated using ΔΔC(t) method. The data show that at d7 post infection, more than 70% of TGFb2 is downregulated. The infected cells were cultured up to 30 days and observe sustained knockdown of TFGb2.

For vector stability, naïve U87 cells were seeded at 2E5 cell per well in 6-well plates the day prior infection. The first cycle of infection was performed at MOI 0.1 according to calculated titers (TU/mL) in the presence of 4 μg/mL polybrene. In subsequent infections, one tenth of the viral supernatant produced by infected cells was used for infecting naïve cells. In each infection cycle, infected cells were passaged at d4 post infection into 6-well plates. Viral supernatants from infected cells at d7 post infection were collected for subsequent infection, and cells were harvested for genomic extraction for assessment of vector stability by IRES-PCR. The primers used for PCR were: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55). The data show that stability of pAC3-mtS1.yCD2-polIII promoter-shRNATGFb2 vector is comparable to pAC3-yCD2 and pAC3-mtS1.yCD2 vectors.

Example 16

Construction and Configuration of pAC3-Based Vectors Containing Optimized S1 Core Promoter Driving yCD2 Expression and Optimized S1 Core Promoter Driving tko An optimized thymidine kinase, tko, is used in this example due its high vector stability. The pAC3-mtS1.yCD2-mtS1.tko vector is derived from the backbone of pAC3-yCD2. The pAC3 backbone is isolated by endonuclease digestion of the pAC3-yCD2 plasmid DNA with Mlu I and Not I. The DNA sequence of mtS1.yCD2-mtS1.tko is synthesized with Mlu I and Not I restriction enzyme site present at each end of the DNA fragment for subsequent cloning to the corresponding sites in the pAC3 backbone.

Example 17

Vector Stability and Transgene Expression of pAC3 Based Vectors Containing an Optimized S1 Core Promoter Driving yCD2 Expression and an Optimized S1 Core Promoter Driving tko Infectious pAC3-mtS1.yCD2-mtS1.tko vector is prepared by transient transfection in 293T cells as before. Naïve U87 cells infected with pAC3-kozakS1.yCD2 vector at MOI of 0.1. At day 7 post infection, cells are harvested and lysed to obtain cell lysates, Protein concentration of cell lysates is determined to allow equal protein loading as indicated by GAPDH in the immunoblot. The data show that the yCD2 and TK expression from cell extracts of U87 cells infected with pAC3-mtS1.yCD2-mtS1.tko vector is comparable to those from pAC3-yCD2 and pAC3-tko vectors mediated by IRES.

To correlate CD expression with 5-FC sensitivity, U87 cells with no vector, with pAC3-yCD2, and pAC3-mtS1.yCD2-mtS1.tko vector, respectively, are seeded at 1E3 cells per well in 96-well plates. They are monitored over an eight day period following treatment with various concentrations of 5-FC, which is first added one day after plating and then replenished with whole medium plus 5-FC every two days. Cell viability is assessed every two days by MTS assay. The data show that IC50 value for U87 cells infected with pAC3-mtS1.yCD2-mtS1.tko vector is comparable to those infected with pAC3-yCD2 vector.

To correlate tko expression with ganciclovir sensitivity, U87 cells with no vector, with pAC3-tko, and pAC3-mtS1.yCD2-mtS1.tko vector, respectively, are seeded at 1e3 cells per well in 96-well plates. They are monitored over an eight day period following treatment with various concentrations of ganciclovir, which is first added one day after plating and then replenished with whole medium plus ganciclovir every two days. Cell viability is assessed every two days by MTS assay. The data show that IC50 value for U87 cells infected with pAC3-mtS1.yCD2-mtS1.tko vector is comparable to those infected with pAC3-tko vector.

For vector stability, naïve U87 cells are seeded at 2E5 cell per well in 6-well plates the day prior infection. The first cycle of infection is performed at MOI 0.1 according to calculated titers (TU/mL) in the presence of 4 μg/mL polybrene. In subsequent infections, one tenth of the viral supernatant produced by infected cells is used for infecting naïve cells. In each infection cycle, infected cells are passaged at d4 post infection into 6-well plates. Viral supernatants from infected cells at d7 post infection are collected for subsequent infection, and cells are harvested for genomic extraction for assessment of vector stability by IRES-PCR. The primers used for PCR were: IRES-F: 5'-CTGATCTTACTCTTTGGACCTTG-3' (SEQ ID NO:54) and IRES-R: 5'-CCCCTTTTTCTGGAGACTAAATAA-3' (SEQ ID NO:55). The data show that stability of pAC3-mtS1.yCD2-mtS1.tko vector is comparable to pAC3-yCD2 vector and much superior than pAC3-tko vector.

Example 18

Construction, Configuration and Testing of pAC3 Based Vectors, pAC3-HOE1.yCD2, pAC3-HOE2.yCD Etc. Containing a Hybrid Promoter with the Human Hemoxygenase Gene Core Promoter, Selected Enhancer Segments and a Kozak Sequence, Driving expression of the yCD2 gene The pAC3 backbone in the vector was isolated by endonuclease digestion of the pAC3-yCD2 plasmid DNA with Mlu I and Not I.

Six double-stranded synthetic DNA fragments coding for the elements listed in Table 2 and a double-stranded synthetic DNA fragment containing the Mlu1 recognition site (ACGCGT) were used. Each fragment from Table 2 also has a 5'protrusion of 5-GATC-3 for ligating each other, as did the Mlu1 site. The individual fragments are annealed by heating up to 90° C. and slow cooling, phophorylated at the 5' end by a T4 polynucleotide kinase reaction, then mixed in equimolar amounts along with 1/10 and 1/100 molar kinased Mlu1 sites and ligated. The ligation mixes are digested with Mlu1, the product electrophoresed on a gel and the 40-200 bp portion excised and purified from the gel.

A sequence corresponding to the human heme oxygenase 1 gene core promoter fused with a Kozak start site and the yCD2 gene is synthesized with a Not1 site on the 3' end and a Mlu1 site on the 5' end and digested with both enzymes.

The synthesized fragment is:

(SEQ ID NO: 56)

5' -

ACGCGTGGGGCGGGCTGGGCGCGGGCCCCTGCGGGTGTTGCAACGCCCGG

CCAGAAAGTGGGCATCAGCTGTTCCGCCTGGCCCACGTGACCCGCCGAGC

ATAAATGTGACCGGCCGCGGCTCCGGCAGTCAACGCCACC*ATG*GTGACCG

GCGGCATGGCCTCCAAGTGGGATCAAAAGGGCATGGATATCGCTTACGAG

GAGGCCCTGCTGGGCTACAAGGAGGGCGGCGTGCCTATCGGCGGCTGTCT

GATCAACAACAAGGACGGCAGTGTGCTGGGCAGGGGCCACAACATGAGGT

TCCAGAAGGGCTCCGCCACCCTGCACGGCGAGATCTCCACCCTGGAGAAC

TGTGGCAGGCTGGAGGGCAAGGTGTACAAGGACACCACCCTGTACACCAC

CCTGTCCCCTTGTGACATGTGTACCGGCGCTATCATCATGTACGGCATCC

CTAGGTGTGTGATCGGCGAGAACGTGAACTTCAAGTCCAAGGGCGAGAAG

TACCTGCAAACCAGGGGCCACGAGGTGGTGGTTGTTGACGATGAGAGGTG

TAAGAAGCTGATGAAGCAGTTCATCGACGAGAGGCCTCAGGACTGGTTCG

AGGATATCGGCGAGTGAGCGGCCGC-3';

where the large C is the transcription start site, the first underlined sequence is the Kozak sequence including the ATG start codon (italics) of the yCD2 gene, and the second underlined sequence is the stop codon for yCD2. This fragment is 625 nucleotides, with a 126 bp fragment upstream of the transcription start site which is the heme oxygenase promoter. This fragment is ligated to the pAC3Mlu1—Not backbone fragment isolated above, in the presence of excess of the Mlu1 fragments carrying the transcription factor binding site mixtures, and individual clones isolated by bacterial transfections followed by analyses of restriction digest of DNA mini-preps to identify plasmids with the pAC3 backbone the heme oxygenase promoter and CD, and a single copy of the binding site mix, below about 200 bp.

The plasmids that carry the desired sequences are then used to make infectious vector by transient transfection and U87 cells infected and assayed by Western blot for CD protein. Vectors expressing equivalent CD protein to pAC3-yCD2 or above are identified and sequenced to characterize the transcription factor binding site mix. Suitable identified binding site mixes as small as 40 bp are used to make vectors with other genes. Stability of the vectors are tested by serial passage as before.

Alternatively the ligation mix of transcription factor binding sites, core promoter-CD and pAC3 back bone is used with the PALA selection method in target cells such as U87, to select vectors that express high levels of CD protein.

Example 19

Construction, Configuration and Testing of pAC3 Based Vectors, pAC3-cTK.yCD2, Containing a Hybrid Promoter with the Herpes Virus 1Thymidine Kinase Gene Promoter, Selected Enhancer Segments and a Kozak Sequence, Driving Expression of the yCD2 Gene The Herpes Thymidine Kinase gene sequence is known to have a cryptic core promoter between the first and third ATG of the normal mRNA coding sequence (Al-shawi et al. Mol. Cell. Biol. 11: 4207 1991, Salamon et al Mol. Cell. Biol. 15:5322 1995). This 180 bp sequence:

```
                                                (SEQ ID NO: 57)
ATGGCTTCGTACCCCTGCCATCAACACGCGTCTGCGTTCGACCAGGCTGC

GCGTTCTCGCGGCCATAGCAACCGACGTACGGCGTTGCGCCCTCGCCGGC

AGCAAGAAGCCACGGAAGTCCGCCTGGAGCAGAAAATGCCCACGCTACTG

CGGGTTTATATAGACGGTCCTCACGGGATG
```

is co-synthesized with both enhancers such as those mixtures isolated in example 18 or in this case with the 72 bp enhancer repeats from SV40 (Gruss et al PNAS 78: 943-9471981, NCBI Reference Sequence: NC_001669.1) a single copy of which is:

```
                                                (SEQ ID NO: 58)
5'-

TGGTTGCTGACTAATTGAGATGCATGCTTTGCATACTTCTGCCTGCTGGG

GAGCCTGGGGACTTTCCACACC-3',
```

upstream of the TK cryptic promoter, and with the yCD2 sequence downstream, starting at the ATG start codon on the 3' end of the cryptic promoter. The total synthesized sequence has MLu1 and Not1 sites on the 5' and 3' ends respectively and is inserted into the pAC3 MLu1—Not 1 backbone fragment isolated as in example 18. The ligation mix is used to transfect bacteria and desired molecular clones isolated and tested for stability and CD expression by Western blot as described in example X. Levels of CD expression are as least as good as for pAC3-yCD2.

Example 20

Construction, Configuration and Testing of Transgene Expression of pAC3 Based Vectors Containing SV40 Promoter, RSV Promoter, a Synthetic Promoter with Selected Enhancer Segments The pAC3 backbone in the vector was isolated by endonuclease digestion of the pAC3-yCD2 plasmid DNA with Mlu I and Not I sites as described above or by endonuclease digestion of the pAC3-Gluc plasmid DNA with Mlu I and Psi I sites.

The retroviral replicating vectors, pAC3-SV40-GFP-R, pAC3-SV40-Gluc, pAC3-RSV-Gluc, and pAC3.ES1-Gluc were derived from the backbone of pAC3-yCD2. The pAC3 backbone was isolated by endonuclease digestion of the pAC3-yCD2 plasmid DNA with Mlu I and Not I. The DNA sequence of SV40-GFP-R was synthesized or amplified by polymerase chain reaction (PCR) with Mlu I and Psi I at each end of DNA fragment for subcloning into the pAC3-Gluc backbone to replace the IRES sequence at the corresponding restriction sites.

Figure 7:
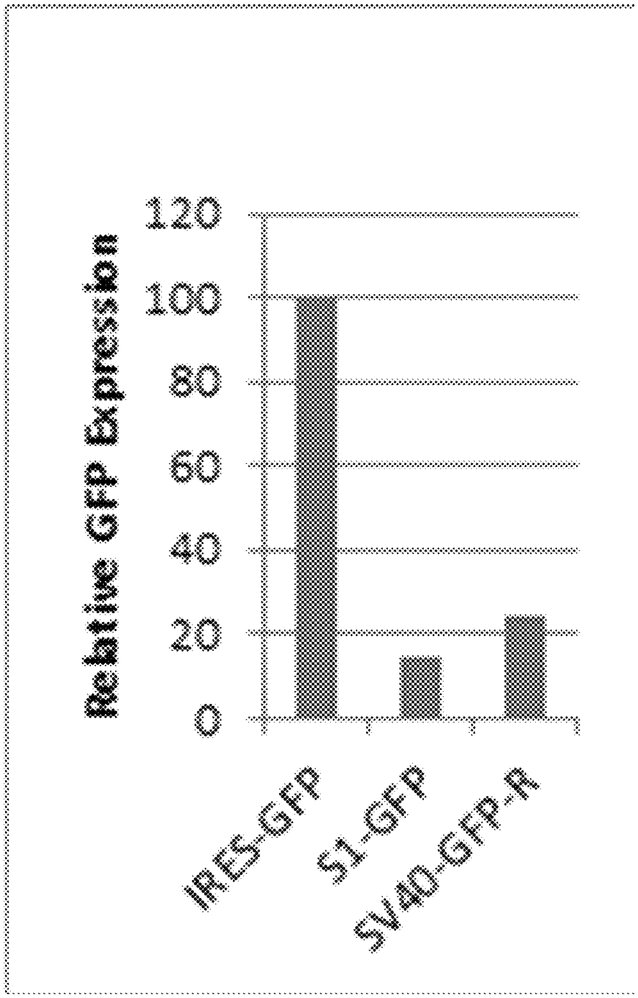
FIG. 7 shows GFP expression from an IRES-cassette, S1 cassette and SV40 cassette.

In pAC3-SV40-GFP-R construct, the SV40-GFP cassette was placed in a reversed orientation in the 3'UTR to minimize promoter interference in proviral DNA configuration.

pAC3-SV40-GFP-R viruses are prepared by transient transfection in 293T cells as before. Naïve U87 cells are infected with these vectors at MI of 0.01. At day 13 post infection, cells are harvested and analyzed by flow cytometry by gating GFP-positive cells and measuring the mean fluorescent intensity of the GFP-positive population. FIG. 7 shows that the GFP expression level of pAC3-SV40-GFP-R is higher than pAC3-S1-GFP, but still significantly less than that of pAC3-GFP mediated by IRES.

pAC3-Gluc, pAC3-SV40-Gluc, pAC3-RSV-Gluc, and pAC3.ES1-Gluc viruses are prepared by transient transfection in 293T cells as before. Naïve U87 cells are infected with these vectors at MI of 0.01. Supernatant from each cell passage (day 3, day 6 and day 9 post infection) is collected. At each cell passage, same number of cells are seeded and cultured in equal volume of culture medium. A 1:5 serial dilutions of the supernatant of each sample from each time point are made to measure the intensity of luminescence in the presence of the substrate, colenterazine, at a final concentration of 15 uM. The data show that Gluc expression levels mediated by SV40, RSV, and ES1 promoters are 2-3 times less than that mediated by IRES.

Example 21

Construction, Configuration and Testing of Transgene Expression of pAC3 Based Vectors Containing RSV Promoter, SV40 Promoter, S1 Core Promoter, EC1 Synthetic Promoter and ES1 Synthetic Promoter The pAC3 backbone in the vector was isolated by endonuclease digestion of the pAC3-yCD2 plasmid DNA with Mlu I and Not I sites as described above or by endonuclease digestion of the pAC3-Gluc plasmid DNA with Mlu I and Psi I sites.

The retroviral replicating vectors, pAC3-SV40-Gluc, pAC3-RSV-Gluc, and pAC3.ES1-Gluc were derived from the backbone of pAC3-yCD2. The pAC3 backbone was isolated by endonuclease digestion of the pAC3-yCD2 plasmid DNA with Mlu I and Not I. The DNA sequence of SV40-GFP-R, SV40-Gluc, RSV-Gluc, and ES1-Gluc, respectively, were synthesized or amplified by polymerase chain reaction (PCR) with Mlu I and Psi I at each end of DNA fragment for subcloning into the pAC3-Gluc backbone to replace the IRES sequence at the corresponding restriction sites. In pAC3-SV40-GFP-R construct, the SV40-GFP cassette was placed in a reversed orientation in the 3'UTR to minimize promoter interference in proviral DNA configuration.

SV40-Gluc, RSV-Gluc and EC1-Gluc, S1-Gluc and ES1-Gluc cassette with Mlu I and Psi I sites are place in the same orientation as LTR. RVS promoter is 271 nts in length; SV40 promoter is 324 nts in length. Synthetic S1 core promoter is 80 nts in length. EC1, which is a hybrid promoter consists of tandem repeats of CRE (Schlabach et al., 2010 PNAS) and the C1 core promoter (Juven-Gershon et al., 2006 Nature Methods) is 181 nts in length. ES1, which is hybrid of tandem repeats of CRE and S1 core promoter (Juven-Gershon et al., 2006 Nature Methods) is 188 nts in length.

Gluc expression from pAC3-Gluc, pAC3-RSV-Gluc, pAC3-SV40-Gluc, pAC3-EC1-Gluc, pAC3-S1-Gluc and pAC3-ES1-Gluc were evaluated in transiently transfected 293T or Hela cells. At 48 hours post transfection, the supernatant was collected and Gluc expression level is determined by co-incubation of 1:3 or 1:4 serially diluted supernatant with colenterazine at a final concentration of 15 uM.

Figure 9:
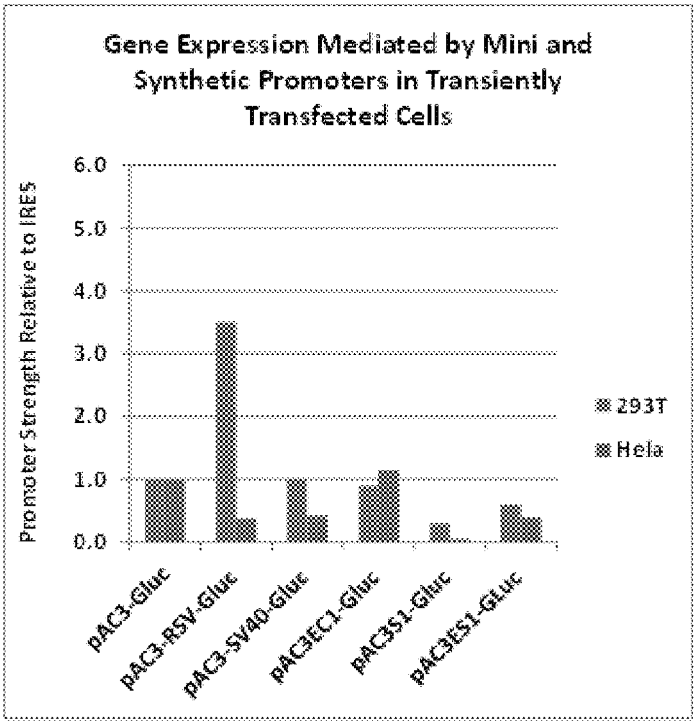
FIG. 9 shows gene expression mediated by mini- and synthetic-promoters in transiently transfected cells (293T, left side; Hela cells right side).

The data is shown in FIG. 9. 293T cells, Gluc expression levels mediated by RSV is approximately 3 fold higher than Gluc expression mediated by IRES. Gluc expression level mediated by SV40, EC1 and promoters are comparable to that of IRES. As expected, Gluc expression mediated by S1 core promoter is 3-fold less than that of IRES. For ES1, the promoter activity is about ⅓ less than IRES and EC1, but 2-fold higher than S1 alone.

In Hela cells, Gluc expression levels mediated by RSV, SV40, and ES1 is approximately 2.5 fold lower than Gluc expression mediated by IRES. The disparity of the RSV results with those seen in 293T cells (3 fold greater than IRES) is expected as, although the RSV LTR promoter is known to be ubiquitously expressed, unusually, in Hela cells it is specifically suppressed by a 21kD inhibitory protein, not present in most other cell types. The Gluc expression level mediated by the S1 core promoter alone is approximately 10-fold less than that mediated by IRES. However, inclusion of the synthetic enhancer (ES1) increases the promoter activity by 4-fold. The Gluc expression level mediated by EC1 is slightly higher than that mediated by IRES (FIG. 9).

pAC3-Gluc, pAC3-CMV-Gluc, pAC3-RSV-Gluc, and pAC3-SV40-Gluc viruses are prepared by transient transfection in 293T cells as before. Naïve U87 cells are infected with these vectors at MOI of 0.01. Supernatant from each cell passage (day 3, day 6 and day 9 post infection) is collected. At each cell passage, same number of cells are seeded and cultured in equal volume of culture medium. A 1:3 serial dilutions of the supernatant of each sample from each time point are made to measure the intensity of luminescence in the presence of the substrate, colenterazine, at a final concentration of 15 uM. The data show that Gluc expression levels mediated by RSV, SV40, EC1 and ES1 promoters are comparable to that mediated by IRES.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A recombinant replication competent gammaretrovirus comprising:

a retroviral GAG protein;

a retroviral POL protein;

a retroviral envelope;

a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain;

a therapeutic cassette comprising at least one mini-promoter cassette having a mini-promoter that is regulated by an RNA polymerase II, wherein the mini-promoter is about 70-500 bp in length and operably linked to a heterologous polynucleotide, wherein the therapeutic cassette is positioned 5' to the 3' LTR and 3' to the env nucleic acid domain encoding the retroviral envelope, and wherein when only one mini-promoter cassette is present the heterologous polynucleotide is 1.2kb to 2.0 kb in length; and cis-acting sequences necessary for reverse transcription, packaging and integration in a target cell, and wherein the mini-promoter comprises an RSV promoter.

2. The recombinant replication competent gammaretrovirus of claim 1, wherein the retroviral polynucleotide sequence is engineered from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, avian reticuloendotheliosis virus (REV), or Gibbon ape leukemia virus (GALV).

3. The recombinant replication competent gammaretrovirus of claim 1, wherein the retroviral envelope is an amphotropic MLV envelope.

4. The recombinant replication competent gammaretrovirus of claim 1, wherein the target cell is a cancer cell.

5. The recombinant replication competent gammaretrovirus of claim 1, wherein the target cell is a neoplastic cell.

6. The recombinant replication competent gammaretrovirus of claim 4, wherein the cancer cell is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer, lymphoma, and leukemia.

7. The recombinant replication competent gammaretrovirus of claim 1, wherein the promoter sequence is a growth regulatory gene promoter.

8. The recombinant replication competent gammaretrovirus of claim 1, wherein the promoter sequence comprises a tissue-specific promoter sequence.

9. The recombinant replication competent gammaretrovirus of claim 1, wherein the promoter comprises a CMV-R-U5 domain polynucleotide.

10. The recombinant replication competent gammaretrovirus of claim 1, wherein the mini-promoter is a core promoter.

11. The recombinant replication competent gammaretrovirus of claim 1, wherein the mini-promoter is an optimized core promoter.

12. The recombinant replication competent gammaretrovirus of claim 1, wherein the therapeutic cassette comprises (a) at least two mini-promoter cassettes, (b) at least one minipromoter cassette and a polIII promoter cassette or (c) at least one mini-promoter cassette and an IRES cassette.

13. The recombinant replication competent gammaretrovirus of claim 1, wherein the mini promoter comprises a core promoter and further comprises an enhancer element.

14. The recombinant replication competent gammaretrovirus of claim 1, wherein the mini-promoter comprises a TATA box, and initiator site, a Motif Ten Element (MTE), a Downstream promoter element (DPE) and at least one additional element selected from the group consisting of: (a) TFIIB recognition element, upstream (BREu); (b) TFIIB recognition element downstream (BREd); (c) HBV X core promoter element 1 (XCPE1); (d) HBV X core promoter element 2 (XCPE2); (d) downstream core element site I (CDE SI); (e) downstream core element site II (CDE SII); and (f) downstream core element site III (CDE SIII).

15. The recombinant replication competent gammaretrovirus of claim 14, wherein the mini-promoter further comprises an enhancer element.

16. The recombinant replication competent gammaretrovirus of claim 1, wherein the heterologous nucleic acid comprises a polynucleotide having a sequence as set forth in SEQ ID NO:3, 5, 11, 13, 15 or 17.

17. The recombinant replication competent gammaretrovirus of claim 1, wherein the heterologous nucleic acid is human codon optimized and encodes a polypeptide as set forth in SEQ ID NO:4.

18. The recombinant replication competent gammaretrovirus of claim 1, wherein the 3' LTR is engineered from a gammaretrovirus.

19. The recombinant replication competent gammaretrovirus of claim 18, wherein the 3' LTR comprises a U3-R-U5 domain.

20. The recombinant replication competent gammaretrovirus of claim 1, wherein the heterologous nucleic acid sequence encodes a biological response modifier or an immunopotentiating cytokine.

21. The recombinant replication competent gammaretrovirus of claim 20, wherein the immunopotentiating cytokine is selected from the group consisting of interleukins 1 through 15, interferon, tumor necrosis factor (TNF), and granulocyte-macrophage-colony stimulating factor (GM-CSF).

22. The recombinant replication competent gammaretrovirus of claim 20, wherein the immunopotentiating cytokine is interferon gamma.

23. The recombinant replication competent gammaretrovirus of claim 1, wherein the heterologous nucleic acid encodes a polypeptide that converts a nontoxic prodrug in to a toxic drug.

24. The recombinant replication competent gammaretrovirus of claim 23, wherein the polypeptide that converts a nontoxic prodrug in to a toxic drug is thymidine kinase, purine nucleoside phosphorylase (PNP), or cytosine deaminase.

25. The recombinant replication competent gammaretrovirus of claim 1, wherein the heterologous nucleic acid sequence comprises an inhibitory polynucleotide.

26. The recombinant replication competent gammaretrovirus of claim 25, wherein the inhibitory polynucleotide comprises an miRNA, siRNA sequence or other RNAi construct.

27. The recombinant replication competent gammaretrovirus of claim 26, wherein the therapeutic cassette comprises a mini-promoter operably linked to heterologous nucleic acid and a polIII promoter operably linked to the miRNA, siRNA sequence or other RNAi coding domain.

28. A method of delivering a therapeutic molecule to a subject comprising contacting the subject with a recombinant replication competent gammaretrovirus of claim 1.

29. A method of treating a cell proliferative disorder comprising contacting the subject with the recombinant replication competent gammaretrovirus of claim 16 under conditions such that the polynucleotide is expressed and contacting the subject with 5-fluorocytosine.

30. The method of claim 29, wherein the cell proliferative disorder is glioblastoma multiforme.

31. The method of claim 29, wherein the cell proliferative disorder is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer.

32. A method of treating a cell proliferative disorder in a subject comprising contacting the subject with the recombinant replication competent gammaretrovirus of claim 1, wherein the heterologous nucleic acid sequence encodes a therapeutic protein that inhibits proliferation of a neoplastic cell.

33. The method of claim 32, wherein the therapeutic protein comprises a polypeptide that converts a non-cytotoxic drug to a cytotoxic drug.

34. The method of claim 33, wherein the polypeptide has cytosine deaminase activity.

35. The method of claim 34, wherein the polypeptide comprises a sequence as set forth in SEQ ID NO:4, 12, 14, 16, or 18.

36. The method of claim 33, wherein the non-cytotoxic drug is 5-fluorocytosine.

37. A method of treating a cell proliferative disorder comprising administering the recombinant replication competent gammaretrovirus of claim 1 to a subject having a cell proliferative disorder under conditions such that the retrovirus infects cells with the disorder and contacting the subject with an anti-cancer agent or chemotherapeutic agent.

38. The method of claim 37, wherein the anti-cancer agent is selected from the group consisting of bevacizumab, pegaptanib, ranibizumab, sorafenib, sunitinib, AE-941, VEGF Trap, pazopanib, vandetanib, vatalanib, cediranib, fenretinide, squalamine, INGN-241, oral tetrathiomolybdate, tetrathiomolybdate, Panzem NCD, 2-methoxyestradiol, AEE-788, AG-013958, bevasiranib sodium, AMG-706, axitinib, BIBF-1120, CDP-791, CP-547632, PI-88, SU-14813, SU-6668, XL-647, XL-999, IMC-1121B, ABT-869, BAY-57-9352, BAY-73-4506, BMS-582664, CEP-7055, CHIR-265, CT-322, CX-3542, E-7080, ENMD-1198, OSI-930, PTC-299, Sirna-027, TKI-258, Veglin, XL-184, and ZK-304709.

39. The method of claim 37, wherein the gammaretrovirus is administered from about $10^3$ to $10^7$ TU/g brain weight.

40. The method of claim 39, wherein the gammaretrovirus is administered from about $10^4$ to $10^6$ TU/g brain weight.

* * * * *